United States Patent
Bowman et al.

(10) Patent No.: US 11,970,543 B2
(45) Date of Patent: Apr. 30, 2024

(54) ANTI-CD39 ANTIBODIES AND USE THEREOF

(71) Applicants: ARCUS BIOSCIENCES, INC., Hayward, CA (US); WUXI BIOLOGICS IRELAND LIMITED, Mullagharlin (IE)

(72) Inventors: Christine Elizabeth Bowman, San Francisco, CA (US); Ada Pei Xian Chen, San Francisco, CA (US); Ester Fernandez-Salas, San Mateo, CA (US); Nigel Pelham Clinton Walker, Burlingame, CA (US); Xiaoning Zhao, San Jose, CA (US); Yaohua Hu, Shanghai (CN); Siwei Nie, Shanghai (CN); JiJie Gu, Shanghai (CN)

(73) Assignees: ARCUS BIOSCIENCES, INC., Hayward, CA (US); WUXI BIOLOGICS IRELAND LIMITED, Mullagharlin (IE)

( * ) Notice: Subject to any disclaimer, the term of this patent is extended or adjusted under 35 U.S.C. 154(b) by 0 days.

(21) Appl. No.: 18/177,729

(22) Filed: Mar. 2, 2023

(65) Prior Publication Data
US 2024/0034803 A1  Feb. 1, 2024

(51) Int. Cl.
*A61P 35/00* (2006.01)
*C07K 16/28* (2006.01)

(52) U.S. Cl.
CPC .......... *C07K 16/2896* (2013.01); *A61P 35/00* (2018.01); *C07K 2317/21* (2013.01); *C07K 2317/24* (2013.01)

(58) Field of Classification Search
CPC ............ C07K 16/2896; C07K 2317/21; C07K 2317/24; A61P 35/00
USPC .................................................... 424/133.1
See application file for complete search history.

(56) References Cited

U.S. PATENT DOCUMENTS

| | | |
|---|---|---|
| 2016/0137747 A1 | 5/2016 | Levy et al. |
| 2017/0335007 A1 | 11/2017 | Chen et al. |
| 2021/0363268 A1 | 11/2021 | Chappel et al. |

FOREIGN PATENT DOCUMENTS

| | | |
|---|---|---|
| CN | 111448211 A | 7/2020 |
| CN | 112262155 A | 1/2021 |
| CN | 113754768 A | 12/2021 |
| SG | 11202008390 | 9/2020 |
| WO | WO-2009/095478 A1 | 8/2009 |
| WO | WO-2012/085132 A1 | 6/2012 |
| WO | WO-2016/073845 A1 | 5/2016 |
| WO | WO-2017/089334 A1 | 6/2017 |
| WO | WO-2017/157948 A1 | 9/2017 |
| WO | WO-2017/191300 A1 | 11/2017 |
| WO | WO-2018/065552 A1 | 4/2018 |
| WO | WO-2018/167267 A1 | 9/2018 |
| WO | WO-2019/027935 A1 | 2/2019 |
| WO | WO-2019/068907 A1 | 4/2019 |
| WO | WO-2019/096900 A1 | 5/2019 |
| WO | WO-2019/178269 A1 | 9/2019 |
| WO | WO-2019/241707 A1 | 12/2019 |
| WO | WO-2019/243252 A1 | 12/2019 |
| WO | WO-2020/172597 A1 | 8/2020 |
| WO | WO-2021/030251 A1 | 2/2021 |
| WO | WO-2021/037037 A1 | 3/2021 |
| WO | WO-2021/055329 A1 | 3/2021 |
| WO | WO-2021/056610 A1 | 4/2021 |
| WO | WO-2021/088838 A1 | 5/2021 |
| WO | WO-2021/203058 A1 | 10/2021 |
| WO | WO-2022/056200 A1 | 3/2022 |
| WO | WO-2022/111576 A1 | 6/2022 |

OTHER PUBLICATIONS

Hayes, et al. "CD39 is a promising therapeutic antibody target for the treatment of soft tissue sarcoma" AM J Transl Red 7(2):1181-1188 (Jun. 30, 2015).
International Search Report and Written Opinion in PCT/CN2023/079295 on Jun. 13, 2023, 10 pages.
Allard et al., "On the mechanism of anti-CD39 immune checkpoint therapy," Journal for Immuno Therapy of Cancer, 2020, 8:e000186 (11 pages).
Allard et al., "The adenosine pathway in immuno-oncology," Nature Reviews Clinical Oncology, 2020, 17(10):611-629.
Allard et al., "The ectonucleotidases CD39 and CD73: Novel checkpoint inhibitor targets," Immunological Reviews, 2017, 276:121-144.
Clayton et al., "Cancer exosomes express CD39 and CD73, which suppresses T cells through adenine production," Journal of Immunology, 2011, 187:676-683.
Del Barrio, et al., "Adenosine-generating ovarian cancer cells attract myeloid cells which differentiate into adenosine-generating tumor associated macrophages—a selfamplifying, CD39- and CD73-dependent mechanism for tumor immune escape," Journal for Immuno Therapy of Cancer, 2016, 4:49 (16 pages).
International Search Report and Written Opinion on PCT/CN2022/079021 Dtd Dec. 8, 2022, 20 pages.
Li et al., "Targeting CD39 in cancer reveals an extracellular ATP- and inflammasome-driven tumor immunity," Cancer Discovery, 2019, 9(12):1754-1773.
Mao et al., "Delivery of an ectonucleotidase inhibitor with ROS-responsive nanoparticles overcomes adenosine-mediated cancer immunosuppression," Science Translational Medicine, 2022, 14(648) : eabh1261 (18 pages).
Moesta et al., "Targeting CD39 in cancer," Nature Reviews Immunology, 2020, 20(12):739-755.
Perrot et al., "Blocking Antibodies Targeting the CD39/CD73 Immunosuppressive Pathway Unleash Immune Responses in Combination Cancer Therapies," Cell Reports, 2019, 27(8):2411-2425. e9.

(Continued)

*Primary Examiner* — Yan Xiao
(74) *Attorney, Agent, or Firm* — Foley & Lardner LLP; Erin Hill

(57) ABSTRACT

Provided herein are anti-CD39 antibodies that inhibit the enzymatic activity of human CD39 and methods of using the same.

13 Claims, 42 Drawing Sheets

Specification includes a Sequence Listing.

(56) References Cited

OTHER PUBLICATIONS

Spatola et al., "Fully human anti-CD39 antibody potently inhibits ATPase activity in cancer cells via uncompetitive allosteric mechanism," MAbs, 2020, 12(1):e1838036, 16 pages.

Wei et al., "A humanized monoclonal antibody targeting CD39 with novel mechanism for cancer treatment," Medicine in Drug Discovery, 2021, 11:10009.

Yan et al., "Control of metastases via myeloid CD39 and NK cell effector function," Cancer Immunology Research, 2020, 8(3):356-367.

Zanin et al., "Differential macrophage activation alters the expression profile of NTPDase and ecto-5'-nucleotidase," PLoS ONE, 2012, 7(2):e31205.

Bastid, et al., "Inhibition of CD39 Enzymatic Function at the Surface of Tumor Cells Alleviates Their Immunosuppressive Activity," Cancer Immunol Res., 3(3):254-265 (Mar. 2015).

Chiarella, et al., "Extracellular ATP and Adenosine in Cancer Pathogenesis and Treatment.," Trends in Cancer, 7(8):731-750 (2021).

Galluzzi, et al., "Immunostimulation with chemotherapy in the era of Immune Checkpoint Inhibitors," Nat. Rev. Clin. Oncol., 17:725-741 (2020).

Junger W.G., "Immune Cell Regulation by Autocrine Purinergic Signalling," Nat Rev. Immunol. 11:201-212 (Mar. 2011).

Nakanishi K., "Unique Action of Interleukin-18 on T Cells and Other Immune Cells," Front. Immunol., 9(763):1-7 (Apr. 2018).

Pelegrin P., "P2X7 Receptor and the NLRP3 Inflammasome: Partners in Crime," Biochem. Pharmacol., 187:114385, 9 pages (2021).

Pellegatti, et al., "Increased Level of Extracellular ATP at Tumor Sites: In Vivo Imaging with Plasma Membrane Luciferase," PLoS ONE 3(7):e2599, 9 pages (2008).

Queen, et al., "A Humanized Antibody That Binds to the Interleukin 2 Receptor," Proc. Natl. Acad. Sci. USA, 86:10029-10033 (Dec. 1989).

Wang, et al., "A Bioorthogonal System Reveals Antitumour Immune Function of Pyroptosis," Nature, 579:421-426 (Mar. 19, 2020).

Wilkin, et al., "The P2Y11 Receptor Mediates the ATP-Induced Maturation of Human Monocyte-Derived Dendritic Cells," J Immunol., 166(12):7172-7177 (2001).

Young, et al., "P2RX7 Purinoceptor as a Therapeutic Target—The Second Coming?," Front. Chem., 6(248):1-14 (Jun. 2018).

Zebisch, et al., "Characterization of Rat NTPDase1, -2, and -3 Ectodomains Refolded from Bacterial Inclusion Bodies," Biochemistry, 46:11945-11956 (2007).

Zhou, et al., "IL-18BP is a Secreted Immune Checkpoint and Barrier to IL-18 Immunotherapy," Nature. 583:609-14 (Jul. 23, 2020).

```
                         SEQUENCE LISTING

Sequence total quantity: 74
SEQ ID NO: 1            moltype = AA   length = 330
FEATURE                 Location/Qualifiers
source                  1..330
                        mol_type = protein
                        organism = synthetic construct
                        note = Description of Artificial Sequence: Synthetic
                          polypeptide
SEQUENCE: 1
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 2            moltype = AA   length = 330
FEATURE                 Location/Qualifiers
source                  1..330
                        mol_type = protein
                        organism = synthetic construct
                        note = Description of Artificial Sequence: Synthetic
                          polypeptide
SEQUENCE: 2
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 3            moltype = AA   length = 330
FEATURE                 Location/Qualifiers
source                  1..330
                        mol_type = protein
                        organism = synthetic construct
                        note = Description of Artificial Sequence: Synthetic
                          polypeptide
SEQUENCE: 3
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PDVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPLPEEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 4            moltype = AA   length = 327
FEATURE                 Location/Qualifiers
source                  1..327
                        mol_type = protein
                        organism = synthetic construct
                        note = Description of Artificial Sequence: Synthetic
                          polypeptide
```

-continued

```
SEQUENCE: 4
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                     327

SEQ ID NO: 5            moltype = AA  length = 327
FEATURE                 Location/Qualifiers
source                  1..327
                        mol_type = protein
                        organism = synthetic construct
                        note = Description of Artificial Sequence: Synthetic
                        polypeptide
SEQUENCE: 5
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                     327

SEQ ID NO: 6            moltype = AA  length = 107
FEATURE                 Location/Qualifiers
source                  1..107
                        mol_type = protein
                        organism = synthetic construct
                        note = Description of Artificial Sequence: Synthetic
                        polypeptide
SEQUENCE: 6
RTVAAPSVFI FPPSDEQLKS GTASVVCLLN NFYPREAKVQ WKVDNALQSG NSQESVTEQD   60
SKDSTYSLSS TLTLSKADYE KHKVYACEVT HQGLSSPVTK SFNRGEC                107

SEQ ID NO: 7            moltype = AA  length = 510
FEATURE                 Location/Qualifiers
source                  1..510
                        mol_type = protein
                        organism = Homo sapiens
SEQUENCE: 7
MEDTKESNVK TFCSKNILAI LGFSSIIAVI ALLAVGLTQN KALPENVKYG IVLDAGSSHT   60
SLYIYKWPAE KENDTGVVHQ VEECRVKGPG ISKFVQKVNE IGIYLTDCME RAREVIPRSQ  120
HQETPVYLGA TAGMRLLRME SEELADRVLD VVERSLSNYP FDFQGARIIT GQEEGAYGWI  180
TINYLLGKFS QKTRWFSIVP YETNNQETFG ALDLGGASTQ VTFVPQNQTI ESPDNALQFR  240
LYGKDYNVYT HSFLCYGKDQ ALWQKLAKDI QVASNEILRD PCFHPGYKKV VNVSDLYKTP  300
CTKRFEMTLP FQQFEIQGIG NYQQCHQSIL ELFNTSYCPY SQCAFNGIFL PPLQGDFGAF  360
SAFYFVMKFL NLTSEKVSQE KVTEMMKKFC AQPWEEIKTS YAGVKEKYLS EYCFSGTYIL  420
SLLLQGYHFT ADSWEHIHFI GKIQGSDAGW TLGYMLNLTN MIPAEQPLST PLSHSTYVFL  480
MVLFSLVLFT VAIIGLLIFH KPSYFWKDMV                                  510

SEQ ID NO: 8            moltype = AA  length = 517
FEATURE                 Location/Qualifiers
source                  1..517
                        mol_type = protein
                        organism = Macaca fascicularis
SEQUENCE: 8
MKGTKDLTSQ QKESNVKTFC SKNILAILGF SSIAVIALL AVGLTQNKAL PENIKYGIVL    60
DAGSSHTSLY IYKWPAEKEN DTGVVHQVEE CRVKGPGISK YVQKVNEIGI YLTDCMERAR  120
EVIPRSQHQE TPVYLGATAG MRLLRMESEE LADRVLDVVE RSLSNYPPDF QGARIITGQE  180
EGAYGWITIN YLLGKFSQKT RWFSIVPYET NNQETFGALD LGGASTQITF VPQNQTTESP  240
DNALQFRLYG KDYNVYTHSF LCYGKDQALW QKLAKDIQVA SNEILRDPCF HPGYKKVVNV  300
SDLYKTPCTK RFEMTLPFQQ FEIQGIGNYQ QCHQSVLELF NTSYCPYSQC AFNGIFPPL   360
QGDFGAFSAF YFVMNFLNLT SEKVSQEKVT EMMKKFCSQP WEEIKTSYAG VKEKYLSEYC  420
FSGTYILSLL LQGYHFTADS WEHIHFIGKI QGSDAGWTLG YMLNLTNMIP AEQPLSTPLS  480
HSTYVFLMVL FSLVLVIVAI IGLLIFHKPS YFWKDMV                          517

SEQ ID NO: 9            moltype = AA  length = 123
FEATURE                 Location/Qualifiers
source                  1..123
                        mol_type = protein
                        organism = synthetic construct
                        note = Description of Artificial Sequence: Synthetic
                        polypeptide
SEQUENCE: 9
QVQLKETGPG LVQPTQTLSI TCTVSGFSLT SYFTQWVRQT PGKGLEWMGF IRSGGSTQYN   60
SAFKSRLSIS RDTSKNQVFL KMNSLKTEDT GVYYCARDRP DYHDGTYGVL DVWGQGASVT  120
VSS                                                               123

SEQ ID NO: 10           moltype = AA  length = 10
```

```
FEATURE                 Location/Qualifiers
source                  1..10
                        mol_type = protein
                        organism = synthetic construct
                        note = Description of Artificial Sequence: Synthetic peptide
SEQUENCE: 10
GFSLTSYFTQ                                                              10

SEQ ID NO: 11           moltype = AA   length = 16
FEATURE                 Location/Qualifiers
source                  1..16
                        mol_type = protein
                        organism = synthetic construct
                        note = Description of Artificial Sequence: Synthetic peptide
SEQUENCE: 11
FIRSGGSTQY NSAFKS                                                       16

SEQ ID NO: 12           moltype = AA   length = 15
FEATURE                 Location/Qualifiers
source                  1..15
                        mol_type = protein
                        organism = synthetic construct
                        note = Description of Artificial Sequence: Synthetic peptide
SEQUENCE: 12
DRPDYHDGTY GVLDV                                                        15

SEQ ID NO: 13           moltype = AA   length = 107
FEATURE                 Location/Qualifiers
source                  1..107
                        mol_type = protein
                        organism = synthetic construct
                        note = Description of Artificial Sequence: Synthetic
                         polypeptide
SEQUENCE: 13
DIRMTQSPAS LSASLGETVN IECLASEDID SDLAWYQKKP GKSPQLLIYN GNALQNGVPS        60
RFSGSGSGTH FSLKINSLQS EDVATYFCQQ YINYPYTFGG GTKLELR                    107

SEQ ID NO: 14           moltype = AA   length = 11
FEATURE                 Location/Qualifiers
source                  1..11
                        mol_type = protein
                        organism = synthetic construct
                        note = Description of Artificial Sequence: Synthetic peptide
SEQUENCE: 14
LASEDIDSDL A                                                            11

SEQ ID NO: 15           moltype = AA   length = 7
FEATURE                 Location/Qualifiers
source                  1..7
                        mol_type = protein
                        organism = synthetic construct
                        note = Description of Artificial Sequence: Synthetic peptide
SEQUENCE: 15
NGNALQN                                                                  7

SEQ ID NO: 16           moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 16
QQYINYPYT                                                                9

SEQ ID NO: 17           moltype = AA   length = 119
FEATURE                 Location/Qualifiers
source                  1..119
                        mol_type = protein
                        organism = synthetic construct
                        note = Description of Artificial Sequence: Synthetic
                         polypeptide
SEQUENCE: 17
EVHLQQSGAA LVRPGTSVKL PCKVSGDSIT AYFMHFVRQR PGQGLEWMGR IDPDHERTKY        60
AEKFKNRASL TSETSSNTVF LQLTSLTSED TATYFCTTER VPGFETDYWG QGVMVTVSS       119

SEQ ID NO: 18           moltype = AA   length = 10
FEATURE                 Location/Qualifiers
source                  1..10
                        mol_type = protein
```

```
                                organism = synthetic construct
                                note = Description of Artificial Sequence: Synthetic peptide
SEQUENCE: 18
GDSITAYFMH                                                              10

SEQ ID NO: 19           moltype = AA   length = 17
FEATURE                 Location/Qualifiers
source                  1..17
                                mol_type = protein
                                organism = synthetic construct
                                note = Description of Artificial Sequence: Synthetic peptide
SEQUENCE: 19
RIDPDHERTK YAEKFKN                                                      17

SEQ ID NO: 20           moltype = AA   length = 10
FEATURE                 Location/Qualifiers
source                  1..10
                                mol_type = protein
                                organism = synthetic construct
                                note = Description of Artificial Sequence: Synthetic peptide
SEQUENCE: 20
ERVPGFETDY                                                              10

SEQ ID NO: 21           moltype = AA   length = 109
FEATURE                 Location/Qualifiers
source                  1..109
                                mol_type = protein
                                organism = synthetic construct
                                note = Description of Artificial Sequence: Synthetic
                                 polypeptide
SEQUENCE: 21
DIVLTQSPTL AVSLGQRATI SCRTNQTVDH YGTTYMNWYQ QKPGQQPKLL IYLASSLASG        60
IPARFSGRGS GTDFTLTIDP VEADDTATYY CQQSRNLWTF GGGTKLELK                   109

SEQ ID NO: 22           moltype = AA   length = 15
FEATURE                 Location/Qualifiers
source                  1..15
                                mol_type = protein
                                organism = synthetic construct
                                note = Description of Artificial Sequence: Synthetic peptide
SEQUENCE: 22
RTNQTVDHYG TTYMN                                                        15

SEQ ID NO: 23           moltype = AA   length = 15
FEATURE                 Location/Qualifiers
source                  1..15
                                mol_type = protein
                                organism = synthetic construct
                                note = Description of Artificial Sequence: Synthetic peptide
SEQUENCE: 23
RTNPTVDHYG TTYMN                                                        15

SEQ ID NO: 24           moltype = AA   length = 15
FEATURE                 Location/Qualifiers
source                  1..15
                                mol_type = protein
                                organism = synthetic construct
                                note = Description of Artificial Sequence: Synthetic peptide
SEQUENCE: 24
RTQQTVDHYG TTYMN                                                        15

SEQ ID NO: 25           moltype = AA   length = 7
FEATURE                 Location/Qualifiers
source                  1..7
                                mol_type = protein
                                organism = synthetic construct
                                note = Description of Artificial Sequence: Synthetic peptide
SEQUENCE: 25
LASSLAS                                                                 7

SEQ ID NO: 26           moltype = AA   length = 8
FEATURE                 Location/Qualifiers
source                  1..8
                                mol_type = protein
                                organism = synthetic construct
                                note = Description of Artificial Sequence: Synthetic peptide
SEQUENCE: 26
QQSRNLWT                                                                8
```

| | |
|---|---|
| SEQ ID NO: 27<br>FEATURE<br>source | moltype = AA   length = 123<br>Location/Qualifiers<br>1..123<br>mol_type = protein<br>organism = synthetic construct<br>note = Description of Artificial Sequence: Synthetic<br>  polypeptide |

SEQUENCE: 27
```
EVQLVESGGG LVQPGRSLKL SCLASGFTFN NYGMNWIRQA PGKGLEWVAS FSSSSTYISY   60
ADTVKGRFTI SRENAKNTLY LQMTSLRSED TALYYCVRHG RYGGYGGFYF DYWGQGVMVT  120
VSS                                                                123
```

| | |
|---|---|
| SEQ ID NO: 28<br>FEATURE<br>source | moltype = AA   length = 10<br>Location/Qualifiers<br>1..10<br>mol_type = protein<br>organism = synthetic construct<br>note = Description of Artificial Sequence: Synthetic peptide |

SEQUENCE: 28
```
GFTFNNYGMN                                                          10
```

| | |
|---|---|
| SEQ ID NO: 29<br>FEATURE<br>source | moltype = AA   length = 17<br>Location/Qualifiers<br>1..17<br>mol_type = protein<br>organism = synthetic construct<br>note = Description of Artificial Sequence: Synthetic peptide |

SEQUENCE: 29
```
SFSSSSTYIS YADTVKG                                                  17
```

| | |
|---|---|
| SEQ ID NO: 30<br>FEATURE<br>source | moltype = AA   length = 14<br>Location/Qualifiers<br>1..14<br>mol_type = protein<br>organism = synthetic construct<br>note = Description of Artificial Sequence: Synthetic peptide |

SEQUENCE: 30
```
HGRYGGYGGF YFDY                                                     14
```

| | |
|---|---|
| SEQ ID NO: 31<br>FEATURE<br>source | moltype = AA   length = 105<br>Location/Qualifiers<br>1..105<br>mol_type = protein<br>organism = synthetic construct<br>note = Description of Artificial Sequence: Synthetic<br>  polypeptide |

SEQUENCE: 31
```
DTVLTQSPAL AVSPGERVSI SCRASEGVKS YMHWYQQKPG QQPKLLIYKA SNLASGVPAR   60
FSGSGSGTDF TLTIDPVEAD DTATYFCQQS WNDPTFGAGT KLELK                 105
```

| | |
|---|---|
| SEQ ID NO: 32<br>FEATURE<br>source | moltype = AA   length = 11<br>Location/Qualifiers<br>1..11<br>mol_type = protein<br>organism = synthetic construct<br>note = Description of Artificial Sequence: Synthetic peptide |

SEQUENCE: 32
```
RASEGVKSYM H                                                        11
```

| | |
|---|---|
| SEQ ID NO: 33<br>FEATURE<br>source | moltype = AA   length = 7<br>Location/Qualifiers<br>1..7<br>mol_type = protein<br>organism = synthetic construct<br>note = Description of Artificial Sequence: Synthetic peptide |

SEQUENCE: 33
```
KASNLAS                                                              7
```

| | |
|---|---|
| SEQ ID NO: 34<br>FEATURE<br>source | moltype = AA   length = 8<br>Location/Qualifiers<br>1..8<br>mol_type = protein<br>organism = synthetic construct<br>note = Description of Artificial Sequence: Synthetic peptide |

SEQUENCE: 34
```
QQSWNDPT                                                             8
```

| | |
|---|---|
| SEQ ID NO: 35<br>FEATURE | moltype = AA   length = 450<br>Location/Qualifiers |

```
source                  1..450
                        mol_type = protein
                        organism = synthetic construct
                        note = Description of Artificial Sequence: Synthetic
                              polypeptide
SEQUENCE: 35
QVQLKETGPG LVQPTQTLSI TCTVSGFSLT SYFTQWVRQT PGKGLEWMGF IRSGGSTQYN    60
SAFKSRLSIS RDTSKNQVFL KMNSLKTEDT GVYYCARDRP DYHDGTYGVL DVWGQGASVT   120
VSSASTKGPS VFPLAPCSRS TSESTAALGC LVKDYFPEPV TVSWNSGALT SGVHTFPAVL   180
QSSGLYSLSS VVTVPSSSLG TKTYTCNVDH KPSNTKVDKR VESKYGPPCP PCPAPEFLGG   240
PSVFLFPPKP KDTLMISRTP EVTCVVVDVS QEDPEVQFNW YVDGVEVHNA KTKPREEQFN   300
STYRVVSVLT VLHQDWLNGK EYKCKVSNKG LPSSIEKTIS KAKGQPREPQ VYTLPPSQEE   360
MTKNQVSLTC LVKGFYPSDI AVEWESNGQP ENNYKTTPPV LDSDGSFFLY SRLTVDKSRW   420
QEGNVFSCSV MHEALHNHYT QKSLSLSLGK                                    450

SEQ ID NO: 36           moltype = AA  length = 214
FEATURE                 Location/Qualifiers
source                  1..214
                        mol_type = protein
                        organism = synthetic construct
                        note = Description of Artificial Sequence: Synthetic
                              polypeptide
SEQUENCE: 36
DIRMTQSPAS LSASLGETVN IECLASEDID SDLAWYQKKP GKSPQLLIYN GNALQNGVPS    60
RFSGSGSGTH FSLKINSLQS EDVATYFCQQ YINYPYTFGG GTKLELRRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 37           moltype = AA  length = 446
FEATURE                 Location/Qualifiers
source                  1..446
                        mol_type = protein
                        organism = synthetic construct
                        note = Description of Artificial Sequence: Synthetic
                              polypeptide
SEQUENCE: 37
EVHLQQSGAA LVRPGTSVKL PCKVSGDSIT AYFMHFVRQR PGQGLEWMGR IDPDHERTKY    60
AEKFKNRASL TSETSSNTVF LQLTSLTSED TATYFCTTER VPGFETDYWG QGVMVTVSSA   120
STKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEFLGGPSVF   240
LFPPKPKDTL MISRTPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLTCLVKG FYPSDIAVEW ESNGQPENNY KTTPPVLDSD GSFFLYSRLT VDKSRWQEGN   420
VFSCSVMHEA LHNHYTQKSL SLSLGK                                        446

SEQ ID NO: 38           moltype = AA  length = 216
FEATURE                 Location/Qualifiers
source                  1..216
                        mol_type = protein
                        organism = synthetic construct
                        note = Description of Artificial Sequence: Synthetic
                              polypeptide
SEQUENCE: 38
DIVLTQSPTL AVSLGQRATI SCRTNQTVDH YGTTYMNWYQ QKPGQQPKLL IYLASSLASG    60
IPARFSGRGS GTDFTLTIDP VEADDTATYY CQQSRNLWTF GGGTKLELKR TVAAPSVFIF   120
PPSDEQLKSG TASVVCLLNN FYPREAKVQW KVDNALQSGN SQESVTEQDS KDSTYSLSST   180
LTLSKADYEK HKVYACEVTH QGLSSPVTKS FNRGEC                             216

SEQ ID NO: 39           moltype = AA  length = 450
FEATURE                 Location/Qualifiers
source                  1..450
                        mol_type = protein
                        organism = synthetic construct
                        note = Description of Artificial Sequence: Synthetic
                              polypeptide
SEQUENCE: 39
EVQLVESGGG LVQPGRSLKL SCLASGFTFN NYGMNWIRQA PGKGLEWVAS FSSSSTYISY    60
ADTVKGRFTI SRENAKNTLY LQMTSLRSED TALYYCVRHG RYGGYGGPYF DYWGQGVMVT   120
VSSASTKGPS VFPLAPCSRS TSESTAALGC LVKDYFPEPV TVSWNSGALT SGVHTFPAVL   180
QSSGLYSLSS VVTVPSSSLG TKTYTCNVDH KPSNTKVDKR VESKYGPPCP PCPAPEFLGG   240
PSVFLFPPKP KDTLMISRTP EVTCVVVDVS QEDPEVQFNW YVDGVEVHNA KTKPREEQFN   300
STYRVVSVLT VLHQDWLNGK EYKCKVSNKG LPSSIEKTIS KAKGQPREPQ VYTLPPSQEE   360
MTKNQVSLTC LVKGFYPSDI AVEWESNGQP ENNYKTTPPV LDSDGSFFLY SRLTVDKSRW   420
QEGNVFSCSV MHEALHNHYT QKSLSLSLGK                                    450

SEQ ID NO: 40           moltype = AA  length = 212
FEATURE                 Location/Qualifiers
source                  1..212
                        mol_type = protein
```

```
                            organism = synthetic construct
                            note = Description of Artificial Sequence: Synthetic
                               polypeptide
SEQUENCE: 40
DTVLTQSPAL AVSPGERVSI SCRASEGVKS YMHWYQQKPG QQPKLLIYKA SNLASGVPAR   60
FSGSGSGTDF TLTIDPVEAD DTATYFCQQS WNDPTFGAGT KLELKRTVAA PSVFIFPPSD  120
EQLKSGTASV VCLLNNFYPR EAKVQWKVDN ALQSGNSQES VTEQDSKDST YSLSSTLTLS  180
KADYEKHKVY ACEVTHQGLS SPVTKSFNRG EC                                212

SEQ ID NO: 41           moltype = AA   length = 453
FEATURE                 Location/Qualifiers
source                  1..453
                        mol_type = protein
                        organism = synthetic construct
                        note = Description of Artificial Sequence: Synthetic
                           polypeptide
SEQUENCE: 41
EVQLVESGGG LVQPGRSLKL SCLASGFTFN NYGMNWIRQA PGKGLEWVAS FSSSSTYISY   60
ADTVKGRFTI SRENAKNTLY LQMTSLRSED TALYYCVRHG RYGGYGGFYF DYWGQGVMVT  120
VSSAKTTAPS VYPLAPVCGD TTGSSVTLGC LVKGYFPEPV TLTWNSGSLS SGVHTFPAVL  180
QSDLYTLSSS VTVTSSTWPS QSITCNVAHP ASSTKVDKKI EPRGPTIKPC PPCKCPAPNA  240
AGGPSVFIFP PKIKDVLMIS LSPIVTCVVV DVSEDDPDVQ ISWFVNNVEV HTAQTQTHRE  300
DYNSTLRVVS ALPIQHQDWM SGKEFKCKVN NKDLGAPIER TISKPKGSVR APQVYVLPPP  360
EEEMTKKQVT LTCMVTDFMP EDIYVEWTNN GKTELNYKNT EPVLDSDGSY FMYSKLRVEK  420
KNWVERNSYS CSVVHEGLHN HHTTKSFSRT PGK                               453

SEQ ID NO: 42           moltype = AA   length = 212
FEATURE                 Location/Qualifiers
source                  1..212
                        mol_type = protein
                        organism = synthetic construct
                        note = Description of Artificial Sequence: Synthetic
                           polypeptide
SEQUENCE: 42
DTVLTQSPAL AVSPGERVSI SCRASEGVKS YMHWYQQKPG QQPKLLIYKA SNLASGVPAR   60
FSGSGSGTDF TLTIDPVEAD DTATYFCQQS WNDPTFGAGT KLELKRADAA PTVSIFPPSS  120
EQLTSGGASV VCFLNNFYPK DINVKWKIDG SERQNGVLNS WTDQDSKDST YSMSSTLTLT  180
KDEYERHNSY TCEATHKTST SPIVKSFNRN EC                                212

SEQ ID NO: 43           moltype = AA   length = 119
FEATURE                 Location/Qualifiers
source                  1..119
                        mol_type = protein
                        organism = synthetic construct
                        note = Description of Artificial Sequence: Synthetic
                           polypeptide
SEQUENCE: 43
QVQLVQSGAE VKKPGASVKV SCKVSGDSIT AYFMHWVRQA PGKGLEWMGR IDPDHERTKY   60
AEKFKNRVTM TSDTSTNTVY MELSSLRSED TAVYYCATER VPGFETDYWG QGTMVTVSS   119

SEQ ID NO: 44           moltype = AA   length = 119
FEATURE                 Location/Qualifiers
source                  1..119
                        mol_type = protein
                        organism = synthetic construct
                        note = Description of Artificial Sequence: Synthetic
                           polypeptide
SEQUENCE: 44
EVQLVQSGAE VKKPGATVKI SCKVSGDSIT AYFMHWVQQA PGKGLEWMGR IDPDHERTKY   60
AEKFKNRVTI TADTSTNTVY MELSSLRSED TAVYYCATER VPGFETDYWG QGVMVTVSS   119

SEQ ID NO: 45           moltype = AA   length = 109
FEATURE                 Location/Qualifiers
source                  1..109
                        mol_type = protein
                        organism = synthetic construct
                        note = Description of Artificial Sequence: Synthetic
                           polypeptide
SEQUENCE: 45
DIVLTQSPAL AVSPGQRATI TCRTNPTVDH YGTTYMNWYQ QKPGQPPKLL IYLASSLASG   60
VPARFSGSGS GTDFTLTINP VEANDTANYY CQQSRNLWTF GGGTKVEIK              109

SEQ ID NO: 46           moltype = AA   length = 109
FEATURE                 Location/Qualifiers
source                  1..109
                        mol_type = protein
                        organism = synthetic construct
                        note = Description of Artificial Sequence: Synthetic
                           polypeptide
```

```
SEQUENCE: 46
DIVLTQSPAL AVSPGQRATI TCRTQQTVDH YGTTYMNWYQ QKPGQPPKLL IYLASSLASG    60
VPARFSGSGS GTDFTLTINP VEANDTANYY CQQSRNLWTF GGGTKVEIK              109

SEQ ID NO: 47           moltype = AA  length = 109
FEATURE                 Location/Qualifiers
source                  1..109
                        mol_type = protein
                        organism = synthetic construct
                        note = Description of Artificial Sequence: Synthetic
                            polypeptide
SEQUENCE: 47
DIVLTQSPAL AVSPGQRATI TCRTNPTVDH YGTTYMNWYQ QKPGQPPKLL IYLASSLASG    60
VPARFSGSGS GTDFTLTINP VEADDTANYY CQQSRNLWTF GGGTKVEIK              109

SEQ ID NO: 48           moltype = AA  length = 109
FEATURE                 Location/Qualifiers
source                  1..109
                        mol_type = protein
                        organism = synthetic construct
                        note = Description of Artificial Sequence: Synthetic
                            polypeptide
SEQUENCE: 48
DIVLTQSPAL AVSPGQRATI TCRTQQTVDH YGTTYMNWYQ QKPGQPPKLL IYLASSLASG    60
VPARFSGSGS GTDFTLTINP VEADDTANYY CQQSRNLWTF GGGTKVEIK              109

SEQ ID NO: 49           moltype = AA  length = 109
FEATURE                 Location/Qualifiers
source                  1..109
                        mol_type = protein
                        organism = synthetic construct
                        note = Description of Artificial Sequence: Synthetic
                            polypeptide
SEQUENCE: 49
DIVMTQSPDL AVSLGERATI NCRTQQTVDH YGTTYMNWYQ QKPGQPPKLL IYLASSLASG    60
VPDRFSGSGS GTDFTLTISS LQAEDVAVYY CQQSRNLWTF GGGTKVEIK              109

SEQ ID NO: 50           moltype = AA  length = 446
FEATURE                 Location/Qualifiers
source                  1..446
                        mol_type = protein
                        organism = synthetic construct
                        note = Description of Artificial Sequence: Synthetic
                            polypeptide
SEQUENCE: 50
QVQLVQSGAE VKKPGASVKV SCKVSGDSIT AYFMHWVRQA PGKGLEWMGR IDPDHERTKY    60
AEKFKNRVTM TSDTSTNTVY MELSSLRSED TAVYYCATER VPGFETDYWG QGTMVTVSSA   120
STKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEFLGGPSVF   240
LFPPKPKDTL MISRTPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLTCLVKG FYPSDIAVEW ESNGQPENNY KTTPPVLDSD GSFFLYSRLT VDKSRWQEGN   420
VFSCSVMHEA LHNHYTQKSL SLSLGK                                       446

SEQ ID NO: 51           moltype = AA  length = 449
FEATURE                 Location/Qualifiers
source                  1..449
                        mol_type = protein
                        organism = synthetic construct
                        note = Description of Artificial Sequence: Synthetic
                            polypeptide
SEQUENCE: 51
QVQLVQSGAE VKKPGASVKV SCKVSGDSIT AYFMHWVRQA PGKGLEWMGR IDPDHERTKY    60
AEKFKNRVTM TSDTSTNTVY MELSSLRSED TAVYYCATER VPGFETDYWG QGTMVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPEAAGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 52           moltype = AA  length = 446
FEATURE                 Location/Qualifiers
source                  1..446
                        mol_type = protein
                        organism = synthetic construct
                        note = Description of Artificial Sequence: Synthetic
                            polypeptide
SEQUENCE: 52
```

```
EVQLVQSGAE VKKPGATVKI SCKVSGDSIT AYFMHWVQQA PGKGLEWMGR IDPDHERTKY   60
AEKFKNRVTI TADTSTNTVY MELSSLRSED TAVYYCATER VPGFETDYWG QGVMVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPPCPA PEFLGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGK                                      446

SEQ ID NO: 53           moltype = AA   length = 216
FEATURE                 Location/Qualifiers
source                  1..216
                        mol_type = protein
                        organism = synthetic construct
                        note = Description of Artificial Sequence: Synthetic
                        polypeptide
SEQUENCE: 53
DIVLTQSPAL AVSPGQRATI TCRTNPTVDH YGTTYMNWYQ QKPGQPPKLL IYLASSLASG   60
VPARFSGSGS GTDFTLTINP VEANDTANYY CQQSRNLWTF GGGTKVEIKR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                           216

SEQ ID NO: 54           moltype = AA   length = 216
FEATURE                 Location/Qualifiers
source                  1..216
                        mol_type = protein
                        organism = synthetic construct
                        note = Description of Artificial Sequence: Synthetic
                        polypeptide
SEQUENCE: 54
DIVLTQSPAL AVSPGQRATI TCRTQQTVDH YGTTYMNWYQ QKPGQPPKLL IYLASSLASG   60
VPARFSGSGS GTDFTLTINP VEANDTANYY CQQSRNLWTF GGGTKVEIKR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                           216

SEQ ID NO: 55           moltype = AA   length = 216
FEATURE                 Location/Qualifiers
source                  1..216
                        mol_type = protein
                        organism = synthetic construct
                        note = Description of Artificial Sequence: Synthetic
                        polypeptide
SEQUENCE: 55
DIVLTQSPAL AVSPGQRATI TCRTNPTVDH YGTTYMNWYQ QKPGQPPKLL IYLASSLASG   60
VPARFSGSGS GTDFTLTINP VEADDTANYY CQQSRNLWTF GGGTKVEIKR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                           216

SEQ ID NO: 56           moltype = AA   length = 216
FEATURE                 Location/Qualifiers
source                  1..216
                        mol_type = protein
                        organism = synthetic construct
                        note = Description of Artificial Sequence: Synthetic
                        polypeptide
SEQUENCE: 56
DIVLTQSPAL AVSPGQRATI TCRTQQTVDH YGTTYMNWYQ QKPGQPPKLL IYLASSLASG   60
VPARFSGSGS GTDFTLTINP VEADDTANYY CQQSRNLWTF GGGTKVEIKR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                           216

SEQ ID NO: 57           moltype = AA   length = 216
FEATURE                 Location/Qualifiers
source                  1..216
                        mol_type = protein
                        organism = synthetic construct
                        note = Description of Artificial Sequence: Synthetic
                        polypeptide
SEQUENCE: 57
DIVMTQSPDL AVSLGERATI NCRTQQTVDH YGTTYMNWYQ QKPGQPPKLL IYLASSLASG   60
VPDRFSGSGS GTDFTLTISS LQAEDVAVYY CQQSRNLWTF GGGTKVEIKR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                           216

SEQ ID NO: 58           moltype = AA   length = 123
FEATURE                 Location/Qualifiers
source                  1..123
                        mol_type = protein
                        organism = synthetic construct
```

```
                        note = Description of Artificial Sequence: Synthetic
                        polypeptide
SEQUENCE: 58
EVQLVESGGG LVQPGRSLRL SCAASGFTFN NYGMNWVRQA PGKGLEWVSS FSSSSTYISY    60
ADTVKGRFTI SRDNAKNSLY LQMNSLRAED TALYYCARHG RYGGYGGFYF DYWGQGTMVT   120
VSS                                                                 123

SEQ ID NO: 59           moltype = AA  length = 123
FEATURE                 Location/Qualifiers
source                  1..123
                        mol_type = protein
                        organism = synthetic construct
                        note = Description of Artificial Sequence: Synthetic
                        polypeptide
SEQUENCE: 59
QVQLVESGGG VVQPGRSLRL SCAASGFTFN NYGMNWVRQA PGKGLEWVAS FSSSSTYISY    60
ADTVKGRFTI SRDNSKNTLY LQMSSLRAED TAVYYCARHG RYGGYGGFYF DYWGQGTMVT   120
VSS                                                                 123

SEQ ID NO: 60           moltype = AA  length = 106
FEATURE                 Location/Qualifiers
source                  1..106
                        mol_type = protein
                        organism = synthetic construct
                        note = Description of Artificial Sequence: Synthetic
                        polypeptide
SEQUENCE: 60
DTVLTQSPAS LAVSPGQRAT ITCRASEGVK SYMHWYQQKP GQPPKLLIYK ASNLASGVPA    60
RFSGSGSGTD FTLTINPVEA DDTANYYCQQ SWNDPTFGQG TKLEIK                  106

SEQ ID NO: 61           moltype = AA  length = 106
FEATURE                 Location/Qualifiers
source                  1..106
                        mol_type = protein
                        organism = synthetic construct
                        note = Description of Artificial Sequence: Synthetic
                        polypeptide
SEQUENCE: 61
DIVLTQSPAS LAVSPGQRAT ITCRASEGVK SYMHWYQQKP GQPPKLLIYK ASNLASGVPA    60
RFSGSGSGTD FTLTINPVEA DDTANYYCQQ SWNDPTFGQG TKLEIK                  106

SEQ ID NO: 62           moltype = AA  length = 106
FEATURE                 Location/Qualifiers
source                  1..106
                        mol_type = protein
                        organism = synthetic construct
                        note = Description of Artificial Sequence: Synthetic
                        polypeptide
SEQUENCE: 62
EIVMTQSPAT LSVSPGERAT LSCRASEGVK SYMHWYQQKP GQAPRLLIYK ASNLASGIPA    60
RFSGSGSGTE FTLTISSLQS EDFAVYYCQQ SWNDPTFGQG TKLELK                  106

SEQ ID NO: 63           moltype = AA  length = 106
FEATURE                 Location/Qualifiers
source                  1..106
                        mol_type = protein
                        organism = synthetic construct
                        note = Description of Artificial Sequence: Synthetic
                        polypeptide
SEQUENCE: 63
ETVMTQSPAT LSVSPGERAT LSCRASEGVK SYMHWYQQKP GQAPRLLIYK ASNLASGIPA    60
RFSGSGSGTE FTLTISSLQS EDFAVYYCQQ SWNDPTFGQG TKLELK                  106

SEQ ID NO: 64           moltype = AA  length = 450
FEATURE                 Location/Qualifiers
source                  1..450
                        mol_type = protein
                        organism = synthetic construct
                        note = Description of Artificial Sequence: Synthetic
                        polypeptide
SEQUENCE: 64
EVQLVESGGG LVQPGRSLRL SCAASGFTFN NYGMNWVRQA PGKGLEWVSS FSSSSTYISY    60
ADTVKGRFTI SRDNAKNSLY LQMNSLRAED TALYYCARHG RYGGYGGFYF DYWGQGTMVT   120
VSSASTKGPS VFPLAPCSRS TSESTAALGC LVKDYFPEPV TVSWNSGALT SGVHTFPAVL   180
QSSGLYSLSS VVTVPSSSLG TKTYTCNVDH KPSNTKVDKR VESKYGPPCP PCPAPEFLGG   240
PSVFLFPPKP KDTLMISRTP EVTCVVVDVS QEDPEVQFNW YVDGVEVHNA KTKPREEQFN   300
STYRVVSVLT VLHQDWLNGK EYKCKVSNKG LPSSIEKTIS KAKGQPREPQ VYTLPPSQEE   360
MTKNQVSLTC LVKGFYPSDI AVEWESNGQP ENNYKTTPPV LDSDGSFFLY SRLTVDKSRW   420
QEGNVFSCSV MHEALHNHYT QKSLSLSLGK                                    450
```

```
SEQ ID NO: 65            moltype = AA   length = 450
FEATURE                  Location/Qualifiers
source                   1..450
                         mol_type = protein
                         organism = synthetic construct
                         note = Description of Artificial Sequence: Synthetic
                         polypeptide
SEQUENCE: 65
QVQLVESGGG VVQPGRSLRL SCAASGFTFN NYGMNWVRQA PGKGLEWVAS FSSSSTYISY    60
ADTVKGRFTI SRDNSKNTLY LQMSSLRAED TAVYYCARHG RYGGYGGFYF DYWGQGTMVT   120
VSSASTKGPS VFPLAPCSRS TSESTAALGC LVKDYFPEPV TVSWNSGALT SGVHTFPAVL   180
QSSGLYSLSS VVTVPSSSLG TKTYTCNVDH KPSNTKVDKR VESKYGPPCP PCPAPEFLGG   240
PSVFLFPPKP KDTLMISRTP EVTCVVVDVS QEDPEVQFNW YVDGVEVHNA KTKPREEQFN   300
STYRVVSVLT VLHQDWLNGK EYKCKVSNKG LPSSIEKTIS KAKGQPREPQ VYTLPPSQEE   360
MTKNQVSLTC LVKGFYPSDI AVEWESNGQP ENNYKTTPPV LDSDGSFFLY SRLTVDKSRW   420
QEGNVFSCSV MHEALHNHYT QKSLSLSLGK                                   450

SEQ ID NO: 66            moltype = AA   length = 453
FEATURE                  Location/Qualifiers
source                   1..453
                         mol_type = protein
                         organism = synthetic construct
                         note = Description of Artificial Sequence: Synthetic
                         polypeptide
SEQUENCE: 66
QVQLVESGGG VVQPGRSLRL SCAASGFTFN NYGMNWVRQA PGKGLEWVAS FSSSSTYISY    60
ADTVKGRFTI SRDNSKNTLY LQMSSLRAED TAVYYCARHG RYGGYGGFYF DYWGQGTMVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGK                                453

SEQ ID NO: 67            moltype = AA   length = 213
FEATURE                  Location/Qualifiers
source                   1..213
                         mol_type = protein
                         organism = synthetic construct
                         note = Description of Artificial Sequence: Synthetic
                         polypeptide
SEQUENCE: 67
DTVLTQSPAS LAVSPGQRAT ITCRASEGVK SYMHWYQQKP GQPPKLLIYK ASNLASGVPA    60
RFSGSGSGTD FTLTINPVEA DDTANYYCQQ SWNDPTFGQG TKLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 68            moltype = AA   length = 213
FEATURE                  Location/Qualifiers
source                   1..213
                         mol_type = protein
                         organism = synthetic construct
                         note = Description of Artificial Sequence: Synthetic
                         polypeptide
SEQUENCE: 68
DIVLTQSPAS LAVSPGQRAT ITCRASEGVK SYMHWYQQKP GQPPKLLIYK ASNLASGVPA    60
RFSGSGSGTD FTLTINPVEA DDTANYYCQQ SWNDPTFGQG TKLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 69            moltype = AA   length = 213
FEATURE                  Location/Qualifiers
source                   1..213
                         mol_type = protein
                         organism = synthetic construct
                         note = Description of Artificial Sequence: Synthetic
                         polypeptide
SEQUENCE: 69
EIVMTQSPAT LSVSPGERAT LSCRASEGVK SYMHWYQQKP GQAPRLLIYK ASNLASGIPA    60
RFSGSGSGTE FTLTISSLQS EDFAVYYCQQ SWNDPTFGQG TKLELKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 70            moltype = AA   length = 213
FEATURE                  Location/Qualifiers
source                   1..213
                         mol_type = protein
                         organism = synthetic construct
```

```
                         note = Description of Artificial Sequence: Synthetic
                         polypeptide
SEQUENCE: 70
ETVMTQSPAT  LSVSPGERAT  LSCRASEGVK  SYMHWYQQKP  GQAPRLLIYK  ASNLASGIPA    60
RFSGSGSGTE  FTLTISSLQS  EDFAVYYCQQ  SWNDPTFGQG  TKLELKRTVA  APSVFIFPPS   120
DEQLKSGTAS  VVCLLNNFYP  REAKVQWKVD  NALQSGNSQE  SVTEQDSKDS  TYSLSSTLTL   180
SKADYEKHKV  YACEVTHQGL  SSPVTKSFNR  GEC                                  213

SEQ ID NO: 71            moltype = AA   length = 510
FEATURE                  Location/Qualifiers
source                   1..510
                         mol_type = protein
                         organism = Mus musculus
SEQUENCE: 71
MEDIKDSKVK  RFCSKNILII  LGFTSILAVI  ALIAVGLTQN  KPLPENVKYG  IVLDAGSSHT    60
NLYIYKWPAE  KENDTGVVQQ  LEECQVKGPG  ISKYAQKTDE  IGAYLAECME  LSTELIPTSK   120
HHQTPVYLGA  TAGMRLLRME  SEQSADEVLA  AVSTSLKSYF  FDFQGAKIIT  GQEEGAYGWI   180
TINYLLGRFT  QEQSWLSLIS  DSQKQETFGA  LDLGGASTQI  TFVPQNSTIE  SPENSLQFRL   240
YGEDYTVYTH  SFLCYGKDQA  LWQKLAKDIQ  VSSGGVLKDP  CFNPGYEKVV  NVSELYGTPC   300
TKRFEKKLPF  DQFRIQGTGD  YEQCHQSILE  LFNNSHCPYS  QCAFNGVFLP  PLHGSFGAFS   360
AFYFVMDFFK  KVAKNSVISQ  EKMTEITKNF  CSKSWEETKT  SYPSVKEKYL  SEYCFSGAYI   420
LSLLQGYNFT  DSSWEQIHFM  GKIKDSNAGW  TLGYMLNLTN  MIPAEQPLSP  PLPHSTYIGL   480
MVLFSLLLVA  VAITGLFIYS  KPSYFWKEAV                                       510

SEQ ID NO: 72            moltype = AA   length = 452
FEATURE                  Location/Qualifiers
source                   1..452
                         mol_type = protein
                         organism = synthetic construct
                         note = Description of Artificial Sequence: Synthetic
                         polypeptide
SEQUENCE: 72
TQNKALPENV  KYGIVLDAGS  SHTSLYIYKW  PAEKENDTGV  VHQVEECRVK  GPGISKFVQK    60
VNEIGIYLTD  CMERAREVIP  RSQHQETPVY  LGATAGMRLL  RMESEELADR  VLDVVERSLS   120
NYPFDFQGAR  IITGQEEGAY  GWITINYLLG  KFSQKTRWFS  IVPYETNNQE  TFGALDLGGA   180
STQVTFVPQN  QTIESPDNAL  QFRLYGKDYN  VYTHSFLCYG  KDQALWQKLA  KDIQVASNEI   240
LRDPCFHPGY  KKVVNVSDLY  KTPCTKRFEM  TLPFQQFEIQ  GIGNYQQCHQ  SILELFNTSY   300
CPYSQCAFNG  IFLPPLQGDF  GAFSAFYFVM  KFLNLTSEKV  SQEKVTEMMK  KFCAQPWEEI   360
KTSYAGVKEK  YLSEYCFSGT  YILSLLLQGY  HFTADSWEHI  HFIGKIQGSD  AGWTLGYMLN   420
LTNMIPAEQP  LSTPLSHSTY  VAHHHHHHHH  HH                                   452

SEQ ID NO: 73            moltype = AA   length = 446
FEATURE                  Location/Qualifiers
source                   1..446
                         mol_type = protein
                         organism = synthetic construct
                         note = Description of Artificial Sequence: Synthetic
                         polypeptide
SEQUENCE: 73
QVQLVQSGAE  VKKPGASVKV  SCKASGYTFT  DYNMHWVRQA  PGQRLEWIGY  IVPLNGGSTF    60
NQKFKGRATI  TVDTSARTAY  MELSSLRSED  TAVYYCARGG  TRFAYWGQGT  LVTVSSASTK   120
GPSVFPLAPS  SKSTSGGTAA  LGCLVKDYFP  EPVTVSWNSG  ALTSGVHTFP  AVLQSSGLYS   180
LSSVVTVPSS  SLGTQTYICN  VNHKPSNTKV  DKRVEPKSCD  KTHTCPPCPA  PEAEGAPSVF   240
LFPPKPKDTL  MISRTPEVTC  VVVDVSHEDP  EVKFNWYVDG  VEVHNAKTKP  REEQYNSTYR   300
VVSVLTVLHQ  DWLNGKEYKC  KVSNKALPSS  IEKTISKAKG  QPREPQVYTL  PPSREEMTKN   360
QVSLTCLVKG  FYPSDIAVEW  ESNGQPENNY  KTTPPVLDSD  GSFFLYSKLT  VDKSRWQQGN   420
VFSCSVMHEA  LHNHYTQKSL  SLSPGK                                           446

SEQ ID NO: 74            moltype = AA   length = 218
FEATURE                  Location/Qualifiers
source                   1..218
                         mol_type = protein
                         organism = synthetic construct
                         note = Description of Artificial Sequence: Synthetic
                         polypeptide
SEQUENCE: 74
DIVMTQSPDS  LAVSLGERAT  INCRASESVD  NFGVSFMYWF  QQKPGQPPKL  LIYGASNQGS    60
GVPDRFSGSG  SGTDFTLTIS  SLQAEDVAVY  YCQQTKEVPY  TFGGGTKVEI  KRTVAAPSVF   120
IFPPSDEQLK  SGTASVVCLL  NNFYPREAKV  QWKVDNALQS  GNSQESVTEQ  DSKDSTYSLS   180
STLTLSKADY  EKHKVYACEV  THQGLSSPVT  KSFNRGEC                             218
```

ANTI-CD39 ANTIBODIES AND USE THEREOF

CROSS REFERENCE STATEMENT

This application claims priority to international application PCT/CN2022/079021, filed Mar. 3, 2022, and international application PCT/CN2022/126070, filed Oct. 19, 2022, the disclosures of which are incorporated herein by reference.

SEQUENCE LISTING

The instant application contains a Sequence Listing which has been submitted electronically in XML file format and is hereby incorporated by reference in its entirety. Said XML copy, created on Mar. 23, 2023, is named 129802-0333_SL.xml and is 94,016 bytes in size.

FIELD

Provided herein are anti-CD39 antibodies that inhibit the enzymatic activity of human CD39 and methods of using the same.

BACKGROUND

Present in negligible concentrations under healthy conditions (10-100 nM), dying or stressed cells release ATP extracellularly. Once released, extracellular ATP signals through type 2 purinergic (P2) receptors to provide inflammatory signals crucial for effective innate and adaptive immune responses. CD39 is the rate-limiting ecto-enzyme in the hydrolysis of extracellular ATP. By catabolizing the conversion of extracellular ATP into AMP, CD39 is a critical regulator of extracellular ATP levels.

CD39 is also an important contributor to extracellular adenosine levels. Adenosine is an immunosuppressive metabolite and thus has a converse relationship to extracellular ATP. CD39 contributes to increased extracellular adenosine levels by hydrolyzing ATP into AMP, which is converted to adenosine by CD73. Extracellular adenosine then signals through type 1 purinergic receptors to create an immunosuppressive environment.

Hydrolysis of extracellular ATP by CD39 therefore has the potential to influence immune responses via two distinct signaling pathways at opposing ends of a signaling axis. Notably, dysregulation of this signaling axis, referred to herein as the ATP-adenosine signaling axis, has been observed in several diseases. As such, there is a need in the art for agents that target CD39 and inhibit its enzymatic activity for beneficial therapeutic purposes.

SUMMARY

Among the various aspects of the present disclosure is the provision of anti-CD39 antibodies. The anti-CD39 antibodies are optionally (i) labeled with one or more detectable signal, including but not limited to fluorescent molecules, spin-labeled molecules, enzymes or radioisotopes, and/or (ii) conjugated to one more therapeutic agent, including but not limited to chemotherapeutic agents, radioisotopes, or nucleic acids. In some embodiments, an anti-CD39 antibody of the present disclosure is provided as an isolated antibody. In some embodiments, an anti-CD39 antibody of the present disclosure is provided in a composition. In some embodiments, an anti-CD39 antibody of the present disclosure is provided in a composition that further comprises a pharmaceutically acceptable excipient.

In one embodiment, the present disclosure provides an anti-CD39 antibody that specifically binds to human CD39, comprising a heavy chain variable region comprising a complementarity determining region 1 (H1) having at least 80% sequence identity to SEQ ID NO: 10, a complementarity determining region 2 (H2) having at least 80% sequence identity to SEQ ID NO: 11, and a complementarity determining region 3 (H3) having at least 80% sequence identity to SEQ ID NO: 12; and a light chain variable region comprising a complementarity determining region 1 (L1) having at least 80% sequence identity to SEQ ID NO: 14, a complementarity determining region 2 (L2) having at least 80% sequence identity to SEQ ID NO: 15, and a complementarity determining region 3 (L3) having at least 80% sequence identity to SEQ ID NO: 16. In another embodiment, the present disclosure provides an anti-CD39 antibody that specifically binds to human CD39, comprising a heavy chain variable region comprising an H1 having at least 90% sequence identity to SEQ ID NO: 10, an H2 having at 90% sequence identity to SEQ ID NO: 11, and an H3 having at least 90% sequence identity to SEQ ID NO: 12; and a light chain variable region comprising an L1 having at least 90% sequence identity to SEQ ID NO: 14, an L2 having at least 90% sequence identity to SEQ ID NO: 15, and an L3 having at least 90% sequence identity to SEQ ID NO: 16. In some of the aforementioned embodiments, the antibody's heavy chain variable region has at least 90% sequence identity to SEQ ID NO: 9, and a light chain variable region has at least 90% sequence identity to SEQ ID NO: 13. In some embodiments, the antibody's heavy chain variable region has at least 95% sequence identity to SEQ ID NO: 9, and a light chain variable region has at least 95% sequence identity to SEQ ID NO: 13.

In one embodiment, the present disclosure provides an anti-CD39 antibody that specifically binds to human CD39, comprising a heavy chain variable region comprising an H1 having at least 80% sequence identity to SEQ ID NO: 18, an H2 having at least 80% sequence identity to SEQ ID NO: 19, and an H3 having at least 80% sequence identity to SEQ ID NO: 20; and a light chain variable region comprising an L1 having at least 80% sequence identity to SEQ ID NO: 22, SEQ ID NO: 23, or SEQ ID NO: 24, an L2 having at least 80% sequence identity to SEQ ID NO: 25, and an L3 having at least 80% sequence identity to SEQ ID NO: 26. In another embodiment, the present disclosure provides an anti-CD39 antibody that specifically binds to human CD39, comprising a heavy chain variable region comprising an H1 having at least 90% sequence identity to SEQ ID NO: 18, an H2 having at least 80% sequence identity to SEQ ID NO: 19, and an H3 having at least 90% sequence identity to SEQ ID NO: 20; and a light chain variable region comprising an L1 having at least 90% sequence identity to SEQ ID NO: 22, SEQ ID NO: 23, or SEQ ID NO: 24, an L2 having at least 90% sequence identity to SEQ ID NO: 25, and an L3 having at least 80% sequence identity to SEQ ID NO: 26. In some of the aforementioned embodiments, the antibody's heavy chain variable region and light chain variable region have at least 90% sequence identity (e.g., 90%, 91%, 92%, 93%, 94%, 95%, 96%, 97%, 98%, 99%, or 100%) or at least 95% sequence identity to: SEQ ID NO: 17 and SEQ ID NO: 21, respectively; or to SEQ ID NO: 43 and SEQ ID NO: 45, respectively; or to SEQ ID NO: 43 and SEQ ID NO: 46, respectively; or to SEQ ID NO: 43 and SEQ ID NO: 47, respectively; or to SEQ ID NO: 43 and SEQ ID NO: 48, respectively; or to SEQ ID NO: 43 and SEQ ID NO: 49, respectively; or to SEQ ID NO: 44 and SEQ ID NO: 48, respectively; or to SEQ ID NO: 44 and SEQ ID NO: 49, respectively.

In one embodiment, the present disclosure provides an anti-CD39 antibody that specifically binds to human CD39, comprising a heavy chain variable region comprising an H1 having at least 80% sequence identity to SEQ ID NO: 28, an H2 having at least 80% sequence identity to SEQ ID NO: 29, and an H3 having at least 80% sequence identity to SEQ ID NO: 30; and a light chain variable region comprising an L1 having at least 80% sequence identity to SEQ ID NO: 32, an L2 having at least 80% sequence identity to SEQ ID NO: 33, and an L3 having at least 80% sequence identity to SEQ ID NO: 34. In some of the aforementioned embodiments, the antibody's heavy chain variable region and light chain variable region have at least 90% sequence identity (e.g., 90%, 91%, 92%, 93%, 94%, 95%, 96%, 97%, 98%, 99%, or 100%) or at least 95% sequence identity to SEQ ID NO: 27 and SEQ ID NO: 31; or to SEQ ID NO: 58 and SEQ ID NO: 60; or to SEQ ID NO: 58 and SEQ ID NO: 61; or to SEQ ID NO: 58 and SEQ ID NO: 62; or to SEQ ID NO: 58 and SEQ ID NO: 63; or to SEQ ID NO: 59 and SEQ ID NO: 61; or to SEQ ID NO: 59 and SEQ ID NO: 60; or to SEQ ID NO: 59 and SEQ ID NO: 62; or to SEQ ID NO: 59 and SEQ ID NO: 63.

For any of the disclosed antibodies of the present disclosure, the anti-CD39 antibody may be a monoclonal antibody or antigen-binding fragment thereof, a chimeric, humanized, or veneered antibody or antigen-binding fragment thereof, or a human antibody or antigen-binding fragment thereof. In addition, the anti-CD39 antibody may further comprise a heavy chain constant region selected from human IgG1, human IgG2, human IgG3, or human IgG4, and optionally a human light chain constant region. The variant heavy chain constant region may be a wild-type heavy chain constant region, or may be a heavy chain constant region with enhanced or decreased effector function with reference to the wild-type heavy chain constant region. In various embodiments, the IgG heavy chain constant region may comprise SEQ ID NO: 1, SEQ ID NO: 2, SEQ ID NO: 3, SEQ ID NO: 4, or SEQ ID NO: 5; and the human light chain kappa constant region may comprise SEQ ID NO: 6.

In one embodiment, the present disclosure provides an anti-CD39 antibody comprising a heavy chain variable region and a light chain comprising the light chain variable region, wherein (a) the heavy chain has an amino acid sequence comprising SEQ ID NO: 50, and the light chain has an amino acid sequence comprising SEQ ID NO: 53; (b) the heavy chain has an amino acid sequence comprising SEQ ID NO: 50, and the light chain has an amino acid sequence comprising SEQ ID NO: 54; (c) the heavy chain has an amino acid sequence comprising SEQ ID NO: 50, and the light chain has an amino acid sequence comprising SEQ ID NO: 55; (d) the heavy chain has an amino acid sequence comprising SEQ ID NO: 50, and the light chain has an amino acid sequence comprising SEQ ID NO: 56; (e) the heavy chain has an amino acid sequence comprising SEQ ID NO: 51, and the light chain has an amino acid sequence comprising SEQ ID NO: 56; (f) the heavy chain has an amino acid sequence comprising SEQ ID NO: 50, and the light chain has an amino acid sequence comprising SEQ ID NO: 57; (g) the heavy chain has an amino acid sequence comprising SEQ ID NO: 52, and the light chain has an amino acid sequence comprising SEQ ID NO: 56; or (h) the heavy chain has an amino acid sequence comprising SEQ ID NO: 52, and the light chain has an amino acid sequence comprising SEQ ID NO: 57.

In one embodiment, the present disclosure provides an anti-CD39 antibody comprising a heavy chain variable region and a light chain comprising the light chain variable region, wherein (a) the heavy chain has an amino acid sequence comprising SEQ ID NO: 64, and the light chain has an amino acid sequence comprising SEQ ID NO: 67; (b) the heavy chain has an amino acid sequence comprising SEQ ID NO: 64, and the light chain has an amino acid sequence comprising SEQ ID NO: 68; (c) the heavy chain has an amino acid sequence comprising SEQ ID NO: 64, and the light chain has an amino acid sequence comprising SEQ ID NO: 69; (d) the heavy chain has an amino acid sequence comprising SEQ ID NO: 64, and the light chain has an amino acid sequence comprising SEQ ID NO: 70; (e) the heavy chain has an amino acid sequence comprising SEQ ID NO: 65, and the light chain has an amino acid sequence comprising SEQ ID NO: 68; (f) the heavy chain has an amino acid sequence comprising SEQ ID NO: 65, and the light chain has an amino acid sequence comprising SEQ ID NO: 67; (g) the heavy chain has an amino acid sequence comprising SEQ ID NO: 66, and the light chain has an amino acid sequence comprising SEQ ID NO: 67; (h) the heavy chain has an amino acid sequence comprising SEQ ID NO: 65, and the light chain has an amino acid sequence comprising SEQ ID NO: 69; or (i) the heavy chain has an amino acid sequence comprising SEQ ID NO: 65, and the light chain has an amino acid sequence comprising SEQ ID NO: 70.

In another aspect, the present disclosure provides any of the antibodies disclosed herein for use as a medicament. In some embodiments, an anti-CD39 antibody is provided for use in treating cancer. In some embodiments, an anti-CD39 antibody is provided for use in preventing cancer.

In another aspect, the present disclosure provides any of the antibodies disclosed herein for use as a medicament in combination with an additional therapy. In some embodiments, an aforementioned anti-CD39 antibody is provided for use in treating cancer. In some embodiments, an aforementioned anti-CD39 antibody is provided for use in preventing cancer. In certain embodiments, the additional therapy may be an immune checkpoint inhibitor, an immunogenic cell death inducing therapy, an ATP-adenosine axis targeting agent, an HIF-2α inhibitor, an arginase inhibitor, an AXL inhibitor, or a PI3K inhibitor. In further embodiments, the additional therapy may be chemotherapy, radiation therapy, durvalumab, zimberelimab, domvanalimab, AB308, AB521, or quemliclustat.

In another aspect, the present disclosure provides any of the antibodies disclosed herein for use as a medicament in combination with two or more additional therapies. In some embodiments, an aforementioned anti-CD39 antibody is provided for use in treating cancer. In some embodiments, an aforementioned anti-CD39 antibody is provided for use in preventing cancer. In certain embodiments, each additional therapy may be a chemotherapeutic agent, an immune checkpoint inhibitor, an immunogenic cell death inducing therapy, an ATP-adenosine axis targeting agent, an HIF-2α inhibitor, an arginase inhibitor, an AXL inhibitor, or a PI3K inhibitor. In further embodiments, the additional therapy may be chemotherapy, radiation therapy, durvalumab, zimberelimab, domvanalimab, AB308, AB521, or quemliclustat. In some embodiments, the one or more additional therapeutic agents includes (a) pemetrexed, carboplatin, and either an antagonist anti-PD-1 antibody or an antagonist anti-PD-L1 antibody, or (b) FOLFOX and either an antagonist anti-PD-1 antibody or an antagonist anti-PD-L1 antibody.

In another aspect, the present disclosure provides a method for treating or preventing cancer, the method comprising administering any of the antibodies disclosed herein to a subject in need thereof. In some embodiments, the method further comprises administering one or more additional therapy. In certain embodiments, each additional therapy may be an immune checkpoint inhibitor, an immunogenic cell death inducing therapy, an ATP-adenosine axis targeting agent, an HIF-2α inhibitor, an arginase inhibitor, an AXL inhibitor, or a PI3K inhibitor. In further embodiments, the additional therapy may be chemotherapy, radiation therapy, durvalumab, zimberelimab, domvanalimab, AB308, AB521, or quemliclustat.

In each of the above aspects, the cancer may be breast cancer, gastrointestinal cancer, genitourinary tract cancer, head and neck cancer, kidney cancer, lung cancer, lymphoma, ovarian cancer, pancreatic cancer, skin cancer, or thyroid cancer. In some embodiments, the cancer may be acute myeloid lymphoma, colorectal cancer, gastric cancer, esophageal cancer, castration-resistant prostate cancer, non-small cell lung cancer, ovarian cancer, pancreatic cancer, triple negative breast cancer, head and neck squamous cell carcinoma, pancreatic ductal adenocarcinoma, clear cell renal carcinoma, or melanoma.

In some embodiments, the cancer is non-small cell lung cancer and the method may further comprise administering the anti-CD39 antibody in combination with pemetrexed, carboplatin, and either an antagonist anti-PD-1 antibody or an antagonist anti-PD-L1 antibody. In some embodiments, the cancer is gastric cancer or gastroesophageal cancer and the method may further comprise administering the anti-CD39 antibody in combination with FOLFOX and either an antagonist anti-PD-1 antibody or an antagonist anti-PD-L1 antibody. These embodiments may further comprise administering one or more additional agent selected from the group consisting of an antagonistic anti-TIGIT antibody, an $A_{2a}R$ antagonist, an $A_{2b}R$ antagonist, an $A_{2a/2b}R$ antagonist, and a CD73 inhibitor, optionally where the additional agents are selected from the group consisting of domvanalimab, AB308, etrumadenant, and quemliclustat.

Other aspects and iterations of the disclosure are provided in more detail below.

BRIEF DESCRIPTION OF THE DRAWINGS

FIG. 15B: 4T1 tumors) or peripheral whole blood cells (FIG. 15C) obtained from hCD39KI mice treated as indicated along the x-axis. ATP levels were measured by detecting relative luminescence units (RLU).

DETAILED DESCRIPTION

Figure 1:
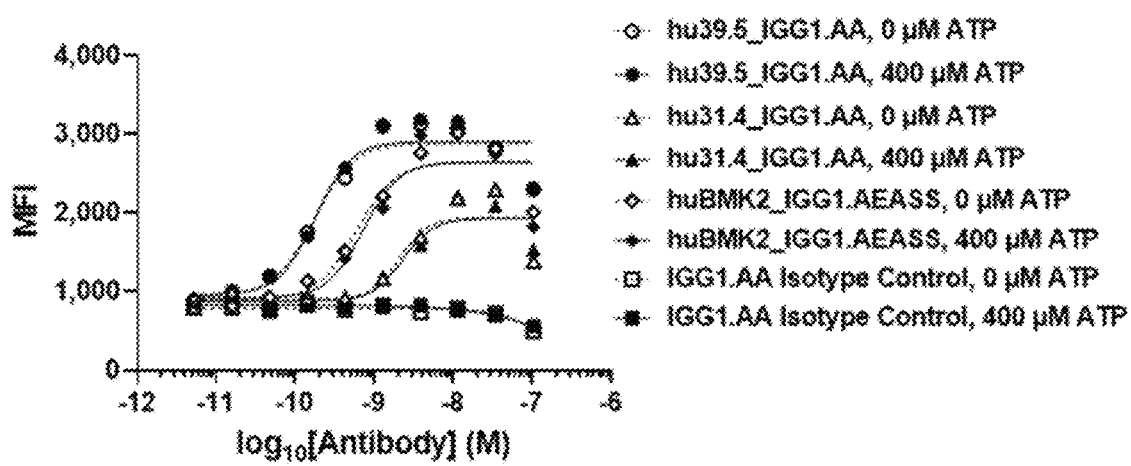
FIG. 1 is a graph depicting binding of several antibodies to human CD39 expressed on the surface of B cells from peripheral blood mononuclear cells (PBMCs). The graph shows representative data from a single human donor. Mean fluorescent intensity (MFI) is on the y-axis and antibody concentration (M) is on the x-axis.

The present disclosure provides antibodies that specifically bind to human CD39, more particularly to epitopes within the extracellular domain of human CD39, and inhibit human CD39 enzymatic activity. Also contemplated are methods for using the anti-CD39 antibodies disclosed herein to bind to cells expressing human CD39 and to inhibit soluble and cell-surface expressed human CD39 enzymatic activity. The present disclosure demonstrates use of the anti-CD39 antibodies disclosed herein to inhibit human CD39 enzymatic activity and thereby influence one end, or both ends, of the ATP-adenosine signaling axis. Accordingly, the present disclosure also provides medical uses of the anti-CD39 antibodies disclosed herein for therapeutic and diagnostic purposes.

I. Definitions

Unless otherwise defined, all terms of art, notations and other scientific terms or terminology used herein are intended to have the meanings commonly understood by those of skill in the art to which this disclosure pertains. It is understood that aspects of the invention described herein include "comprising," "consisting," and "consisting essentially of" aspects. The terms "comprising", "including" and "having" are intended to be inclusive and mean that there may be additional elements other than the listed elements.

Unless otherwise indicated, the term "about" as used herein refers to the usual error range for the respective value as understood by a skilled person in this technical field. For the avoidance of doubt, reference to "about" a value or parameter herein includes (and describes) aspects that are directed to that value or parameter per se.

Also as used herein, "and/or" refers to and encompasses any and all possible combinations of one or more of the associated listed items, as well as the lack of combinations when interpreted in the alternative ("or"). Similarly, a phrase in the form "A/B" or in the form "A and/or B" means (A), (B), or (A and B); a phrase in the form "at least one of A, B, and C" means (A), (B), (C), (A and B), (A and C), (B and C), or (A, B, and C).

The term "CD39" refers to human CD39, unless otherwise indicated. An exemplary human CD39 sequence is SEQ ID NO: 7 (UniProtKB reference: P49961). CD39 is a double-pass transmembrane protein. The extracellular domain of CD39 comprises residues 38-478 of SEQ ID NO: 7. An exemplary cynomolgus monkey CD39 sequence is SEQ ID NO: 8. The term "CD39 enzymatic activity" refers to the hydrolysis of ATP to ADP or AMP.

The terms "anti-CD39 antibody" and "an antibody that binds to CD39" are used herein interchangeably to refer to an antibody that is capable of binding human CD39 with sufficient affinity such that the antibody is useful as a diagnostic and/or therapeutic agent in targeting human CD39 and inhibiting human CD39 enzymatic activity. Anti-CD39 antibodies of the present disclosure have an equilibrium dissociation constant (KD) of $10^{-6}$ M or lower for CD39. An anti-CD39 antibody of the present disclosure can be a monospecific antibody or a multispecific antibody, and in some examples can be a polyepitopic antibody.

The term "antibody," as used herein, is used in the broadest sense and encompasses various antibody and antibody-like structures that specifically bind to a single antigen or to multiple antigens, including but not limited to full-length antibodies, antigen-binding fragments, heavy chain antibodies, single-chain antibodies, and higher order variants of single-chain antibodies. Thus, any reference to an antibody should be understood to refer to the antibody in intact form or an antigen-binding fragment unless the context requires otherwise. Preferably, but not necessarily, antibodies useful herein are isolated and can be produced recombinantly.

The terms "full-length antibody," "intact antibody," and "whole antibody" are used herein interchangeably to refer to an antibody having a structure substantially similar to a native antibody structure or having heavy chains that contain an Fc region.

"Native antibodies" are naturally occurring immunoglobulin molecules with varying structures. For example, native IgG antibodies are heterotetrameric glycoproteins of about 150,000 daltons, composed of two identical light chains (each about 25 kDa) and two identical heavy chains (each about 50-70 kDa) that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain. Heavy chains are classified as gamma, mu, alpha, delta, or epsilon, and define the antibody's isotype as IgG, IgM, IgA, IgD and IgE, respectively. The amino-terminal portion of each light and heavy chain includes a variable region of about 100 to 110 or more amino acid sequences primarily responsible for antigen recognition (VL and VH, respectively). The carboxy-terminal portion of each chain defines a constant region primarily responsible for effector function. Within light and heavy chains, the variable and constant regions are joined by a "J" region of about 12 or more amino acid sequences, with the heavy chain also including a "D" region of about 10 more amino acid sequences.

The term "variable region" or "variable domain" refers to the domain of an antibody heavy or light chain that is involved in binding the antibody to antigen. The variable domains of the heavy chain and light chain of an antibody generally have similar structures, with each domain comprising four conserved framework regions (FRs) and three hypervariable regions (CDRs). (See, e.g., Kindt et al. Kuby Immunology, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

"Framework region" or "FR" refers to variable domain residues other than hypervariable region residues. The FR of a variable domain generally consists of four FR domains: FR1, FR2, FR3, and FR4. Accordingly, the CDR and FR sequences generally appear in the following sequence: FR1-CDR1-FR2-CDR2-FR3-CDR3-FR4. The FR domains of a heavy chain and a light chain may differ, as is known in the art.

As used herein, the terms "hypervariable region" or "HVR", also commonly referred to as "complementarity determining region" or "CDR", are used interchangeably and refer to each of the regions of a variable domain which are hypervariable in sequence and/or form structurally defined loops ("hypervariable loops") and/or contain the antigen-contacting residues ("antigen contacts"). Generally, antibodies comprise six CDRs: three in the VH (H1, H2, H3), and three in the VL (L1, L2, L3). As used herein, "a CDR derived from a variable region" refers to a CDR that has no more than two amino acid substitutions, as compared to the corresponding CDR from the original variable region. Exemplary CDRs herein include: (a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987)); (b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991)); (c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), as defined below for various antibodies of this disclosure. Unless otherwise indicated, CDR residues and other residues in the variable domain (e.g., FR residues) are Eu numbered herein according to Kabat et al., supra.

The term "isolated antibody" refers to an antibody that has been separated from a component of its natural environment. In some embodiments, an isolated antibody is purified to greater than 95% or 99% purity as determined by, for example, electrophoresis or chromatography (e.g., ion exchange or reverse phase HPLC).

The term "chimeric" antibody refers to an antibody in which a portion of the heavy and/or light chain is derived from a particular source or species, while the remainder of the heavy and/or light chain is derived from a different source or species.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. Human antibodies can be produced using various techniques known in the art, including phage-display libraries. Hoogenboom and Winter. J. Mol. Biol. 227:381, 1991; Marks et al. J. Mol. Biol. 222:581, 1991. Also available for the preparation of human monoclonal antibodies are methods described in Cole et al. Monoclonal Antibodies and Cancer Therapy, Alan R. Liss, p. 77 (1985); Boerner et al. J. Immunol., 147(1):86-95, 1991. See also van Dijk and van de Winkel. Curr. Opin. Pharmacol. 5:368-74, 2001.

A "humanized" antibody refers to an antibody comprising amino acid residues from non-human CDRs and amino acid residues from human FRs. In certain aspects, a humanized antibody will comprise variable domains, in which all or substantially all of the CDRs correspond to those of a non-human antibody, and all or substantially all of the FRs correspond to those of a human antibody. In certain aspects in which all or substantially all of the FRs of a humanized antibody correspond to those of a human antibody, any of the FRs of the humanized antibody may contain one or more amino acid residues from non-human FR(s), for example at one or more Vernier position residues of FRs, and/or at one or more other chosen residue. A humanized antibody optionally may comprise at least a portion of an antibody constant region derived from a human antibody. A "humanized form" of an antibody, e.g., a non-human antibody, refers to an antibody that has undergone humanization. A humanized antibody retains similar binding specificity and affinity as the starting non-human antibody.

The term "monoclonal antibody" refers to an antibody that is derived from a single copy or clone, including e.g., any eukaryotic, prokaryotic, or phage clone. The term "monoclonal antibody" is not limited to antibodies produced through hybridoma technology. Monoclonal antibodies can be produced using hybridoma techniques well known in the art, as well as recombinant technologies, phage display technologies, synthetic technologies or combinations of such technologies and other technologies readily known in the art.

The term "epitope" refers to the particular site on an antigen to which an antibody binds. The particular site on an antigen to which an antibody binds can be determined, for example, by crystallography. Methods such as hydroxyl radical protein footprinting and alanine scanning mutagenesis can also be used but may provide less resolution.

The term "monospecific antibody" refers to an antibody that specifically binds to only one antigen. A monospecific antibody can bind to only one epitope of an antigen or can bind to two or more epitopes of an antigen. A monospecific antibody that binds to two or more epitopes of an antigen is a monospecific polyepitopic antibody.

The term "multispecific antibody" refers to an antibody that specifically binds two or more antigens (e.g., a bispecific antibody, a trispecific antibody, etc.). Non-limiting examples of multispecific antibodies include, but are not limited to, an antibody comprising a heavy chain variable domain (VH) and a light chain variable domain (VL), where the VH/VL unit has polyepitopic specificity, antibodies having two or more VL and VH domains with each VH/VL unit binding to a different epitope, antibodies having two or more single variable domains with each single variable domain binding to a different epitope, diabodies, triabodies, etc., as well as full-length antibodies and/or antibody fragments that have been linked covalently or non-covalently.

The terms "polyepitopic antibody" and "antibody having polyepitopic specificity" are used herein interchangeably to refer to an antibody that binds to two or more epitopes on the same or different antigen.

The term "Fc region" is used herein to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the Eu numbering system) of the Fc region may be removed, for example, during production or purification of the antibody, or by recombinantly engineering the nucleic acid encoding a heavy chain of the antibody. Accordingly, a composition of intact antibodies may comprise antibody populations with all Lys447 residues removed, antibody populations with no Lys447 residues removed, and antibody populations having a mixture of antibodies with and without the Lys447 residue.

A "functional Fc region" possesses an effector function of a native sequence Fc region. Exemplary effector functions include C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions generally require the Fc region to be combined with a binding domain (e.g., an antibody variable domain) and can be assessed using various assays disclosed herein or otherwise known in the art. A functional Fc region may possess effector function substantially similar to a wild-type IgG, reduced effector function compared to a wild-type IgG, or enhanced effector function compared to a wild-type IgG. For antibodies comprising a human Fc region, the comparison is typically to a wild-type human IgG1.

A "native sequence Fc region" comprises an amino acid sequence identical to the amino acid sequence of an Fc region found in nature. Native sequence human Fc regions include a native sequence human IgG1 Fc region (non-A and A allotypes); native sequence human 1gG2 Fc region; native sequence human 1gG3 Fc region; and native sequence human 1gG4 Fc region as well as naturally occurring variants thereof.

A "variant Fc region" comprises an amino acid sequence which differs from that of a native sequence Fc region by virtue of at least one amino acid modification (e.g., from about one to about ten amino acid modifications, and in some embodiments from about one to about five amino acid modifications), preferably one or more amino acid substitution(s). The variant Fc region herein will preferably possess at least about 80% homology with a native sequence Fc region and/or with an Fc region of a parent polypeptide, preferably at least about 90% homology therewith, or preferably at least about 95% homology therewith. In some embodiments, variant Fc regions may possess reduced or enhanced effector function, as compared to a wild-type IgG. For antibodies comprising a human Fc region, the comparison is typically to a wild-type human IgG1.

"Fc component" as used herein refers to a hinge region, a CH2 domain or a CH3 domain of an Fc region.

"Hinge region" is generally defined as stretching from about residue 216 to 230 of an IgG (Eu numbering), from about residue 226 to 243 of an IgG (Kabat numbering), or from about residue 1 to 15 of an IgG (IMGT unique numbering).

The term "antibody fragment" refers to a molecule other than an intact antibody that comprises a portion of an intact antibody that binds the antigen to which the intact antibody binds. Examples of antigen-binding fragment include, without limitation, a diabody, a Fab, a Fab', a F(ab')$_2$, a F(ab)$_c$, an Fv fragment, a disulfide stabilized Fv fragment (dsFv), a (dsFv)$_2$, a bispecific dsFv (dsFv-dsFv'), a disulfide stabilized diabody (ds diabody), a triabody, a tetrabody, a single-chain antibody, an scFv, an scFv dimer, a single domain antibody, a single-domain antibody, and a multivalent domain antibody. Typically, binding fragments compete with the intact antibody from which they were derived for specific binding. Binding fragments can be produced by recombinant DNA techniques, or by enzymatic or chemical separation of intact immunoglobulins.

The term "Fab" refers to that portion of an antibody consisting of a single light chain (both variable and constant regions) bound to the variable region and first constant region of a single heavy chain by a disulfide bond.

The term "Fab'" refers to a Fab fragment that includes a portion of the hinge region.

The term "F(ab')$_2$" refers to a dimer of Fab'. F(ab')$_2$ antibody fragments originally were produced as pairs of Fab' fragments which have hinge cysteines between them. Other chemical couplings of antibody fragments are also known.

The term "Fv" refers to the smallest fragment of an antibody to bear the complete antigen binding site. An Fv fragment consists of the variable region of a single light chain bound to the variable region of a single heavy chain.

The term "single-chain antibody" refers to an antibody consisting of a heavy chain variable region and a light chain variable region connected by a linker. In most instances, but not all, the linker may be a peptide. The length of the linker varies depending upon the type of single-chain antibody. Covalently or non-covalently linking two or more single-chain antibodies together results in higher order forms. Single-chain antibodies, and their higher order forms, may include, but are not limited to, single-domain antibodies, multivalent domain antibodies, single chain variant fragments (scFvs), divalent scFvs (di-scFvs), trivalent scFvs (tri-scFvs), tetravalent scFvs (tetra-scFvs), diabodies, and triabodies and tetrabodies.

The terms "single-chain Fv antibody" and "scFv" are used herein interchangeably to refer to a single-chain antibody consisting of heavy variable region and a light chain variable region connected by a linker. In most instances, but not all, the linker may be a peptide. The linker peptide is preferably from about 5 to 30 amino acids in length, or from about 10 to 25 amino acids in length. Typically, the linker allows for stabilization of the variable domains without interfering with the proper folding and creation of an active binding site. In preferred embodiments, a linker peptide is rich in glycine, as well as serine or threonine. Covalently or non-covalently linking two or more scFvs together results in higher order forms di-scFvs, tri-scFvs, tetra-scFvs, etc. The antigen-binding sites of each scFv in a higher order form can target the same or different antigen or epitope.

The term "single-chain Fv-Fc antibody" or "scFv-Fc" refers to a full-length antibody consisting of a scFv connected to an Fc region.

A "diabody" is a higher order variant of a single-chain antibody consisting of two single-chain antibodies. For each single-chain antibody, a linker is used that is too short to allow pairing between the two domains on the same chain, forcing the domains to pair with the complementary domains of another chain, thereby creating two antigen-binding sites. In most instances, but not all, the linker may be a peptide. The antigen-binding sites can target the same or different antigens or epitopes. Triabodies (three single chain antibodies assembled to form three antigen-binding sites), tetrabodies (four single chain antibodies assembled to form four antigen-binding sites), and higher order variants can similarly be produced. See, for example, Holliger P. et al., *Proc Natl Acad Sci USA*. July 15; 90(14):6444-8 (1993); EP404097; WO93/11161.

A "single-domain antibody" refers to an antibody fragment containing only the variable region of a heavy chain or the variable region of a light chain. In certain instances, two or more $V_H$ domains are covalently joined with a peptide linker to create a multivalent domain antibody. The two or more $V_H$ domains of a multivalent domain antibody can target the same or different antigens or epitopes.

The term "heavy chain antibody" refers to an antibody that consists of two heavy chains. A heavy chain antibody may be an IgG-like antibody from camels, llamas, alpacas, sharks, etc., or an IgNAR from a cartilaginous fish. See, for example, Riechmann L. and Muyldermans S., *J Immunol Methods*. December 10; 231(1-2): 25-38 (1999); Muyldermans S., J Biotechnol. June; 74(4):277-302 (2001); WO94/04678; WO94/25591; or U.S. Pat. No. 6,005,079. Heavy chain antibodies were originally derived from Camelidae (camels, dromedaries, and llamas). Although devoid of light chains, camelized antibodies have an authentic antigen-binding repertoire (Hamers-Casterman C. et al., *Nature*. June 3; 363(6428):446-8 (1993); Nguyen V. K. et al. "Heavy-chain antibodies in Camelidae; a case of evolutionary innovation," *Immunogenetics*. April; 54(1):39-47 (2002); Nguyen V. K. et al. *Immunology*. May; 109(1):93-101 (2003)). The variable domain of a heavy chain antibody (VHH domain) represents the smallest known antigen-binding unit generated by adaptive immune responses (Koch-Nolte F. et al., *FASEB J*. November; 21(13):3490-8. Epub 2007 Jun. 15 (2007)).

A "nanobody" refers to an antibody that consists of a VHH domain from a heavy chain antibody and two constant domains, CH2 and CH3.

"Percent (%) identity" with respect to a reference amino acid sequence is defined as the percentage of amino acid residues in a candidate sequence that are identical with the amino acid residues in the reference sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, or CLUSTAL software. Those skilled in the art can determine appropriate parameters for aligning sequences, including any algorithms needed to achieve maximal alignment over the full length of the sequences being compared. Generally speaking, the % sequence identity of a given amino acid sequence A to, with, or against a given amino acid sequence B is calculated as follows: 100 times the fraction X/Y where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

The terms "patient" and "subject" are used herein interchangeably to refer to a human or a non-human animal (e.g., a mammal) expressing human CD39.

The terms "treat", "treating", treatment" and the like refer to a course of action that eliminates, reduces, suppresses, mitigates, or ameliorates, or prevents the worsening of, either temporarily or permanently, a disease, disorder or condition to which the term applies, or at least one of the symptoms associated therewith. Treatment includes, as examples, inhibiting (e.g., arresting the development or further development of the disease, disorder or condition or clinical symptoms association therewith) an active disease, improving the quality of life, and/or prolonging survival of a subject.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention", "prophylaxis" and the like refer to a course of action initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state. Prevention also refers to a course of action initiated in a subject after the subject has been treated for a disease, disorder, condition or a symptom associated therewith in order to prevent relapse of that disease, disorder, condition or symptom.

The term "in need of prevention" as used herein refers to a judgment made by a physician or other caregiver that a subject requires or will benefit from preventative care. This judgment is made based on a variety of factors that are in the realm of a physician's or caregiver's expertise.

II. Antibodies of the Disclosure

The present disclosure provides antibodies that specifically bind to human CD39, more particularly to the extracellular domain of human CD39. Antibodies of the present disclosure may specifically bind to soluble and/or membrane-bound human CD39. In some embodiments, an anti-CD39 antibody of the present disclosure is monospecific. In other embodiments, an anti-CD39 antibody of the present disclosure is multispecific. Additional antigen binding specificity contemplated in the context of the present disclosure includes but is not limited to TGFβ. Anti-CD39 antibodies of the present application can be isolated or part of a composition.

Anti-CD39 antibodies of the present disclosure, whether monospecific or multispecific, specifically bind to human CD39, meaning the antibody has an equilibrium dissociation constant ($K_D$) of $10^{-6}$ M or lower for CD39, measured by surface plasmon resonance (SPR). In certain embodiments, the anti-CD39 antibodies of the present disclosure have a $K_D$ for human CD39 of $10^{-8}$ M or lower (e.g., $10^{-8}$, $10^{-9}$, $10^{-10}$, etc.), measured by SPR. See, for instance, Example 3 for detailed methodology. In various embodiments, the anti-CD39 antibodies of the present disclosure have a $K_D$ for human CD39 that is about $1\times10^{-9}$ M to about $1\times10^{-14}$ M, or about $1\times10^{-9}$ M to about $1\times10^{-13}$ M, or about $1\times10^{-9}$ M to about $1\times10^{-12}$ M, or about $1\times10^{-9}$ M to about $1\times10^{-11}$ M. In some embodiments, an anti-CD39 antibody of the present disclosure has a $K_D$ for human CD39 that is about $1\times10^{-10}$ M to about $1\times10^{-14}$ M, or about $1\times10^{-10}$ M to about $1\times10^{-13}$ M, or about $1\times10^{-10}$ M to about $1\times10^{-12}$ M. In some embodiments, an anti-CD39 antibody of the present disclosure has a $K_D$ for human CD39 that is about $1\times10^{-11}$ M to about $1\times10^{-14}$ M, about $1\times10^{-11}$ M to about $1\times10^{-13}$ M. In some embodiments, an anti-CD39 antibody of the present disclosure has a $K_D$ for human CD39 that is about $1\times10^{-12}$ M to about $1\times10^{-14}$ M, or about $1\times10^{-12}$ M to about $1\times10^{-13}$ M. In some embodiments, an anti-CD39 antibody of the present disclosure has a $K_D$ for human CD39 that is about $1\times10^{-10}$ M to about $1\times10^{-11}$ M, or about $1\times10^{-11}$ M to about $1\times10^{-12}$ M.

Anti-CD39 antibodies of the present disclosure also inhibit CD39 enzymatic activity. In some embodiments, an anti-CD39 antibody of the present disclosure inhibits human CD39 enzymatic activity with an $IC_{50}$ value of about 5 nM or less, measured as in Example 5 For example, an anti-CD39 antibody may inhibit recombinant human CD39 enzymatic activity with an $IC_{50}$ value of about 5 nM, about 4 nM, about 3 nM, about 2 nM, about 1 nM, or less, measured as in Example 5. As another example, an anti-CD39 antibody may inhibit recombinant human CD39 enzymatic activity with an $IC_{50}$ value of about 1 nM or less, for example, about 1.0 nM, about 0.9 nM, about 0.8 nM, about 0.7 nM, about 0.6 nM, about 0.5 nM, or less. As another example, an anti-CD39 antibody may inhibit recombinant human CD39 enzymatic activity with an $IC_{50}$ value of about 0.5 nM or less, for example, about 0.5 nM, about 0.4 nM, about 0.3 nM, about 0.2 nM, about 0.1 nM, about 0.09 nM, about 0.08 nM, about 0.07 nM, about 0.06 nM, about 0.05 nM, or less, measured as in Example 5. The $IC_{50}$ values above may also be expressed as individual values, or as ranges. For example, an anti-CD39 antibody may inhibit recombinant human CD39 enzymatic activity with an $IC_{50}$ value of about 0.05 nM to about 5 nM, about 0.05 nM to about 1 nM, 0.05 nM to about 0.5 nM, about 1 nM to about 5 nM, about 0.5 nM to about 1.0 nM, or sub-ranges thereof. In one embodiment, an anti-CD39 antibody of the present disclosure inhibits human CD39 enzymatic activity with an $IC_{50}$ value of about 0.5 nM to about 1.0 nM, or about 0.6 nM to about 1.0 nM. In one embodiment, an anti-CD39 antibody of the present disclosure inhibits human CD39 enzymatic activity with an $IC_{50}$ value of about 0.05 nM to about 0.5 nM, about 0.05 nM to about 0.4 nM, or about 0.05 nM to about 0.3 nM. In one embodiment, an anti-CD39 antibody of the present disclosure inhibits human CD39 enzymatic activity with an $IC_{50}$ value of about 0.07 nM to about 0.5 nM, about 0.07 nM to about 0.4 nM, about 0.07 nM to about 0.3 nM, or about 0.07 nM to about 0.2 nM. In the aforementioned embodiments, (i) the human CD39 may be recombinant, soluble CD39 or may be cell-surface expressed CD39, and/or (ii) inhibition may be assessed in the presence of low ATP (e.g., 20 μM) and/or high ATP (e.g., 400 μM).

A. Exemplary Variable Regions

The present disclosure provides anti-CD39 antibodies comprising a VH, or a VH and a VL, as described herein. In the following embodiments, "at least X % sequence identity" encompasses individual values and ranges thereof. For example, "at least 90% sequence identity" includes at least 91%, at least 92%, at least 93%, at least 94%, at least 95%, at least 96%, at least 97%, at least 98%, at least 99% sequence identity, as well as individual values (e.g., 90%, 91%, 92%, 93%, 94%, 95%, 96%, 97%, 98%, 99%, 100% sequence identity) and ranges thereof.

In one example, an anti-CD39 antibody of the present disclosure comprises a heavy chain variable region (VH) that has one or more CDRs derived from SEQ ID NO: 9 and optionally a light chain variable region (VL) that has one or more CDRs derived from SEQ ID NO: 13. The CDR derived from SEQ ID NO: 9 may be H1, H2, H3, or any combination thereof. In certain embodiments, the VH may comprise an H1 having at least 90% sequence identity to SEQ ID NO: 10, an H2 having at least 90% sequence identity to SEQ ID NO: 11, an H3 having at least 90% sequence identity to SEQ ID NO: 12, or any combination thereof. The CDR derived from SEQ ID NO: 13 may be L1, L2, L3, or any combination thereof. In certain embodiments, the VL may comprise an L1 having at least 90% sequence identity to SEQ ID NO: 14, an L2 having at least 90% sequence identity to SEQ ID NO: 15, an L3 having at least 90% sequence identity to SEQ ID NO: 16, or any combination thereof. An antibody comprising one or more CDRs derived from SEQ ID NO: 9 may further comprise a VL comprising one or more CDRs derived from SEQ ID NO: 13. The CDR may be L1, L2, L3, or any combination thereof. In a preferred embodiment, the VL may comprise an L1 with an amino acid sequence having at least 90% sequence identity to SEQ ID NO: 14, an L2 with an amino acid sequence having at least 90% sequence identity to SEQ ID NO: 15, an L3 with an amino acid sequence having at least 90% sequence identity to SEQ ID NO: 16, or any combination thereof. In a specific example, an anti-CD39 antibody of the present disclosure comprises a VH comprising an H1 with an amino acid sequence having at least 90% sequence identity to SEQ ID NO: 10, an H2 with an amino acid sequence having at least 90% sequence identity to SEQ ID NO: 11, an H3 with an amino acid sequence having at least 90% sequence identity to SEQ ID NO: 12, and a VL comprising an L1 with an amino acid sequence having at least 90% sequence identity to SEQ ID NO: 14, an L2 with an amino acid sequence having at least 90% sequence identity to SEQ ID NO: 15, and an L3 with an amino acid sequence having at least 90% sequence identity to SEQ ID NO: 16. In another specific example, an anti-CD39 antibody of the present disclosure comprises a VH comprising an H1 having an amino acid sequence comprising SEQ ID NO: 10, an H2 having an amino acid sequence comprising SEQ ID NO: 11, an H3 having an amino acid sequence comprising SEQ ID NO: 12, and a VL comprising an L1 having an amino acid sequence comprising SEQ ID NO: 14, an L2 having an amino acid sequence comprising SEQ ID NO: 15, and an L3 having an amino acid sequence comprising SEQ ID NO: 16.

In some of the aforementioned embodiments, the antibody may further comprise (i) a mature VH having an amino acid sequence with at least 80% sequence identity to SEQ ID NO: 9 and/or a mature VL having an amino acid sequence with at least 80% sequence identity to SEQ ID NO: 13. In an exemplary embodiment, the antibody comprises a mature VH and a mature VL, and is an antibody of Table A.

TABLE A

| Antibody | mature VH | mature VL |
|---|---|---|
| A | SEQ ID NO: 9 | SEQ ID NO: 13 |

In each of the aforementioned embodiments, the anti-CD39 antibody may be (i) an intact antibody or an antigen-binding fragment, and/or (ii) a chimeric antibody, a humanized antibody, or a human antibody. Suitable chimeric, humanized, and human antibodies are described further in Section IIC, IID, and IE. In certain embodiments, the anti-CD39 antibody may optionally comprise one or more constant regions, or a portion of a constant region, that is substantially human. Suitable constant regions are described in further detail in Section II(F).

In another exemplary embodiment, the antibody is an antibody of Table B.

TABLE B

| Antibody | mature HC | mature LC |
| --- | --- | --- |
| ch19_IGG4.P | SEQ ID NO: 35 | SEQ ID NO: 36 |

In another example, an anti-CD39 antibody of the present disclosure comprises a heavy chain variable region (VH) that has one or more CDRs derived from SEQ ID NO: 17, SEQ ID NO: 43, or SEQ ID NO: 44 and optionally a light chain variable region (VL) that has one or more CDRs derived from SEQ ID NO: 21, SEQ ID NO: 45, SEQ ID NO: 46, SEQ ID NO: 47, SEQ ID NO: 48, or SEQ ID NO: 49. The CDR derived from SEQ ID NO: 17, SEQ ID NO: 43, or SEQ ID NO: 44 may be H1, H2, H3, or any combination thereof. In certain embodiments, the VH may comprise an H1 having at least 90% sequence identity to SEQ ID NO: 18, an H2 having at least 90% sequence identity to SEQ ID NO: 19, an H3 having at least 90% sequence identity to SEQ ID NO: 20, or any combination thereof. The CDR derived from SEQ ID NO: 21, SEQ ID NO: 45, SEQ ID NO: 46, SEQ ID NO: 47, SEQ ID NO: 48, or SEQ ID NO: 49 may be L1, L2, L3, or any combination thereof. In certain embodiments, the VL may comprise an L1 having at least 90% sequence identity to SEQ ID NO: 22, SEQ ID NO: 23, or SEQ ID NO: 24, an L2 having at least 90% sequence identity to SEQ ID NO: 25, an L3 having at least 90% sequence identity to SEQ ID NO: 26, or any combination thereof. An antibody comprising one or more CDRs derived from SEQ ID NO: 17, SEQ ID NO: 43, or SEQ ID NO: 44 may further comprise a VL comprising one or more CDRs derived from SEQ ID NO: 21, SEQ ID NO: 45, SEQ ID NO: 46, SEQ ID NO: 47, SEQ ID NO: 48, or SEQ ID NO: 49. The CDR may be L1, L2, L3, or any combination thereof. In a preferred embodiment, the VL may comprise an L1 having at least 90% sequence identity to SEQ ID NO: 22, SEQ ID NO: 23, or SEQ ID NO: 24, an L2 having at least 90% sequence identity to SEQ ID NO: 25, an L3 having at least 90% sequence identity to SEQ ID NO: 26, or any combination thereof. In a specific example, an anti-CD39 antibody of the present disclosure comprises a VH comprising an H1 with an amino acid sequence having at least 90% sequence identity to SEQ ID NO: 18, an H2 with an amino acid sequence having at least 90% sequence identity to SEQ ID NO: 19, an H3 with an amino acid sequence having at least 90% sequence identity to SEQ ID NO: 20, and a VL comprising an L1 with an amino acid sequence having at least 90% sequence identity to SEQ ID NO: 22, SEQ ID NO: 23, or SEQ ID NO: 24, an L2 with an amino acid sequence having at least 90% sequence identity to SEQ ID NO: 25, and an L3 with an amino acid sequence having at least 90% sequence identity to SEQ ID NO: 26. In another specific example, an anti-CD39 antibody of the present disclosure comprises a VH comprising an H1 having an amino acid sequence comprising SEQ ID NO: 18, an H2 having an amino acid sequence comprising SEQ ID NO: 19, an H3 having an amino acid sequence comprising SEQ ID NO: 20, and a VL comprising an L1 having an amino acid sequence comprising SEQ ID NO: 22, SEQ ID NO: 23, or SEQ ID NO: 24, an L2 having an amino acid sequence comprising SEQ ID NO: 25, and an L3 having an amino acid sequence comprising SEQ ID NO: 26.

In some of the aforementioned embodiments, the antibody may further comprise (i) a VH having an amino acid sequence with at least 80% sequence identity to SEQ ID NO: 17 and/or a VL having an amino acid sequence with at least 80% sequence identity to SEQ ID NO: 21; or (ii) a VH having an amino acid sequence with at least 80% sequence identity to SEQ ID NO: 43 or SEQ ID NO: 44 and/or a VL having an amino acid sequence with at least 80% sequence identity to SEQ ID NO: 45, SEQ ID NO: 46, SEQ ID NO: 47, SEQ ID NO: 48, or SEQ ID NO: 49. In an exemplary embodiment, the antibody comprises a VH and a VL, and is an antibody of Table C.

TABLE C

| Antibody | mature VH | mature VL |
| --- | --- | --- |
| B | SEQ ID NO: 17 | SEQ ID NO: 21 |
| C | SEQ ID NO: 43 | SEQ ID NO: 45 |
| D | SEQ ID NO: 43 | SEQ ID NO: 46 |
| E | SEQ ID NO: 43 | SEQ ID NO: 47 |
| F | SEQ ID NO: 43 | SEQ ID NO: 48 |
| G | SEQ ID NO: 43 | SEQ ID NO: 49 |
| H | SEQ ID NO: 44 | SEQ ID NO: 48 |
| I | SEQ ID NO: 44 | SEQ ID NO: 49 |

In each of the aforementioned embodiments, the anti-CD39 antibody may be (i) an intact antibody or an antigen-binding fragment, and/or (ii) a chimeric antibody, a humanized antibody, or a human antibody. Suitable chimeric, humanized, and human antibodies are described further in Section IIC, IID, and IE. In certain embodiments, the anti-CD39 antibody may optionally comprise one or more constant regions, or a portion of a constant region, that is substantially human. Suitable constant regions are described in further detail in Section II(F).

In another exemplary embodiment, the antibody is an antibody of Table D.

TABLE D

| Antibody | mature HC | mature LC |
| --- | --- | --- |
| ch31_IGG4.P | SEQ ID NO: 37 | SEQ ID NO: 38 |
| hu31.1_IGG4.P | SEQ ID NO: 50 | SEQ ID NO: 53 |
| hu31.2_IGG4.P | SEQ ID NO: 50 | SEQ ID NO: 54 |
| hu31.3_IGG4.P | SEQ ID NO: 50 | SEQ ID NO: 55 |
| hu31.4_IGG4.P | SEQ ID NO: 50 | SEQ ID NO: 56 |
| hu31.4_IGG1.AA | SEQ ID NO: 51 | SEQ ID NO: 56 |
| hu31.5_IGG4.P | SEQ ID NO: 50 | SEQ ID NO: 57 |
| hu31.6_IGG4.P | SEQ ID NO: 52 | SEQ ID NO: 56 |
| hu31.7_IGG4.P | SEQ ID NO: 52 | SEQ ID NO: 57 |

In another example, an anti-CD39 antibody of the present disclosure comprises a heavy chain variable region (VH) that has one or more CDRs derived from SEQ ID NO: 27, SEQ ID NO: 58 or SEQ ID NO: 59 and optionally a light chain variable region (VL) that has one or more CDRs derived from SEQ ID NO: 31, SEQ ID NO: 60, SEQ ID NO: 61, SEQ ID NO: 62, or SEQ ID NO: 63. The CDR derived from SEQ ID NO: 58 or SEQ ID NO: 59 may be H1, H2, H3, or any combination thereof. In certain embodiments, the VH may comprise an H1 having at least 90% sequence identity to SEQ ID NO: 28, an H2 having at least 90% sequence identity to SEQ ID NO: 29, an H3 having at least 90% sequence identity to SEQ ID NO: 30, or any combination thereof. The CDR derived from SEQ ID NO: 60, SEQ ID NO: 61, SEQ ID NO: 62, SEQ ID NO: 63 may be L1, L2, L3, or any combination thereof. In certain embodiments, the VL may comprise an L1 having at least 90% sequence identity to SEQ ID NO: 32, an L2 having at least 90% sequence identity to SEQ ID NO: 33, an L3 having at least 90% sequence identity to SEQ ID NO: 34, or any combination thereof. An antibody comprising one or more CDRs derived from SEQ ID NO: 58 or SEQ ID NO: 59 may further comprise a VL comprising one or more CDRs derived from SEQ ID NO: 60, SEQ ID NO: 61, SEQ ID NO: 62, SEQ ID NO: 63. The CDR may be L1, L2, L3, or any combination thereof. In a preferred embodiment, the VL may comprise an L1 with an amino acid sequence having at least 90% sequence identity to SEQ ID NO: 32, an L2 with an amino acid sequence having at least 90% sequence identity to SEQ ID NO: 33, an L3 with an amino acid sequence having at least 90% sequence identity to SEQ ID NO: 34, or any combination thereof. In a specific example, an anti-CD39 antibody of the present disclosure comprises a VH comprising an H1 with an amino acid sequence having at least 90% sequence identity to SEQ ID NO: 28, an H2 with an amino acid sequence having at least 90% sequence identity to SEQ ID NO: 29, an H3 with an amino acid sequence having at least 90% sequence identity to SEQ ID NO: 30, and a VL comprising an L1 with an amino acid sequence having at least 90% sequence identity to SEQ ID NO: 32, an L2 with an amino acid sequence having at least 90% sequence identity to SEQ ID NO: 33, and an L3 with an amino acid sequence having at least 90% sequence identity to SEQ ID NO: 34. In another specific example, an anti-CD39 antibody of the present disclosure comprises a VH comprising an H1 having an amino acid sequence comprising SEQ ID NO: 28, an H2 having an amino acid sequence comprising SEQ ID NO: 29, an H3 having an amino acid sequence comprising SEQ ID NO: 30, and a VL comprising an L1 having an amino acid sequence comprising SEQ ID NO: 32, an L2 having an amino acid sequence comprising SEQ ID NO: 33, and an L3 having an amino acid sequence comprising SEQ ID NO: 34.

In some of the aforementioned embodiments, the antibody may further comprise (i) a VH having an amino acid sequence with at least 80% sequence identity to SEQ ID NO: 27 and/or a VL having an amino acid sequence with at least 80% sequence identity to SEQ ID NO: 31; or (ii) a VH having an amino acid sequence with at least 80% sequence identity to SEQ ID NO: 58 or SEQ ID NO: 59 and/or a VL having an amino acid sequence with at least 80% sequence identity to SEQ ID NO: 60, SEQ ID NO: 61, SEQ ID NO: 62, or SEQ ID NO: 63. In an exemplary embodiment, the antibody comprises a VH and a VL, and is an antibody of Table E.

TABLE E

| Antibody | mature VH | mature VL |
|---|---|---|
| J | SEQ ID NO: 27 | SEQ ID NO: 31 |
| K | SEQ ID NO: 58 | SEQ ID NO: 60 |
| L | SEQ ID NO: 58 | SEQ ID NO: 61 |
| M | SEQ ID NO: 58 | SEQ ID NO: 62 |
| N | SEQ ID NO: 59 | SEQ ID NO: 61 |
| O | SEQ ID NO: 59 | SEQ ID NO: 60 |
| P | SEQ ID NO: 59 | SEQ ID NO: 62 |
| Q | SEQ ID NO: 59 | SEQ ID NO: 63 |
| R | SEQ ID NO: 58 | SEQ ID NO: 63 |

In each of the aforementioned embodiments, the anti-CD39 antibody may be (i) an intact antibody or an antigen-binding fragment, and/or (ii) a chimeric antibody, a humanized antibody, or a human antibody. Suitable chimeric, humanized, and human antibodies are described further in Section IIC, IID, and IIE, respectively. In certain embodiments, the anti-CD39 antibody may optionally comprise one or more constant regions, or a portion of a constant region, that is substantially human. Suitable constant regions are described in further detail in Section II(F).

In another exemplary embodiment, the antibody is an antibody of Table F.

TABLE F

| Antibody | mature HC | mature LC |
|---|---|---|
| ch39_IGG4.P | SEQ ID NO: 39 | SEQ ID NO: 40 |
| ch39_mIGG2A.AAG | SEQ ID NO: 41 | SEQ ID NO: 42 |
| hu39.1_IGG4.P | SEQ ID NO: 64 | SEQ ID NO: 67 |
| hu39.2_IGG4.P | SEQ ID NO: 64 | SEQ ID NO: 68 |
| hu39.3_IGG4.P | SEQ ID NO: 64 | SEQ ID NO: 69 |
| hu39.4_IGG4.P | SEQ ID NO: 65 | SEQ ID NO: 68 |
| hu39.5_IGG4.P | SEQ ID NO: 65 | SEQ ID NO: 67 |
| hu39.5_IGG1.AA | SEQ ID NO: 66 | SEQ ID NO: 67 |
| hu39.6_IGG4.P | SEQ ID NO: 65 | SEQ ID NO: 69 |
| hu39.7_IGG4.P | SEQ ID NO: 65 | SEQ ID NO: 70 |
| hu39.8_IGG4.P | SEQ ID NO: 64 | SEQ ID NO: 70 |

B. Antibodies with Similar Binding Specificity

The present disclosure also provides anti-CD39 antibodies that bind to the same or overlapping epitope as an antibody designated above as 19 or ch19_IGG4.P, or an antibody designated above as 31, ch31_IGG4.P, hu31.1_IGG4.P, hu31.2_IGG4.P, hu31.3_IGG4.P, hu31.4_IGG4.P, hu31.4_IGG1.AA, hu31.5_IGG4.P, hu31.6_IGG4.P, or hu31.7_IGG4.P, or an antibody designated above as 39, ch39_IGG4.P, ch39_mIGG2A.AAG, hu39.1_IGG4.P, hu39.2_IGG4.P, hu39.3_IGG4.P, hu39.4_IGG4.P, hu39.5_IGG4.P, hu39.5_IGG1.AA, hu39.6_IGG4.P, hu39.7_IGG4.P, or hu39.8_IGG4.P. Epitopes may be identified by methods known in the art, such as X-ray crystallography of the antibody bound to its antigen to identify contact residues. A competition assay may be used to identify such antibodies. For example, an anti-CD39 antibody may competitively inhibit binding of a reference antibody to human CD39, the reference antibody selected from 19, ch19_IGG4.P, 31, ch31_IGG4.P, hu31.1_IGG4.P, hu31.2_IGG4.P, hu31.3_IGG4.P, hu31.4_IGG4.P, hu31.4_IGG1.AA, hu31.5_IGG4.P, hu31.6_IGG4.P, or hu31.7_IGG4.P, 39, ch39_IGG4.P, ch39_mIGG2A.AAG, hu39.1_IGG4.P, hu39.2_IGG4.P, hu39.3_IGG4.P, hu39.4_IGG4.P, hu39.5_IGG4.P, hu39.5_IGG1.AA, hu39.6_IGG4.P, hu39.7_IGG4.P, or hu39.8_IGG4.P. An antibody is said to competitively inhibit binding of a reference antibody to human CD39 if the antibody blocks binding of the reference antibody to human CD39 by at least 50%, at least 60%, at least 70%, at least 80%, or at least 90%. Competitive inhibition can be determined, for example, by a competition flow assay, as described in Example 7.

In further embodiments, an antibody that competitively inhibits binding of a reference antibody to human CD39, as described above, comprises a VH, or a VH and a VL, as described Section II (A).

Other antibodies having such a binding specificity can be produced by immunizing mice with human CD39 or a portion thereof including the desired epitope, and screening resulting antibodies for binding to the extracellular domain of human CD39, optionally in competition with antibody 19 or a variant thereof (e.g., ch19_IGG4.P, etc.), antibody 31 or a variant thereof (e.g., ch31_IGG4.P, hu31.1_IGG4.P, hu31.2_IGG4.P, hu31.3_IGG4.P, hu31.4_IGG4.P, hu31.4_IGG1.AA, hu31.5_IGG4.P, hu31.6_IGG4.P, hu31.7_IGG4.P, etc.), or antibody 39 or a variant thereof (e.g., ch39_IGG4.P, ch39_mIGG2A.AAG, hu39.1_IGG4.P, hu39.2_IGG4.P, hu39.3_IGG4.P, hu39.4_IGG4.P, hu39.5_IGG4.P, hu39.5_IGG1.AA, hu39.6_IGG4.P, hu39.7_IGG4.P, hu39.8_IGG4.P, etc.). Antibodies can also be screened against mutagenized forms of human CD39 to identify an antibody showing the same or similar binding profile to collection of mutational changes as 19, ch19_IGG4.P, 31, ch31_IGG4.P, hu31.1_IGG4.P, hu31.2_IGG4.P, hu31.3_IGG4.P, hu31.4_IGG4.P, hu31.4_IGG1.AA, hu31.5_IGG4.P, hu31.6_IGG4.P, hu31.7_IGG4.P, 39, ch39_IGG4.P, ch39_mIGG2A.AAG, hu39.1_IGG4.P, hu39.2_IGG4.P, hu39.3_IGG4.P, hu39.4_IGG4.P, hu39.5_IGG4.P, hu39.5_IGG1.AA, hu39.6_IGG4.P, hu39.7_IGG4.P, or hu39.8_IGG4.P. The mutations can be systematic replacement substitution with alanine (or serine if an alanine is present already) one residue at a time, or more broadly spaced intervals, throughout the extracellular domain of CD39 antibody or through a section thereof in which an epitope is known to reside.

Other antibodies can be obtained by mutagenesis of cDNA encoding the heavy and light chains of an exemplary antibody, such as 19, ch19_IGG4.P, 31, ch31_IGG4.P, hu31.1_IGG4.P, hu31.2_IGG4.P, hu31.3_IGG4.P, hu31.4_IGG4.P, hu31.4_IGG1.AA, hu31.5_IGG4.P, hu31.6_IGG4.P, hu31.7_IGG4.P, 39, ch39_IGG4.P, ch39_mIGG2A.AAG, hu39.1_IGG4.P, hu39.2_IGG4.P, hu39.3_IGG4.P, hu39.4_IGG4.P, hu39.5_IGG4.P, hu39.5_IGG1.AA, hu39.6_IGG4.P, hu39.7_IGG4.P, or hu39.8_IGG4.P. Antibodies that are at least any of about 80%, 81%, 82%, 83%, 84%, 85%, 86%, 87%, 88%, 89%, 90%, 91%, 92%, 93%, 94%, 95%, 96%, 97%, 98%, 99% or 100% identical to 19, ch19_IGG4.P, 31, ch31_IGG4.P, hu31.1_IGG4.P, hu31.2_IGG4.P, hu31.3_IGG4.P, hu31.4_IGG4.P, hu31.4_IGG1.AA, hu31.5_IGG4.P, hu31.6_IGG4.P, hu31.7_IGG4.P, 39, ch39_IGG4.P, ch39_mIGG2A.AAG, hu39.1_IGG4.P, hu39.2_IGG4.P, hu39.3_IGG4.P, hu39.4_IGG4.P, hu39.5_IGG4.P, hu39.5_IGG1.AA, hu39.6_IGG4.P, hu39.7_IGG4.P, or hu39.8_IGG4.P in amino acid sequence of the mature heavy and/or light chain variable regions and maintain its functional properties, and/or which differ from the respective antibody by a small number of functionally inconsequential amino acid substitutions (e.g., conservative substitutions), deletions, or insertions are also included in the present disclosure. Amino acids in the variable region frameworks likely important for binding can be identified as described in the sections on humanization below.

Antibodies having the binding specificity of a selected rodent antibody (e.g., 19, 31, or 37) or of a selected humanized antibody (e.g., hu31.1_IGG4.P, hu31.2_IGG4.P, hu31.3_IGG4.P, hu31.4_IGG4.P, hu31.4_IGG1.AA, hu31.5_IGG4.P, hu31.6_IGG4.P, hu31.7_IGG4.P, hu39.1_IGG4.P, hu39.2_IGG4.P, hu39.3_IGG4.P, hu39.4_IGG4.P, hu39.5_IGG4.P, hu39.5_IGG1.AA, hu39.6_IGG4.P, hu39.7_IGG4.P, or hu39.8_IGG4.P) can also be produced using a variant of the phage display method. See Winter, WO 92/20791. This method is particularly suitable for producing human antibodies. In this method, either the heavy or light chain variable region of the selected antibody is used as a starting material. If, for example, a light chain variable region is selected as the starting material, a phage library is constructed in which members display the same light chain variable region (i.e., the light chain of the starting material) and a different heavy chain variable region. The heavy chain variable regions can, for example, be obtained from a library of rearranged human heavy chain variable regions. A phage showing strong specific binding for human CD39 (e.g., at least $10^8$ or at least $10^9$ $M^{-1}$) is selected. The heavy chain variable region from this phage then serves as a starting material for constructing a further phage library. In this library, each phage displays the same heavy chain variable region (i.e., the region identified from the first display library) and a different light chain variable region. The light chain variable regions can be obtained, for example, from a library of rearranged human variable light chain regions. Again, phage showing strong specific binding for human CD39 are selected. The resulting antibodies usually have the same or similar epitope specificity as the murine starting material.

In addition to antibodies described herein, it may be possible to design an antibody mimetic or an aptamer that has the same binding specificity using methods known in the art that functions substantially the same as an antibody of the invention. An "antibody mimetic" refers to a polypeptide or a protein that can specifically bind to an antigen but is not structurally related to an antibody. Antibody mimetics have a mass of about 3 kDa to about 20 kDa. Non-limiting examples of antibody mimetics are affibody molecules, affilins, affimers, alphabodies, anticalins, avimers, DARPins, and monobodies. Aptamers are a class of small nucleic acid ligands that are composed of RNA or single-stranded DNA oligonucleotides and have high specificity and affinity for their targets. Aptamers interact with and bind to their targets through structural recognition, a process similar to that of an antigen-antibody reaction. Aptamers have a lower molecular weight than antibodies, typically about 8-25 kDa.

C. Chimeric and Veneered Antibodies

As described above, the present disclosure provides chimeric and veneered forms of non-human antibodies, including but not limited to the chimeric anti-CD39 antibodies of an antibody designated herein as antibody 19, antibody 31 or antibody 39.

In certain embodiments, a chimeric antibody is an antibody in which the mature variable regions of light and heavy chains of a non-human antibody (e.g., a mouse, a rat, etc.) are combined with human light and heavy chain constant regions. Such antibodies substantially or entirely retain the binding specificity of the non-human antibody and are about two-thirds human sequence.

A veneered antibody is a type of humanized antibody that retains some and usually all of the CDRs and some of the non-human variable region framework residues of a non-human antibody but replaces other variable region framework residues that can contribute to B- or T cell epitopes, for example, exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions. Veneered forms of anti-CD39 antibodies are included in the present disclosure.

In some embodiments, an anti-CD39 chimeric antibody is a rat-human chimera having rat variable domains and human IgG1 and kappa constant domains (or variants thereof) or human IgG4 and kappa constant domains (or variants thereof). Suitable human constant domains are known in the art, and further described in Section II(F). In a specific embodiment, an anti-CD39 chimeric antibody is ch19_IGG4.P, ch31_IGG4.P, and ch39_IGG4.P.

D. Humanized Antibodies

As described herein, the present disclosure provides humanized antibodies of an antibody designated herein as 19, 31 or 39, optionally wherein the humanized antibody inhibits human CD39 enzymatic activity with an $IC_{50}$ value of about 5 nM or less, about 0.05 nM to about 5 nM, about 1 nM or less, about 0.05 nM to about 1 nM, about 0.5 nM or less, or about 0.05 nM to about 0.5 nM, measured as in Example 5. Typically, a non-human antibody is humanized to reduce immunogenicity to humans, while retaining the specificity and affinity of the parental non-human antibody. A humanized antibody comprises one or more variable domains in which CDRs or portions thereof are derived from a non-human antibody, and FRs or portions thereof are derived from human antibody sequences. A humanized antibody optionally may also comprise at least a portion of a human constant region. In some embodiments, some FR residues in a humanized antibody are substituted with corresponding residues from a non-human antibody (e.g., the antibody from which the CDR residues are derived), e.g., to restore or improve antibody specificity or affinity.

Thus, a humanized antibody is an antibody having some or all CDRs entirely or substantially from a donor antibody and variable region framework sequences and constant regions, if present, entirely or substantially from human antibody sequences. For example, a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly, a humanized light chain has at least one, two and usually all three CDRs entirely or substantially from a donor antibody light chain, and a light chain variable region framework sequence and light chain constant region, if present, substantially from human light chain variable region framework and constant region sequences. Here as elsewhere in the application, a CDR in a subject antibody is substantially from a corresponding CDR in a reference antibody when at least about 80%, 81%, 82%, 83%, 84%, 85%, 86%, 87%, 88%, 89%, 90%, 91%, 92%, 93%, 94%, 95%, 96%, 97%, 98%, 99% or 100% of corresponding residues (as defined by Kabat) are identical between the respective CDRs; however, a CDR H2 as defined by Kabat in a subject antibody is substantially from a corresponding CDR in a reference antibody when at least about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of corresponding residues (as defined by Kabat) are identical between the respective CDRs. The variable region framework sequences of an antibody chain or the constant region of an antibody chain are substantially from a human variable region framework sequence or human constant region respectively when at least about 80%, 81%, 82%, 83%, 84%, 85%, 86%, 87%, 88%, 89%, 90%, 91%, 92%, 93%, 94%, 95%, 96%, 97%, 98%, 99% or 100% of corresponding residues defined by Kabat are identical.

Generally speaking, a humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539, Carter, U.S. Pat. No. 6,407,213, Adair, U.S. Pat. No. 5,859,205 6,881, 557, Foote, U.S. Pat. No. 6,881,557). The acceptor antibody sequences can be, for example, a mature human antibody sequence, a composite of such sequences, a consensus sequence of human antibody sequences, or a germline region sequence. Although humanized antibodies may incorporate all six CDRs from a non-human (e.g. mouse, rat, etc.) antibody, they can also be made with less than all CDRs (e.g., at least 3, 4, or 5) CDRs from a non-human antibody (e.g., Pascalis et al., *J. Immunol.* 169:3076, 2002; Vajdos et al., *Journal of Molecular Biology,* 320: 415-428, 2002; Iwahashi et al., *Mol. Immunol.* 36:1079-1091, 1999; Tamura et al, *Journal of Immunology,* 164:1432-1441, 2000).

In some antibodies only part of the CDRs, namely the subset of CDR residues required for binding, termed the SDRs, are needed to retain binding in a humanized antibody. CDR residues not contacting antigen and not in the SDRs can be identified based on previous studies (for example, residues H60-H65 in CDR H2 are often not required), from regions of Kabat CDRs lying outside Chothia hypervariable loops (Chothia, *J Mol. Biol.* 196:901, 1987), by molecular modeling and/or empirically, or as described in Gonzales et al., *Mol. Immunol.* 41: 863, 2004. In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. In some antibodies, potential sites for post-translational modification (e.g., glycosylation) in the CDR can be substituted to eliminate the post-translational modification. Positions for substitution within CDRs and amino acids to substitute can also be selected empirically.

While the acceptor can be identical in sequence to the human framework sequence selected, whether that is from a human immunoglobulin or a human consensus framework, the present disclosure contemplates that the acceptor sequence can include pre-existing amino acid substitutions relative to the human immunoglobulin sequence or human consensus framework sequence. These pre-existing substitutions can be minimal; generally four, three, two or one amino acid differences only relative to the human immunoglobulin sequence or consensus framework sequence. The human acceptor antibody sequences can optionally be selected from among the many known human antibody sequences to provide a high degree of sequence identity (e.g., 65-85% identity) between a human acceptor sequence variable region frameworks and corresponding variable region frameworks of a donor antibody chain.

Certain amino acids from the human variable region framework residues can be selected for substitution based on their possible influence on CDR conformation and/or binding to antigen. Investigation of such possible influences may be conducted by modeling, examination of the characteristics of the amino acids at particular locations, or empirical observation of the effects of substitution or mutagenesis of particular amino acids. For example, when an amino acid differs between a non-human variable region framework residue and a selected human variable region framework residue, the human framework amino acid can be substituted by the equivalent framework amino acid from the non-human antibody when it is reasonably expected that the amino acid: (1) noncovalently binds antigen directly, (2) is adjacent to a CDR region, (3) otherwise interacts with a CDR region (e.g. is within about 6 Å of a CDR region). Other candidates for substitution are acceptor human framework amino acids that are unusual for a human immunoglobulin at that position. These amino acids can be substituted with amino acids from the equivalent position of the non-human donor antibody or from the equivalent positions of more typical human immunoglobulins.

In some embodiments, a humanized anti-CD39 antibody has a mature VH comprising an H1 comprising an amino acid sequence of SEQ ID NO: 10 with zero to two amino acid substitutions or deletions, an H2 comprising an amino acid sequence of SEQ ID NO: 11 with zero to two amino acid substitutions or deletions, a H3 comprising an amino acid sequence of SEQ ID NO: 12 with zero to two amino acid substitutions or deletions, and framework regions having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity to an acceptor human framework region; and has a mature VL comprising an L1 comprising an amino acid sequence of SEQ ID NO: 14 with zero to two amino acid substitutions or deletions, a L2 comprising an amino acid sequence of SEQ ID NO: 15 with zero to two amino acid substitutions or deletions, a L3 comprising an amino acid sequence of SEQ ID NO: 16 with zero to two amino acid substitutions or deletions, and framework regions having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity to an acceptor human framework region. Framework regions may be determined according to Kabat definitions.

In some embodiments, a humanized anti-CD39 antibody has a mature VH comprising an H1 comprising an amino acid sequence of SEQ ID NO: 18 with zero to two amino acid substitutions or deletions, an H2 comprising an amino acid sequence of SEQ ID NO: 19 with zero to two amino acid substitutions or deletions, a H3 comprising an amino acid sequence of SEQ ID NO: 20 with zero to two amino acid substitutions or deletions, and framework regions having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity to an acceptor human framework region; and has a mature VL comprising an L1 comprising an amino acid sequence of SEQ ID NO: 22 with zero to two amino acid substitutions or deletions, a L2 comprising an amino acid sequence of SEQ ID NO: 25 with zero to two amino acid substitutions or deletions, a L3 comprising an amino acid sequence of SEQ ID NO: 26 with zero to two amino acid substitutions or deletions, and framework regions having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity to an acceptor human framework region. For example, the above-referenced humanized anti-CD39 antibody may have an L1 comprising SEQ ID NO: 23 or SEQ ID NO: 24. Framework regions may be determined according to Kabat definitions. In some embodiments, the VH human acceptor is M99642 or KF698734 and/or the VL human acceptor is X12682 or Z00023.

In some embodiments, a humanized anti-CD39 antibody has a mature VH comprising an H1 comprising an amino acid sequence of SEQ ID NO: 28 with zero to two amino acid substitutions or deletions, an H2 comprising an amino acid sequence of SEQ ID NO: 29 with zero to two amino acid substitutions or deletions, a H3 comprising an amino acid sequence of SEQ ID NO: 30 with zero to two amino acid substitutions or deletions, and framework regions having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity to an acceptor human framework region; and has a mature VL comprising an L1 comprising an amino acid sequence of SEQ ID NO: 32 with zero to two amino acid substitutions or deletions, a L2 comprising an amino acid sequence of SEQ ID NO: 33 with zero to two amino acid substitutions or deletions, a L3 comprising an amino acid sequence of SEQ ID NO: 34 with zero to two amino acid substitutions or deletions, and framework regions having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity to an acceptor human framework region. Framework regions may be determined according to Kabat definitions. In some embodiments, the VH human acceptor is M99651 or M77327 and/or the VL human acceptor is X12682 or M23090.

In the aforementioned embodiments, the mature heavy chain variable region may be linked to at least a portion of a heavy chain constant region and the mature light chain variable region may be linked to at least a portion of a light chain constant region. In some embodiments, the mature heavy chain variable region is linked to a heavy chain constant region and the mature light chain variable region is linked to a light chain constant region. Suitable constant regions are described in further detail in Section II(F). In certain embodiments, the heavy chain constant region has an effector function substantially similar to a wild-type human IgG1. In other embodiments, the heavy chain constant region reduced or enhanced effector function, as compared to a wild-type human IgG1. In a specific example, the heavy chain constant region comprises or consists of SEQ ID NO: 1 and the light chain constant region comprises or consists of SEQ ID NO: 6. In a specific example, the heavy chain constant region comprises or consists amino acids 1 to 329 of SEQ ID NO: 1 and the light chain constant region comprises or consists of SEQ ID NO: 6. In another specific example, the heavy chain constant region comprises or consists of SEQ ID NO: 4 and the light chain constant region comprises of consists of SEQ ID NO: 6. In another specific example, the heavy chain constant region comprises or consists of amino acids 1 to 326 of SEQ ID NO: 4 and the light chain constant region comprises of consists of SEQ ID NO: 6. In another specific example, the heavy chain constant region comprises or consists of SEQ ID NO: 2 and the light chain constant region comprises of consists of SEQ ID NO: 6. In another specific example, the heavy chain constant region comprises or consists of amino acids 1 to 329 of SEQ ID NO: 2 and the light chain constant region comprises of consists of SEQ ID NO: 6. In another specific example, the heavy chain constant region comprises or consists of SEQ ID NO: 5 and the light chain constant region comprises of consists of SEQ ID NO: 6. In another specific example, the heavy chain constant region comprises or consists of amino acids 1 to 326 of SEQ ID NO: 5 and the light chain constant region comprises of consists of SEQ ID NO: 6. In another specific example, the heavy chain constant region comprises or consists of SEQ ID NO: 3 and the light chain constant region comprises of consists of SEQ ID NO: 6. In another specific example, the heavy chain constant region comprises or consists of amino acids 1 to 329 of SEQ ID NO: 3 and the light chain constant region comprises of consists of SEQ ID NO: 6.

E. Human Antibodies

As described herein, the present disclosure also provides human antibodies that have the binding specificity of an antibody designated herein as 19, ch19_IGG4.P, 31, ch31_IGG4.P, hu31.1_IGG4.P, hu31.2_IGG4.P, hu31.3_IGG4.P, hu31.4_IGG4.P, hu31.4_IGG1.AA, hu31.5_IGG4.P, hu31.6_IGG4.P, hu31.7_IGG4.P, 39, ch39_IGG4.P, ch39_mIGG2A.AAG, hu39.1_IGG4.P, hu39.2_IGG4.P, hu39.3_IGG4.P, hu39.4_IGG4.P, hu39.5_IGG4.P, hu39.5_IGG1.AA, hu39.6_IGG4.P, hu39.7_IGG4.P, or hu39.8_IGG4.P, optionally wherein the human antibody inhibits human CD39 enzymatic activity with an $IC_{50}$ value of about 5 nM or less, about 0.05 nM to about 5 nM, about 1 nM or less, about 0.05 nM to about 1 nM, about 0.5 nM or less, or about 0.05 nM to about 0.5 nM, measured as in Example 5. Human antibodies can be selected by competitive binding experiments, by the phage display method of Winter, WO 92/20791, or otherwise, to have the same epitope specificity as a particular rodent antibody, such as antibody designated herein as 19, 31, or 39, or to have the same epitope specificity as a particular humanized antibody, such as an antibody designated herein as ch19_IGG4.P, ch31_IGG4.P, hu31.1_IGG4.P, hu31.2_IGG4.P, hu31.3_IGG4.P, hu31.4_IGG4.P, hu31.4_IGG1.AA, hu31.5_IGG4.P, hu31.6_IGG4.P, hu31.7_IGG4.P, ch39_IGG4.P, ch39_mIGG2A.AAG, hu39.1_IGG4.P, hu39.2_IGG4.P, hu39.3_IGG4.P, hu39.4_IGG4.P, hu39.5_IGG4.P, hu39.5 IGG1.AA, hu39.6 IGG4.P, hu39.7_IGG4.P, or hu39.8_IGG4.P. Human antibodies can also be screened for a particular epitope specificity by using only a fragment of CD39 as the target antigen, and/or by screening antibodies against a collection of deletion mutants of CD39.

Methods for producing human antibodies include the trioma method of Oestberg et al., *Hybridoma* 2:361-367 (1983); Oestberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. Nos. 5,877,397, 5,874,299, 5,814,318, 5,789,650, 5,770,429, 5,661,016, 5,633,425, 5,625,126, 5,569,825, 5,545,806, *Nature* 148, 1547-1553 (1994), *Nature Biotechnology* 14, 826 (1996), Kucherlapati, WO 91/10741 (1991) and phage display methods (see, e.g., Dower et al., WO 91/17271 and McCafferty et al., WO 92/01047, U.S. Pat. Nos. 5,877,218, 5,871,907, 5,858,657, 5,837,242, 5,733,743 and 5,565,332).

Human antibodies of the present disclosure may comprise a mature heavy chain variable region linked to at least a portion of a heavy chain constant region and a mature light chain variable region linked to at least a portion of a light chain constant region. In some embodiments, the mature heavy chain variable region is linked to a heavy chain constant region and the mature light chain variable region is linked to a light chain constant region. Suitable constant regions are described in further detail in Section II(F). In certain embodiments, the heavy chain constant region has an effector function substantially similar to a wild-type human IgG1. In other embodiments, the heavy chain constant region reduced or enhanced effector function, as compared to a wild-type human IgG1. In a specific example, the heavy chain constant region comprises or consists of SEQ ID NO: 1 and the light chain constant region comprises or consists of SEQ ID NO: 6. In another specific example, the heavy chain constant region comprises or consists of SEQ ID NO: 4 and the light chain constant region comprises of consists of SEQ ID NO: 6. In another specific example, the heavy chain constant region comprises or consists of SEQ ID NO: 2 and the light chain constant region comprises of consists of SEQ ID NO: 6. In another specific example, the heavy chain constant region comprises or consists of SEQ ID NO: 5 and the light chain constant region comprises of consists of SEQ ID NO: 6. In another specific example, the heavy chain constant region comprises or consists of SEQ ID NO: 3 and the light chain constant region comprises of consists of SEQ ID NO: 6.

F. Selection of Constant Region(s)

The heavy and light chain variable regions of chimeric, humanized (including veneered), or human antibodies can each be linked to at least a portion of a human constant region. In some embodiments, a heavy chain variable domain described in the sections above is linked to a portion of a human heavy chain constant region and a light chain variable domain described in the sections above is linked to a portion of a human light chain constant region. In some embodiments, a heavy chain variable domain described in the sections above is linked to a portion of a human heavy chain constant region and a light chain variable domain described in the sections above is linked to a full-length human light chain constant region. In some embodiments, a heavy chain variable domain described in the sections above is linked to a full-length human heavy chain constant region and a light chain variable domain described in the sections above is linked to a full-length human light chain constant region.

The choice of constant region (or truncation thereof) depends, in part, on whether effector functions are desired, or even need to be enhanced. "Effector functions" refer to biological activities attributable to a light chain or heavy chain constant region of an antibody and vary depending on the antibody isotype. Non-limiting examples of antibody effector functions include: C1q binding on the C1 complex and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation. Human antibodies are classified into five isotypes (IgM, IgD, IgG, IgA, and IgE) according to their heavy chain, with each providing different functions. IgG consists of four human subclasses (IgG1, IgG2, IgG3 and IgG4) each containing a different heavy chain. They are highly homologous and differ mainly in the hinge region and the extent to which they activate the host immune system. For example, human isotopes IgG1 and IgG3 can mediate complement-mediated cytotoxicity and human isotypes IgG2 and IgG4 do not or do so at very low levels. Light chain constant regions can be of subclasses lambda or kappa.

Antibodies of the present disclosure comprising a human constant region, or portion thereof, are typically IgG antibodies, preferably IgG1 or IgG4 antibodies. Human constant regions show allotypic variation and isoallotypic variation between different individuals, that is, the constant regions can differ in different individuals at one or more polymorphic positions. Isoallotypes differ from allotypes in that sera recognizing an isoallotype bind to a non-polymorphic region of a one or more other isotypes. Reference to a human constant region includes a constant region with any natural allotype or any permutation of residues occupying polymorphic positions in natural allotypes.

One or several amino acids at the amino or carboxy terminus of the light and/or heavy chain, such as the C-terminal lysine of the heavy chain, may be missing or derivatized in a proportion or all of the molecules. An N-terminal glutamine of the heavy or light chain can be substituted with a glutamate residue to prevent the formation of pyroglutamate.

In some embodiments, an antibody of the present disclosure is an IgG4 antibody. For human IgG4, inclusion of a S228P (Eu numbering) engineered mutation on the heavy chain to prevent Fab-arm exchange can be used. Suitable sequences for human IgG4 include but are not limited to SEQ ID NO: 4 and SEQ ID NO: 5. In some embodiments, the C-terminal lysine of an IgG4 antibody is absent.

In some embodiments, an antibody of the present disclosure is an IgG1 or an IgG3 antibody. Suitable sequences for human IgG1 or IgG3 are known in the art and include but are not limited to SEQ ID NO: 1, SEQ ID NO: 2, SEQ ID NO: 3, and human IgG3 disclosed in U.S. Pat. No. 5,624,821. In some embodiments, the C-terminal lysine of an IgG1 antibody or an IgG3 antibody is absent.

In certain embodiments, substitutions can be made in a constant region to prolong half-life in humans (see, e.g., Hinton et al., *J. Biol. Chem.* 279:6213, 2004). Exemplary substitutions include a Gln at position 250 and/or a Leu at position 428 (Eu numbering) for increasing the half-life of an antibody.

Alternatively or in addition, substitutions can be made in a constant region to reduce or increase effector function such as complement-mediated cytotoxicity (CDC) or antibody-dependent cell-mediated cytotoxicity (ADCC) (see, e.g., Winter et al., U.S. Pat. No. 5,624,821; Tso et al., U.S. Pat. No. 5,834,597; and Lazar et al., *Proc. Natl. Acad. Sci. USA*, 103:4005, 2006).

Some antibodies of the disclosure are engineered by introduction of constant region mutation(s) to have reduced Fc effector function, such as CDC, ADCC, and antibody-dependent cellular phagocytosis (ADCP), compared with the same antibody without the mutation(s). In some embodiments, each or all of these effector functions are reduced at least 50%, 75%, 90% or 95% compared with antibodies without the mutation. Effector function can be assayed as described in the examples. Other assays are described by Shields et al, 2001 *J. Biol. Chem.*, Vol. 276, p 6591-6604; Chappel et al, 1993 *J. Biol. Chem.*, Vol 268, p 25124-25131; Lazar et al, 2006 *PNAS,* 103; 4005-4010.

Substitution of any or all of positions 234, 235, 236 and/or 237 reduces affinity for Fc7 receptors, particularly FcγRI receptor (see, e.g., U.S. Pat. No. 6,624,821). In some embodiments, an alanine residue is used for substitution, such as an L234A/L235A dual mutation to reduce effector function. Other combinations of mutations with reduced effector functions include L234A/L235A/G237A, E233P/L234V/L235A/AG236, A327G/A330S/P331S, K322A, L234A/L235A, L234F/L235E/P331S and L234A/L235E/G237A/A330S/P331S (Eu numbering). Optionally, positions 234, 236 and/or 237 in human IgG2 are substituted with alanine and position 235 with glutamine. (see, e.g., U.S. Pat. No. 5,624,821.) Two amino acid substitutions in the complement C1q binding site at Eu index positions 330 and 331 reduce complement fixation (see Tao et al., *J. Exp. Med.* 178:661 (1993) and Canfield and Morrison, *J. Exp. Med.* 173:1483 (1991)). Substitution into human IgG1 of IgG2 residues at positions 233-236 and IgG4 residues at positions 327, 330 and 331 reduces ADCC and CDC (see, for example, Armour K L. Et al., 1999 *Eur J Immunol.* 29(8): 2613-24; and Shields R L. Et al., 2001. *J Biol Chem.* 276(9):6591-604). N297A, N297Q, or N297G (Eu numbering) mutations reduce glycosylation and thereby effector functions.

Some antibodies of the disclosure are engineered by introduction of constant region mutation(s) to have enhanced Fc effector function. For example, FcγR binding can be enhanced by amino acid engineering. In some embodiments, this can be done by substitution of one or more amino acids in the Fc region. Desirable mutations can be determined by, for example, either alanine scanning or rational design and library screening. IgG variants with enhanced binding to FcγRs and enhanced effector function can be identified using these technologies. Alternatively, several mutations to the Fc receptor region are known in the art, for example, as described in Smith P. et al (2012) PNAS 6181-6186.

In some embodiments, the antibodies described herein include a modified IgG1 constant domain that increases the ability of the antibody to mediate ADCC compared to wild-type IgG1 without the modification. The modified IgG1 domain can be characterized by amino acid substitutions at one or more of L235V, S239D, F243L, R292P, A330L, I332E, P396L (Eu numbering). In other embodiments, the modified IgG1 domain is characterized by substitutions at S239D, A330L, and I332E (Eu numbering).

Alternatively, glycoform perturbation can be used to enhance Fc-mediated therapeutic antibody function. The N-linked Fc glycosylations on IgG1 antibodies are important for effector function. Sialylation, galactosylation, bisecting sugars, and fucosylation can all affect binding and activity of IgG molecules. Controlling the glycosylation patterns on therapeutic antibodies can be done a number of different ways. The type of cell producing the recombinant antibody and its culture conditions can affect glycosylation and activity of therapeutic antibodies.

Furthermore, bioreactor conditions and downstream processing can also affect the glycan microheterogeneity. Low or afucosylated antibodies have been shown to enhance Fc-mediating properties. Numerous ways to achieve this reduction of fucose levels by glycoengineering are well known in the art. One way is to manipulate the enzymes involved in the post-translational modification of antibodies. This can involve overexpression of glucosidases, such as β-1-4-N-acetylglucosaminyltransferase III, knocking out fucosyltransferases, or using cell lines that are naturally fucose-deficient or have been mutated to express low fucosylation levels. In addition, inhibitors of N-linked glucosidases, such as castanospermine, can also be used to obtain low fucose bearing IgG molecules.

In some embodiments amino acid engineered variants can have more broadly enhanced affinity for multiple FcγR, whereas glycoform engineered antibody can generally have more specific affinity for enhanced FcγRIIIa binding. Glycoforms interact with proximal amino acids on the Fc portion and replacement of the amino acid that come in contact with Ig oligosaccharides can result in different glycoform structures.

G. Expression of Recombinant Antibodies

Chimeric, humanized (including veneered) and human antibodies are typically produced by recombinant expression. Accordingly, the present disclosure also provides polynucleotides that encode the anti-CD39 antibodies of Section IIA-F, vectors comprising the polynucleotides, and host cells comprising the vectors.

Polynucleotides encoding the anti-CD39 antibodies of the present disclosure can be inserted into a vector for amplification, expression, or further optimization. Many vectors are available. In some embodiments, the vector system includes mammalian, bacterial, yeast systems, etc., and comprises plasmids such as, but not limited to, pALTER, pBAD, pcDNA, pCal, pL, pET, pGEMEX, pGEX, pCI, pCMV, pEGFP, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS420, pLexA, pACT2.2 etc, and other laboratory and commercially available vectors. Suitable vectors may include, plasmid, or viral vectors (e.g., replication defective retroviruses, adenoviruses and adeno-associated viruses). The vector components generally include, but are not limited to, one or more of the following: a signal sequence, an origin of replication, one or more marker genes, an enhancer element, a promoter (e.g. SV40, CMV, EF-1α), and a transcription termination sequence. For expression, recombinant polynucleotide constructs typically include an expression control sequence operably linked to the coding sequences of antibody chains, including naturally-associated or heterologous promoter regions. In some embodiments, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the recombinant antibodies.

Vectors comprising the polynucleotide sequence encoding an anti-CD39 antibody of the present disclosure can be introduced to a host cell for cloning or gene expression. Suitable host cells for cloning or expressing the polynucleotide sequences in the vectors herein include prokaryote and eukaryote cells. Non-limiting examples of suitable prokaryotes include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. In addition to prokaryotes, eukaryotic microbes such as filamentous fungi or yeast are suitable cloning or expression hosts for anti-CD39 antibody-encoding vectors. Non-limiting examples include *Saccharomyces cerevisiae, Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma* reesia (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*. Suitable host cells can also be derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruit fly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts. In some embodiments, mammalian cells are used as host cells for expressing nucleotide segments encoding immunoglobulins or fragments thereof. See Winnacker, From Genes to Clones, (VCH Publishers, N Y, 1987). A number of suitable host cell lines capable of secreting intact heterologous proteins have been developed in the art, and include CHO cell lines, various COS cell lines, HeLa cells, HEK293 cells, L cells, and non-antibody-producing myelomas including Sp2/0 and NS0. In some embodiments, the cells are nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. In some embodiments, expression control sequences are promoters derived from endogenous genes, cytomegalovirus, SV40, adenovirus, bovine papillomavirus, and the like. See Co et al., *J. Immunol.* 148:1149 (1992).

Host cells are transformed with the above-described expression or cloning vectors for anti-CD39 antibody production and cultured in conventional nutrient media modified as appropriate for inducing promoters, selecting transformants, or amplifying the genes encoding the desired sequences. Once expressed, antibodies can be purified according to standard procedures of the art, including HPLC purification, column chromatography, gel electrophoresis and the like (see generally, Scopes, Protein Purification (Springer-Verlag, NY, 1982)).

H. Labeled Antibodies

The disclosed anti-CD39 antibodies can optionally be labeled with one or more detectable signal, including but not limited to fluorescent molecules, spin-labeled molecules, enzymes, or radioisotopes. Such antibodies may be used for the detection or isolation of human CD39 in any number of in vitro, in vivo, or ex vivo assays.

For example, when any one of the disclosed anti-CD39 antibodies are labeled with a detectable signal such as a fluorescent molecule, spin-labeled molecule, enzyme, or radioisotope, such a detectable antibody may be used in pharmacodynamic assays, immunohistochemistry, receptor occupancy assays, ELISA (enzyme-linked immunosorbent assay), EIA (enzyme immunoassay), RIA (radioimmunoassay), and the like.

III. Methods of Use

The present disclosure provides methods for using the anti-CD39 antibodies described herein in the preparation of a medicament for inhibition of CD39 enzymatic activity. As used herein, the terms "inhibit", "inhibition" and the like refer to the ability of an antagonist to decrease the function or activity of a particular target, e.g., CD39. The decrease is preferably at least a 50% and may be, for example, at least about 55%, at least about 60%, at least about 65%, at least about 70%, at least about 75%, at least about 80%, at least about 85%, at least about 90%, or at least about 95%. The present disclosure also encompasses the use of anti-CD39 antibodies described herein in the preparation of a medicament for the treatment or prevention of diseases, disorders, and/or conditions that would benefit from inhibition of CD39 enzymatic activity. As one example, the present disclosure encompasses the use of anti-CD39 antibodies described herein in the preparation of a medicament for the treatment of a disease characterized by (i) high extracellular ATP (as compared to non-diseased tissue), (ii) expression or increased expression of ENTPD1, P2RX7, P2RY11, or a combination thereof in diseased tissue, (iii) expression or increased expression of CD39, P2X7, P2Y11, or a combination thereof in diseased tissue, (iv) myeloid infiltration into diseased tissue, or any combination of (i) to (iv). In another example, the present disclosure encompasses the use of anti-CD39 antibodies described herein in the preparation of a medicament for the treatment of cancer. Optionally, the cancer may be characterized by (i) high extracellular ATP (as compared to a non-diseased sample), (ii) expression or increased expression of ENTPD1, P2RX7, P2RY11, or a combination thereof in diseased tissue, (iii) expression or increased expression of CD39, P2X7, P2Y11, or a combination thereof in diseased tissue, (iv) myeloid infiltration into diseased tissue, or any combination of (i) to (iv). In some embodiments of the aforementioned methods, the anti-CD39 antibodies described herein are used in combination with at least one additional therapy, examples of which are set forth elsewhere herein.

Extracellular ATP is present in negligible concentrations under healthy conditions (e.g., about 10-100 nM) but rapidly increases in response to tissue injury, stress, hypoxia, and agents used in the treatment of cancer and may be found at high concentrations in tumors. ATP released by dying or stressed cells, including but not limited to cancer cells and other cells in the tumor microenvironment, provides inflammatory signals important for effective innate and adaptive immune responses. Conversely, hydrolysis of extracellular ATP into adenosine, for example in the tumor microenvironment, limits immune responses. CD39 is the rate-limiting ecto-enzyme in the hydrolysis of extracellular ATP. By catabolizing the conversion of extracellular ATP into AMP, CD39 also increases extracellular adenosine production via CD73 (ecto-5'-nucleotidase), the rate-limiting ecto-enzyme in extracellular AMP hydrolysis. Adenosine signals through type 1 purinergic receptors and has opposing effects to those mediated by ATP receptors. In particular, the $A_{2a}$ and $A_{2b}$ receptors, expressed on the surface of immune cells, help mediate the immunosuppressive effects of adenosine. For example, in the tumor microenvironment, adenosine elicits immunosuppressive effects through direct interaction with $A_{2a}$ and $A_{2b}$ receptors on tumor-infiltrating immune cells. The opposing roles of adenosine and ATP are reviewed in Chiarella et al., "Extracellular ATP and Adenosine in Cancer Pathogenesis and Treatment," *Trends in Cancer*, 2021, 7(8): 731-750. As demonstrated herein, the use of anti-CD39 antibodies of the present disclosure potently inhibits CD39 enzymatic activity, resulting in immunostimulation from ATP build-up and prevention of the formation of immunosuppressive adenosine. Diseases, disorders, and/or conditions that would benefit from inhibition of CD39 enzymatic activity may include those where release of extracellular ATP may be high, for example due to tissue injury, stress, hypoxia treatment with an additional therapy, or any combination thereof. Additional diseases, disorders and/or conditions that would benefit from inhibition of CD39 enzymatic activity may include those where extracellular adenosine levels in a diseased tissue sample are high, for example due to increased hydrolysis of ATP as compared to a healthy control and/or due to increased hydrolysis of AMP to adenosine as compared to a healthy control, for example as measured by increased CD39 enzymatic activity in a peripheral blood sample or a tissue (e.g., tumor) sample, and/or where CD39 and/or CD73 expression is detectable, and optionally high as compared to a healthy control, for example as measured by immunohistochemistry, immunophenotyping, RNA sequencing, or other clinically validated method in a peripheral blood sample or a tissue (e.g., tumor) sample.

Accordingly, in some embodiments, anti-CD39 antibodies described herein are administered to a subject in need thereof in an amount effective to inhibit CD39 enzymatic activity. CD39 enzymatic activity may be assessed using a peripheral blood sample or a tissue (e.g., tumor) sample obtained from the subject, or both. As a non-limiting example, commercial assays such as Kinase-Glo® or AMP-Glo® may be used to measure CD39 activity in cellular and non-cellular compartments of peripheral blood samples or tumor samples. Alternatively, or in addition, CD39 enzymatic activity in tumor tissue may be measured by enzyme histochemistry. Inhibition may be determined, for example, by comparison to a previous sample obtained from the subject (i.e., prior to administration of the anti-CD39 antibody) or by comparison to a reference sample or reference value for a control group (e.g., subjects administered an isotype control antibody, an anti-CD39 antibody that binds to but does not inhibit CD39 enzymatic activity, standard of care, a placebo, etc.). In some embodiments, anti-CD39 antibodies described herein are administered to a subject in need thereof in an amount effective to inhibit CD39 enzymatic activity in the tumor microenvironment. In some embodiments, anti-CD39 antibodies described herein are administered to a subject in need thereof in an amount effective to inhibit CD39 enzymatic activity peripheral to a tumor. In some embodiments, anti-CD39 antibodies described herein are administered to a subject in need thereof in an amount effective to inhibit CD39 enzymatic activity in or on immune cells. In some embodiments, anti-CD39 antibodies described herein are administered to a subject in need thereof in an amount effective to inhibit CD39 enzymatic activity in or on cells of myeloid lineage. Myeloid lineage cells expressing CD39 include those detailed in the Examples. In some embodiments, anti-CD39 antibodies described herein are administered to a subject in need thereof in an amount effective to inhibit CD39 enzymatic activity in or on stroma and/or vasculature.

Alternatively or in addition, in some embodiments, anti-CD39 antibodies described herein are administered to a subject in need thereof in an amount effective to increase ATP-mediated immunostimulation, as compared to a suitable control (e.g., a subject administered an isotype control antibody, a subject administered an anti-CD39 antibody that binds to but does not inhibit CD39 enzymatic activity, a subject receiving standard of care, a subject receiving no treatment). ATP-mediated immunostimulation may be assessed using a peripheral blood sample and/or a tissue (e.g., tumor) sample obtained from the subject. ATP-mediated immunostimulation may be identified, for example, by (i) measuring an increase in ATP-dependent signaling through one or more type 2 purinergic (P2) receptor, such as a P2Y G-protein coupled receptor or a P2X cation-selective channel receptors, (ii) measuring an increase in NLRP3 inflammasome activation; (iii) measuring an increase in cell surface markers of dendritic cells; (iv) measuring an increase in CD4+ and/or CD8+ T cell activity and/or proliferation, and/or (v) measuring an increase in activation, maturation, cytokine secretion, or any combination thereof in one or more cell type of myeloid lineage. In one example, anti-CD39 antibodies described herein are administered to a subject in need thereof in an amount effective to increase ATP-dependent signaling through one or more P2X receptor or P2Y receptor selected from P2X4, P2X5, P2X7, P2Y2 or P2Y11, as compared to a suitable control (e.g., a subject administered an isotype control antibody, a subject administered an anti-CD39 antibody that binds to but does not inhibit CD39 enzymatic activity, a subject receiving standard of care, a subject receiving no treatment). In one example, anti-CD39 antibodies described herein are administered to a subject in need thereof in an amount effective to increase ATP-dependent signaling through P2X7, as compared to a suitable control (e.g., a subject administered an isotype control antibody, a subject administered an anti-CD39 antibody that binds to but does not inhibit CD39 enzymatic activity, a subject receiving standard of care, a subject receiving no treatment). In one example, anti-CD39 antibodies described herein are administered to a subject in need thereof in an amount effective to increase ATP-dependent signaling through P2Y11, as compared to a suitable control (e.g., a subject administered an isotype control antibody, a subject administered an anti-CD39 antibody that binds to but does not inhibit CD39 enzymatic activity, a subject receiving standard of care, a subject receiving no treatment). In one example, anti-CD39 antibodies described herein are administered to a subject in need thereof in an amount effective to increase ATP-dependent signaling through P2X7 and/or P2Y11, as compared to a suitable control (e.g., a subject administered an isotype control antibody, a subject administered an anti-CD39 antibody that binds to but does not inhibit CD39 enzymatic activity, a subject receiving standard of care, a subject receiving no treatment). In one example, anti-CD39 antibodies described herein are administered to a subject in need thereof in an amount effective to increase NLRP3 inflammasome activation. Measures of NLRP3 inflammasome activation are known in the art and include those detailed in the Examples (e.g., IL-1β and IL-18 secretion). In one embodiment, anti-CD39 antibodies described herein are administered to a subject in need thereof in an amount effective to increase myeloid cell activation, maturation, cytokine secretion, or any combination thereof. Measures of myeloid cell activation, maturation, cytokine secretion are known in the art and include those detailed in the Examples.

Alternatively, or in addition to the above, in some embodiments, anti-CD39 antibodies described herein are administered to a subject in need thereof in an amount effective to decrease or prevent adenosine-mediated immunosuppression, as compared to a suitable control (e.g., a subject administered an isotype control antibody, a subject administered an anti-CD39 antibody that binds to but does not inhibit CD39 enzymatic activity, a subject receiving standard of care, a subject receiving no treatment). Adenosine-mediated immunosuppression may be identified, for example, by measuring an increase adenosine signaling through $A_{2a}R$ and/or $A_{2b}R$. Adenosine-mediated immunosuppression also includes adenosine-mediated inhibition of lymphoid (e.g., T cells, B cells) and/or myeloid (e.g., monocytes, macrophages, dendritic cells, NK cells) cell activity. For instance, one measure of adenosine-mediated immunosuppression may be NECA-induced pCREB activation in CD8+ T cells in human blood.

Alternatively, or in addition to the above, in some embodiments, anti-CD39 antibodies described herein are administered to a subject in need thereof in an amount effective to achieve at least 60%, at least 65%, at least 70%, at least 75%, at least 80%, at least 85%, at least 90%, at least 95%, or 100% target (i.e., CD39) engagement, as measured by a receptor occupancy assay. In some embodiments, anti-CD39 antibodies described herein are administered to a subject in need thereof in an amount effective to achieve at least at least 85%, at least 86%, at least 87%, at least 88%, at least 89%, at least 90%, at least 91%, at least 92%, at least 93%, at least 94%, at least 95%, at least 96%, at least 97% at least, 98%, or at least 99 target (i.e., CD39) engagement, as measured by a receptor occupancy assay. Exemplary receptor occupancy assays are detailed in the Examples.

Alternatively, or in addition to the above, in some embodiments, anti-CD39 antibodies described herein are administered to a subject in need thereof in an amount effective to decrease CD39 expression. In some embodiments, anti-CD39 antibodies described herein are administered to a subject in need thereof in an amount effective to decrease cell surface CD39 expression. CD39 expression (intracellular and/or extracellular) can be evaluated, for example, by immunohistochemistry or immunophenotyping, including by those methods further detailed in the Examples.

Alternatively, or in addition to the above, in some embodiments, anti-CD39 antibodies described herein are administered to a subject in need thereof in an amount effective to treat or prevent cancer. Without wishing to be bound by theory, applicants believe increasing ATP-mediated immunostimulation and/or decreasing (or preventing) adenosine-mediated immunosuppression can result in tumor death and may result in improved outcomes.

A. Oncology and Oncology-Related Disorders

In one or more embodiments, the antibodies described herein are useful in the treatment and/or prophylaxis of cancer (e.g., carcinomas, sarcomas, leukemias, lymphomas, myelomas, etc.). In certain embodiments, the cancer may be locally advanced and/or unresectable, metastatic, or at risk of becoming metastatic. Alternatively, or in addition, the cancer may be recurrent or no longer responding to a treatment, such as a standard of care or a checkpoint inhibitor. Exemplary types of cancer contemplated by this disclosure include cancer of the genitourinary tract (e.g., bladder, kidney, renal cell, penile, prostate, testicular, Von Hippel-Lindau disease, etc.), uterus, cervix, ovary, breast, gastrointestinal tract (e.g., esophagus, oropharynx, stomach, small or large intestines, colon, or rectum), bone, bone marrow, skin (e.g., melanoma), head and neck, liver, gall bladder, bile ducts, heart, lung, pancreas, salivary gland, adrenal gland, thyroid, brain (e.g., gliomas), ganglia, central nervous system (CNS), peripheral nervous system (PNS), the hematopoietic system (i.e., hematological malignancies), and the immune system (e.g., spleen or thymus).

In some embodiments, the antibodies according to this disclosure are useful in the treatment and/or prophylaxis of hematological malignancies. Exemplary types of cancer affecting the hematopoietic system include leukemias, lymphomas and myelomas, including acute myeloid leukemia, adult T cell leukemia, T cell large granular lymphocyte leukemia, acute lymphoblastic leukemia, chronic lymphocytic leukemia, chronic myelogenous leukemia, acute monocytic leukemia, Hodgkin's and Non-Hodgkin's lymphoma, Diffuse large B Cell lymphoma, and multiple myeloma.

In another embodiment, the antibodies according to this disclosure are useful in the treatment and/or prophylaxis of solid tumors. The solid tumor may be, for example, ovarian cancer, endometrial cancer, breast cancer, lung cancer (small cell or non-small cell), colon cancer, prostate cancer, cervical cancer, biliary cancer, pancreatic cancer, gastric cancer, esophageal cancer, liver cancer (hepatocellular carcinoma), kidney cancer (renal cell carcinoma), head-and-neck tumors, mesothelioma, melanoma, sarcomas, central nervous system (CNS) hemangioblastomas, and brain tumors (e.g., gliomas, such as astrocytoma, oligodendroglioma and glioblastomas).

In another embodiment, the antibodies according to this disclosure are useful in the treatment and/or prophylaxis of lung cancer, genitourinary cancer, gastrointestinal cancer, or a combination thereof. In another embodiment, the antibodies according to this disclosure are useful in the treatment and/or prophylaxis of lung cancer, genitourinary cancer, gastrointestinal cancer, skin cancer, or a combination thereof.

In some embodiments, the antibodies according to this disclosure are useful in the treatment and/or prophylaxis of skin cancer. In further embodiments, the skin cancer is melanoma.

In some embodiments, the antibodies according to this disclosure are useful in the treatment and/or prophylaxis of breast cancer. In further embodiments, the breast cancer is hormone receptor positive (e.g., ERα-positive breast cancer, PR-positive breast cancer, ERα-positive and PR-positive breast cancer), HER2 positive breast cancer, HER2 overexpressing breast cancer, or any combination thereof. In still further embodiments, the breast cancer is triple negative breast cancer.

In some embodiments, the antibodies according to this disclosure are useful in the treatment and/or prophylaxis of kidney cancer. In further embodiments, the kidney cancer is renal cell carcinoma. In still further embodiments, the renal cell carcinoma is clear cell renal carcinoma.

In some embodiments, the antibodies according to this disclosure are useful in the treatment and/or prophylaxis of lung cancer. In further embodiments, the lung cancer is non-small cell lung cancer (NSCLC). In still further embodiments, the NSCLC is lung squamous cell carcinoma or lung adenocarcinoma.

In some embodiments, the disclosed methods of treating non-small cell lung cancer may further comprise administering any of the disclosed anti-CD39 antibody in combination with pemetrexed, carboplatin, and either an antagonist anti-PD-1 antibody or an antagonist anti-PD-L1 antibody. Such method may further comprise comprising administering one or more additional agent selected from the group consisting of an antagonistic anti-TIGIT antibody, an A2aR antagonist, an A2bR antagonist, an A2a/2bR antagonist, and a CD73 inhibitor, optionally where the additional agents are selected from the group consisting of domvanalimab, AB308, etrumadenant, and quemliclustat.

In some embodiments, the antibodies according to this disclosure are useful in the treatment and/or prophylaxis of pancreatic cancer. In further embodiments, the pancreatic cancer is pancreatic neuroendocrine tumor or pancreatic adenocarcinoma.

In some embodiments, the antibodies according to this disclosure are useful in the treatment and/or prophylaxis of a neuroendocrine tumor. In further embodiments, the neuroendocrine tumor is pancreatic neuroendocrine tumor, pheochromocytoma, paraganglioma, or a tumor of the adrenal gland.

In some embodiments, the antibodies according to this disclosure are useful in the treatment and/or prophylaxis of brain cancer. In further embodiments, the brain cancer is a glioma. In still further embodiments, the glioma is an astrocytoma, an oligodendroglioma, or a glioblastoma.

In some embodiments, the antibodies according to this disclosure are useful in the treatment and/or prophylaxis of an upper GI cancer, such as esophageal or gastric cancer. In further embodiments, the upper GI cancer is an adenocarcinoma, a squamous cell carcinoma, or any combination thereof. In still further embodiments, the upper GI cancer is esophageal adenocarcinoma (EAC), esophageal squamous cell carcinoma (ESCC), gastroesophageal junction adenocarcinoma (GEJ), gastric adenocarcinoma (also referred to herein as "gastric cancer") or any combination thereof.

In some embodiments, the disclosed methods of treating gastric cancer or gastroesophageal cancer may further comprise administering any of the disclosed anti-CD39 antibody in combination with FOLFOX and either an antagonist anti-PD-1 antibody or an antagonist anti-PD-L1 antibody. Such method may further comprise comprising administering one or more additional agent selected from the group consisting of an antagonistic anti-TIGIT antibody, an A2aR antagonist, an A2bR antagonist, an A2a/2bR antagonist, and a CD73 inhibitor, optionally where the additional agents are selected from the group consisting of domvanalimab, AB308, etrumadenant, and quemliclustat.

In some embodiments, the antibodies according to this disclosure are useful in the treatment and/or prophylaxis of lymphoma. In further embodiments, the hematological malignancy is acute myeloid lymphoma.

In some embodiments, the antibodies according to this disclosure are useful in the treatment of breast cancer, gastrointestinal cancer, genitourinary tract cancer, lung cancer, lymphoma, or ovarian cancer. In further embodiments, the antibodies according to this disclosure are useful in the treatment of acute myeloid lymphoma, colorectal cancer, gastric cancer, esophageal cancer, castration-resistant prostate cancer, non-small cell lung cancer, ovarian cancer, pancreatic cancer, or triple negative breast cancer.

In some embodiments, the antibodies according to this disclosure are useful in the treatment of lung cancer, head and neck cancer, thyroid cancer, pancreatic cancer, kidney cancer, or skin cancer. In still further embodiments, the antibodies according to this disclosure are useful in the treatment of non-small cell lung cancer, head and neck squamous cell carcinoma, pancreatic ductal adenocarcinoma, clear cell renal carcinoma, melanoma.

In some embodiments, the antibodies according to this disclosure are useful in the treatment of lower GI cancer, upper GI cancer, head and neck cancer, kidney cancer, lung cancer, or pancreatic cancer. In further embodiments, the antibodies according to this disclosure are useful in the treatment of esophageal carcinoma, head and neck squamous cell carcinoma, kidney renal clear cell carcinoma, lung adenocarcinoma, lung squamous cell carcinoma, pancreatic adenocarcinoma, gastric (stomach) adenocarcinoma.

In the aforementioned embodiments, the methods of the present disclosure may be practiced in an adjuvant setting or neoadjuvant setting. The methods described herein may be indicated as a first line, second line, third line, or greater line of treatment. In some embodiments, the methods of the present disclosure may be practiced in a second or greater line of treatment, wherein an earlier line of treatment included a checkpoint inhibitor (i.e., the subject is checkpoint inhibitor (CPI) experienced). In further embodiments, the checkpoint inhibitor is a CTLA-4 antagonist, a PD-1 antagonist, a PD-L1 antagonist, a TIM-3 antagonist, or a TIGIT antagonist.

The present disclosure also provides methods of treating or preventing other cancer-related diseases, disorders or conditions. The use of the term(s) cancer-related diseases, disorders and conditions is meant to refer broadly to conditions that are associated, directly or indirectly, with cancer and non-cancerous proliferative disease, and includes, e.g., angiogenesis, precancerous conditions such as dysplasia, and non-cancerous proliferative diseases disorders or conditions, such as benign proliferative breast disease and papillomas. For clarity, the term(s) cancer-related disease, disorder and condition do not include cancer per se.

In general, the disclosed methods for treating or preventing cancer, or a cancer-related disease, disorder or condition, in a subject in need thereof comprise administering to the subject an anti-CD39 antibody of Section II. Administration of an anti-CD39 antibody of Section II may comprise one or more (e.g., one, two, or three or more) dosing cycles. In some embodiments, the present disclosure provides methods for treating or preventing cancer, or a cancer-related disease, disorder or condition with an anti-CD39 antibody of Section II and at least one additional therapy, examples of which are set forth elsewhere herein.

Selection of patients. In some instances, the methods according to this disclosure may be provided in selected patients, for example patients identified as having, for example, detectable PD-L1, CD73, and/or CD39 expression, having high microsatellite instability, having high tumor mutational burden, or any combination thereof. In some instances, the patient is identified as having an oncogene driven cancer that has a mutation in at least one gene associated with the cancer. In some instances, patients are selected by determining a patient's P2X7 variant. Commonly expressed P2X7 splice variants, distinct SNPs and post-translational receptor modifications can affect the function of P2X7. For example, certain modifications have been shown to result in partial or complete loss of P2X7 function and other modifications have been shown to increase P2X7 function. See, for instance, Lara et al., Front Pharmacol, 2020, 11:793.

In some embodiments, patients are selected by measuring PD-L1 (CD274), P2X7 (P2RX7), P2Y11 (P2RY11), IL-2, CXCL1 (CXCL1), MIP-2a (CXCL2), CXCL3 (CXCL3), IL-8 (CXCL8), COX2 (PTGS2), CD73 (NT5E) and/or CD39 (ENTPD1) expression in a relevant sample, such as a peripheral blood sample or a tumor sample. Expression may be measured by quantifying nucleic acid or protein, using methods known in the art including but not limited to immunohistochemistry, immunophenotyping, RNA sequencing, gene expression analysis, single-molecule imaging or other clinically validated assay. In some embodiments, patients are selected by measuring PD-L1, CD73, and/or CD39 expression (at the nucleic or protein level) in a relevant sample, such as a peripheral blood sample or a tumor sample, using immunohistochemistry, immunophenotyping, RNA sequencing, gene expression analysis, single-molecule imaging or other clinically validated assay. Alternatively or in addition, patients can be selected by measuring CD39 enzymatic activity, for example in a peripheral blood sample or a tumor sample. In one embodiment, the disclosure provides a method of treating cancer in a patient having (i) detectable PD-L1, P2X7, P2Y11, IL-2, CXCL1, CXCL2, CXCL3, CXCL8, COX2, CD73, and/or CD39 expression, for example by immunohistochemistry, immunophenotyping, or other clinically validated test, (ii) elevated PD-L1, P2X7, P2Y11, IL-2, CXCL1, CXCL2, CXCL3, CXCL8, COX2, CD73, and/or CD39 expression, for example by immunohistochemistry, immunophenotyping, or other clinically validated test, (iii) detectable CD39 enzymatic activity, or (iv) any combination of (i) to (iii), by administering an anti-CD39 antibody described herein. In another embodiment, the disclosure provides a method of treating cancer in a patient having (i) detectable PD-L1, P2X7, P2Y11, IL-2, CXCL1, CXCL2, CXCL3, CXCL8, COX2, CD73, and/or CD39 expression, for example by immunohistochemistry, immunophenotyping, or other clinically validated test, (ii) elevated PD-L1, CD73, and/or CD39 expression, for example by immunohistochemistry, immunophenotyping, or other clinically validated test, (iii) detectable CD39 enzymatic activity, or (iv) any combination of (i) to (iii), by administering a therapeutically effective amount of anti-CD39 antibody described herein. In another embodiment, the disclosure provides a method of administering a therapeutically effective amount of an anti-CD39 antibody described herein to an individual for the treatment of cancer the method comprising measuring based on a determination of PD-L1, P2X7, P2Y11, IL-2, CXCL1, CXCL2, CXCL3, CXCL8, COX2, CD73, and/or CD39 expression. In still another embodiment, the disclosure provides a method of administering a therapeutically effective amount of an anti-CD39 antibody described herein to an individual for the treatment of cancer, the method comprising measuring PD-L1, P2X7, P2Y11, IL-2, CXCL1, CXCL2, CXCL3, CXCL8, COX2, CD73, and/or CD39 expression in a sample obtained from an individual, for example by immunohistochemistry, immunophenotyping, or other clinically validated test, and administering a therapeutically effective amount of the antibody to the individual whose sample contained detectable PD-L1 (CD274), P2X7 (P2RX7), P2Y11 (P2RY11), IL-2, CXCL1 (CXCL1), MIP-2a (CXCL2), CXCL3 (CXCL3), IL-8 (CXCL8), COX2 (PTGS2), CD73 (NT5E) and/or CD39 (ENTPD1) expression.

B. Route of Administration

In some embodiments, pharmaceutical compositions containing an antibody according to this disclosure may be in a form suitable for oral administration. Oral administration may involve swallowing the formulation thereby allowing the antibody to be absorbed into the bloodstream in the gastrointestinal tract. Alternatively, oral administration may involve buccal, lingual or sublingual administration, thereby allowing the antibody to be absorbed into the blood stream through oral mucosa.

In another embodiment, the pharmaceutical compositions containing an antibody according to this disclosure may be in a form suitable for parenteral administration. Forms of parenteral administration include, but are not limited to, intravenous, intraarterial, intramuscular, intradermal, intraperitoneal, intrathecal, intracisternal, intracerebral, intracerebroventricular, intraventricular, and subcutaneous. Pharmaceutical compositions suitable for parenteral administration may be formulated using suitable aqueous or non-aqueous carriers. Depot injections, which are generally administered subcutaneously or intramuscularly, may also be utilized to release the antibodies disclosed herein over a defined period of time.

Other routes of administration are also contemplated by this disclosure, including, but not limited to, nasal, vaginal, intraocular, rectal, topical (e.g., transdermal), and inhalation.

Particular embodiments of the present disclosure contemplate oral administration or parenteral administration.

C. Pharmaceutical Compositions

The anti-CD39 antibodies of the present disclosure may be in the form of compositions suitable for administration to a subject. In general, such compositions are pharmaceutical compositions comprising an anti-CD39 antibody according to this disclosure and one or more pharmaceutically acceptable excipients. In certain embodiments, the anti-CD39 antibody may be present in an effective amount. The pharmaceutical compositions may be used in the methods of the present disclosure; thus, for example, the pharmaceutical compositions comprising an anti-CD39 antibody according to this disclosure can be administered to a subject in order to practice the therapeutic and prophylactic methods and uses described herein.

The pharmaceutical compositions of the present disclosure can be formulated to be compatible with the intended method or route of administration. Routes of administration may include those known in the art. Exemplary routes of administration are oral and parenteral. Furthermore, the pharmaceutical compositions may be used in combination with one or more other therapy as described herein in order to treat or prevent the diseases, disorders and conditions as contemplated by the present disclosure. In one embodiment, the one or more other additional therapeutic agents contemplated by this disclosure are included in the same pharmaceutical composition that comprises the anti-CD39 antibody according to this disclosure. In another embodiment, the one or more other therapeutic agents are in a composition that is separate from the pharmaceutical composition comprising the anti-CD39 antibody according to this disclosure.

In one aspect, the anti-CD39 antibodies described herein may be administered orally, Oral administration may be via, for example, capsule or tablets. In making the pharmaceutical compositions that include the anti-CD39 antibody, the tablet or capsule typically includes at least one pharmaceutically acceptable excipient. Non-limiting examples of pharmaceutically acceptable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, sterile water, syrup, and methyl cellulose. Additional pharmaceutically acceptable excipients include lubricating agents such as talc, magnesium stearate, and mineral oil: wetting agents; emulsifying and suspending agents; preserving agents such as methyl and propylhydroxy-benzoates Some oral administration forms include taste masking, sweetening or flavoring agents. An oral dosage form may be formulated as a solution or suspension.

In another aspect, the antibodies described herein may be administered parenterally, for example by intravenous injection. A pharmaceutical composition appropriate for parenteral administration may be formulated in solution for injection or may be reconstituted for injection in an appropriate system such as a physiological solution. Such solutions may include sterile water for injection, salts, buffers, and tonicity excipients in amounts appropriate to achieve isotonicity with the appropriate physiology.

The pharmaceutical compositions described herein may be stored in an appropriate sterile container or containers. In some embodiments, the container is designed to maintain stability for the pharmaceutical composition over a given period of time.

D. Dosing

In general, the disclosed methods comprise administering an anti-CD39 antibody described herein, or a composition thereof, in an effective amount to a subject in need thereof. An "effective amount" with reference to an anti-CD39 antibody of the present disclosure means an amount of the antibody that is sufficient to engage the target (e.g., by binding to and inhibiting CD39 enzymatic activity) at a level that is indicative of the potency of the antibody. For CD39, target engagement can be determined by one or more biochemical or cellular assays resulting in an $EC_{50}$, $ED_{50}$, $EC_{90}$, $IC_{50}$, or similar value which can be used as one assessment of the potency of the antibody. Assays for determining target engagement include, but are not limited to, those described in the Examples. The effective amount may be administered as a single quantity or as multiple, smaller quantities (e.g., as one tablet with "x" amount, as two tablets each with "x/2" amount, etc.).

In some embodiments, the disclosed methods comprise administering a therapeutically effective amount of an anti-CD39 antibody described herein to a subject in need thereof. As used herein, the phrase "therapeutically effective amount" with reference to an anti-CD39 antibody means a dose regimen (i.e., amount and interval) of the antibody that provides the specific pharmacological effect for which the antibody is administered to a subject in need of such treatment. For prophylactic use, a therapeutically effective amount may be effective to eliminate or reduce the risk, lessen the severity, or delay the onset of the disease, including biochemical, histological and/or behavioral signs or symptoms of the disease. For treatment, a therapeutically effective amount may be effective to reduce, ameliorate, or eliminate one or more signs or symptoms associated with a disease, delay disease progression, prolong survival, decrease the dose of other medication(s) required to treat the disease, or a combination thereof. With respect to cancer specifically, a therapeutically effective amount may, for example, result in the killing of cancer cells, reduce cancer cell counts, reduce tumor burden, eliminate tumors or metastasis, or reduce metastatic spread. A therapeutically effective amount of an anti-CD39 antibody need not always be effective in treating every individual subject to be deemed to be a therapeutically effective amount by those of skill in the art. A therapeutically effective amount may vary based on, for example, one or more of the following: the age and weight of the subject, the subject's overall health, the stage of the subject's disease, the route of administration, and prior or concomitant treatments.

In certain embodiments, an anti-CD39 antibody contemplated by the present disclosure may be administered (e.g., orally, parenterally, etc.) at about 0.01 mg/kg to about 50 mg/kg, or about 1 mg/kg to about 25 mg/kg, of subject's body weight per day, one or more times a day, a week, or a month, to obtain the desired effect. In some embodiments, a suitable weight-based dose of an anti-CD39 antibody contemplated by the present disclosure is used to determine a dose that is administered independent of a subject's body weight (i.e., a fixed-dose. In certain embodiments, an anti-CD39 antibody of the present disclosure may be administered (e.g., orally, parenterally, etc.) at fixed dosage levels of about 1 mg to about 1000 mg, particularly 1, 3, 5, 10, 15, 20, 25, 50, 75, 100, 150, 200, 250, 300, 400, 500, 600, 750, 800, 900, or 1000 mg, one or more times a day, a week, or a month, to obtain the desired effect. In some embodiments, an anti-CD39 antibody of the present disclosure may be administered (e.g., orally, parenterally, etc.) at fixed dosage levels of about 3 mg to about 3000 mg, particularly 3, 5, 10, 15, 20, 25, 50, 75, 100, 150, 200, 250, 300, 400, 500, 600, 750, 800, 900, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, 2500 mg, 2600 mg, 2700 mg, 2800 mg, 2900 mg, or 3000 mg one or more times a day, a week, or a month, to obtain the desired effect. The term "about" when used herein in reference to a dose means the numerical value stated as well as plus or minus 10% of the numerical value. For example, "about 10" should be understood as both "10" and "9-11.

In certain embodiments, an anti-CD39 antibody of the present disclosure is contained in a "unit dosage form". The phrase "unit dosage form" refers to physically discrete units, each unit containing a predetermined amount of the anti-CD39 antibody, either alone or in combination with one or more additional agents, sufficient to produce the desired effect. It will be appreciated that the parameters of a unit dosage form will depend on the particular agent and the effect to be achieved.

IV. Combinations with a Disclosed Anti-CD39 Antibody

The present disclosure contemplates the use of anti-CD39 antibodies of Section II alone or in combination with one or more additional therapy. Each additional therapy can be a therapeutic agent or another treatment modality. In embodiments comprising one or more additional therapeutic agent, each agent may target a different, but complementary, mechanism of action. The additional therapeutic agents can be small chemical molecules; macromolecules such as proteins, antibodies, peptibodies, peptides, DNA, RNA or fragments of such macromolecules; or cellular or gene therapies. Non-limiting examples of additional treatment modalities include surgical resection of a tumor, bone marrow transplant, radiation therapy, and photodynamic therapy. The use of anti-CD39 antibodies of Section II in combination with one or more additional therapies may have a synergistic or additive therapeutic effect or a prophylactic effect on the underlying disease, disorder, or condition. In addition or alternatively, the combination therapy may allow for a dose reduction of one or more of the therapies, thereby ameliorating, reducing or eliminating adverse effects associated with one or more of the agents.

In embodiments comprising one or more additional treatment modality, the anti-CD39 antibodies of Section II can be administered before, after or during treatment with the additional treatment modality. In embodiments comprising one or more additional therapeutic agent, the therapeutic agents used in such combination therapy can be formulated as a single composition or as separate compositions. If administered separately, each therapeutic agent in the combination can be given at or around the same time, or at different times. Furthermore, the therapeutic agents are administered "in combination" even if they have different forms of administration (e.g., oral capsule and intravenous), they are given at different dosing intervals, one therapeutic agent is given at a constant dosing regimen while another is titrated up, titrated down or discontinued, or each therapeutic agent in the combination is independently titrated up, titrated down, increased or decreased in dosage, or discontinued and/or resumed during a patient's course of therapy. If the combination is formulated as separate compositions, in some embodiments, the separate compositions are provided together in a kit.

Cancer Therapies

The present disclosure contemplates the use of anti-CD39 antibodies of Section II in combination with one or more additional therapies useful in the treatment of cancer, or a cancer-related disease, disorder or condition. In some embodiments, one or more of the additional therapies is an additional treatment modality. Exemplary treatment modalities include but are not limited to surgical resection of a tumor, bone marrow transplant, radiation therapy, and photodynamic therapy. In some embodiments, one or more of the additional therapies is a therapeutic agent. Exemplary therapeutic agents include chemotherapeutic agents, radiopharmaceuticals, hormone therapies, epigenetic modulators, ATP-adenosine axis-targeting agents, targeted therapies, signal transduction inhibitors, RAS signaling inhibitors, PI3K inhibitors, arginase inhibitors, HIF inhibitors, AXL inhibitors, PAK4 inhibitors, immunotherapeutic agents, cellular therapies, gene therapies, immune checkpoint inhibitors, and agonists of stimulatory or co-stimulatory immune checkpoints.

In some embodiments, one or more of the additional therapeutic agents is a chemotherapeutic agent. Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, pomalidomide, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pemetrexed, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel, nab paclitaxel, and docetaxel; chlorambucil; gemcitabine; 6-thioguanine; mercaptopurine; methotrexate; platinum and platinum coordination complexes (collectively referred to as "platinum agents") such as cisplatin, carboplatin and oxaliplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; proteasome inhibitors such as bortezomib, carfilzomib and ixazomib; topoisomerase inhibitors such as irinotecan, topotecan, etoposide, mitoxantrone, teniposide; difluoromethylornithine (DMFO); retinoic acid; esperamicins; capecitabine; anthracyclines and pharmaceutically acceptable salts, acids or derivatives of any of the above. In certain embodiments, combination therapy comprises a chemotherapy regimen that includes one or more chemotherapeutic agents. In one embodiment, combination therapy comprises a chemotherapeutic regimen comprising FOLFOX (folinic acid, fluorouracil, and oxaliplatin), FOLFIRI (folinic acid, fluorouracil, and irinotecan), a taxane (e.g., docetaxel, paclitaxel, nab-paclitaxel, etc.), CAPOX (capecitabine and oxaliplatin), XELOX (capecitabine and oxaliplatin), irinotecan, a platinum-based chemotherapeutic agent, or gemcitabine. In another embodiment, combination therapy comprises a chemotherapeutic regimen comprising an alkylating agent (e.g., cyclophosphamide), an anthracycline (e.g., doxorubicin, epirubicin, idarubicin, mitoxantrone), a platinum agent (e.g., oxaliplatin), a proteasome inhibitor (e.g., bortezomib), or any combination thereof. In another embodiment, combination therapy comprises a chemotherapeutic regimen comprising an alkylating agent (e.g., cyclophosphamide), an anthracycline (e.g., doxorubicin, epirubicin, idarubicin, mitoxantrone), a platinum agent (e.g., carboplatin, cisplatin, oxaliplatin), a taxane (e.g., docetaxel, paclitaxel), a proteasome inhibitor (e.g., bortezomib), or any combination thereof. In another embodiment, combination therapy comprises a chemotherapeutic regimen comprising bortezomib, cyclophosphamide, doxorubicin, epirubicin, idarubicin, mitoxantrone, oxaliplatin, or any combination thereof.

In some embodiments, one or more of the additional therapeutic agents is a radiopharmaceutical. A radiopharmaceutical is a form of internal radiation therapy in which a source of radiation (i.e., one or more radionuclide) is put inside a subject's body. The radiation source can be in solid or liquid form. Non-limiting examples of radiopharmaceuticals include sodium iodide I-131, radium-223 dichloride, lobenguane iodine-131, radioiodinated vesicles (e.g., saposin C-dioleoylphosphatidylserine (SapC-DOPS) nanovesicles), various forms of brachytherapy, and various forms of targeted radionuclides. Targeted radionuclides comprise a radionuclide associated (e.g., by covalent or ionic interactions) with a molecule ("a targeting agent") that specifically binds to a target on a cell, typically a cancer cell or an immune cell. The targeting agent may be a small molecule, a saccharide (inclusive of oligosaccharides and polysaccharides), an antibody, a lipid, a protein, a peptide, a non-natural polymer, or an aptamer. In some embodiments, the targeting agent is a saccharide (inclusive of oligosaccharides and polysaccharides), a lipid, a protein, or a peptide and the target is a tumor-associated antigen (enriched but not specific to a cancer cell), a tumor-specific antigen (minimal to no expression in normal tissue), or a neo-antigen (an antigen specific to the genome of a cancer cell generated by non-synonymous mutations or gene fusions in the tumor cell genome). In some embodiments, the targeting agent is an antibody and the target is a tumor-associated antigen (i.e., an antigen enriched but not specific to a cancer cell), a tumor-specific antigen (i.e., an antigen with minimal to no expression in normal tissue), or a neo-antigen (i.e., an antigen specific to the genome of a cancer cell generated by non-synonymous mutations or gene fusions in the tumor cell genome). Non-limiting examples of targeted radionuclides include radionuclides attached to: somatostatin or peptide analogs thereof (e.g., 177Lu-Dotatate, etc.); prostate specific membrane antigen or peptide analogs thereof (e.g., 177Lu-PSMA-617, 225Ac-PSMA-617, 177Lu-PSMA-I&T, 177Lu-MIP-1095, etc.); a receptor's cognate ligand, peptide derived from the ligand, or variants thereof (e.g., 188Re-labeled VEGF$_{125-136}$ or variants thereof with higher affinity to VEGF receptor, etc.); antibodies targeting tumor antigens (e.g., 131I-tositumomab, 90Y-ibritumomab tiuxetan, CAM-H2-I131 (Precirix NV), I131-omburtamab, etc.).

In some embodiments, one or more of the additional therapeutic agents is a hormone therapy. Hormone therapies act to regulate or inhibit hormonal action on tumors. Examples of hormone therapies include, but are not limited to: selective estrogen receptor degraders such as fulvestrant, GDC-9545, SAR439859, RG6171, AZD9833, rintodestrant, ZN-c5, LSZ102, D-0502, LY3484356, SHR9549; selective estrogen receptor modulators such as tamoxifen, raloxifene, 4-hydroxytamoxifen, trioxifene, keoxifene, toremifene; aromatase inhibitors such as anastrozole, exemestane, letrozole and other aromatase inhibiting 4(5)-imidazoles; gonadotropin-releasing hormone agonists such as nafarelin, triptorelin, goserelin; gonadotropin-releasing hormone antagonists such as degarelix; antiandrogens such as abiraterone, enzalutamide, apalutamide, darolutamide, flutamide, nilutamide, bicalutamide, leuprolide; 5α-reductase inhibitors such as finasteride, dutasteride; and the like. In certain embodiments, combination therapy comprises administration of a hormone or related hormonal agent. In one embodiment, combination therapy comprises administration of enzalutamide.

In some embodiments, one or more of the additional therapeutic agents is an epigenetic modulator. An epigenetic modulator alters an epigenetic mechanism controlling gene expression, and may be, for example, an inhibitor or activator of an epigenetic enzyme. Non-limiting examples of epigenetic modulators include DNA methyltransferase (DNMT) inhibitors, hypomethylating agents, and histone deacetylase (HDAC) inhibitors. In one or more embodiments, an anti-CD39 antibody of Section II can be combined with DNA methyltransferase (DNMT) inhibitors or hypomethylating agents. Exemplary DNMT inhibitors include decitabine, zebularine and azacitadine. In one or more embodiments, combinations of an anti-CD39 antibody of Section II with a histone deacetylase (HDAC) inhibitor are also contemplated. Exemplary HDAC inhibitors include vorinostat, givinostat, abexinostat, panobinostat, belinostat and trichostatin A.

In some embodiments, one or more of the additional therapeutic agents is an ATP-adenosine axis-targeting agent. ATP-adenosine axis-targeting agents alter signaling mediated by adenine nucleosides and nucleotides (e.g., adenosine, AMP, ADP, ATP), for example by modulating the level of adenosine or targeting adenosine receptors. Adenosine and ATP, acting at different classes of receptors, often have opposite effects on inflammation, cell proliferation and cell death. For instance, ATP and other adenine nucleotides have antitumor effects via activation of the PS2Y1 receptor subtype, while accumulation of adenosine in the tumor microenvironment has been shown to inhibit the antitumor function of various immune cells and to augment the immunosuppressive activity of myeloid and regulatory T cells by binding to cell surface adenosine receptors. In certain embodiments, an ATP-adenosine axis-targeting agent is an inhibitor of an ectonucleotidase involved in the conversion of ATP to adenosine or an antagonist of adenosine receptor. Ectonucleotidases involved in the conversion of ATP to adenosine include the ectonucleoside triphosphate diphosphohydrolase 1 (ENTPD1, also known as CD39 or Cluster of Differentiation 39) and the ecto-5'-nucleotidase (NT5E or 5NT, also known as CD73 or Cluster of Differentiation 73). Exemplary small molecule CD73 inhibitors include CB-708, ORIC-533, LY3475070 and AB680. Exemplary anti-CD73 antibodies include CPI-006, oleclumab (MEDI9447), NZV930, IPH5301, GS-1423, uliledlimab (TJD5, TJ004309), and BMS-986179. In one embodiment, the present disclosure contemplates combination of an anti-CD39 antibody of Section II with a CD73 inhibitor such as those described in WO 2017/120508, WO 2018/067424, WO 2018/094148, and WO 2020/046813. In further embodiments, the CD73 inhibitor is quemliclustat. Adenosine can bind to and activate four different G-protein coupled receptors: $A_1R$, $A_{2A}R$, $A_{2B}R$, and $A_3R$. $A_2R$ antagonists include etrumadenant, inupadenant, taminadenant, caffeine citrate, NUV-1182, TT-702, DZD-2269, INCB-106385, EVOEXS-21546, AZD-4635, imaradenant, RVU-330, ciforadenant, PBF-509, PBF-999, PBF-1129, and CS-3005. In some embodiments, the present disclosure contemplates the combination of an anti-CD39 antibody of Section II with an A2AR antagonist, an A2BR antagonist, or an antagonist of A2AR and A2MR. In some embodiments, the present disclosure contemplates the combination of an anti-CD39 antibody of Section II with the adenosine receptor antagonists described in WO 2018/136700, WO 2018/204661, WO 2018/213377, or WO 2020/023846, WO 2020/102646. In one embodiment, the adenosine receptor antagonist is etrumadenant.

In some embodiments, one or more of the additional therapeutic agents is a targeted therapy. In one aspect, a targeted therapy may comprise a chemotherapeutic agent, a radionuclide, a hormone therapy, or another small molecule drug attached to a targeting agent. The targeting agent may be a small molecule, a saccharide (inclusive of oligosaccharides and polysaccharides), an antibody, a lipid, a protein, a peptide, a non-natural polymer, or an aptamer. In some embodiments, the targeting agent is a saccharide (inclusive of oligosaccharides and polysaccharides), a lipid, a protein, or a peptide and the target is a tumor-associated antigen (enriched but not specific to a cancer cell), a tumor-specific antigen (minimal to no expression in normal tissue), or a neo-antigen (an antigen specific to the genome of a cancer cell generated by non-synonymous mutations in the tumor cell genome). In some embodiments, the targeting agent is an antibody and the target is a tumor-associated antigen (enriched but not specific to a cancer cell), a tumor-specific antigen (minimal to no expression in normal tissue), or a neo-antigen (an antigen specific to the genome of a cancer cell generated by non-synonymous mutations in the tumor cell genome). In some embodiments, the targeted therapy is an antibody-drug conjugate comprising an antibody and a drug, wherein the antibody specifically binds to HER2, HER3, nectin-4, or Trop-2. Specific examples of a targeted therapy comprising an antibody and a drug include but are not limited to patritumab deruxtecan, sacituzumab govitecan-hziy, telisotuzumab vedotin, and trastuzumab deruxtecan. In other aspects, a targeted therapy may inhibit or interfere with a specific protein that helps a tumor survive, grow and/or spread. Non-limiting examples of such targeted therapies include signal transduction inhibitors, RAS signaling inhibitors, inhibitors of oncogenic transcription factors, activators of oncogenic transcription factor repressors, angiogenesis inhibitors, immunotherapeutic agents, ATP-adenosine axis-targeting agents, AXL inhibitors, PARP inhibitors, PAK4 inhibitors, PI3K inhibitors, HIF2α inhibitors, CD73 inhibitors, A2R antagonists, TIGIT antagonists, and PD-1 antagonists. ATP-adenosine axis-targeting agents are described above, while other agents are described in further detail below.

In some embodiments, one or more of the additional therapeutic agents is a signal transduction inhibitor. Signal transduction inhibitors are agents that selectively inhibit one or more steps in a signaling pathway. Signal transduction inhibitors (STIs) contemplated by the present disclosure include but are not limited to: (i) BCR-ABL kinase inhibitors (e.g., imatinib); (ii) epidermal growth factor receptor tyrosine kinase inhibitors (EGFR TKIs), including small molecule inhibitors (e.g., CLN-081, gefitinib, erlotinib, afatinib, icotinib, and osimertinib), and anti-EGFR antibodies; (iii) inhibitors of the human epidermal growth factor (HER) family of transmembrane tyrosine kinases, e.g., HER-2/neu receptor inhibitors (e.g., trastuzumab and HER-3 receptor inhibitors); (iv) vascular endothelial growth factor receptor (VEGFR) inhibitors including small molecule inhibitors (e.g., axitinib, regorafenib, sunitinib and sorafenib), VEGF kinase inhibitors (e.g., lenvatinib, cabozantinib, pazopanib, tivozanib, XL092, etc.), anti-VEGF antibodies (e.g., bevacizumab) and anti-VEGFR antibodies (e.g., ramucirumab); (v) inhibitors of AKT family kinases or the AKT pathway (e.g., rapamycin); (vi) inhibitors of serine/threonine-protein kinase B-Raf (BRAY), such as, for example, vemurafenib, dabrafenib and encorafenib; (vii) inhibitors of rearranged during transfection (RET), including, for example, selpercatinib and pralsetinib; (viii) tyrosine-protein kinase Met (MET) inhibitors (e.g., tepotinib, tivantinib, cabozantinib and crizotinib); (ix) anaplastic lymphoma kinase (ALK) inhibitors (e.g., ensartinib, ceritinib, lorlatinib, crizotinib, and brigatinib); (x) inhibitors of the RAS signaling pathway (e.g., inhibitors of KRAS, HRAS, RAF, MEK, ERK) as described elsewhere herein; (xi) FLT-3 inhibitors (e.g., gilteritinib); (xii) inhibitors of Trop-2; (xiii) inhibitors of the JAK/STAT pathway, e.g., JAK inhibitors including tofacitinib and ruxolitinib, or STAT inhibitors such as napabucasin; (xiv) inhibitors of NF-kB; (xv) cell cycle kinase inhibitors (e.g., flavopiridol); (xvi) phosphatidyl inositol kinase (PI3K) inhibitors; (xix) protein kinase B (AKT) inhibitors (e.g., capivasertib, miransertib); (xx) platelet-derived growth factor receptor (PDGFR) inhibitors (e.g., imatinib, sunitinib, regorafenib, avapritinib, Lenvatinib, nintedanib, famitinib, ponatinib, axitinib, repretinib, etc.); and (xxi) insulin-like growth factor receptor (IGFR) inhibitors (e.g., erlotinib, afatinib, gefitinib, osimertinib, dacomitinib). In one or more embodiments, the additional therapeutic agent comprises an inhibitor of EGFR, VEGFR, HER-2, HER-3, BRAF, RET, MET, ALK, RAS (e.g., KRAS, MEK, ERK), FLT-3, JAK, STAT, NF-kB, PI3K, AKT, or any combinations thereof.

In some embodiments, one or more of the additional therapeutic agents is a RAS signaling inhibitor. Oncogenic mutations in the RAS family of genes, e.g., HRAS, KRAS, and NRAS, are associated with a variety of cancers. For example, mutations of G12C, G12D, G12V, G12A, G13D, Q61H, G13C and G12S, among others, in the KRAS family of genes have been observed in multiple tumor types. Direct and indirect inhibition strategies have been investigated for the inhibition of mutant RAS signaling. Indirect inhibitors target effectors other than RAS in the RAS signaling pathway, and include, but are not limited to, inhibitors of RAF, MEK, ERK, PI3K, PTEN, SOS (e.g., SOS1), mTORC1, SHP2 (PTPN11), and AKT. Non-limiting examples of indirect inhibitors under development include RMC-4630, RMC-5845, RMC-6291, RMC-6236, JAB-3068, JAB-3312, TNO155, RLY-1971, BI1701963. Direct inhibitors of RAS mutants have also been explored, and generally target the KRAS-GTP complex or the KRAS-GDP complex. Exemplary direct RAS inhibitors under development include, but are not limited to, sotorasib (AMG510), MRTX849, mRNA-5671 and ARS1620. In some embodiments, the one or more RAS signaling inhibitors are selected from the group consisting of RAF inhibitors, MEK inhibitors, ERK inhibitors, PI3K inhibitors, PTEN inhibitors, SOS1 inhibitors, mTORC1 inhibitors, SHP2 inhibitors, and AKT inhibitors. In other embodiments the one or more RAS signaling inhibitors directly inhibit RAS mutants.

In some embodiments one or more of the additional therapeutic agents is an inhibitor of a phosphatidylinositol 3-kinase (PI3K), particularly an inhibitor of the PI3K7 isoform. PI3K7 inhibitors can stimulate an anti-cancer immune response through the modulation of myeloid cells, such as by inhibiting suppressive myeloid cells, dampening immune-suppressive tumor-infiltrating macrophages or by stimulating macrophages and dendritic cells to make cytokines that contribute to effective T cell responses thereby decreasing cancer development and spread. Exemplary PI3Kγ inhibitors include copanlisib, duvelisib, AT-104, ZX-101, tenalisib, eganelisib, SF-1126, AZD3458, and pictilisib. In some embodiments, an anti-CD39 antibody of Section II can be combined with one or more PI3K7 inhibitors described in WO 2020/0247496A1.

In some embodiments, one or more of the additional therapeutic agents is an inhibitor of arginase. Arginase has been shown to be either responsible for or participate in inflammation-triggered immune dysfunction, tumor immune escape, immunosuppression and immunopathology of infectious disease. Exemplary arginase compounds include CB-1158 and OAT-1746. In some embodiments, an anti-CD39 antibody of Section II can be combined with one or more arginase inhibitors described in WO/2019/173188 and WO 2020/102646.

In some embodiments, one or more of the additional therapeutic agents is an inhibitor of an oncogenic transcription factor or an activator of an oncogenic transcription factor repressor. Suitable agents may act at the expression level (e.g., RNAi, siRNA, etc.), through physical degradation, at the protein/protein level, at the protein/DNA level, or by binding in an activation/inhibition pocket. Non-limiting examples include inhibitors of one or more subunit of the MLL complex (e.g., HDAC, DOT1L, BRD4, Menin, LEDGF, WDR5, KDM4C (JMJD2C) and PRMT1), inhibitors of hypoxia-inducible factor (HIF) transcription factor, and the like.

In some embodiments, one or more of the additional therapeutic agents is an inhibitor of a hypoxia-inducible factor (HIF) transcription factor, particularly HIF-2α. Exemplary HIF-2α inhibitors include belzutifan, ARO-HIF2, PT-2385, AB521, and those described in WO 2021113436 and WO 2021188769. In some embodiments, an anti-CD39 antibody of Section II can be combined with one or more HIF-2α inhibitors described in WO 2021188769.

In some embodiments, one or more of the additional therapeutic agents is an inhibitor of anexelekto (AXL). The AXL signaling pathway is associated with tumor growth and metastasis, and is believed to mediate resistance to a variety of cancer therapies. There are a variety of AXL inhibitors under development that also inhibit other kinases in the TAM family (i.e., TYRO3, MERTK), as well as other receptor tyrosine kinases including MET, FLT3, RON and AURORA, among others. Exemplary multikinase inhibitors include sitravatinib, rebastinib, glesatinib, gilteritinib, merestinib, cabozantinib, foretinib, BMS777607, LY2801653, S49076, GSK1363089, and RXDX-106. AXL specific inhibitors have also been developed, e.g., small molecule inhibitors including DS-1205, SGI-7079, SLC-391, TP-0903 (i.e., dubermatinib), BGB324 (i.e., bemcentinib), and DP3975; anti-AXL antibodies such as ADCT-601; and antibody drug conjugates (ADCs) such as BA3011. Another strategy to inhibit AXL signaling involves targeting AXL's ligand, GAS6. For example, AVB-500 is under development as is a Fc fusion protein that binds the GAS6 ligand thereby inhibiting AXL signaling.

In some embodiments, one or more of the additional therapeutic agents is an inhibitor of p21-activated kinase 4 (PAK4). PAK4 overexpression has been shown across a variety of cancer types, notably including those resistant to PD-1 therapies. While no PAK4 inhibitors have been approved, some are in development, and exhibit dual PAK4/NAMPT inhibitor activity, e.g., ATG-019 and KPT-9274. In some embodiments, the antibodies according to this disclosure are combined with a PAK4 selective inhibitor. In some embodiments, the antibodies according to this disclosure are combined with a PAK4/NAMPT dual inhibitor, e.g., ATG-019 or KPT-9274.

In some embodiments, one or more of the additional therapeutic agents is (i) an agent that inhibits the enzyme poly (ADP-ribose) polymerase (e.g., olaparib, niraparib and rucaparib, etc.); (ii) an inhibitor of the Bcl-2 family of proteins (e.g., venetoclax, navitoclax, etc.); (iii) an inhibitor of MCL-1; (iv) an inhibitor of the CD47-SIRPα pathway (e.g., the anti-CD47 antibody, magrolimab, etc.); (v) an isocitrate dehydrogenase (IDH) inhibitor, e.g., IDH-1 or IDH-2 inhibitor (e.g., ivosidenib, enasidenib, etc.).

In some embodiments, one or more of the additional therapeutic agents is an immunotherapeutic agent. Immunotherapeutic agents useful in the treatment of cancers typically elicit or amplify an immune response to cancer cells. Non-limiting examples of suitable immunotherapeutic agents include: immunomodulators; cellular immunotherapies; vaccines; gene therapies; ATP-adenosine axis-targeting agents; immune checkpoint modulators; and certain signal transduction inhibitors. ATP-adenosine axis-targeting agents are described above. Immunomodulators, signal transduction inhibitors, cellular immunotherapies, vaccines, gene therapies, and immune checkpoint modulators are described further below.

In some embodiments, one or more of the additional therapeutic agents is an immunotherapeutic agent, more specifically a cytokine or chemokine, such as, IL1, IL2, IL12, IL18, ELC/CCL19, SLC/CCL21, MCP-1, IL-4, IL-18, TNF, IL-15, MDC, IFNa/b, M-CSF, IL-3, GM-CSF, IL-13, and anti-IL-10; bacterial lipopolysaccharides (LPS); an organic or inorganic adjuvant that activates antigen-presenting cells and promote the presentation of antigen epitopes on major histocompatibility complex molecules including, but not limited to Toll-like receptor (TLR) agonists, antagonists of the mevalonate pathway, agonists of STING; indoleamine 2,3-dioxygenase 1 (IDO1) inhibitors and immune-stimulatory oligonucleotides, as well as other T cell adjuvants.

In some embodiments, one or more of the additional therapeutic agents is an immunotherapeutic agent, more specifically a cellular therapy. Cellular therapies are a form of treatment in which viable cells are administered to a subject. In certain embodiments, one or more of the additional therapeutic agents is a cellular immunotherapy that activates or suppresses the immune system. Cellular immunotherapies useful in the treatment of cancers typically elicit or amplify an immune response. The cells can be autologous or allogenic immune cells (e.g., monocytes, macrophages, dendritic cells, NK cells, T cells, etc.) collected from one or more subject. Alternatively, the cells can be "(re)programmed" allogenic immune cells produced from immune precursor cells (e.g., lymphoid progenitor cells, myeloid progenitor cells, common dendritic cell precursor cells, stem cells, induced pluripotent stem cells, etc.). In some embodiments, such cells may be an expanded subset of cells with distinct effector functions and/or maturation markers (e.g., adaptive memory NK cells, tumor infiltrating lymphocytes, immature dendritic cells, monocyte-derived dendritic cells, plasmacytoid dendritic cells, conventional dendritic cells (sometimes referred to as classical dendritic cells), M1 macrophages, M2 macrophages, etc.), may be genetically modified to target the cells to a specific antigen and/or enhance the cells' anti-tumor effects (e.g., engineered T cell receptor (TCR) cellular therapies, chimeric antigen receptor (CAR) cellular therapies, lymph node homing of antigen-loaded dendritic cells, etc.), may be engineered to express of have increased expression of a tumor-associated antigen, or may be any combination thereof. Non-limiting types of cellular therapies include CAR-T cell therapy, CAR-NK cell therapy, TCR therapy, and dendritic cell vaccines. Exemplary cellular immunotherapies include sipuleucel-T, tisagenlecleucel, lisocabtagene maraleucel, idecabtagene vicleucel, brexucabtagene autoleucel, and axicabtagene ciloleucel, as well as CTX110, JCAR015, JCAR017, MB- CART19.1, MB-CART20.1, MB-CART2019.1, UniCAR02-T-CD123, BMCA-CAR-T, JNJ-68284528, BNT211, and NK-92/5.28.z.

In some embodiments, one or more of the additional therapeutic agents is an immunotherapeutic agent, more specifically a gene therapy. Gene therapies comprise recombinant nucleic acids administered to a subject or to a subject's cells ex vivo in order to modify the expression of an endogenous gene or to result in heterologous expression of a protein (e.g., small interfering RNA (siRNA) agents, double-stranded RNA (dsRNA) agents, micro RNA (miRNA) agents, viral or bacterial gene delivery, etc.), as well as gene editing therapies that may or may not comprise a nucleic acid component (e.g., meganucleases, zinc finger nucleases, TAL nucleases, CRISPR/Cas nucleases, etc.), oncolytic viruses, and the like. Non-limiting examples of gene therapies that may be useful in cancer treatment include Gendicine® (rAd-p53), Oncorine® (rAD5-H101), talimogene laherparepvec, Mx-dnGI, ARO-HIF2 (Arrowhead), quaratusugene ozeplasmid (Immunogene), CTX110 (CRISPR Therapeutics), CTX120 (CRISPR Therapeutics), and CTX130 (CRISPR Therapeutics).

In some embodiments, one or more of the additional therapeutic agents is an immunotherapeutic agent, more specifically an agent that modulates an immune checkpoint.

Immune checkpoints are a set of inhibitory and stimulatory pathways that directly affect the function of immune cells (e.g., B cells, T cells, NK cells, etc.). Immune checkpoints engage when proteins on the surface of immune cells recognize and bind to their cognate ligands. The present invention contemplates the use of an anti-CD39 antibody of Section II in combination with agonists of stimulatory or co-stimulatory pathways and/or antagonists of inhibitory pathways. Agonists of stimulatory or co-stimulatory pathways and antagonists of inhibitory pathways may have utility as agents to overcome distinct immune suppressive pathways within the tumor microenvironment, inhibit T regulatory cells, reverse/prevent T cell anergy or exhaustion, trigger innate immune activation and/or inflammation at tumor sites, or combinations thereof.

In some embodiments, one or more of the additional therapeutic agents is an immune checkpoint inhibitor. As used herein, the term "immune checkpoint inhibitor" refers to an antagonist of an inhibitory or co-inhibitory immune checkpoint. The terms "immune checkpoint inhibitor", "checkpoint inhibitor" and "CPI" may be used herein interchangeably. Immune checkpoint inhibitors may antagonize an inhibitory or co-inhibitory immune checkpoint by interfering with receptor-ligand binding and/or altering receptor signaling. Examples of immune checkpoints (ligands and receptors), some of which are selectively upregulated in various types of cancer cells, that can be antagonized include PD-1 (programmed cell death protein 1); PD-L1 (PD-1 ligand); BTLA (B and T lymphocyte attenuator); CTLA-4 (cytotoxic T-lymphocyte associated antigen 4); TIM-3 (T cell immunoglobulin and mucin domain-containing protein 3); LAG-3 (lymphocyte activation gene 3); TIGIT (T cell immunoreceptor with Ig and ITIM domains); CD276 (B7-H3), PD-L2, Galectin 9, CEACAM-1, BTLA, CD69, Galectin-1, CD113, GPR56, VISTA, 2B4, CD48, GARP, PD1H, LAIR1, TIM-1, and TIM-4, and Killer Inhibitory Receptors, which can be divided into two classes based on their structural features: i) killer cell immunoglobulin-like receptors (KIRs), and ii) C-type lectin receptors (members of the type II transmembrane receptor family). Also contemplated are other less well-defined immune checkpoints that have been described in the literature, including both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)).

In some embodiments, an immune checkpoint inhibitor is a CTLA-4 antagonist. In further embodiments, the CTLA-4 antagonist can be an antagonistic CTLA-4 antibody. Suitable antagonistic CTLA-4 antibodies include, for example, monospecific antibodies such as ipilimumab or tremelimumab, as well as bispecific antibodies such as MEDI5752 and KN046.

In some embodiments, an immune checkpoint inhibitor is a PD-1 antagonist. In further embodiments, the PD-1 antagonist can be an antagonistic PD-1 antibody, small molecule or peptide. Suitable antagonistic PD-1 antibodies include, for example, monospecific antibodies such as balstilimab, budigalimab, camrelizumab, cosibelimab, dostarlimab, cemiplimab, ezabenlimab, MEDI-0680 (AMP-514; WO2012/145493), nivolumab, pembrolizumab, pidilizumab, pimivalimab, retifanlimab, sasanlimab, spartalizumab, sintilmab, tislelizumab, toripalimab, and zimberelimab; as well as bi-specific antibodies such as LY3434172. In still further embodiments, the PD-1 antagonist can be a recombinant protein composed of the extracellular domain of PD-L2 (B7-DC) fused to the Fc portion of IgG1 (AMP-224). In certain embodiments, an immune checkpoint inhibitor is zimberelimab.

In some embodiments, an immune checkpoint inhibitor is a PD-L1 antagonist. In further embodiments, the PD-L1 antagonist can be an antagonistic PD-L1 antibody. Suitable antagonistic PD-L1 antibodies include, for example, monospecific antibodies such as avelumab, atezolizumab, durvalumab, BMS-936559, and envafolimab as well as bi-specific antibodies such as LY3434172 and KN046.

In some embodiments, an immune checkpoint inhibitor is a TIGIT antagonist. In further embodiments, the TIGIT antagonist can be an antagonistic TIGIT antibody. Suitable antagonistic anti-TIGIT antibodies include monospecific antibodies such as AGEN1327, AB308 (WO2021247591), BMS 986207, COM902, domvanalimab, EOS-448, etigilimab, IBI-929, JS006, M6223, ociperlimab, SEA-TGT, tiragolumab, vibostolimab; as well as bi-specific antibodies such as AGEN1777 and AZD2936. In certain embodiments, an immune checkpoint inhibitor is an antagonistic anti-TIGIT antibody disclosed in WO2017152088 or WO2021247591. In certain embodiments, an immune checkpoint inhibitor is domvanalimab or AB308.

In some embodiments, an immune checkpoint inhibitor is a LAG-3 antagonist. In further embodiments, the LAG-3 antagonist can be an antagonistic LAG-3 antibody. Suitable antagonistic LAG-3 antibodies include, for example, BMS-986016 (WO10/19570, WO14/08218), or IMP-731 or IMP-321 (WO08/132601, WO09/44273).

In some embodiments, an immune checkpoint inhibitor is a B7-H3 antagonist. In further embodiments, the B7-H3 antagonist is an antagonistic B7-H3 antibody. Suitable antagonist B7-H3 antibodies include, for example, MGA271 (WO 11/109400), omburtumab, enoblituzumab, DS-7300a, ABBV-155, and SHR-A1811.

In some embodiments, an immune checkpoint inhibitor is a TIM-3 antagonist. In further embodiments, the TIM-3 antagonist can be an antagonistic TIM-3 antibody. Suitable antagonistic TIM-3 antibodies include, for example, dostarlimab, sabatolimab, BMS-986258. and RG7769/RO7121661.

In some embodiments, one or more of the additional therapeutic agents activates a stimulatory or co-stimulatory immune checkpoint. Examples of stimulatory or co-stimulatory immune checkpoints (ligands and receptors) include B7-1, B7-2, CD28, 4-1BB (CD137), 4-1BBL, ICOS, ICOS-L, OX40, OX40L, GITR, GITRL, CD70, CD27, CD40, DR3 and CD2.

In some embodiments, an agent that activates a stimulatory or co-stimulatory immune checkpoint is a CD137 (4-1BB) agonist. In further embodiments, the CD137 agonist can be an agonistic CD137 antibody. Suitable CD137 antibodies include, for example, urelumab and PF-05082566 (WO12/32433). In some embodiments, an agent that activates a stimulatory or co-stimulatory immune checkpoint is a GITR agonist. In further embodiments, the GITR agonist can be an agonistic GITR antibody. Suitable GITR antibodies include, for example, BMS-986153, BMS-986156, TRX-518 (WO06/105021, WO09/009116) and MK-4166 (WO11/028683). In some embodiments, an agent that activates a stimulatory or co-stimulatory immune checkpoint is an OX40 agonist. In further embodiments, the OX40 agonist can be an agonistic OX40 antibody. Suitable OX40 antibodies include, for example, MEDI-6383, MEDI-6469, MEDI-0562, PF-04518600, GSK3174998, BMS-986178, and MOXR0916. In some embodiments, an agent that activates a stimulatory or co-stimulatory immune checkpoint is a CD40 agonist. In further embodiments, the CD40 agonist can be an agonistic CD40 antibody, such as dacetuzumab, selicrelumab, APX005M, ADC-1013, or CDX-1140. In some embodiments, an agent that activates a stimulatory or co-stimulatory immune checkpoint is a CD27 agonist. In further embodiments, the CD27 agonist can be an agonistic CD27 antibody. Suitable CD27 antibodies include, for example, varlilumab.

In some embodiments, one or more of the additional therapies is an immunotherapeutic agent, more specifically a signal transduction inhibitor. Intracellular signaling molecules that influence immune cell functions may also be suitable targets for improving antitumor immunity. For example, one or more of the additional therapies may be an inhibitor of an intracellular signaling molecule is an inhibitor of hematopoietic progenitor kinase 1 (HPK1). HPK1 is serine/threonine kinase that functions as a negative regulator of activation signals generated by the T cell antigen receptor. As another example, one or more of the additional therapies may be an inhibitor of Cb1-b, an E3 ubiquitin ligase involved in the regulation of TCR signaling (e.g., AP401). As another example, one or more of the additional therapies may be an inhibitor of diacylglycerol kinase (DGK). In some embodiments, the inhibitor is a small molecule. Non-limiting examples of small molecule HPK1 inhibitors in clinical development include CFI-402411 and BGB-15025; non-limiting examples of Cb1-b inhibitors in clinical development include AP401. Non-limiting examples of small molecule DAG inhibitors include those described in WO2020006016A1 and WO2021130638.

In some embodiments, one or more of the additional therapeutic agents is an agent that inhibits or depletes immune-suppressive immune cells. For example, to inhibit or deplete immunosuppressive macrophages or monocytes the agent may be CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264), or an antibody disclosed in WO14/036357. As another example, to inhibit or deplete Tregs, the agent may be anti-CD25 beads used to deplete Tregs ex vivo.

In some embodiments, the present disclosure contemplates the use of an anti-CD39 antibody of Section II in combination with an immunogenic cell death (ICD) inducing therapy. ICD can be defined as a functionally unique regulated cell death subtype that is sufficient for the elicitation of adaptive immunity specifically directed toward antigens derived from cell "corpses". Criteria for identifying ICD-inducing therapies may include those described in Vanmeerbeek et al., *OncoImmunology*, 2020, 9:1, DOI: 10.1080/2162402X.2019.1703449; Keep et al., *OncoImmunology*, 2014, 3(9)::e955691. Non-limiting examples of ICD-inducing therapies are described in Galluzzi et al., *Nature Reviews Clinical Oncology*, 2020 17: 725-742. In some embodiments, an ICD-inducing therapy may be radiation therapy, photodynamic therapy, extracorporeal photochemotherapy, oncolytic virotherapy, bortezomib, cyclophosphamide, doxorubicin, epirubicin, idarubicin, mitoxantrone, cetuximab, crizotinib, or oxaliplatin. In some embodiments, an ICD-inducing therapy may be radiation therapy, photodynamic therapy, extracorporeal photochemotherapy, oncolytic virotherapy, bleomycin, bortezomib, carboplatin, cetuximab, crizotinib, cyclophosphamide, docetaxel, doxorubicin, epirubicin, gemcitabine, idarubicin, irinotecan, mitoxantrone, oxaliplatin, paclitaxel, vemurafenib, or vorinostat.

In some embodiments, each additional therapy can independently be radiation therapy, a chemotherapeutic agent, a radiopharmaceutical, a hormone therapy, an epigenetic modulator, a targeted agent, an immunotherapeutic agent, a cellular therapy, a gene therapy, or an ICD-inducing therapy. For example, in one embodiment, the present disclosure contemplates the use of an anti-CD39 antibody of Section II in combination with one or more ICD-inducing therapy and optionally one or more additional therapies, wherein each additional therapy is independently selected from radiation therapy, a radiopharmaceutical, a chemotherapeutic agent, a hormone therapy, a targeted agent, an immunotherapeutic agent, a cellular therapy, or a gene therapy. In another example, in one embodiment, the present disclosure contemplates the use of an anti-CD39 antibody of Section II in combination with one or more chemotherapeutic agent and optionally one or more additional therapies, wherein each additional therapy is independently selected from radiation therapy, a radiopharmaceutical, a hormone therapy, a targeted agent, an immunotherapeutic agent, a cellular therapy, or a gene therapy. In another embodiment, the present disclosure contemplates the use of an anti-CD39 antibody of Section II in combination with one or more chemotherapeutic agent and one or more tyrosine kinase inhibitor, and optionally one or more additional therapy, wherein each additional therapy is independently a targeted agent, an immunotherapeutic agent, or a cellular therapy. In another embodiment, the present disclosure contemplates the use of an anti-CD39 antibody of Section II in combination with one or more chemotherapeutic agent and one or more inhibitor independently selected from (i) BCR-ABL kinase inhibitor; (ii) an EGFR inhibitor (e.g., EGFR TKI or anti-EGFR antibody); (iii) HER-2/neu receptor inhibitor; (iv) an anti-angiogenic agent (e.g., anti-VEGF antibody, VEGFR TKI, VEGF kinase inhibitors, etc.); (v) AKT inhibitor; (vi) BRAF inhibitor; (vii) RET inhibitor; (viii) MET inhibitor; (ix) RAS inhibitor; and (x) ALK inhibitor, and optionally one or more additional therapies, wherein each additional therapy is independently selected from radiation therapy, a radiopharmaceutical, a targeted agent, an immunotherapeutic agent, or a cellular therapy. In another embodiment, the present disclosure contemplates the use of an anti-CD39 antibody of Section II in combination with one or more immunotherapeutic agent and optionally one or more additional therapy, wherein each additional therapy is independently selected from radiation therapy, a radiopharmaceutical, a hormone therapy, a targeted agent, a chemotherapeutic agent, a cellular therapy, or a gene therapy. In another embodiment, the present disclosure contemplates the use of an anti-CD39 antibody of Section II in combination with one or more immunotherapeutic agents and one or more chemotherapeutic agent, and optionally one or more additional therapy, wherein each additional therapy is independently selected from radiotherapy, a radiopharmaceutical, a hormone therapy, a targeted agent, a cellular therapy, or a gene therapy. In another embodiment, the present disclosure contemplates the use of an anti-CD39 antibody of Section II in combination with one or more immunotherapeutic agents and one or more radiation therapy or radiopharmaceutical, and optionally one or more additional therapy, wherein each additional therapy is independently selected from a chemotherapeutic agent, a hormone therapy, a targeted agent, a cellular therapy, or a gene therapy. In another embodiment, the present disclosure contemplates the use of an anti-CD39 antibody of Section II of the present disclosure in combination with one or more immune checkpoint inhibitors and/or one or more ATP-adenosine axis-targeting agents, and optionally one or more additional therapy, wherein each additional therapy is independently selected from radiation therapy, a radiopharmaceutical, a chemotherapeutic agent, a targeted agent, an immunotherapeutic agent, or a cellular therapy. In another embodiment, the present disclosure contemplates the use of an anti-CD39 antibody of Section II in combination with one or more immune checkpoint inhibitors and/or one or more ATP-adenosine axis-targeting agents and/or one or more chemotherapeutic agent, radiopharmaceutical or radiation therapy. In another embodiment, the present disclosure contemplates the use of an anti-CD39 antibody of Section II in combination with one or more immune checkpoint inhibitors and/or one or more ATP-adenosine axis-targeting agents, and one or more inhibitor independently selected from (i) BCR-ABL kinase inhibitor; (ii) an EGFR inhibitor (e.g., EGFR TKI or anti-EGFR antibody); (iii) HER-2/neu receptor inhibitor; (iv) an anti-angiogenic agent (e.g., anti-VEGF antibody, VEGFR TKI, VEGF kinase inhibitors, etc.); (v) AKT inhibitor; (vi) BRAF inhibitor; (vii) RET inhibitor; (viii) MET inhibitor; (ix) KRAS inhibitor; and (x) ALK inhibitor. In another embodiment, the present disclosure contemplates the use of an anti-CD39 antibody of Section II in combination with one or more immune checkpoint inhibitors and/or one or more ATP-adenosine axis-targeting agents, and one or more ICD-inducing therapy. In further embodiments of the above (a) the targeted agent can be a PI3K inhibitor, an arginase inhibitor, a HIF2α inhibitor, an AXL inhibitor, a PAK4 inhibitor, or an anti-angiogenic agent; (b) the immunotherapeutic agent is an ATP-adenosine axis-targeting agent, cytokine therapy, an immune checkpoint inhibitor, or a combination thereof; (c) the ATP-adenosine axis-targeting agent is an A2AR and/or A2BR antagonist, or a CD73 inhibitor; (d) the ATP-adenosine axis-targeting agent is etrumadenant or quemliclustat; (e) the immunotherapeutic agent is an anti-PD-L1 antagonist antibody or an anti-PD-1 antagonist antibody, optionally selected from the group consisting of budigalimab, camrelizumab, cosibelimab, dostarlimab, cemiplimab, ezabenlimab, nivolumab, pembrolizumab, pidilizumab, pimivalimab, retifanlimab, sasanlimab, spartalizumab, sintilimab, tislelizumab, toripalimab, zimberelimab, LY3434172, avelumab, atezolizumab, balstilimab, durvalumab, envafolimab, LY3434172 and KN046; (f) the immunotherapeutic agent is an anti-TIGIT antagonist antibody, optionally selected from the group consisting of AGEN1327, AB308 (WO2021247591), BMS 986207, COM902, domvanalimab, EOS-448, etigilimab, IBI-929, JS006, M6223, ociperlimab, SEA-TGT, tiragolumab, vibostolimab; as well as bi-specific antibodies such as AGEN1777 and AZD2936; (g) the immunotherapeutic agent is domvanalimab, AB308, zimberelimab, tiragolumab, pembrolizumab, nivolumab, atezolizumab, or durvalumab; (h), the anti-angiogenic agent is pazopanib, sorafenib, sunitinib, bevacizumab, axitinib, lenvatinib, tivozanib, or cabozantinib; (i) the ICD-inducing therapy is radiation therapy (including both external beam therapy and internal radiation therapy), photodynamic therapy, extracorporeal photochemotherapy, oncolytic virotherapy, bortezomib, cyclophosphamide, doxorubicin, epirubicin, idarubicin, mitoxantrone, or oxaliplatin; or (j) any combination thereof. In still further embodiments of the above, the present disclosure contemplates the use of an anti-CD39 antibody of Section II in combination with domvanalimab, AB308, etrumadenant, quemliclustat, zimberelimab, AB521, or any combination thereof. In still further embodiments of the above, the present disclosure contemplates the use of an anti-CD39 antibody of Section II in combination with etrumadenant, quemliclustat, or etrumadenant and quemliclustat. In still further embodiments of the above, the present disclosure contemplates the use of an anti-CD39 antibody of Section II in combination with etrumadenant, AB521, or etrumadenant and AB521. In still further embodiments of the above, the present disclosure contemplates the use of an anti-CD39 antibody of Section II in combination with quemliclustat, AB521, or quemliclustat and AB521.

Selection of the additional therapeutic agent(s) may be informed by current standard of care for a particular cancer and/or mutational status of a subject's cancer and/or stage of disease. Detailed standard of care guidelines are published, for example, by National Comprehensive Cancer Network (NCCN). See, for instance, NCCN Colon Cancer v3.2021, NCCN Hepatobiliary Cancer v5.2021, NCCN Kidney Cancer, v3.2022, NCCN NSCLC v7.2021, NCCN Pancreatic Adenocarcinoma v2.2021, NCCN Esophageal and Esophagogastric Junction Cancers v4.2021, NCCN Gastric Cancer v5.2021, Ovarian Cancer/Fallopian Tube Cancer/Primary Peritoneal Cancer v3.2021, Prostate Cancer v3.2022, Head and Neck Cancers v1.2022, Melanoma: Cutaneous v1.2022, Acute Myeloid Leukemia, v1.2022.

EXPERIMENTAL

The following examples are put forth so as to provide those of ordinary skill in the art with a complete disclosure and description of how to make and use the present disclosure, and are not intended to limit the scope of what the inventors regard as their invention. Additional antibodies within the scope of this disclosure may be made using methods based on those illustrated in these examples or based on other methods described herein. Efforts have been made to ensure accuracy with respect to numbers used (e.g., amounts, temperature, etc.), but some experimental errors and deviations should be accounted for.

Unless indicated otherwise, temperature is in degrees Celsius (° C.), and pressure is at or near atmospheric. Standard abbreviations are used, including the following: rt or r.t.=room temperature; min=minute(s); h or hr=hour(s); ng=nanogram; g=microgram; mg=milligram; g=gram; kg=kilogram; μl or μL=microliter; ml or mL=milliliter; 1 or L=liter; M=micromolar; mM=millimolar; M=molar; mol=mole; mmol=millimole; nM=nanomolar.

Example 1: Generation of Anti-CD39 Antibodies

A human CD39-expressing CHO-K1 cell line, a cynomolgus monkey CD39-expressing HEK-293 cell pool and a murine CD39-expressing HEK-293 cell pool were generated. Briefly, CHO-K1 cells or HEK-293 cells (Flp-In™-293 cells) were transfected with pcDNA3.3 expression vector encoding full-length human, cynomolgus monkey or murine CD39 (SEQ ID NO: 7, SEQ ID NO: 8, SEQ ID NO: 71, respectively) using a Lipofectamine 2000 transfection kit according to the manufacturer's protocol. At 48-72 hours post transfection, the transfected cells were cultured in medium containing blasticidin for selection and tested for CD39 expression, then CD39-expressing cell pools were obtained. Human, cynomolgus monkey and murine CD39-expressing cell lines or cell pool were obtained by limiting dilution and used to screen hybridoma supernatants as described below.

To generate anti-CD39 antibodies, four Sprague Dawley rats of age 6-8 weeks were immunized with 30-200 mg/animal of human CD39 antigen, either protein or plasmid DNA. The adjuvant mixture included Adju-Phos, CpG-ODN or Titer-Max. The animals were injected once every other week via footpad, subcutaneous, intra-peritoneal, intramuscular, and intradermal routes. The serum titer was measured by ELISA or fluorescence activated cell sorting (FACS). The ELISA used to measure serum antibody titers against the given antigen was performed as follows. Plates (Nunc) were coated with 100 μL of human CD39 antigen at 1 μg/mL at 4° C. overnight, and then blocked with blocking buffer (1×PBS/2% BSA) for 1 hour at ambient temperature. Rat serum was 3-fold serially diluted starting at a 1:100 dilution in blocking buffer, and incubated for 1 hour at ambient temperature. A well with no serum sample added was used as a negative control. The plates were then washed and subsequently incubated with secondary antibody, goat anti-rat IgG-Fc-HRP (Bethyl), for 1 hour. After washing, tetramethylbenzidine (TMB) substrate was added and the interaction was stopped by adding 2M HCl. The absorbance at 450 nm was read using a microplate reader (Molecular Device). The FACS assay used to measure serum antibody titers was performed as generally described for screening hybridoma supernatants (described below), except serially diluted serum was used. Serum titer was determined as the final dilution giving a positive signal (i.e., >3-fold over the negative control).

When the serum titer was sufficiently high (≥1:24,300), the animal was given a final boost with protein and cell membrane lysates in sterilized PBS without adjuvant. After 48-96 hours the animals were euthanized, and lymph nodes and spleen were used for cell fusion.

Lymph nodes and spleen from an immunized animal were homogenized and filtered to remove blood clots and cell debris. Sp2/0 myeloma cells in logarithmic growth were collected and centrifuged. B cells and Sp2/0 myeloma cells were treated separately with Pronase solution and the reaction was stopped with 100% FBS. The cells were washed and counted. B cells were fused with Sp2/0 myeloma cells at 1:1 ratio in electric fusion solution following general electro-fusion procedures. The fused cells were re-suspended in DMEM medium supplemented with 20% FBS and 1×HAT, and then transferred into 96-well plates. The fused cells were kept for 10-14 days in an incubator set to 37° C. and 5% $CO_2$.

Hybridoma cells were harvested and 150-200 cells were added to 1.5 mL semi-solid-HAT media. The cells were mixed gently in vortex oscillators for 5-10 seconds and then seeded in 6-well plates. The plates were kept in an incubator set to 37° C., 5% $CO_2$ for 7-8 days. Each visible single colony was picked into 96-well plates with DMEM medium, supplemented with 10% FBS. After 2-3 days, the cell supernatants were collected and screened.

Four rounds of hybridoma generation and antibody screening were performed in which the order of the assay cascade in the screening paradigm was varied. To satisfy the screening criteria, antibodies produced from a given hybridoma clone were required to bind to both human and cynomolgus monkey cellular CD39 with high affinity with no measurable binding to murine CD39 or to any of the other CD39 family members, CD39-L1, CD39-L2, CD39-L3 or CD39-L4. The antibody was also required to demonstrate potent inhibition of cellular human CD39 enzymatic activity in both cell lines engineered to overexpress CD39 and human cell lines that naturally express CD39, e.g., THP-1, SK-MEL-5 and MOLP-8. In the first round of fusion, a CHO-K1 cell-based human CD39 ELISA was the primary screen and binding to cellular overexpression of human, cynomolgus monkey and murine CD39 measured by FACS (using the cell lines described previously), and an in vitro soluble human CD39 enzymatic assay and cellular enzymatic assay were secondary screens. A second round of fusion failed to produce suitable hybridoma material. In the third round of fusion, a soluble human CD39 enzymatic assay was the primary screen and binding to cellular overexpression of human and murine CD39 measured by FACS, a human CD39-L1 binding counter-screen, and a confirmatory soluble human CD39 enzymatic assay were secondary screens. In the fourth round of fusion, a THP-1 cellular enzymatic assay was used as the primary screen and binding to cellular overexpression of human and cynomolgus monkey CD39 measured by FACS, and a confirmatory THP-1 cellular enzymatic assay were secondary screens. Clone 39 from the first round and clones 19 and 31 from the third round were selected for further characterization. No clones were selected from the fourth round.

For the cell-based ELISAs, used to evaluate binding to CD39 expressed on the cell surface, the assays were generally performed as follows. The plates (384-well) were pre-coated with 3-5×$10^4$ of cells per well and cultured for 2 days in an incubator set to 37° C., 5% $CO_2$. The plates were blocked with blocking buffer (1×PBS/5% milk) at ambient temperature for 1 hour. Then 30 μL hybridoma supernatant was added into the plates and incubated for 1 hour at ambient temperature. The plates were washed with PBS three times and subsequently incubated with secondary antibody, goat anti-rat IgG-Fc-HRP (1:500), at ambient temperature for 1 hour. After washing, TMB substrate was added to each well and the plates were incubated at ambient temperature in the dark for 3-5 minutes, and the reaction was stopped by adding 2 M HCl. The absorbance at 450 nm was read using a microplate reader (Molecular Device).

FACS was also used to detect the binding of anti-CD39 antibodies in the supernatant to CD39, using the human CD39-expressing CHO-K1 cell line, cynomolgus monkey CD39-expressing HEK-293 cell line, and murine CD39-expressing HEK-293 cell pool described earlier. Unlabeled cells were used as a control to set the threshold before detection, then the percentage change of each group that exceeded the fluorescence intensity threshold was analyzed. 1×$10^5$ cells/well were incubated with hybridoma supernatant in a volume of 100 μL for 1 hour at 4° C. Anti-human CD39 reference antibody, was used as the positive control. Human/rat IgG isotype antibody was used as the negative control. After washing the cells with 1×PBS/1% BSA, Alexa647-labeled goat anti-human antibody or goat anti-rat antibody (diluted 1:500 in FACS staining buffer) was added. The cells were incubated at 4° C. for 1 hour in the dark. The mean fluorescence intensity (MFI) of the cells was measured by a flow cytometer and analyzed using FlowJo software.

Anti-CD39 antibodies were tested for their ability to block the enzymatic activity of soluble CD39 extracellular domain (ECD) antigen by measuring the inhibition of human CD39 catalytic function for hydrolyzing ATP to AMP+inorganic phosphate, coupled to luciferase activity and light emission as the signal. Enzyme assays were carried out in 96-well multi-well plates in a final volume of 120 µL. Assay mixtures were incubated at an incubator set to 37° C. for the indicated incubation periods. Tris magnesium (TM) buffer contained 25 mM Tris, 5 mM $MgCl_2$ and 0.01% BSA. Serial dilutions of an inhibitory anti-CD39 antibody were prepared starting from 20 nM in a solution of TM buffer containing soluble human CD39 (Sino Biological, Cat. No. 16020-H08B). Dilutions were performed either with or without ATP to determine the impact of premixing antibody and enzyme prior to substrate (ATP) addition. As an isotype control, an unrelated antibody was similarly diluted to examine the specificity of antibody mediated CD39 inhibition. Antibody/enzyme preparations were incubated for 1 hour in an incubator set to 37° C., then the ATP with final concentration of 20 µM was added and incubated for 1 hour at 37° C. The enzyme activity was quantified using CellTiter-Glo (CTG). The CTG luciferase reagent from the CTG Luminescent Cell Viability Assay (Promega Corporation) was used to measure the amount of ATP remaining.

The functional activity of the anti-CD39 antibodies was determined by measuring the CD39-catalyzed hydrolysis of ATP using a human myeloid leukemia mononuclear cell line (THP-1). THP-1 cells were re-suspended in TM buffer and 80 µL/well cells were seeded into the 96-well U-plates at a density of $4×10^4$ cells/well, then 40 µL/well of the antibody CD39 solution (various concentrations, 5-fold serially diluted in TM buffer from 100 nM to 1.28 µM) was added to the plates. Antibody and cells were incubated for 1 hour at an incubator set to 37° C. After incubation, ATP (50 µM in TM buffer) was added to the plates in a volume of 80 µL/well and kept in an incubator set to 37° C. for 1 hour. The plates were placed in a centrifuge set to 1500 rpm for 5 minutes and 50 µL/well of supernatant was transferred into white 96-well plates (Corning, Cat. No. 3903). CellTiter-Glo (50 µL/well) was added to corresponding wells and mixed well. The cellular enzyme inhibition of CD39 was measured on a multilabel reader (Perkin-Elmer Envision Workstation).

To test whether anti-CD39 antibodies specifically bind to human CD39, but do not cross-react with the other CD39 family members (CD39-L1, CD39-L2, CD39-L3, CD39-L4), the binding of anti-CD39 antibodies to human CD39-L1, CD39-L2, CD39-L3, and CD39-L4 was determined by ELISA. Briefly, 96-well high protein binding ELISA plates (Nunc MaxiSorp, ThermoFisher) were pre-coated with His-tagged human CD39 cross family proteins: CD39-L1, CD39-L2, CD39-L3, or CD39-L4 (0.5 µg/mL) in carbonate-bicarbonate buffer (20 mM $Na_2CO_3$, 180 mM $NaHCO_3$, pH 9.2) at left overnight at 4° C. Next day, the plates were washed three times with 300 µL/well of PBS/0.5% (v/v) Tween-20, and then blocked with PBS/2% BSA for 1 hour. After blocking, the plates were washed three times. After washing, various concentrations (6-fold serial dilution in 2% BSA/PBS from 100 nM to 0.36 pM) of test antibody were added to the plates and left in an incubator set at room temperature for 2 hours. An in-house CD39-L1 binding antibody was used as a positive control and human IgG4 isotype antibody was used as a negative control. After washing three times, 100 µL/well goat anti-human IgG Fc-HRP antibody (1:5000) was added and the plates placed in an incubator for 1 hour set to room temperature. For color development, 100 µL/well TMB substrate solution was added to the plates. After 3-5 minutes, reactions were stopped by 100 µL/well of 2M HCl. Absorbance was read at 450 nm using a SpectraMax® M5e microplate spectrophotometer. $EC_{50}$ values were obtained from four-parameter non-linear regression analysis using GraphPad Prism software.

Antibodies from hybridoma clone 19, hybridoma clone 31 and hybridoma clone 39, having a rat Fc domain, were purified from hybridoma supernatant. These antibodies are referred to herein as antibody 19, 31, and 39, respectively. The harvested hybridoma supernatants were loaded onto a Protein A column after being adjusted to pH 7.0. The bound antibodies were eluted by glycine-HCl (pH 3.5) followed immediately by neutralization with 0.1 M Tris (pH 9.0). The protein was dialyzed against PBS and filtered with a 0.22 µm membrane filter. Antibody concentration was measured by Nano Drop. The purity of the antibodies was evaluated by SDS-PAGE and HPLC-SEC.

Total RNA was isolated from hybridoma clones 19, 31 and 39 using RNeasy Plus Mini Kit (Qiagen). The first strand cDNA was reverse transcribed using oligo dT. VH and VL genes of the antibodies were amplified from cDNA using 3'-constant region degenerated primer and 5'-degenerated primer sets. The 5' degenerated primers were designed based on the upstream signal sequence-coding region of Ig variable sequences. The PCR product was then ligated into pMD18-T vector and 10 µL of the ligation product were transformed into Top10 competent cells. Transformed cells were plated on 2×YT plates with carbocinin and incubated overnight in an incubator set to 37° C. 12 positive colonies were randomly picked for DNA sequencing by Biosune.

The genes of the clones were codon optimized for mammalian expression then synthesized by GENEWIZ (Suzhou, China). The resulting plasmids comprised a gene encoding a heavy chain comprising the VH domain of antibody 19, 31, or 39 fused with human IgG4 CH1, hinge, CH2 and CH3 segments (including hinge mutation S228P), or a gene encoding a light chain comprising a VL domain fused with human Ig kappa CK domain in the light chain.

To produce antibodies ch19_IGG4.P, ch31_IGG4.P, and ch39_IGG4.P, the plasmids containing the above-described VH and VL genes were co-transfected into Expi293F cells. $2.94×10^6$/mL Expi293F cells with higher than 95% viability in 40 mL of cell culture medium were prepared for each antibody. Plasmid DNA at the final concentration of 1 µg/mL and ExpiFectamine™ 293 transfection reagent were mixed then added to cell culture medium. The cell culture was incubated in a platform shaker with the rotation rate of 150 rpm. The temperature was maintained in an incubator set to 37° C. and a $CO_2$ level of 8%. After six days of incubation, cells were pelleted using centrifugation at 4000 rpm, 25° C. for 10 minutes. Supernatants was collected for gel electrophoresis, SPR $k_{off}$ ranking and purification, if desired. The supernatant was loaded on SDS-PAGE gel, following the instructions for NuPAGE™ 4-12% Bis-Tris Protein Gels (Thermo Fisher). PageRuler™ Unstained Protein Ladder (Thermo Fisher) was used alongside with the antibody samples to determine the molecular weight of the antibody.

To purify antibody, Protein A column was pre-packed with 1 mL MabSelect Sure resin. The column was equilibrated with five column volumes (CV) of equilibrium buffer (0.1 M Tris, pH 7.0) before being loaded with the cell culture fluid. Following loading, the column was washed with 15 CV of 0.1 M Tris, pH 7.0, followed by elution with 8 CV of 0.1 M glycine, pH 3.5. The eluted samples were buffer exchanged to PBS buffer using a desalting column. Finally, the purified antibodies were analyzed by SDS-PAGE and SEC-HPLC, and then stored at −80° C.

FACS analysis was used to measure the binding of the recombinant anti-CD39 antibodies to the previously described CHO-K1 cells overexpressing human CD39 and HEK293 cells overexpressing cynomolgus monkey or murine CD39. The ability of these antibodies to inhibit cellular CD39 enzymatic activity was also determined. Table 1 shows that all three selected antibodies have high affinity for cellular human CD39 and potently inhibit the enzymatic activity of cellular human CD39.

The kinetic binding of these recombinant anti-CD39 antibodies to human CD39 was determined by surface plasmon resonance (SPR) using a Biacore 8K instrument. Recombinant antibodies were immobilized using a goat anti-human Fc IgG coated CM5 sensor chip (GE, Cat. No. 29-1496-03), and soluble His-tagged CD39 ECD protein SEQ ID NO: 72 (Sino Biological, Cat. No. 16020-H08B) was used as the analyte. The binding constants were determined at 25° C. As shown in Table 2, all three antibodies had similarly high binding affinity as measured by the slow off-rate ($k_d$) and sub-nanomolar equilibrium dissociation constant ($K_D$).

TABLE 1

Recombinant anti-CD39 rat/human chimera antibodies binding to CD39 overexpressed on CHO-K1 or HEK293 cell surface, and their blocking activity to inhibit cellular enzymatic activity.

| anti-CD39 antibody | Human CD39-CHO—K1 $EC_{50}$ (nM) | Cynomolgus Monkey CD39-HEK293 $EC_{50}$ (nM) | Human THP-1 CD39 inhibition $IC_{50}$ (nM) |
| --- | --- | --- | --- |
| ch19_IGG4.P | 9.04 | 4.30 | 0.44 |
| ch31_IGG4.P | 4.44 | 2.55 | 0.090 |
| ch39_IGG4.P | 0.79 | 0.32 | 0.042 |

TABLE 2

Kinetics of recombinant rat/human chimeric anti-CD39 antibodies binding to His-tagged human CD39 ECD.

| anti-CD39 antibody | $k_a$ ($M^{-1}s^{-1}$) | $k_d$ ($s^{-1}$) | $K_D$ (M) |
| --- | --- | --- | --- |
| ch19_IGG4.P | 9.02E+05 | 4.00E−04 | 4.43E−10 |
| ch31_IGG4.P | 1.10E+06 | 1.25E−04 | 1.13E−10 |
| ch39_IGG4.P | 3.48E+05 | 7.45E−05 | 2.14E−10 |

Example 2: Generation of Humanized Anti-CD39 Antibodies

Rat antibodies 31 and 39 were selected for humanization using the CDR grafting technique (Queen et al, Proc. Natl. Acad. Sci. USA. 86:10029-10033, 1989). The rat variable heavy (VH) and variable light (VL) sequences of antibodies 31 and 39 were used to identify the closest human germlines for each chain. Human acceptors for the VH and VL frameworks were searched for within the GenBank database (Benson et al., Nucleic Acids Res. 2005, 33, D34-D38). Frameworks were defined using an extended CDR definition where Kabat CDR1 was extended by 5 amino acids at N-terminus. The top three hits were used to derive sequences of humanized VH-genes and VL-genes and from each of these, two were selected for expressing humanized antibodies. For antibody 31 VH, IGHV4-24*01 with 64.6% sequence identity, and IGHV1-69-2*01 with 63.4% identity were selected, and for VL, IGKV7-3*01 with 84.8% sequence identity, and IGKV4-1*01 with 77.2% identity were selected (Table 3). For antibody 39 VH, IGHV3-9*01 with 87.8% sequence identity, and IGHV3-30*15 with 85.4% identity were selected, and for VL, IGKV7-3*01 with 83.5% sequence identity, and IGKV3-15*01 with 72.2% identity were selected (Table 4).

TABLE 3

Identification of human germlines and acceptors for Clone 31.

| Variable Chain | Human Germline | Human/Rat Identity (%) | Human Acceptor |
| --- | --- | --- | --- |
| VH1 | IGHV1-24*01 | 64.6% | M99642 |
| VH2 | IGHV1-69-2*01 | 63.4% | KF698734 |
| VL1 | IGKV7-3*01 | 84.8% | X12682 |
| VL2 | IGKV4-1*01 | 77.2% | Z00023 |

TABLE 4

Identification of human germlines and acceptors for Clone 39.

| Variable Chain | Human Germline | Human/Rat Identity (%) | Human Acceptor |
| --- | --- | --- | --- |
| VH1 | IGHV3-9*01 | 87.8% | M99651 |
| VH3 | IGHV3-30*15 | 85.4% | M77327 |
| VL1 | IGKV7-3*01 | 83.5% | X12682 |
| VL3 | IGKV3-15*01 | 72.2% | M23090 |

CDR grafting for each human acceptor was performed. For antibody 31, HC-CDR1 (SEQ ID NO: 18), HC-CDR2 (SEQ ID NO: 19), and HC-CDR3 (SEQ ID NO: 20) were used for the VH acceptors, and LC-CDR1 (SEQ ID NO: 22), LC-CDR2 (SEQ ID NO: 25), and LC-CDR3 (SEQ ID NO: 26) were used for the VL acceptors. For antibody 39, HC-CDR1 (SEQ ID NO: 28), HC-CDR2 (SEQ ID NO: 29), and HC-CDR3 (SEQ ID NO: 30) were used for the VH acceptors, and LC-CDR1 (SEQ ID NO: 32), LC-CDR2 (SEQ ID NO: 33), and LC-CDR3 (SEQ ID NO: 34) were used for the VL acceptors. The resultant sequences were examined for the introduction of any potential post-translation modification (PTM) sites such as isomerization, deamination, glycosylation and oxidation. Putative residues suitable for rat sequence back mutation were also identified using antibody homology graphic modeling. Following PTM site removal, antibodies were assayed to determine whether the change(s) affected antigen binding compared to the parental antibody.

Humanized genes were back-translated, codon-optimized for mammalian expression, and synthesized by GENEWIZ. Synthetic genes were re-cloned into an in-house IgG expression vector, expressed, and purified.

The kinetics of purified antibody binding to antigen were determined using Surface Plasmon Resonance (SPR) and used to rank the antibodies. The affinity of anti-CD39 antibodies to human CD39 ECD His-tagged antigen (SEQ ID NO: 72) was measured using a Biacore 8K instrument. The activator was prepared by mixing 400 mM EDC and 100 mM NHS (GE) immediately prior to injection. The CM5 sensor chip (GE, Cat. No. 29-1496-03) was activated for 420 s with the activator. Goat anti-human Fc IgG (30 μg/mL in 10 mM NaAc, pH 4.5) was then injected to the channel for 420 s at a flow rate of 10 μL/minute. The chip was deactivated by 1 M ethanolamine hydrochloric acid. Anti-CD39 antibodies were diluted to 4 μg/mL in running buffer (1×HBS-EP+) and were injected to the channel at a flow rate of 10 μL/minute for 15 s. Six concentrations (8, 4, 2, 1, 0.5 and 0.25 nM) of the CD39 antigen analyte were injected orderly to the channel at a flow rate of 30 μL/minute for an association phase of 180 s, followed by a 2400 s dissociation phase. Glycine (10 mM, pH 1.5) as regeneration buffer was injected following the dissociation phase. The sensorgrams for reference channel and buffer channel were subtracted from the test sensorgrams. The experimental data were fitted with a 1:1 binding model steady state affinity/heterogeneous ligand. The molecular weights of the CD39 antigen and anti-CD39 antibodies used in the calculation were 52 and 145 kDa, respectively.

Humanized variants of antibody 39: The K94R rat sequence back mutation was introduced into the VH1 chain (SEQ ID NO: 58) in order to maintain the binding affinity of ch39_IGG4.P, but an equivalent back mutation was not required for VH3 as R94 was present (SEQ ID NO: 59). The human framework for VL1 also introduced a glycosylation PTM site ($^{81}$NDT$^{83}$) which was removed by introducing an additional rat sequence back mutation N8ID (SEQ ID NO: 61). No rat sequence back mutations were required for VL3 (SEQ ID NO: 62).

All four VH/VL combinations of VH1 (SEQ ID NO: 58) or VH3 (SEQ ID NO: 59) with VL1 (SEQ ID NO: 61) or VL3 (SEQ ID NO: 62) for the humanized variants of 39 were then expressed, however, the VH1+VL3 pair did not express well. The genes of the variants were codon optimized for mammalian expression then synthesized by GENEWIZ: plasmids containing VH, in which the VH domain was fused with human IgG4 CH1, hinge, CH2 and CH3 segments in the heavy chain (including hinge mutation S228P); and plasmids containing VL, in which the VL domain was fused with human Ig kappa CK domain in the light chain.

The humanized IgG4 (S228P) variants of antibody 39, along with the chimera rVH+rVL/human IgG4 (S228P) variant of antibody 39, were analyzed by SPR as described above. The results are shown in Table 5.

TABLE 5

Kinetic binding affinity data for humanized IgG4 (S228P) variants of antibody 39.

| anti-CD39 antibody | VH + VL | $k_a$ (M$^{-1}$s$^{-1}$) | $k_d$ (s$^{-1}$) | $K_D$ (M) |
| --- | --- | --- | --- | --- |
| ch39_IGG4.P | rVH + rVL | 2.80E+05 | 9.40E−05 | 3.36E−10 |
| hu39.2_IGG4.P | VH1 + VL1 | 5.35E+05 | 5.01E−05 | 9.36E−11 |
| hu39.3_IGG4.P | VH1 + VL3 | 4.55E+05 | 1.16E−04 | 2.54E−10 |
| hu39.4_IGG4.P | VH3 + VL1 | 2.79E+05 | 5.15E−05 | 1.85E−10 |
| hu39.6_IGG4.P | VH3 + VL3 | 2.70E+05 | 9.38E−05 | 3.47E−10 |

An additional rat sequence back mutation (I2T) was introduced into the VL1 framework (SEQ ID NO: 60) and VL3 framework (SEQ ID NO: 63), and antibodies were expressed and analyzed, however, the VH1+VL3 pair did not express well. Table 6 shows the SPR data for these antibody variants.

TABLE 6

Kinetic binding affinity data for Clone 39 humanized IgG4 antibodies.

| anti-CD39 antibody | VH + VL | $k_a$ (M$^{-1}$s$^{-1}$) | $k_d$ (s$^{-1}$) | $K_D$ (M) |
| --- | --- | --- | --- | --- |
| hu39.1_IGG4.P | VH1 + VL1 | 3.35E+05 | 4.59E−05 | 1.37E−10 |
| hu39.8_IGG4.P | VH1 + VL3 | 5.67E+05 | 8.50E−05 | 1.50E−10 |
| hu39.5_IGG4.P | VH3 + VL1 | 3.11E+05 | 3.75E−05 | 1.21E−10 |
| hu39.7_IGG4.P | VH3 + VL3 | 3.08E+05 | 5.87E−05 | 1.91E−10 |

Humanized variants of antibody 39 show high affinity for cellular human CD39 and potently inhibit the enzymatic activity of cellular human CD39 (Table 7).

TABLE 7

Humanized IgG4 anti-CD39 antibodies binding to CD39 overexpressed on CHO-K1 or HEK293 cell surface, and their blocking activity to inhibit cellular enzymatic activity.

| anti-CD39 antibody | Human CD39-CHO-K1 EC$_{50}$ (nM) | Cynomolgus Monkey CD39-HEK293 EC$_{50}$ (nM) | Human THP-1 CD39 inhibition IC$_{50}$ (nM) |
| --- | --- | --- | --- |
| hu39.1_IGG4.P | 0.43 | 0.091 | 0.094 |
| hu39.5_IGG4.P | 0.44 | 0.088 | 0.10 |
| hu39.7_IGG4.P | 0.46 | 0.11 | 0.080 |

Humanized variants of antibody 31: The following rat sequence back mutations were introduced into the VH1 chain: E71S, D76N and A78V (SEQ ID NO: 43); and back mutations D76N and A78V were introduced into the VH2 chain (SEQ ID NO: 44), in order to maintain the binding affinity of ch31_IGG4.P. Antibody 31 has a glycosylation PTM site sequence ($^{26}$NQT$^{28}$) in LC CDR1. This was mutated in VL1 to either Q27P (SEQ ID NO: 45) or N26Q (SEQ ID NO: 46), and in VL2 to N26Q (SEQ ID NO: 49). The human framework for VL1 also introduced a glycosylation PTM site ($^{81}$NDT$^{83}$) which was removed by introducing an additional rat sequence back mutation N81D (SEQ ID NO: 47 and SEQ ID NO: 48, respectively). No rat sequence back mutations were required for VL2.

All four VH/VL combinations of VH1 (SEQ ID NO: 43) or VH2 (SEQ ID NO: 44) with VL1 (SEQ ID NO: 45, SEQ ID NO: 46, SEQ ID NO: 47, or SEQ ID NO: 48) or VL2 (SEQ ID NO: 49) for the humanized variants of antibody 31 were expressed, however, the VH1+VL2 pair did not express well. The genes of the variants were codon optimized for mammalian expression then synthesized by GENEWIZ: plasmids containing VH, in which the VH domain was fused with human IgG4 CH1, hinge, CH2 and CH3 segments in the heavy chain (including hinge mutation S228P); and plasmids containing VL, in which the VL domain was fused with human Ig kappa CK domain in the light chain.

The humanized IgG4 (S228P) variants of antibody 31, along with the chimera rVH+rVL/human IgG4 (S228P) variant of antibody 31, were analyzed by SPR as described above. The results are shown in Table 8.

TABLE 8

Kinetic binding affinity data for Clone 31 humanized IgG4 antibodies.

| anti-CD39 antibody | VH + VL | $k_a$ (M$^{-1}$ s$^{-1}$) | $k_d$ (s$^{-1}$) | $K_D$ (M) |
| --- | --- | --- | --- | --- |
| ch31_IGG4.P | rVH + rVL | 1.16E+06 | 1.50E−04 | 1.29E−10 |
| hu31.4_IGG4.P | VH1 + VL1 | 1.11E+06 | 1.96E−04 | 1.76E−10 |
| hu31.6_IGG4.P | VH2 + VL1 | 1.12E+06 | 6.84E−04 | 6.13E−10 |
| hu31.7_IGG4.P | VH2 + VL2 | 1.24E+06 | 6.15E−04 | 4.96E−10 |

Humanized variants of antibody 31 show high affinity for cellular human CD39 and potently inhibit the enzymatic activity of cellular human CD39 (Table 9).

TABLE 9

Humanized IgG4 anti-CD39 antibodies binding to CD39 overexpressed on CHO-K1 or HEK293 cell surface, and their blocking activity to inhibit cellular enzymatic activity.

| anti-CD39 antibody | Human CD39-CHO-K1 $EC_{50}$ (nM) | Cynomolgus Monkey CD39-HEK293 $EC_{50}$ (nM) | Human THP-1 CD39 inhibition $IC_{50}$ (nM) |
|---|---|---|---|
| hu31.4_IGG4.P | 1.70 | 0.78 | 0.26 |
| hu31.6_IGG4.P | 1.69 | 0.81 | 0.30 |
| hu31.7_IGG4.P | 1.83 | 1.01 | 0.25 |

Humanized variants were obtained for both antibody 31 and antibody 39 through the application of CDR grafting, followed by a small number of rat sequence back mutations to the human variable domain frameworks. These antibodies retained or improved upon the binding affinity and inhibitory potency of their respective rat/human chimeric antibody.

Example 3: Full Kinetic Binding Characterization by SPR

The genes for the VH and VL domains of the hu31.4_IGG4.P and hu39.5_IGG4.P humanized antibodies that had been codon optimized for mammalian expression were used to generate human IgG1 variants. Plasmids containing VH, in which the VH domain was fused with human IgG1 CH1, hinge, CH2 and CH3 constant domain segments in the heavy chain (HC) which included L234A and L235A (Eu numbering) mutations (SEQ ID NO: 2), and plasmids containing VL, in which the VL domain was fused with human Ig kappa CK constant domain (SEQ ID NO: 6) in the light chain (LC), were transfected into CHO-K1 cells. Antibodies hu31.4_IGG1.AA (HC with SEQ ID NO: 51 and LC with SEQ ID NO: 56) and hu39.5_IGG1.AA (HC with SEQ ID NO: 66 and LC with SEQ ID NO: 67) were expressed using a fast stable pool protocol and purified by Protein A affinity chromatography followed by size exclusion chromatography (SEC) to >95% purity, confirmed by SEC-HPLC analysis.

Antibodies hu31.4_IGG1.AA and hu39.5_IGG1.AA were analyzed by SPR using a Biacore 4000 instrument. Kinetic binding characterization was performed in two modes. In "monovalent affinity mode", the test antibody was captured using a CM3 sensor chip (GE, Cat. No. 29-1049-90) coated with amine-coupled goat anti-human IgG coated CM3 sensor chip at seven different densities. Soluble human CD39 ECD His-tagged antigen (Sino Biological, Cat. No. 16020-H08B) was the analyte; a stock solution prepared at 33.3 µM was diluted to 33 nM as the highest concentration and tested in triplicate in a three-fold dilution series over the antibody surface. In "bivalent avidity mode", the soluble human CD39 ECD His-tagged antigen was amine-coupled to a CM3 sensor chip at six different densities. The test antibodies for the analyte were prepared as a 33.3 µM stock solution, diluted to 100 nM as the highest concentration and tested in triplicate in a three-fold dilution series over the CD39 surface. The running buffer contained 10 mM HEPES, 150 mM NaCl, 0.05% tween-20 and 0.2 mg/mL BSA. Data were collected using single cycle kinetics where multiple injections were performed with increasing concentration of analyte and the dissociation phase was monitored for 1 h. All data were collected at 25° C. Response data from all six or seven surface densities were fit to a 1:1 interaction model using a local Rmax, the response for the maximal amount of complex formed. Results for experiments performed in monovalent affinity mode are shown in Table 10, and for bivalent avidity mode in Table 11.

Antibodies hu31.4_IGG1.AA and hu39.5_IGG1.AA have similar equilibrium dissociation constants ($K_D$) when analyzed in monovalent affinity mode with antibody captured on the sensor chip and soluble CD39 ECD as the analyte. However, when analyzed in a mode that permits bivalent antibody binding with CD39 ECD captured on the sensor chip and soluble antibody as the analyte, hu31.4_IGG1.AA showed a very similar $K_D$ to that obtained when analyzed in monovalent mode, which was independent of the antigen surface density. By contrast, hu39.5_IGG1.AA exhibited up to three orders of magnitude lower $K_D$, dependent upon the antigen surface density, indicating that this antibody is able to bind in a bivalent mode to more than one immobilized CD39 molecule on the surface of the chip and hence display enhanced kinetic binding affinity due to avidity.

TABLE 10

Kinetic data for hu31.4_IGG1.AA and hu39.5_IGG1.AA from SPR performed with immobilized antibody and soluble CD39 ECD analyte.

| anti-CD39 antibody | Rmax (RU) | $k_a$ (M$^{-1}$s$^{-1}$) | $k_d$ (s$^{-1}$) | $K_D$ (M) |
|---|---|---|---|---|
| hu31.4_IGG1.AA | 244.80(3) | 1.36(1)E+06 | 2.510(1)E−04 | 1.85(1)E−10 |
|  | 177.77(4) | 1.51(2)E+06 | 2.877(1)E−04 | 1.90(2)E−10 |
|  | 125.98(2) | 1.36(1)E+06 | 2.941(1)E−04 | 2.16(2)E−10 |
|  | 120.12(1) | 1.21(1)E+06 | 3.039(1)E−04 | 2.52(1)E−10 |
|  | 50.588(7) | 2.96(1)E+06 | 3.022(1)E−04 | 1.02(1)E−10 |
|  | 48.40(1) | 2.24(2)E+06 | 3.377(1)E−04 | 1.51(1)E−10 |
|  | 31.787(5) | 1.56(1)E+06 | 3.389(1)E−04 | 2.18(1)E−10 |
| Average |  | 1.7[6]E+06 | 3.0[3]E−04 | 1.9[5]E−10 |
| hu39.5_IGG1.AA | 268.14(4) | 2.55(1)E+05 | 7.601(6)E−05 | 2.98(2)E−10 |
|  | 255.16(3) | 3.03(2)E+05 | 7.695(5)E−05 | 2.54(2)E−10 |
|  | 211.73(2) | 3.06(2)E+05 | 7.043(5)E−05 | 2.30(2)E−10 |
|  | 89.36(1) | 3.13(2)E+05 | 7.511(6)E−05 | 2.40(2)E−10 |
|  | 84.17(1) | 3.44(2)E+05 | 7.120(5)E−05 | 2.07(1)E−10 |

TABLE 10-continued

Kinetic data for hu31.4_IGG1.AA and hu39.5_IGG1.AA from SPR performed with immobilized antibody and soluble CD39 ECD analyte.

| anti-CD39 antibody | Rmax (RU) | $k_a$ (M$^{-1}$s$^{-1}$) | $k_d$ (s$^{-1}$) | $K_D$ (M) |
|---|---|---|---|---|
|  | 66.79(1) | 2.75(2)E+05 | 7.149(5)E−05 | 2.60(1)E−10 |
|  | 64.50(1) | 3.34(2)E+05 | 6.581(5)E−05 | 1.97(1)E−10 |
| Average |  | 3.0[3]E+05 | 7.2[4]E−05 | 2.4[3]E−10 |

Note:
The numbers in parentheses represent the standard errors in the last reported digits from the non-linear least squares fitting routine. The numbers in brackets represent the experimental deviation taken from the average of different density surfaces.

TABLE 11

Kinetic data for hu31.4_IGG1.AA and hu39.5_IGG1.AA from SPR performed with immobilized CD39 ECD and soluble antibody analyte.

| anti-CD39 antibody | Rmax (RU) | $k_a$ (M$^{-1}$s$^{-1}$) | $k_d$ (s$^{-1}$) | $K_D$ (M) |
|---|---|---|---|---|
| hu31.4_IGG1.AA | 1568.5(1) | 1.634(4)E+05 | 9.97(2)E−06 | 6.11(2)E−11 |
|  | 896.01(8) | 2.621(4)E+05 | 2.753(4)E−05 | 1.050(2)E−10 |
|  | 225.80(5) | 2.493(8)E+05 | 5.87(1)E−05 | 2.356(9)E−10 |
|  | 38.30(2) | 3.13(2)E+05 | 1.590(2)E−04 | 5.07(4)E−10 |
|  | 9.67(1) | 6.4(1)E+05 | 2.482(7)E−04 | 3.86(7)E−10 |
|  | 1.472(2) | 5.9(1)E+05 | 2.50(1)E−04 | 4.3(1)E−10 |
| Average |  | 4[2]E+05 | 1[1]E−04 | 3[2]E−10 |
| hu39.5_IGG1.AA | 2230.22(5) | 3.331(6)E+05 | 1.2(1)E−07 | 4(3)E−13 |
|  | 524.16(1) | 6.828(9)E+05 | 4.48(1)E−06 | 6.56(2)E−12 |
|  | 420.45(2) | 1.518(5)E+06 | 1.514(2)E−05 | 9.98(3)E−12 |
|  | 96.66(1) | 3.02(2)E+06 | 4.946(7)E−05 | 1.64(1)E−11 |
|  | 58.42(2) | 3.73(5)E+06 | 8.25(1)E−05 | 2.21(3)E−11 |
|  | 7.757(3) | 4.34(7)E+06 | 1.115(2)E−04 | 2.57(4)E−11 |
| Average |  | 2[2]E+06 | 4.4[5]E−05 | 1[1]E−11 |

Note:
The numbers in parentheses represent the standard errors in the last reported digits from the non-linear least squares fitting routine. The numbers in brackets represent the experimental deviation taken from the average of different density surfaces.

Example 4: Binding of Anti-CD39 Antibodies to Endogenous Human CD39

Variants of antibodies 19, 31, and 39 were tested for binding to the surface of primary human cells. Binding was assessed in the absence of ATP and in the presence of high ATP (400 µM).

Purified Monocyte Binding: Antibodies were tested for binding to human CD39 expressed on the cell surface of primary human monocytes (CD14$^+$) by flow cytometry. Monocytes were positively selected from peripheral blood (leukopak or LRS chamber) using EasySep Human CD14 Positive Selection Kit II (Stem Cell, Cat. No. 17858), frozen in Bambanker (Wako, Cat. No. 302-14681), and stored in liquid nitrogen for future use. On the day of the assay, frozen monocytes were defrosted, rinsed, and resuspended in 1:25 Fc block (BD, Cat. No. 564220) and 1:250 aqua viability dye (Invitrogen, Cat. No. L34966A) in DPBS and incubated for 15 minutes at room temperature in the dark. In a polypropylene v-bottom 96-well plate, cells were plated at 0.2-0.5×10$^6$ cells per well. Zero or 400 µM ATP was added and incubated for 30 minutes at 4° C. followed by the addition of test antibodies and an additional 30 minutes incubation at 4° C. After two washes with DPBS, 1 µg/mL of PE-labeled mouse anti-human IgG4 secondary (Southern Biotech, Cat. No. 9200-09) was added for 30 minutes at 4° C. for antibody detection. After two washes with DPBS, cells were fixed with 50 µL IC Fixation Buffer (Invitrogen, Cat. No. 00-8222-49) for 20 minutes at room temperature. Cells were then washed once and resuspended in DPBS and subjected to flow cytometry using the BD LSR Fortessa X-20 Cell Analyzer. The geometric mean of the fluorescence intensity of PE was obtained for the live single cell population. EC$_{50}$ values were calculated using standard 4-parameter curve fitting in GraphPad Prism (Table 12).

TABLE 12

EC$_{50}$ (nM) values of antibodies binding to human CD39 on purified human monocytes. Data in this table represents one biological donor.

| anti-CD39 antibody | 0 µM ATP | 400 µM ATP |
|---|---|---|
| ch19_IGG4.P | 61 | 49 |
| ch31_IGG4.P | 27 | 28 |
| hu31.2_IGG4.P | 15 | 25 |
| hu31.3_IGG4.P | 7.7 | 26 |
| hu31.4_IGG4.P | 16 | 26 |
| ch39_IGG4.P | 0.69 | 1.3 |
| hu39.1_IGG4.P | 1.2 | 1.4 |
| hu39.4_IGG4.P | 1.4 | 10 |
| hu39.5_IGG4.P | 3.9 | 10 |
| hu39.6_IGG4.P | 3.5 | 6.5 |
| hu39.7_IGG4.P | 5.7 | 6.9 |

PBMC Binding: IgG1 isotypic variants of antibody 31 and antibody 39 were also tested for binding to human CD39 expressed on the cell surface of PBMCs, gated on CD14$^+$ (monocyte) and CD19$^+$ (B cell) populations, by flow cytometry. In this experiment, an antibody reported to bind and inhibit human CD39, referred to herein as huBMK2_IGG1.AEASS, was used as a comparator. The amino acid sequence of the mature heavy chain for huBMK2_IGG1.AEASS is SEQ ID NO: 73. The amino acid sequence of the mature light chain for huBMK2_IGG1.AEASS is SEQ ID NO: 74. Previously purified, frozen PBMCs were defrosted, rinsed, and resuspended in 1:25 Fc block (BD, Cat. No. 564220) and 1:250 aqua viability dye (Invitrogen, Cat. No. L34966A) in DPBS and incubated for 15 minutes at room temperature in the dark. Cells were then washed in DPBS and resuspended in filtered staining buffer: DPBS supplemented with 5% goat serum (Gibco, Cat. No. 16210-064). In a polypropylene v-bottom 96-well plate, cells were plated at $0.5 \times 10^6$ cells per well in staining buffer. Zero or 400 µM ATP was added and incubated for 30 minutes at 4° C. followed by the addition of a test antibody and an additional 30-minute incubation at 4° C. After two washes in staining buffer, 0.8 µg/test CD14 FITC (Invitrogen, Cat. No. 11-0149-42, clone 61D3) and 0.5 µg/test CD19 eFluor 450 (eBioscience, Cat. No. 48-0199-42, clone HIB19) were added to the PBMCs. CD39 binding by the test antibodies was detected with 0.5 µg/mL of PE-labeled Goat Anti-Human IgG (Southern Biotech, Cat. No. 2048-09) for 30 minutes at 4° C. Cells were then washed and resuspended in DPBS and subjected to flow cytometry using the BD LSR Fortessa X-20 Cell Analyzer. The geometric mean of the fluorescence intensity of PE was obtained for the live single cell population gated on either monocytes (CD14$^+$) or B cells (CD19$^+$). EC$_{50}$ values (Table 13) were calculated using standard 4-parameter curve fitting in GraphPad Prism. A representative graph from one donor is shown in FIG. 1.

TABLE 13

EC$_{50}$ (nM) of antibodies binding to human CD39 on monocytes and B cells in human PBMCs. Error reported is standard error of the mean (SEM). N is distinct biological donors.

|  | Monocytes | | B cells | |
| --- | --- | --- | --- | --- |
|  | 0 µM ATP | 400 µM ATP | 0 µM ATP | 400 µM ATP |
| hu31.4_IGG1.AA | — | — | 1 ± 0.3, N = 8 | 1 ± 0.3, N = 6 |
| hu39.5_IGG1.AA | 0.3 ± 0.04, N = 8 | 0.5 ± 0.3, N = 6 | 0.2 ± 0.06, N = 8 | 0.3 ± 0.09, N = 6 |
| huBMK2_IGG1.AEASS | 1 ± 0.3, N = 8 | 1 ± 0.2, N = 6 | 0.9 ± 0.09, N = 8 | 0.8 ± 0.08, N = 6 |

Overall, variants of antibodies 19, 31, 39 showed potent binding to the surface of primary cells. The potency was determined to be 39 variants>31 variants>19 variants. The potency ranking of variants of 31 and 39 was maintained with the isotype switch from IGG4.P to IGG1.AA and potency was maintained in the presence of high ATP. A humanized IgG1 variant of antibody 31, hu31.4_IGG1.AA, and a humanized IgG1 variant of antibody 39, hu39.5_IGG1.AA, showed potent binding in comparison to a previously described anti-CD39 antibody, with hu39.5_IGG1.AA>huBMK2_IGG1.AEASS>hu31.4_IGG1.AA.

Example 5: Inhibition of Human CD39 Enzymatic Activity

Variants of antibodies 19, 31, and 39 were tested for inhibition of human CD39 enzymatic activity. Inhibition was assessed using soluble, recombinant CD39 and CD39 expressed on the cell surface of primary human cells or human cell lines derived from patient tumor samples. Inhibition was assessed in the presence of low and high ATP (20 µM and 400 µM, respectively).

Recombinant CD39 Inhibition: The potency with which antibodies described in previous examples inhibited CD39 enzymatic activity was assessed first using recombinant human CD39. Recombinant human CD39 biochemical assay was performed in assay buffer consisting of 25 mM Tris-HCl, pH 7.4, 5 mM MgCl$_2$, and 0.01% BSA. A 14 point, 1:3 master serial dilution of test antibodies was prepared in assay buffer to span a final concentration range of 200 nM to 0.125 pM. Five microliters of test antibodies at 5-fold final concentration in assay buffer was added to each well of a 384-well plate. Ten microliters of 1.56 nM of recombinant human CD39 resuspended in assay buffer were added to each well and the plate incubated for a further 60 minutes at 37° C. prior to addition of 10 µL of 50 µM ATP in assay buffer. Final assay conditions comprised 0.625 nM of recombinant human CD39 and 20 µM of ATP substrate. After a further 30 minutes of incubation at 37° C., 25 µL of Kinase Glo Plus reagent were added to each well of the 384-well plate. The reaction was measured using Kinase-Glo reagent kit (Promega, Cat. No. V3771) according to manufacture protocol. Amount of ATP remaining after CD39 inhibition was assessed as a function of luminescence generated and quantitated using an Envision 2102 Multilabel Reader fitted with a luminescence filter. CD39 enzymatic activity was evaluated as a correlate of ATP levels remaining. Percentage maximum activity in each test well was calculated based on assay buffer (maximum activity, 0% inhibition) and no enzyme control wells (baseline activity, 100% inhibition). The IC$_{50}$ values of the test antibodies were determined from a dose response curve fitted using a standard four parameter fit equation. Data are shown in Table 14.

TABLE 14

Potency of antibodies against soluble, recombinant CD39.

| Anti-CD39 antibody | IC$_{50}$ (nM) | Max Inhibition (%) |
| --- | --- | --- |
| ch19_IGG4.P | 1.8 | 100% |
| ch31_IGG4.P | 1.3 | 100% |
| hu31.4_IGG1.AA | 0.30 | 86% |
| ch39_IGG4.P | 2.3 | 100% |
| hu39.1_IGG4.P | 0.26 | 92% |
| hu39.5_IGG1.AA | 0.19 | 80% |

SK-MEL-5 CD39 Inhibition: Inhibition of CD39 enzymatic activity was also assessed using SK-MEL-5 cells, which is a melanoma cell line established from patient-derived tumor samples. On the day of the experiment, one vial of previously frozen SK-MEL-5 cells was thawed, and cells were resuspended in 10 mL of assay buffer consisting of 20 mM HEPES, pH 7.4, 137 mM NaCl, 5.4 mM KCl, 1.3 mM CaCl$_2$), 4.2 mM NaHCO$_3$ and 0.1% glucose. A 14 point, 1:3 master serial dilution of anti-CD39 antibodies was prepared in assay buffer to span a final concentration range of 100 nM to 0.063 pM. Twenty microliters of test antibodies at 5-fold final concentration in assay buffer was added to each well of a 96-well round-bottomed polypropylene plate. Forty microliters of SK-MEL-5 cells were added to each well and the plate incubated for a further 60 minutes at 37° C. prior to addition of 40 µL of 50 µM ATP in assay buffer. Final assay conditions comprised 10,000 cells per well and 20 µM of ATP substrate. After a further 60 minutes of incubation at 37° C. and 5% $CO_2$, the plate was centrifuged at 225×g for 10 minutes. Thirty microliters of supernatant were transferred to a 96-well assay plate (Corning, Cat. No. 3912) and the amount of ATP remaining in the reaction was measured using Kinase-Glo reagent kit (Promega, Cat. No. V3771) according to manufacture protocol. Amount of ATP remaining after CD39 inhibition was assessed as a function of luminescence generated and quantitated using an Envision 2102 Multilabel Reader fitted with a luminescence filter. CD39 enzymatic activity was evaluated as a correlate of ATP levels remaining. Percentage maximum activity in each test well was calculated based on assay buffer (maximum activity, 0% inhibition) and no cell control wells (baseline activity, 100% inhibition). The $IC_{50}$ values of the test antibodies were determined from a dose response curve fitted using a standard four parameter fit equation. Data are shown in Table 15.

TABLE 15

Potency of antibodies against CD39 expressed on the surface of SK-MEL-5 cells.

| Anti-CD39 antibody | $IC_{50}$ (nM) | Max Inhibition (%) |
|---|---|---|
| ch19_IGG4.P | 5.4 | 55% |
| ch31_IGG4.P | 2.4 | 63% |
| hu31.3_IGG4.P | 0.61 | 71% |
| hu31.4_IGG4.P | 1.1 | 71% |
| ch39_IGG4.P | 0.56 | 63% |
| hu39.1_IGG4.P | 0.16 | 65% |
| hu39.4_IGG4.P | 0.13 | 60% |
| hu39.5_IGG4.P | 0.14 | 66% |
| hu39.6_IGG4.P | 0.12 | 55% |
| hu39.7_IGG4.P | 0.20 | 65% |

THP-1 CD39 Inhibition: Inhibition of CD39 enzymatic activity was assessed in a second tumor cell line, specifically a human monocytic cell line derived from an acute monocytic leukemia patient. On the day of the experiment, one vial of previously frozen THP-1 cells was thawed and cells were resuspended in 10 mL of assay buffer consisting of 20 mM HEPES, pH 7.4, 137 mM NaCl, 5.4 mM KCl, 1.3 mM $CaCl_2$), 4.2 mM $NaHCO_3$ and 0.1% glucose. A 14 point, 1:3 master serial dilution of anti-CD39 antibodies was prepared in assay buffer to span a final concentration range of 100 nM to 0.063 pM. Twenty microliters of test antibodies at 5-fold final concentration in assay buffer was added to each well of a 96-well round-bottomed polypropylene plate. Forty microliters of THP-1 cells were added to each well and the plate incubated for a further 60 minutes at 37° C. prior to addition of 40 µL of 50 µM ATP in assay buffer. Final assay conditions comprised 40,000 cells per well and 20 µM of ATP substrate. After a further 60 minutes of incubation at 37° C. and 5% $CO_2$, the plate was centrifuged at 225×g for 10 minutes. Thirty microliters of supernatant were transferred to a 96-well assay plate (Corning, Cat. No. 3912) and the amount of ATP remaining in the reaction was measured using Kinase-Glo reagent kit (Promega, Cat. No. V3771) according to manufacture protocol. Amount of ATP remaining after CD39 inhibition was assessed as a function of luminescence generated and quantitated using an Envision 2102 Multilabel Reader fitted with a luminescence filter. CD39 enzymatic activity was evaluated as a correlate of ATP levels remaining. Percentage maximum activity in each test well was calculated based on assay buffer (maximum activity, 0% inhibition) and no cell control wells (baseline activity, 100% inhibition). The $IC_{50}$ values of the test antibodies were determined from a dose response curve fitted using a standard four parameter fit equation. Data are shown in Table 16.

TABLE 16

Potency of antibodies against CD39 expressed on the surface of THP-1 cells.

| anti-CD39 antibody | $IC_{50}$ (nM) | Max Inhibition (%) |
|---|---|---|
| ch19_IGG4.P | 0.75 | 75% |
| ch31_IGG4.P | 0.14 | 86% |
| hu31.3_IGG4.P | 0.080 | 79% |
| hu31.4_IGG4.P | 0.095 | 73% |
| hu31.4_IGG1.AA | 0.53 | 62% |
| ch39_IGG4.P | 0.11 | 67% |
| hu39_1 IGG4.P | 0.077 | 78% |
| hu39.4_IGG4.P | 0.064 | 76% |
| hu39.5_IGG4.P | 0.062 | 83% |
| hu39.6_IGG4.P | 0.058 | 79% |
| hu39.7_IGG4.P | 0.071 | 77% |
| hu39.5_IGG1.AA | 0.075 | 55% |

Figure 2:
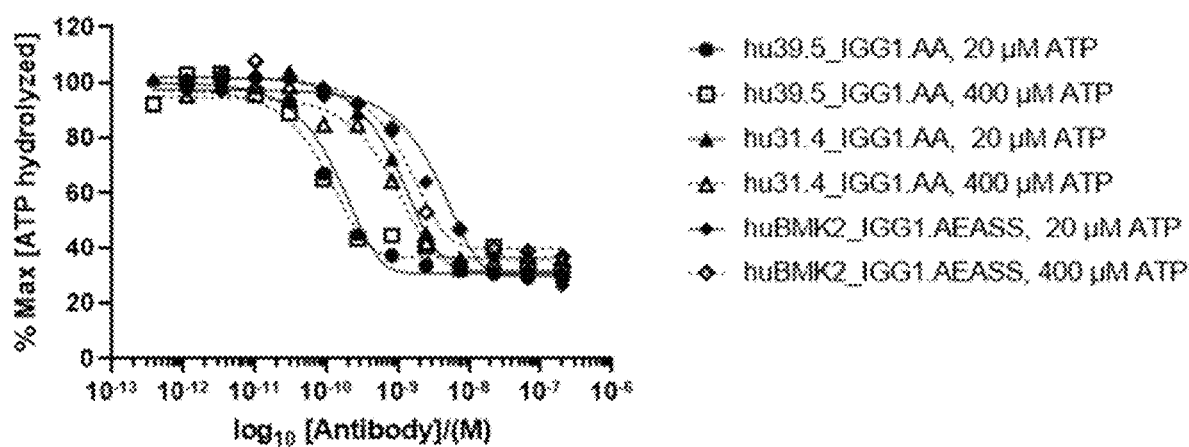
FIG. 2 is a graph depicting inhibition of the enzymatic activity of human CD39 expressed on the surface of human monocytes in the presence of 20 or 400 micromolar ATP. The graph shows representative data from a single human donor. Percent (%) maximum inhibition in on the y-axis and antibody concentration is on the x-axis.

Purified Monocyte CD39 Inhibition: Potency was additionally assessed using primary human monocytes. On the day of the experiment, two vials of previously frozen $CD14^+$ positively selected human monocytes (donor 1003773) cells were thawed, and cells were resuspended in 10 ml of assay buffer consisting of 20 mM HEPES, pH 7.4, 137 mM NaCl, 5.4 mM KCl, 1.3 mM $CaCl_2$), 4.2 mM $NaHCO_3$ and 0.1% glucose. A 14 point, 1:3 master serial dilution of test antibodies was prepared in assay buffer to span a final concentration range of 200 nM to 0.13 pM. Twenty microliters of test antibodies at 5-fold final concentration in assay buffer was added to each well of a 96-well round-bottomed polypropylene plate. Forty microliters of human monocytes cells were added to each well and the plate incubated for a further 60 minutes at 37° C. prior to addition of 40 µL of 50 µM or 1000 µM ATP in assay buffer. Final assay conditions comprised 20,000 cells per well and 20 µM or 400 µM of ATP substrate. After a further 60 minutes of incubation at 37° C. and 5% $CO_2$, the plate was centrifuged at 225×g for 10 minutes. Fifteen microliters of supernatant were transferred to a 96-well assay plate (Corning Cat. No. 3912) and the amount of AMP produced in the reaction was measured using AMP-Glo reagent kit (Promega, Cat. No. 5012) according to manufacture protocol. Supernatant from reaction plate with 400 µM ATP substrate were diluted 1:8 fold with assay buffer before transfer and addition of AMP-Glo reagent. Amount of AMP produced after CD39 inhibition was assessed as a function of luminescence generated and quantitated using an Envision 2102 Multilabel Reader fitted with a luminescence filter. CD39 enzymatic activity was evaluated as a correlate of AMP levels. Percentage maximum activity in each test well was calculated based on assay buffer (maximum activity, 0% inhibition) and no cell control wells (baseline activity, 100% inhibition). The $IC_{50}$ values of the test antibodies were determined from a dose response curve fitted using a standard four parameter fit equation. Data are shown in Table 17 and Table 18, and in FIG. 2.

TABLE 17

Potency of antibodies against CD39 expressed on the surface of human monocytes in the presence of 20 µM ATP.

| anti-CD39 antibody | IC$_{50}$ (nM) | Max Inhibition (%) |
| --- | --- | --- |
| hu31._IGG4.P | 0.42 | 74% |
| hu31.4_IGG4.P | 0.59 | 74% |
| hu39.1_IGG4.P | 0.15 | 74% |
| hu39.4_IGG4.P | 0.13 | 71% |
| hu39.5_IGG4.P | 0.15 | 72% |
| hu39.6_IGG4.P | 0.21 | 68% |
| hu39.7_IGG4.P | 0.20 | 70% |
| hu39.5_IGG1.AA | 0.10 | 69% |
| hu31.4_IGG1.AA | 1.0 | 69% |
| huBMK2_IGG1.AEASS | 2.7 | 74% |

TABLE 18

Potency of antibodies against CD39 expressed on the surface of human monocytes in the presence of 400 µM ATP.

| anti-CD39 antibody | IC$_{50}$ (nM) | Max Inhibition (%) |
| --- | --- | --- |
| hu31.2_IGG4.P | 0.87 | 71% |
| hu39.1_IGG4.P | 0.33 | 76% |
| hu39.2_IGG4.P | 0.14 | 80% |
| hu39.4_IGG4.P | 0.45 | 73% |
| hu39.5_IGG4.P | 0.20 | 60% |
| hu39.6_IGG4.P | 0.38 | 73% |
| hu39.7_IGG4.P | 0.39 | 70% |
| hu39.5_IGG1.AA | 0.083 | 62% |
| hu31.4_IGG1.AA | 0.70 | 63% |
| huBMK2_IGG1.AEASS | 1.40 | 62% |

Overall, variants of antibodies 19, 31, 39 showed potent inhibition of soluble and surface human CD39 enzymatic activity. Importantly, potency was maintained in the presence of high ATP.

Example 6: Immunostimulatory Effects of CD39 Inhibition

To evaluate the effectiveness of the anti-CD39 antibodies produced in Examples 1-3, downstream functional consequences of inhibiting CD39 enzymatic activity at the surface of myeloid cells were evaluated in vitro.

Macrophage IL-1β/IL-18 Release Assay: The NLRP3 inflammasome is a multiprotein, cytosolic complex that once oligomerized allows for the cleavage and activation of pro-caspase-1 proteins into caspase-1. Caspase-1 then facilitates IL-1β and IL-18 maturation via the cleavage of their inactive pro-isomers (pro-IL-1β and pro-IL-18) into their active and secreted form. These cytokines are involved in innate immune responses, creating a generalized pro-inflammatory environment.

Figure 3:
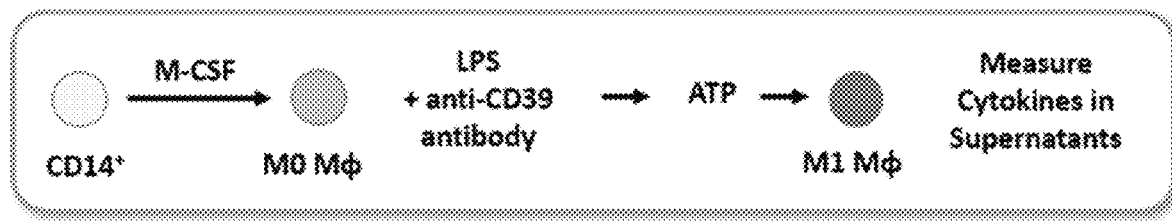
FIG. 3 is a schematic depicting key steps in the macrophage cytokine release assay described in Example 6. Mφ=macrophage.
Figure 4A:
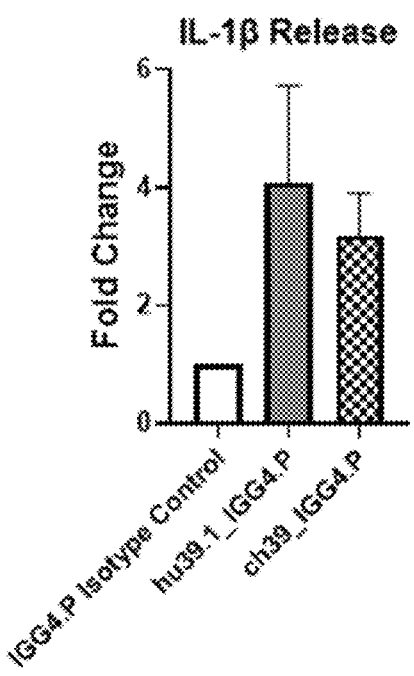
FIG. 4A, FIG. 4B, FIG. 4C, FIG. 4D, FIG. 4E, FIG. 4F depict the results of a macrophage cytokine release assay. Relative amounts of cytokines in the supernatant of macrophages treated with 10 nM (FIG. 4A) or 100 nM (FIG. 4B-F) of anti-CD39 antibodies or isotype control. Fold change is normalized to the isotype control per donor and two (FIG. 4C, FIG. 4D) or three (FIG. 4A, FIG. 4B, FIG. 4E, FIG. 4F) donors were run per test. The height of the bar is the average fold-change among normalized donors and the error bar is the SEM.
Figure 4B:
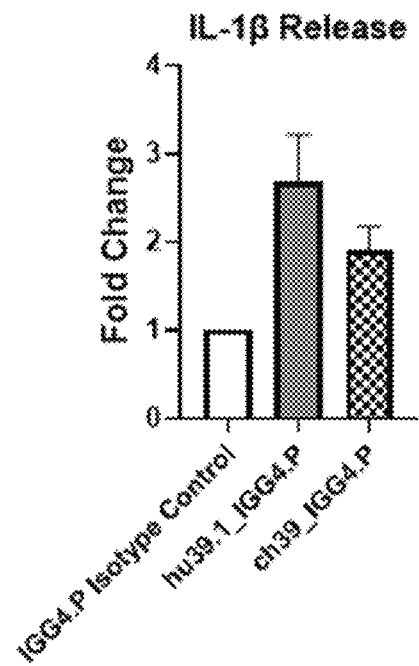
Figure 4C:
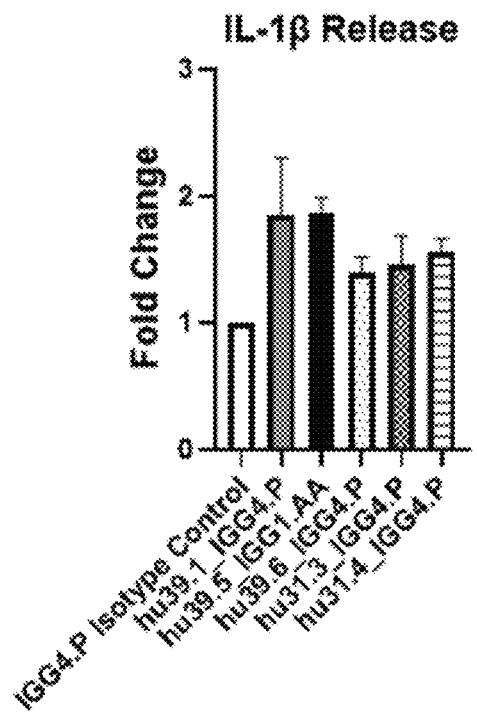
Figure 4D:
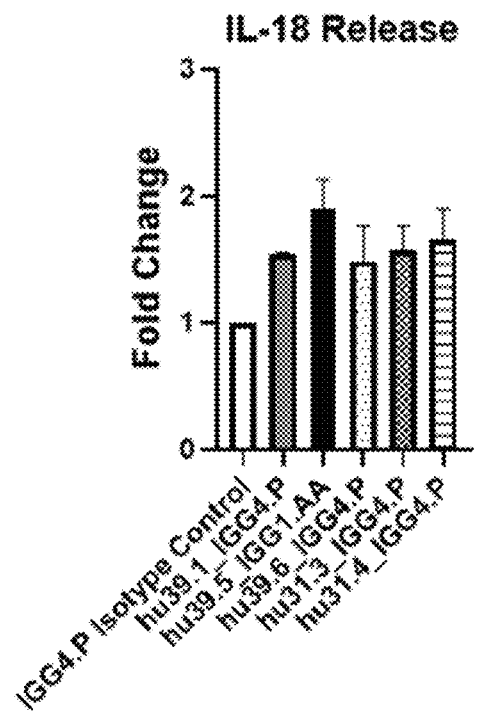
Figure 4E:
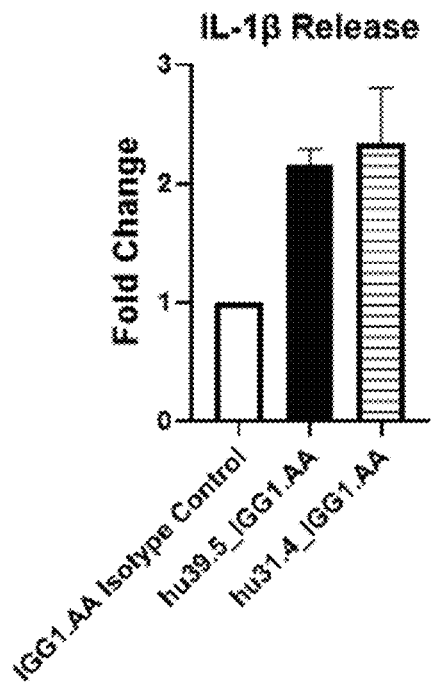
Figure 4F:
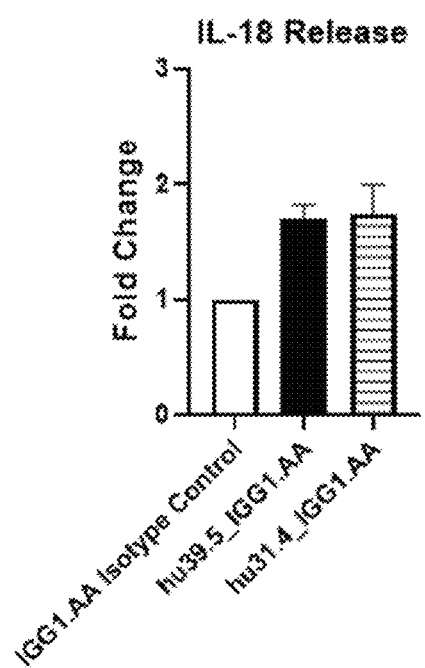

Anti-CD39 antibodies were tested for their ability to activate the NLRP3 inflammasome on macrophages, by measuring the secretion of mature IL-1β and IL-18. A schematic of the assay is shown in FIG. 3. On day 0, previously isolated, positively selected CD14$^+$ monocytes (see Example 4 were defrosted and cultured in RPMI media with 10% heat inactivated FBS, 1% Glutamax, 1% Penicillin/Streptomycin and 50 ng/mL recombinant human M-CSF (R&D, Cat. No. 216MCC/CF) at a density of approximately 15×10$^6$ CD14$^+$ monocytes per 10 cm dish (Thermo Scientific Nunclon Delta Surface, Cat. No. 150464). On day 5, non-adherent cells were washed off and the adherent macrophages were collected by scraping and plated at a density of 0.125×10$^6$ cells per well in 24-well plates. The cells were then incubated overnight to allow adherence. The following day, the cells were treated with 1 ng/mL LPS (InvivoGen, Cat. No. tlrl-peklps) followed by treatment with test antibodies or IgG controls at 10 or 100 nM and incubated for 3 hours at 37° C., 5% CO$_2$. The cells were then treated with 500 µM ATP (Life Technologies, Cat. No. R0441) and incubated for an additional 2-4 hours at 37° C., 5% CO$_2$. The supernatants were collected and IL-1β levels were analyzed by CBA (BD, Cat. No. 558279) or ELISA (R&D, Cat. No. QK201) following manufacturer's instructions. IL-18 levels in the supernatants were analyzed by ELISA (R&D, Cat. No. DL180) following manufacturer's instructions. Experiments were performed in technical quadruplicate per donor, averaged, and then normalized to the isotype control for each donor. As shown in FIG. 4, ch39_IGG4.P, hu39.1_IGG4.P, hu39.5_IGG1.AA, and hu31.4_IGG1.AA, increased IL-1β and IL-18 release, relative to isotype control, from in vitro derived macrophages.

Monocyte-derived Dendritic Cell Assay: Antibodies were also tested for their ability to mature monocyte-derived dendritic cells (moDCs) in the presence of ATP. On day 0, positively selected monocytes were resuspended in RPMI supplemented with 10% heat inactivated FBS, 1% Glutamax, 1% Penicillin/Streptomycin, 100 ng/mL recombinant human GM-CSF (R&D, Cat. No. 215-GM/CF) and 100 ng/mL IL-4 (Peprotech, Cat. No. 200-04), and seeded at 4×10$^6$ cells per well in 6-well plates (Falcon, Cat. No. 353046). On day 6, the moDCs were collected and seeded at 0.5×10$^6$ cells per well in a 24-well Upcell plate (Thermo Fisher, Cat. No. 174899) and treated with 10 µg/mL isotype control or anti-CD39 antibodies for 1 hour at 37° C., 5% CO$_2$ followed by either 0 µM or 300 µM ATP for 18 hours at 37° C., 5% CO$_2$. On Day 7, the moDCs were transferred into a polypropylene v-bottom 96-well plate for staining. All wells were resuspended in 1:25 Fc block (BD, Cat. No. 564220) and 1:250 aqua viability dye (Invitrogen, Cat. No. L34966A) in DPBS and incubated for 15 minutes at room temperature in the dark. After one wash with DPBS, the cells were stained with the following antibodies [1 µg/test CD83 PE-Cy7 (BD, Cat. No. 561132), 1 µg/test CD86 BV605 (BD, Cat. No. 562999), 0.8 µg/test CD14 FITC (Invitrogen, Cat. No. 11-0149-42)] or the corresponding isotype controls [PE-Cy7 Mouse IgG1 κ (BD, Cat. No. 565573), BV605 Mouse IgG1 κ (BD, Cat. No. 562652), FITC Mouse IgG1 κ (eBiosciences, Cat. No. 11-4714-41)] for 30 minutes at 4° C. Surface levels of the dendritic cell maturation markers CD83 and CD86 should increase with the maturation of dendritic cells, while CD14, a monocyte marker, should decrease. After one wash in DPBS, cells were fixed with 50 µL IC Fixation Buffer (Invitrogen, Cat. No. 00-8222-49) for 20 minutes at room temperature. Cells were then washed and resuspended in DPBS and subjected to flow cytometry using the BD LSR Fortessa X-20 Cell Analyzer. For CD83 and CD14 percent of parent gates were set on the isotype controls (<5% of total events) for each donor on the 0 µM ATP condition. For CD86, >90% of the cells were positive compared to isotype control in the control-treated condition, so instead, the geometric mean of the fluorescence intensity of the fluorophore was reported for the live single cell population.

Figure 5A:
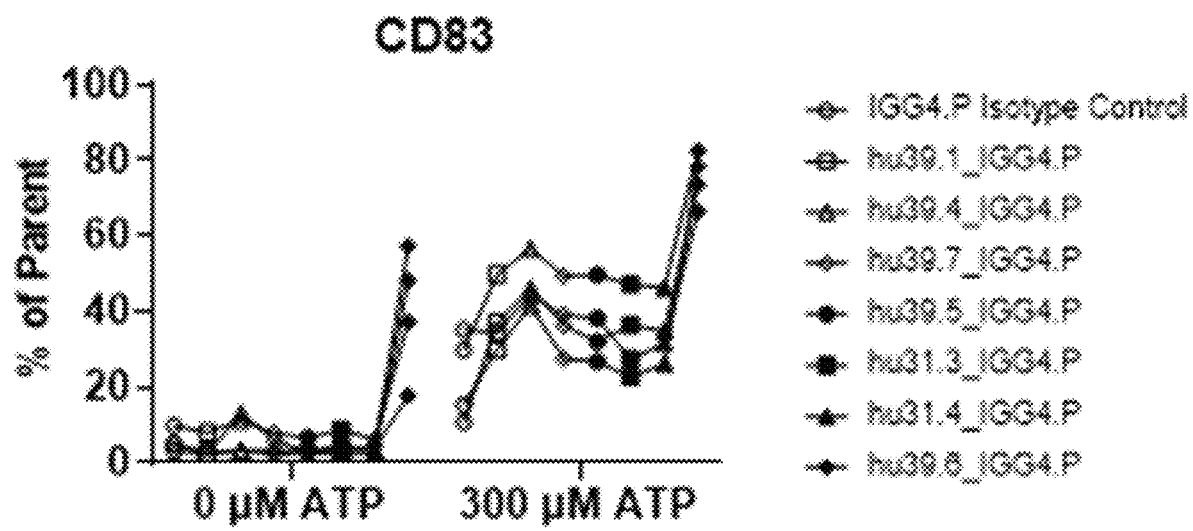
FIG. 5A, FIG. 5B, and FIG. 5C depict the results of a monocyte-derived dendritic cell (moDC) assay. Extracellular markers CD83 (FIG. 5A), CD86 (FIG. 5B), and CD14 (FIG. 5C) were measured on the surface of moDCs in the presence or absence of ATP ±anti-CD39 or isotype control. Each line represents one biological donor, where connected symbols are from the same donor, N=4.
Figure 5B:
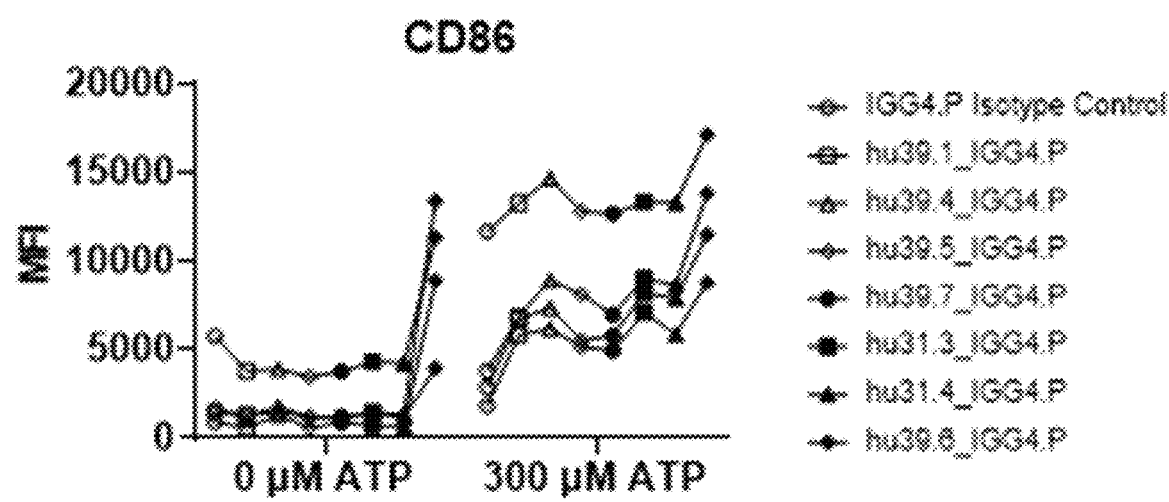
Figure 5C:
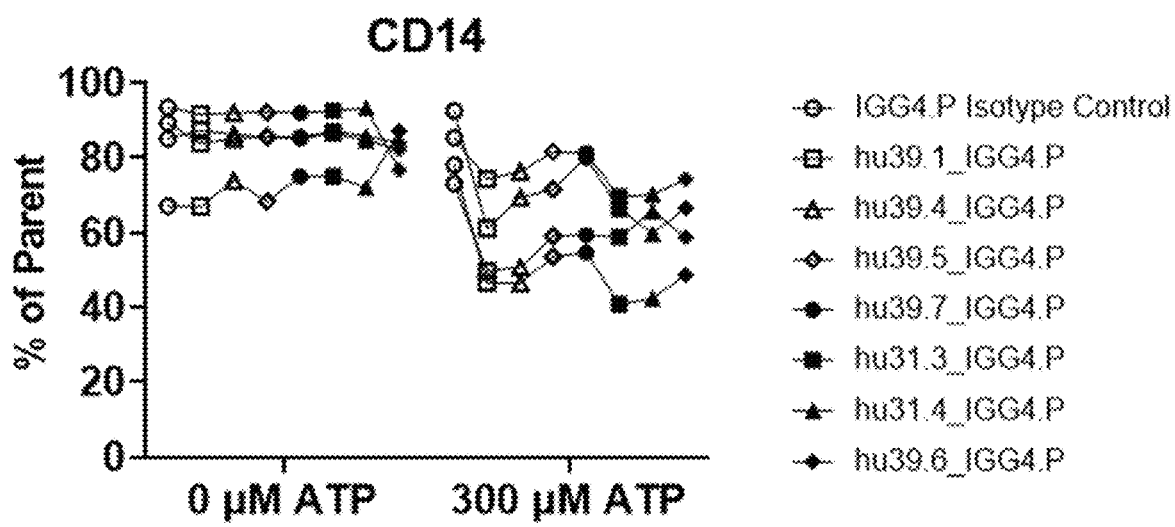

As shown in FIG. 5A and FIG. 5B, ATP matured the moDCs as seen by an increase in the dendritic cell maturation markers CD83 and CD86. Inhibition of CD39 enzymatic activity by the addition of anti-CD39 antibody, but not isotype control, enhanced maturation, further increasing the percentage of cells expressing CD83 and the surface amounts of CD86 per cell. Upon anti-CD39 addition in the presence of ATP, the percentage of cells expressing the monocyte marker CD14 also decreased (FIG. 5C). With the exception of hu39.6_IGG4.P the effect on CD83, CD86, and CD14 was an ATP-dependent effect.

Overall, the above data suggest enzymatic inhibition of human CD39 by antibodies of the present disclosure has an immunostimulatory effect on different myeloid populations in vitro.

Example 7: Antibody Characterization by Competition Flow

This example describes a competition flow assay useful in determining whether two antibodies (a test antibody and a reference antibody) compete for binding to human CD39 expressed on the surface of a cell. The choice of test antibody, reference antibody and cell type can be modified.

Antibody hu39.1_IGG4.P and antibody IGG4.P, an IgG4 (S228P) isotype control (CrownVivo), were directly conjugated to Alexa Fluor 647 ("AF647") utilizing the Alexa Fluor 647 Conjugation Kit-Lightning-Link (Abcam, Cat. No. ab269823). The conjugated antibodies are referred to in this example as "hu39.1_IGG4.P-AF647" and "IGG4.P-AF647". Validation of the binding was performed using a human multiple myeloma, CD39 expressing cell line, MOLP-8. On the day of the assay, frozen MOLP-8 cells were defrosted, rinsed, and resuspended in 1:25 Fc block (BD, Cat. No. 564220) and 1:250 aqua viability dye (Invitrogen, Cat. No. L34966A) in DPBS and incubated for 15 minutes at room temperature in the dark. Cells were plated at $0.2 \times 10^6$ cells per well in a polypropylene v-bottom 96-well plate. An 11-point dose response curve was prepared by a 3-fold serial dilution in DPBS with concentrations ranging from 833-0.0141 nM for each antibody. A twelfth point contained only DPBS and no antibody. The diluted antibody from the dose response was added to the plated cells at a 1:1 ratio and incubated for 30 minutes at 4° C. Cells were then washed three times and resuspended in DPBS and subjected to flow cytometry using the BD LSR Fortessa X-20 Cell Analyzer. The mean fluorescence intensity of AF647 was obtained for the live single cell population. The $EC_{50}$ and $EC_{95}$ values were calculated using standard 4-parameter non-linear regression analysis in GraphPad Prism software.

Antibody hu39.1_IGG4.P-AF647 was then used as a reference antibody in a competition flow assay with unlabeled test antibodies (hu31.1_IGG1.AA, hu39.1_IGG4.P, hu39.5_IGG1.AA, IGG1.AA isotype control, and IGG4.P isotype control (CrownVivo)). On the day of the assay, frozen MOLP-8 cells were defrosted, rinsed, and resuspended in 1:25 Fc block (BD, Cat. No. 564220) and 1:250 aqua viability dye (Invitrogen, Cat. No. L34966A) in DPBS, and incubated for 15 minutes at room temperature in the dark. An 11-point dose response curve was prepared by a 3-fold serial dilution in DPBS with concentrations ranging from 833-0.0141 nM for each test antibody. A twelfth point contained only DPBS and no antibody. 12.5 µL added to each well of a 96-well staining plate. 12.5 µL of reference antibody, hu39.1_IGG4.P-AF647, at a concentration of 93.7 nM was added to each well and gently mixed three times. Cells were plated at $0.2 \times 10^6$ cells per well and incubated for 60 minutes at 4° C. Cells were then washed three times and resuspended in DPBS and subjected to flow cytometry using the BD LSR Fortessa X-20 Cell Analyzer. The mean fluorescence intensity of AF647 was obtained for the live single cell population. The $EC_{50}$ was calculated using standard 4-parameter non-linear regression analysis in GraphPad Prism software. Max competition (%) was calculated using the following formula: Max competition=1−(MFI at the top concentration for the test antibody/MFI at matched concentration of hu39.1_IGG4.P-AF647 only). Only a single concentration of the reference antibody hu39.1_IGG4.P-AF647 was used.

Figure 6:
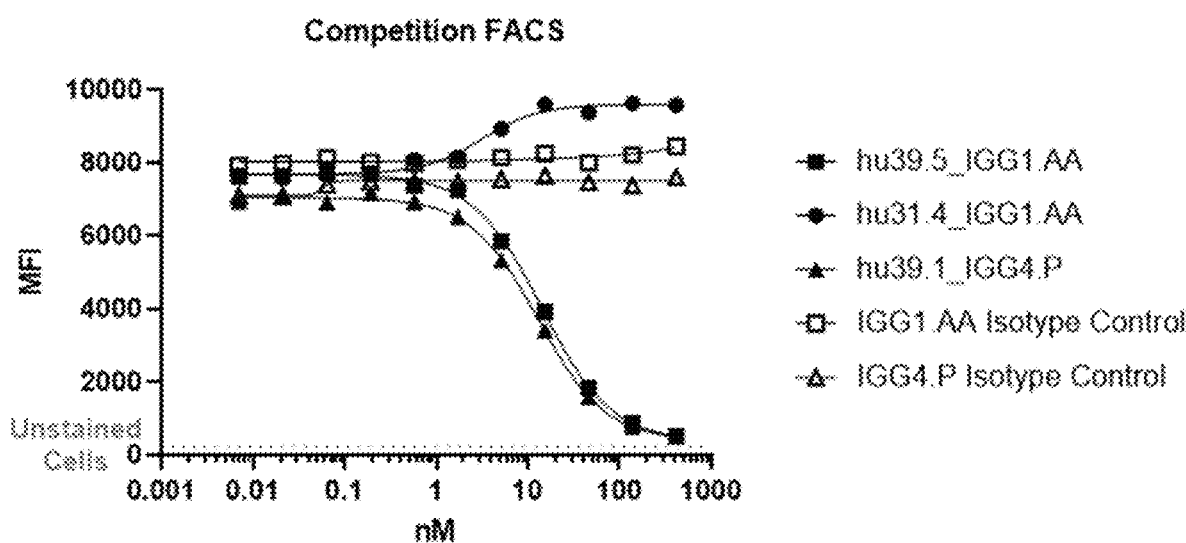
FIG. 6 is a graph depicting the results of a competition flow cytometry assay between a fluorescently labeled reference antibody, hu39.1_IGG4.P-AF647, and unlabeled test antibodies. Mean fluorescent intensity (MFI) is on the y-axis and test antibody concentration (nM) is on the x-axis.

As shown in FIG. 6 and Table 19, the test antibody hu39.5_IGG1.AA competes with the reference antibody hu39.1_IGG4.P-AF647 with maximum competition at 93%. A similar level of competition was observed for hu39.1_IGG4 (unlabeled reference antibody). In contrast, no competition was observed between the test antibody hu31.4_IGG1.AA antibody and the reference antibody hu39.1_IGG4.P-AF647. These data suggest antibodies 31 and 39, and their variants, bind to different non-overlapping epitopes.

TABLE 19

Antibody Competition for CD39 Binding.

| Test Antibody | Min. MFI | MFI at Top Concentration | Max Competition | $EC_{50}$ (nM) |
|---|---|---|---|---|
| hu31.4_IGG1.AA | 7578 | 9591 | −22% | |
| hu39.5_IGG1.AA | 528 | 528 | 93% | 14 |
| unlabeled hu39.1_IGG4.P | 511 | 511 | 93% | 13 |
| hu39.1_IGG4.P-AF647 only | | 7849 | | |

Example 8: Efficacy in Xenograft Models

Figure 7A:
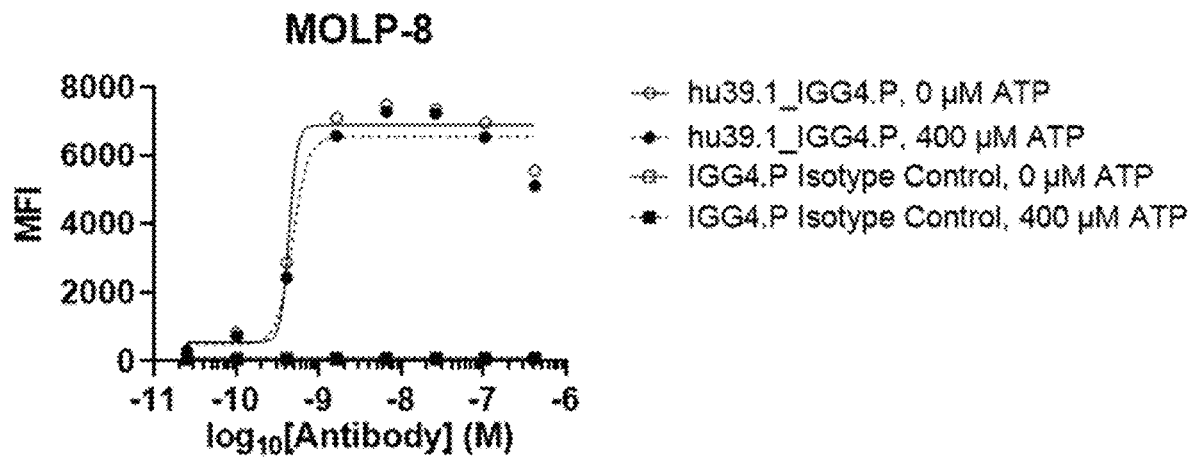
FIG. 7A is a graph depicting the binding of hu39.1_IGG4.P and an isotype control antibody to human CD39 expressed on MOLP-8, human myeloma cells.
Figure 7B:
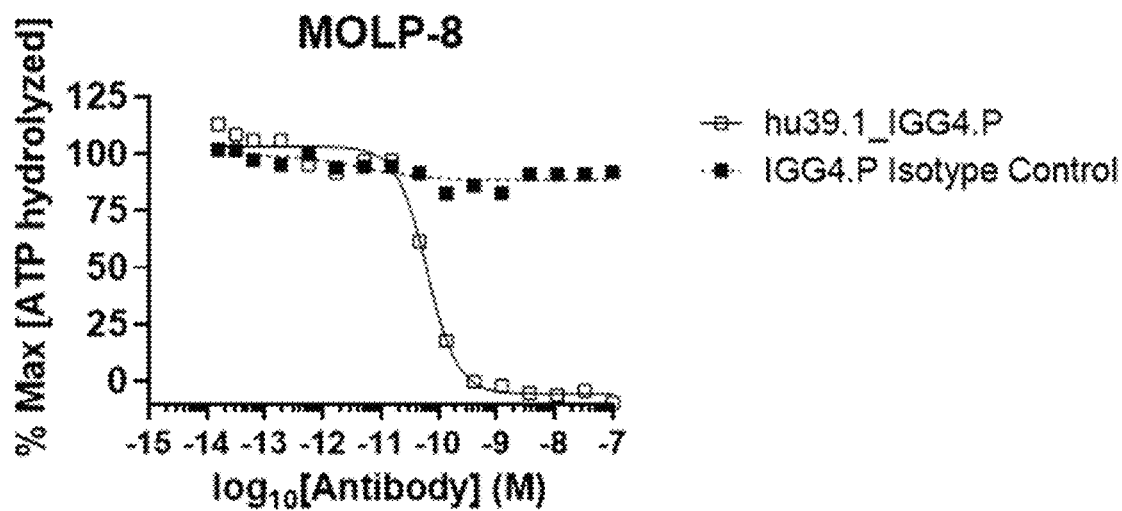
FIG. 7B is a graph depicting enzymatic inhibition of human CD39 expressed on MOLP-8, human myeloma cells, by hu39.1_IGG4.P and an isotype control antibody.
Figure 8A:
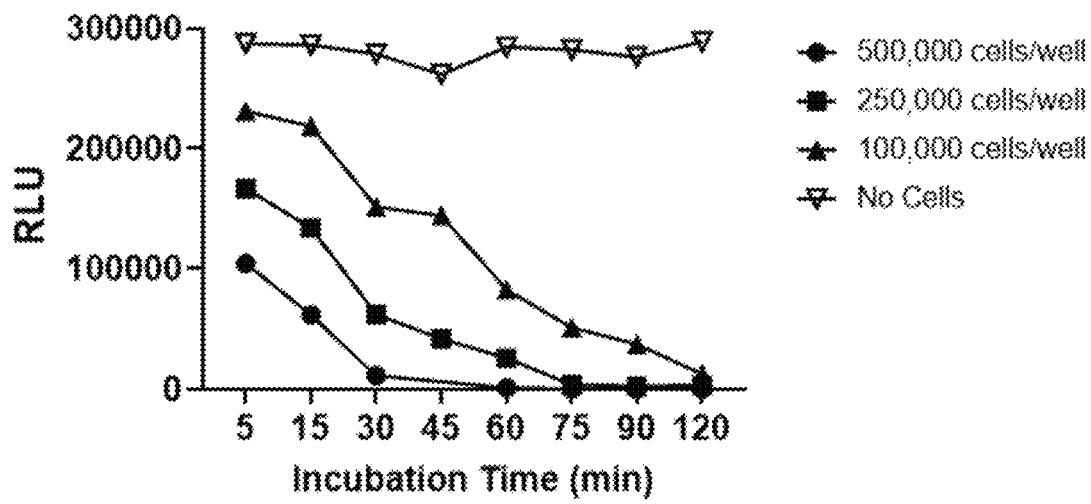
FIG. 8A depicts enzymatic activity (ATP consumption) on splenocytes from a hCD39KI mouse model.
Figure 8B:
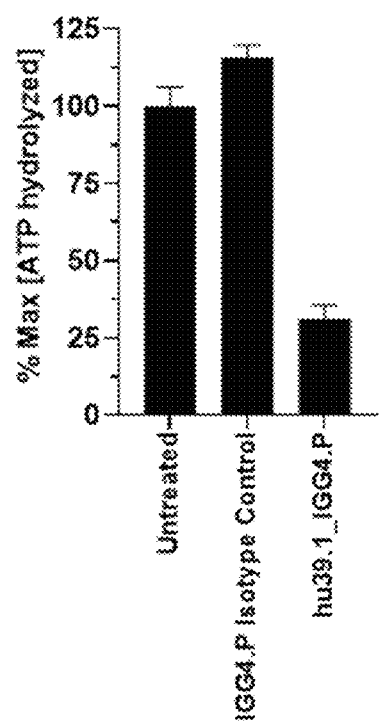
FIG. 8B depicts inhibition of splenocyte enzymatic activity by hu39.1_IGG4.P.

Anti-CD39 antibodies produced as described in Examples 1 and 2 bind human but not murine CD39. Therefore, to assess in vivo efficacy, xenograft mouse models can be used. Half a million to ten million human cancer cells expressing human CD39 are injected subcutaneously or orthotopically into an immunocompromised mouse, such as SCID or nude mice, and monitored for tumor growth. Anti-CD39 antibodies can bind and inhibit CD39 activity on several human cancer cell lines including but not limited to MOLP-8 myeloma (FIG. 7), THP-1 leukemia (Table 16), SK-MEL-5 melanoma (Table 15), and OAW42 ovarian cancer cells. When tumors are less than 150 mm³, mice are treated intraperitoneally (i.p.) with 0.1-30 mg/kg of an anti-CD39 antibody of the present disclosure or an isotype control BIW×4 or until tumor volume reaches 2,000 mm³. Treatment of MOLP-8 tumors expressing human CD39 with an anti-CD39 antibody of the present disclosure resulted in tumor growth inhibition compared to isotype control treated mice. Tumor growth inhibition compared to isotype control treated mice is also expected following treatment of other tumor types expressing human CD39 with an anti-CD39 antibody of the present disclosure.

Example 9: Efficacy in Human CD39 Knock-in Models

Figure 9:
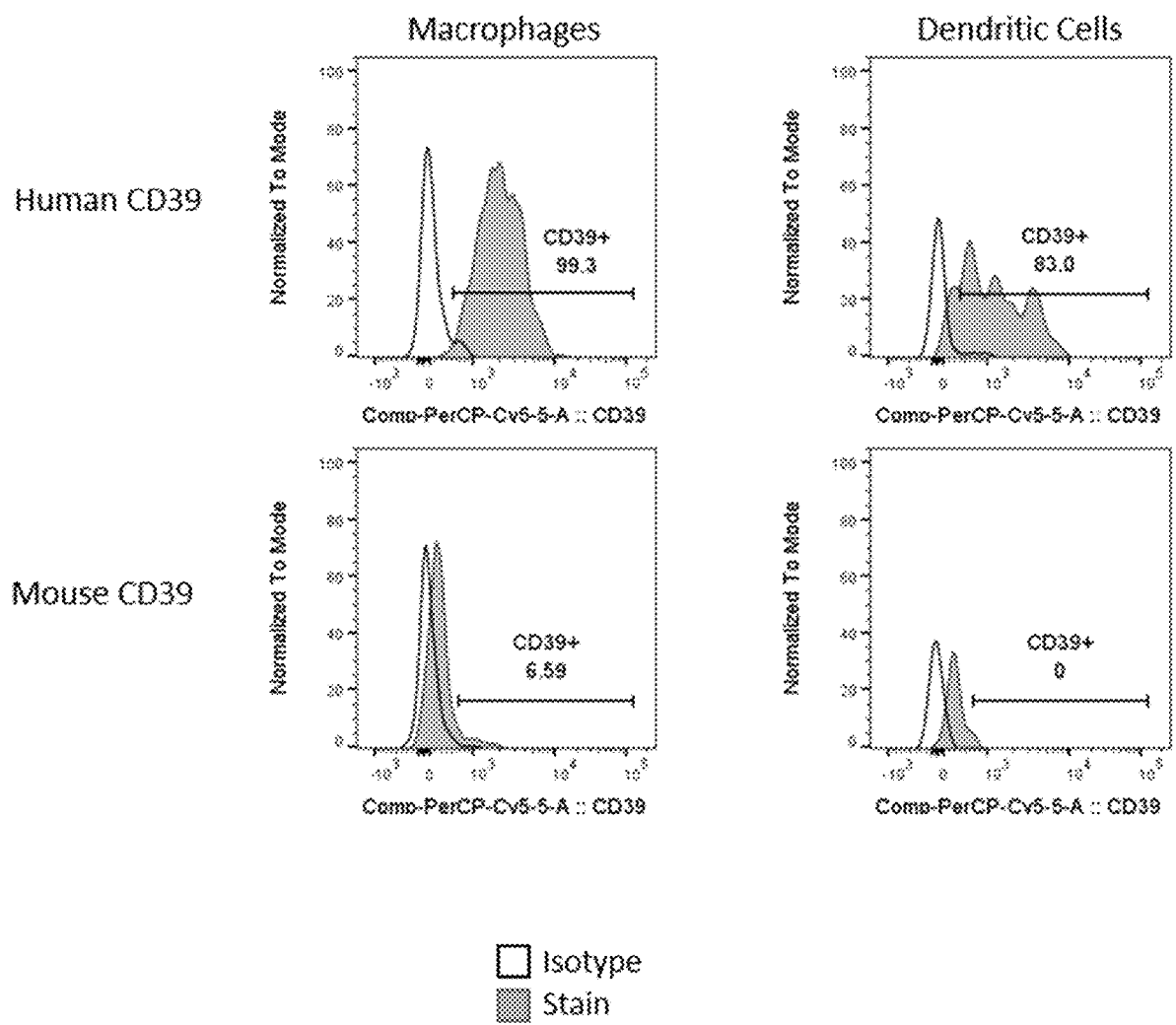
FIG. 9 depicts confirmation that a hCD39KI mouse model expresses human, and not murine, CD39.

To evaluate anti-CD39 antibodies of this disclosure in an immune-competent murine model, the antibodies can be tested in a human CD39 knock-in (hCD39KI) mouse model where fully immune-competent C57BL/6 or BALB/c mice express human CD39 and do not express murine CD39 (FIG. 9). In this mouse model, expression of human CD39 parallels expression of murine CD39 in wild-type mice. This mouse model allows for in vivo testing where anti-CD39 inhibition can act on host cells such as stromal cells, vasculature, and immune cells. The mice are inoculated subcutaneously or orthotopically with a murine wild-type or engineered tumor cell line including, but not limited to, MCA-205 fibrosarcoma, B16-F10 melanoma, MC38 colon adenocarcinoma, ID8 ovarian cancer, 4T1 breast cancer, or CT-26 colon carcinoma cells. Half a million to ten million murine cancer cells are injected and monitored for tumor growth. When tumors are less than 150 mm$^3$ mice are treated intraperitoneally (i.p.) with 0.1-30 mg/kg ch39_mIGG2A.AAG or isotype control BIW×4 or until tumor volume reaches 2,000 mm$^3$. Treatment of tumors with anti-CD39 as a single agent, or in combination with one or more an additional therapy (e.g., an ICD inducing agent, an immunotherapy, etc.) will result in tumor growth inhibition compared to isotype control treated mice.

In one experiment, C57BL/6 hCD39KI mice were inoculated with 1 million MC38 cells on day 0. When tumors reached 80 mm$^3$, mice were dosed intraperitoneally (i.p.) with a loading dose of 20 mg/kg anti-CD39 or isotype control antibody (vehicle: PBS), and then subsequently with 10 mg/kg anti-CD39 or isotype control antibody 2×/week (BIW). Each group consisted of 11-12 mice. In these experiments, anti-CD39 antibody refers to ch39_mIGG2A.AAG. Oxaliplatin (OXA) treatment, 5 mg/kg i.p. (vehicle: saline), was initiated the day following the anti-CD39 or isotype control loading dose and dosed 1×/week. In a similarly designed experiment, BALB/c hCD39KI mice were inoculated with 4T1 cells on day 0 and treated OXA or anti-CD39 antibody as described for the MC38 model. Results from these experiments are described in the following paragraphs.

Anti-CD39 shows efficacy in a hCD39KI model. To evaluate the effectiveness of anti-CD39 treatment, tumor volume, intratumoral and peripheral CD39 enzymatic activity, and CD39 expression were evaluated.

Figure 10A:
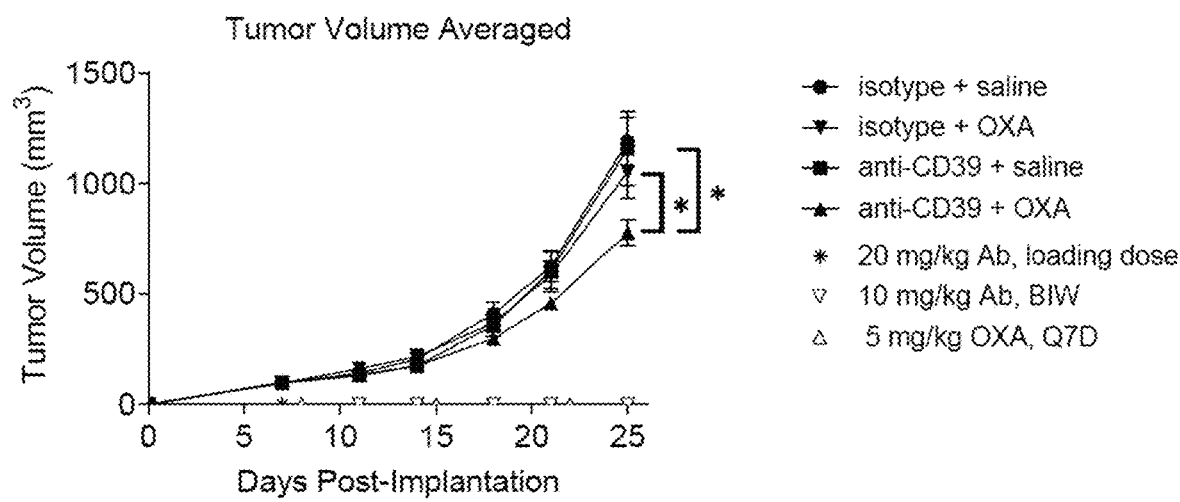
FIG. 10A is a graph depicting the averaged tumor volume in hCD39KI mice with the indicated treatment. The points represent the mean and the errors bars the standard error of the mean (SEM), *=p<0.5.
Figure 10B:
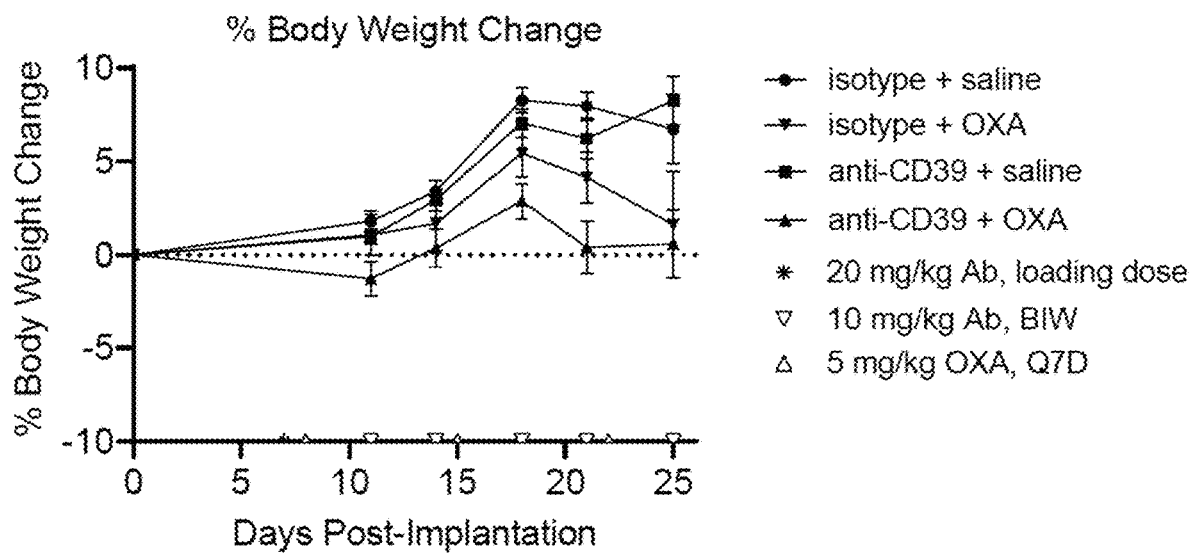
FIG. 10B is a graph depicting the percent change in the body weight of hCD39KI mice with the indicated treatment.
Figure 11:
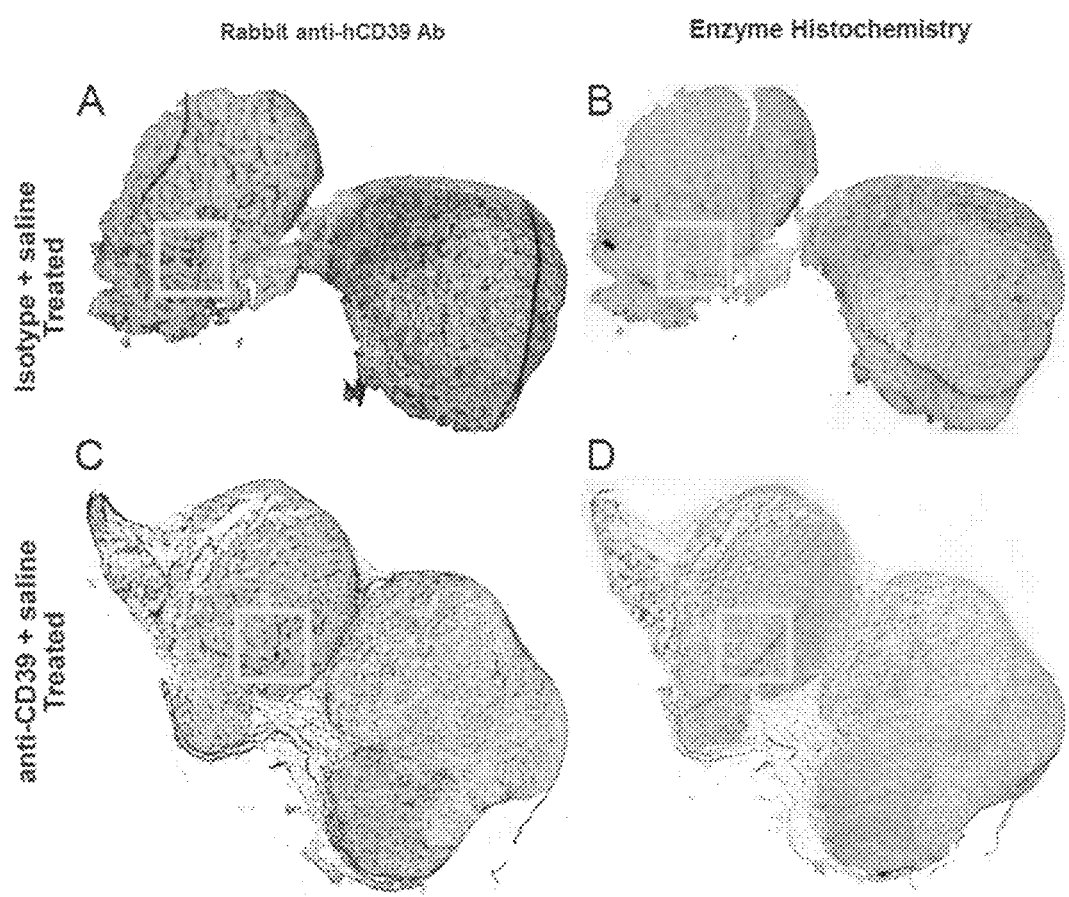
FIG. 11 shows low-magnification images of tumors from hCD39KI mice analyzed for human CD39 expression by immunohistochemistry (panels A and C) and evidence of anti-CD39 enzymatic blocking activity by enzyme histochemistry (panels B and D).
Figure 12:
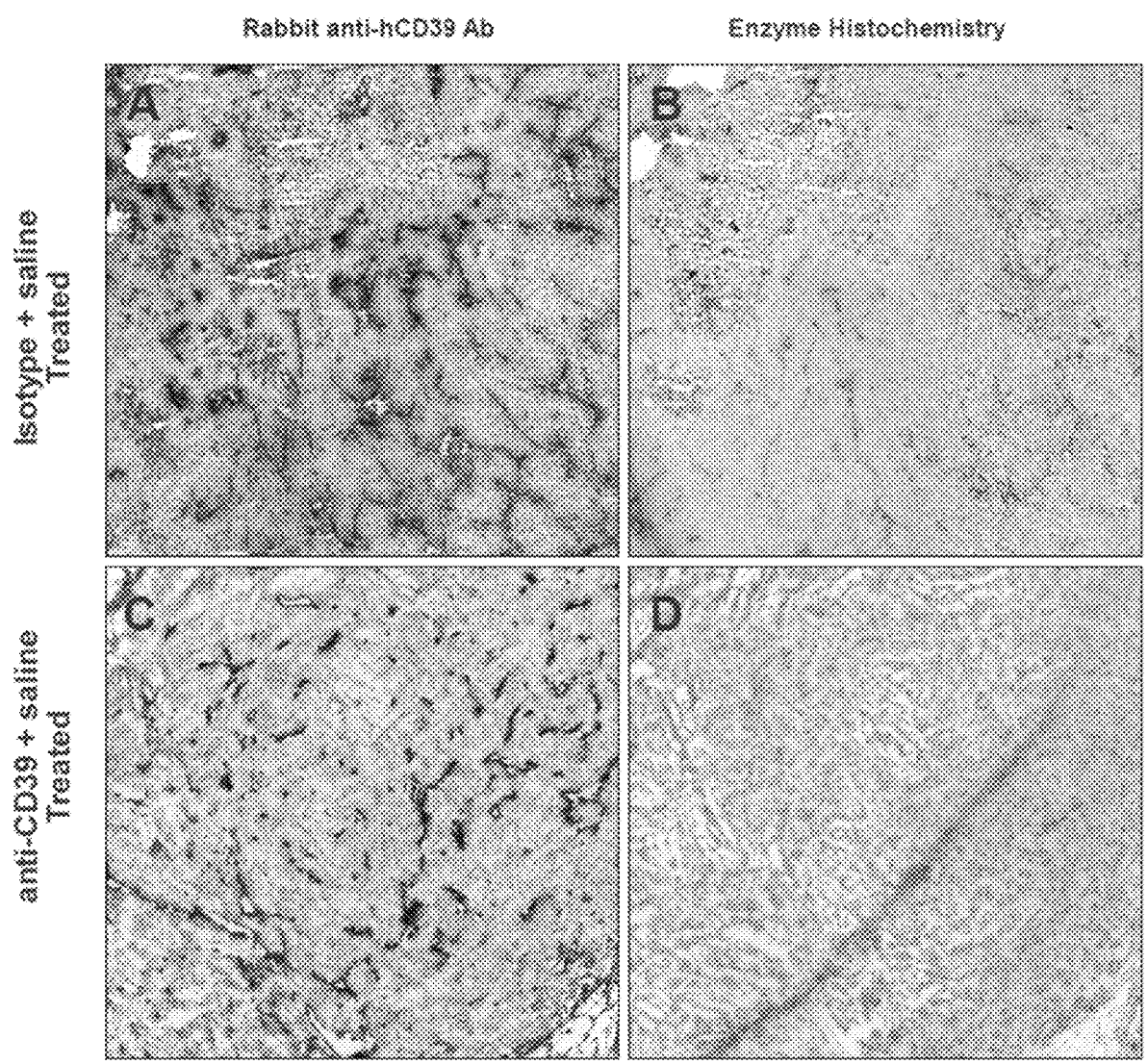
FIG. 12 shows high-magnification images of tumors of hCD39KI mice analyzed for human CD39 expression by immunohistochemistry (panels A and C) and evidence of anti-CD39 enzymatic blocking activity by enzyme histochemistry (panels B and D). The images in FIG. 12 are high-resolution images of the boxed areas in FIG. 11.
Figure 13:
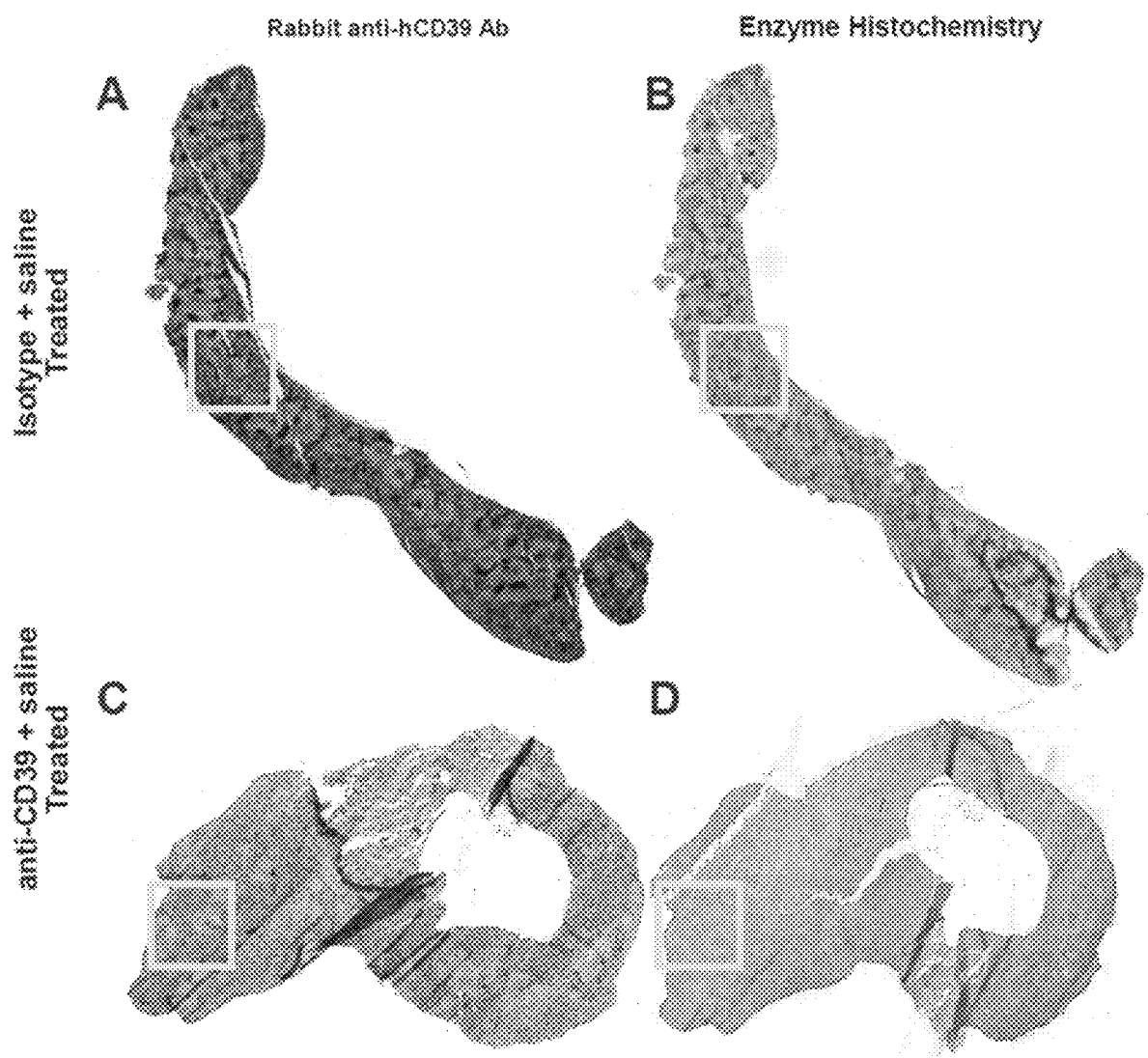
FIG. 13 shows low-magnification images of spleens of hCD39KI mice analyzed for human CD39 expression by immunohistochemistry (panels A and C) and evidence of anti-CD39 enzymatic blocking activity by enzyme histochemistry (panels B and D).
Figure 14:
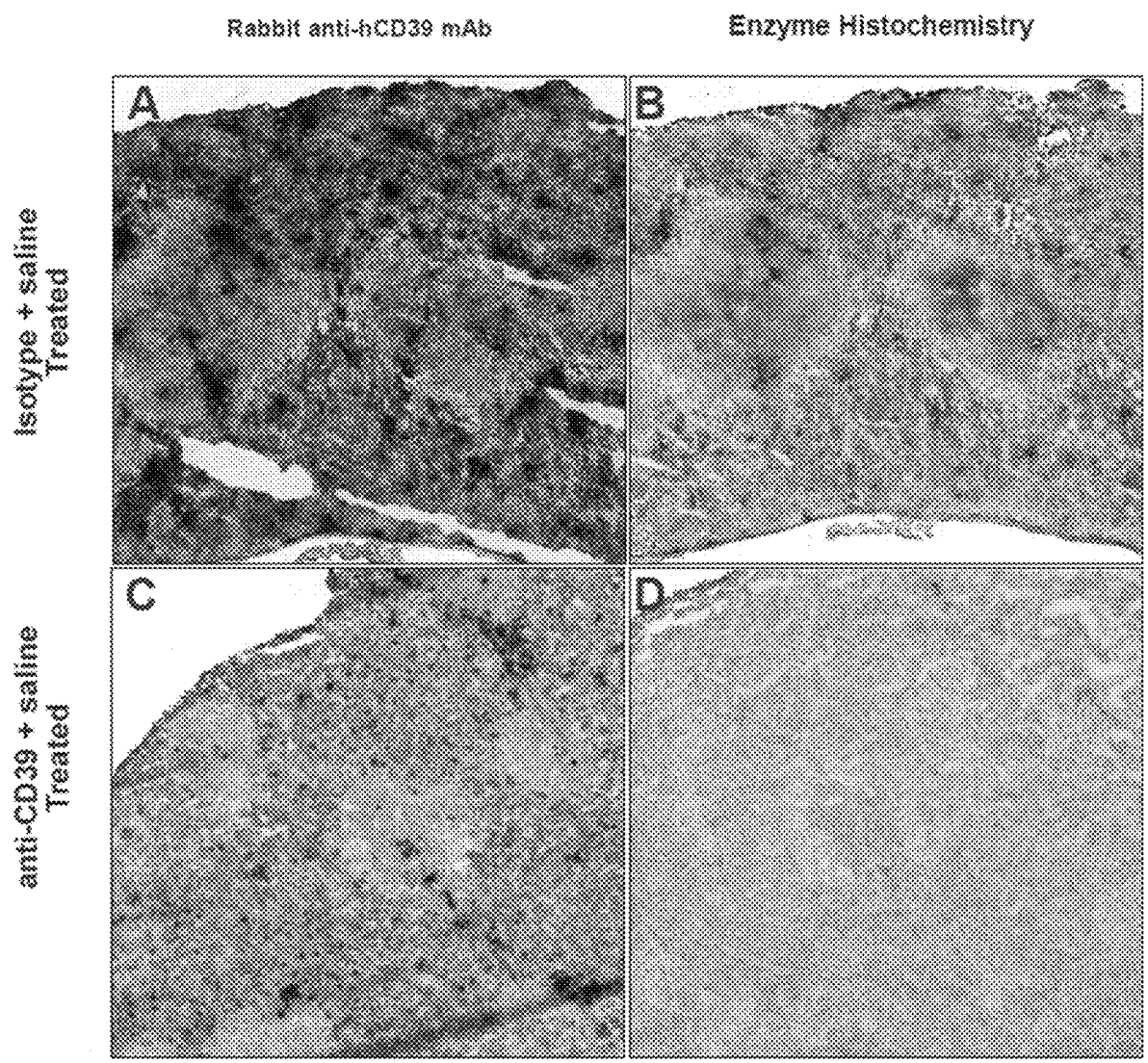
FIG. 14 shows high-magnification images of spleens of hCD39KI mice analyzed for human CD39 expression by immunohistochemistry (panels A and C) and evidence of anti-CD39 enzymatic blocking activity by enzyme histochemistry (panels B and D). The images in FIG. 14 are high-resolution images of the boxed areas in FIG. 13.

Tumor volume and body weight were measured approximately twice a week (BIW) and are shown in FIG. 10A and FIG. 10B respectively, where the points represent the mean and the errors bars the standard error of the mean (SEM) of the respective metrics from each group of mice. Significance was calculated using a mixed-effects model with multiple comparisons. As shown in FIG. 10A, treatment with anti-CD39 and oxaliplatin was statistically significant (p=0.0217) compared to treatment with either single agent alone (p=0.0372 for isotype+OXA vs. anti-CD39+OXA and p=0.0217 for anti-CD39+saline vs. anti-CD39+OXA). Body weight was stable over the course of the experiment indicating anti-CD39 treatment was well tolerated (FIG. 10B).

Tumors and spleens from C57BL/6 hCD39KI MC38 mice at the end of the study were additionally analyzed for human CD39 expression by immunohistochemistry (IHC) and evidence of anti-CD39 antibody enzymatic blocking activity by enzyme histochemistry (EHC). Briefly, frozen OCT-embedded tumor or spleen samples were sectioned at 4 um thickness, mounted on positively charged microscope slides, air dried for 15 minutes, then placed in 4% paraformaldehyde (PFA) fixative for 20 min. After fixation, the slides were washed in Tris-buffered saline and IHC was performed on an automated Leica Bond Rx platform starting with blocking of endogenous peroxidases, followed by incubation with a rabbit anti-CD39 mAb (Abcam, EPR20627), and detected with an anti-rabbit HRP polymer system followed by a diaminobenzidine (DAB) brown chromogen, hematoxylin nuclear counterstain, and then dehydrated and mounted. For the EHC assay, following a 5 minutes fixation in 4% PFA, sections were washed in Tris maleate buffer and incubated 30 minutes at room temperature in a solution of 50 mM Tris maleate, 250 mM sucrose, and 2 mM MgCl$_2$. The sections were then incubated for 2 hours at 37° C. in a solution of 100 mM Tris maleate containing 1 mM ATP, 2.5 mM levamisole, 2 mM lead nitrate, 0.25 mM sucrose, and 5 mM MnCl$_2$. Levamisole was used to inhibit tissue non-specific alkaline phosphatase (TNAP) activity; other inhibitors may also be used. The sections were then developed in a 1% ammonium sulfide solution for 5 min, washed, counterstained with hematoxylin, dehydrated and mounted. Representative images are shown in FIG. 11-14 (tumors, FIG. 11-12; spleens, FIG. 13-14). Human CD39 expression was detected in both isotype treated (FIG. 11, panel A and FIG. 12, panel A, low- and high-power magnification, respectively) and anti-CD39 treated tumors (FIG. 11, panel C and FIG. 11 panel C, low- and high-power magnification, respectively), localized to vascular endothelia, infiltrating immune cells, and stromal components of the tumor microenvironment. The level of human CD39 expression was observed in both isotype treated (FIG. 13, panel A and FIG. 14, panel A, low- and high-power magnification, respectively) and anti-CD39 treated spleens (FIG. 13, panel C and FIG. 14, panel C, low- and high-power magnification, respectively), localized to the red pulp and to a lesser degree in the white pulp. In tumors and spleens treated in vivo with isotype, lead-phosphate deposition is observed by enzyme histochemistry (tumor—FIG. 11, panel B and FIG. 12, panel B, low- and high-power magnifications, respectively; spleen, FIG. 13, panel B and FIG. 14, panel B low- and high-power magnification, respectively). In tumors and spleens treated in vivo with anti-CD39 antibody, lead-phosphate deposition is not observed by enzyme histochemistry, indicating that enzymatic activity has been blocked (tumor—FIG. 11, panel D and FIG. 12, panel D, low- and high-power magnifications, respectively; spleen, FIG. 13, panel D and FIG. 14, panel D low- and high-power magnification, respectively).

Figure 15A:
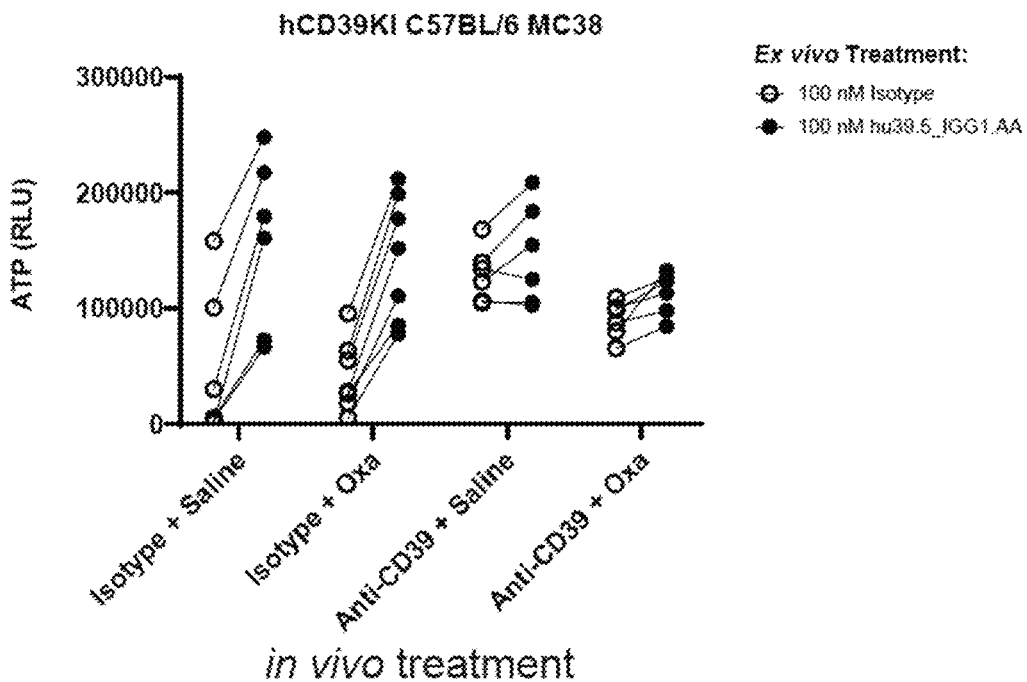
FIG. 15A, FIG. 15B, and FIG. 15C are graphs depicting ATP levels detected in supernatants derived from single cell suspensions of tumors (FIG. 15A: MC38 tumors.
Figure 15B:
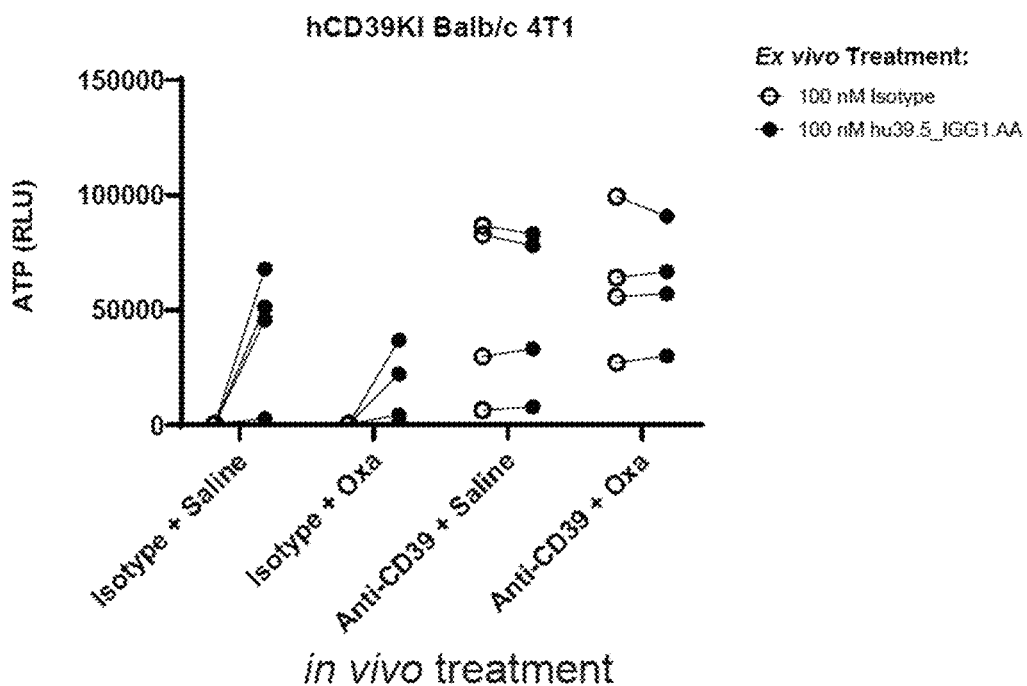

Intratumoral and peripheral CD39 enzymatic activity was also evaluated ex vivo. Upon study completion, tumor samples obtained after sacrificing C57BL/6 hCD39KI MC38 and BALB/c hCD39KI 4T1 mice were placed in RPMI+20% FBS+250 µg/ml collagenase D (Millipore Sigma, Cat. No. 11088858001)+100 KU/ml DNAse 1 (Millipore Sigma Cat. No. D5025-150KU) and enzymatically digested using gentleMACS™ Octo Dissociator to obtain a single cell suspension. Cells were then plated at 2.5×10$^4$ cells per well in a 96-well plate and treated with 100 nM of hu39.5_IGG1.AA or IgG1 Fc silent isotype control antibody (Absolute Antibody, Cat. No. Ab00178-10.3) and incubated for 1 hour at 37° C., 5% CO$_2$. The cells were then treated with 20 µM ATP and incubated for an additional 30 minutes at 37° C., 5% CO$_2$. At the end of the incubation period, the 96-well plate was spun at 1000 rpm for 3 minutes and the supernatant was collected. 2× Kinase-Glo® Plus (Promega, Cat. No. V3771) was then added to the supernatants. ATP levels in the supernatants were then measured by detecting luminescence using Flexstation® 3 microplate reader. Data are presented as relative luminescence units (RLU). No difference between the RLU in the ex vivo hu39.5_IGG1.AA and isotype-treated groups is indicative of complete enzymatic activity inhibition from the in vivo treatment. Anti-CD39 treatment inhibited enzymatic activity in the tumor (FIG. 15A and FIG. 15B).

Figure 15C:
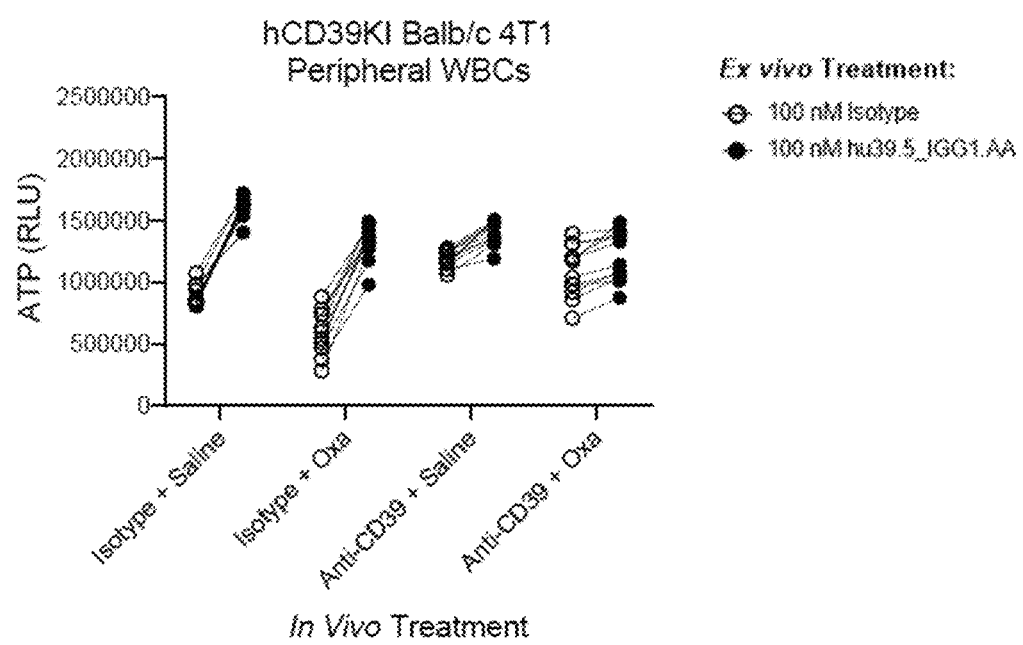

To assay peripheral CD39 enzymatic activity, peripheral white blood cells (WBCs) were isolated from terminal blood samples of hCD39KI mice and assayed as generally described for the tumor cell suspensions. Briefly, whole blood samples were mixed with 1× Pharm Lyse red blood cell lysing solution (BD Biosciences, Cat. No. 555899). WBC pellets were then collected after washing with 1×PBS solution and stored in BamBanker cell freezing medium (Bulldog Bio, Cat. No. BB01). To perform the enzymatic inhibition assay, samples were thawed and then cells were plated at $2.5 \times 10^4$ cells per well in a 96-well plate. Each sample was incubated for 1 hour at room temperature with two treatment conditions: 100 nM of hu39.5_IGG1.AA or IgG1 Fc silent isotype control antibody (Absolute Antibody, Cat. No. Ab00178-10.3). All wells were then treated with 20 µM ATP and incubated for 2 hours at room temperature. At the end of the incubation period, the 96-well plate was spun at 1000 rpm for 3 minutes and the supernatant was collected. 2× Kinase-Glo® Plus (Promega, Cat. No. V3771) was then added to the supernatants. ATP levels in the supernatants were then measured by detecting luminescence using Flexstation® 3 microplate reader. Data are presented as relative luminescence units (RLU). No difference between the RLU in the ex vivo hu39.5_IGG1.AA and isotype-treated groups is indicative of complete enzymatic activity inhibition from the in vivo treatment. Anti-CD39 treatment inhibited enzymatic activity in the periphery of 4T1 tumor-bearing mice (FIG. 15C).

Figure 16:
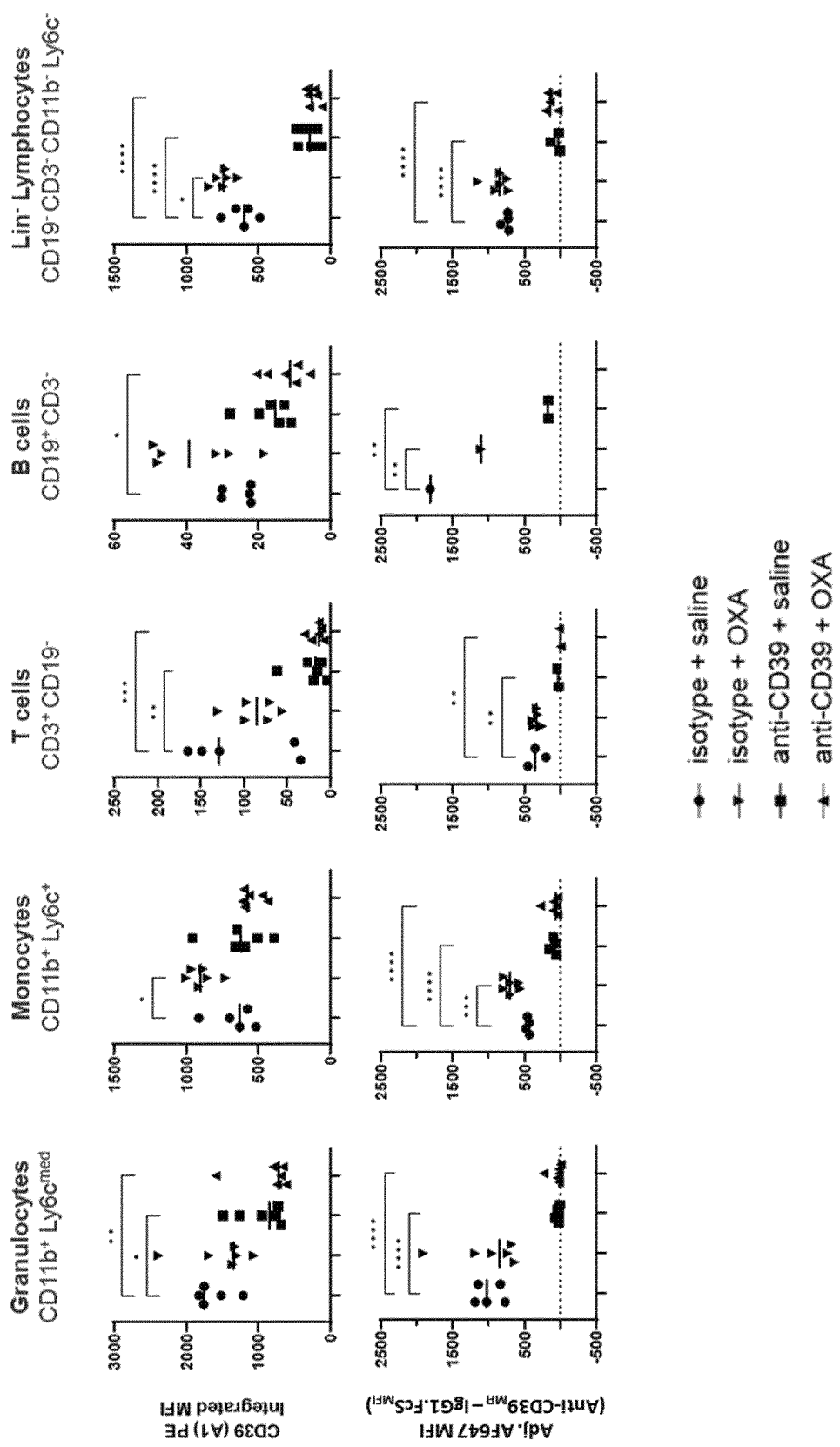
FIG. 16 depicts graphs showing cell surface CD39 and receptor occupancy in hCD39KI mice treated with anti-CD39. The graphs in top panel show a decrease in cell surface CD39 expression, determined by binding of the non-competitive anti-CD39 clone A1-PE, in multiple cell types after in vivo anti-CD39 treatment. The graphs in the bottom panel show binding of a competitive antibody was observed on all CD39(A1)-expressing cells in the in vivo isotype control treated mice, but not on the CD39(A1)-expressing cells in the in vivo anti-CD39 treated mice, indicating complete or near-complete target coverage. Data are shown for populations where >100 CD39(A1)$^+$ events were collected. Statistical analysis was performed with One-way ANOVA (Dunnett's multiple comparison test, with a single pooled variance), *P≤0.05, P≤0.01, *P≤0.001, ****P≤0.0001.

Decrease in cell surface CD39 and complete or near-complete coverage with anti-CD39 treatment in peripheral immune populations of hCD39KI mice. Whole blood samples from terminal bleeds of C57BL/6 hCD39KI MC38 mice were assessed by flow cytometry to evaluate target coverage and CD39 expression changes on peripheral immune cell types expressing CD39, including monocytes (CD3⁻CD19⁻CD11b⁺Ly6c⁺⁺), granulocytes (CD3⁻CD19⁻CD11b⁺Ly6c⁺), T cells (CD3⁺CD19⁻), B cells (CD3⁻CD19⁺), and other lineage negative (Lin⁻) lymphocytes. Target engagement was determined using hu39.5_IGG1.AA-AF647, a reagent which binds competitively with ch39_mIGG2A.AAG. hu39.5_IGG1.AA was conjugated to AF647 using an Abcam AF647 Lightning Link conjugation kit. Whole blood samples from 5-6 mice per treatment group were stained with a cocktail of extracellular antibodies including: CD39 hu39.5_IGG1.AA-AF647 (competitive to anti-CD39), CD39 A1 PE (non-competitive to anti-CD39), CD3 17A2 PerCP-Cy5.5, CD11b M1/70 FITC, CD19 6D5 BV421, and Ly6c HK1.4 PE-Cy7. Antibodies were incubated in whole blood for 30 minutes in the dark on ice, then samples were fixed/lysed using 1× BD FACSLysing solution for 20 minutes in the dark on ice. Samples were then centrifuged at 400×g for 5 minutes and washed once in 1×PBS buffer, resuspended in 1% paraformaldehyde solution, and filtered through a 20 µm strainer prior to data acquisition. Samples were run on a BD FACSCanto Special Order cytometer and analyses were performed using FlowJo and Prism software. Unbound CD39 was detected by competitive clone hu39.5_IGG1.AA-AF647 (measured by MFI of hu39.5_IGG1.AA-AF647 signal over its isotype control, IgG1.FcS-AF647) across cell types in all animals treated with isotype antibody. Significant competitive binding of hu39.5_IGG1.AA-AF647 was observed on all CD39 (A1)-expressing cells in animals treated with anti-CD39, indicating complete or near complete target coverage (FIG. 16, bottom panel). Total CD39 surface protein was detected by non-competitive CD39 antibody (clone A1 PE). Decreases in surface CD39 protein were observed in multiple types of peripheral immune cells of mice treated with anti-CD39 (FIG. 16, top panel).

Figure 17A:
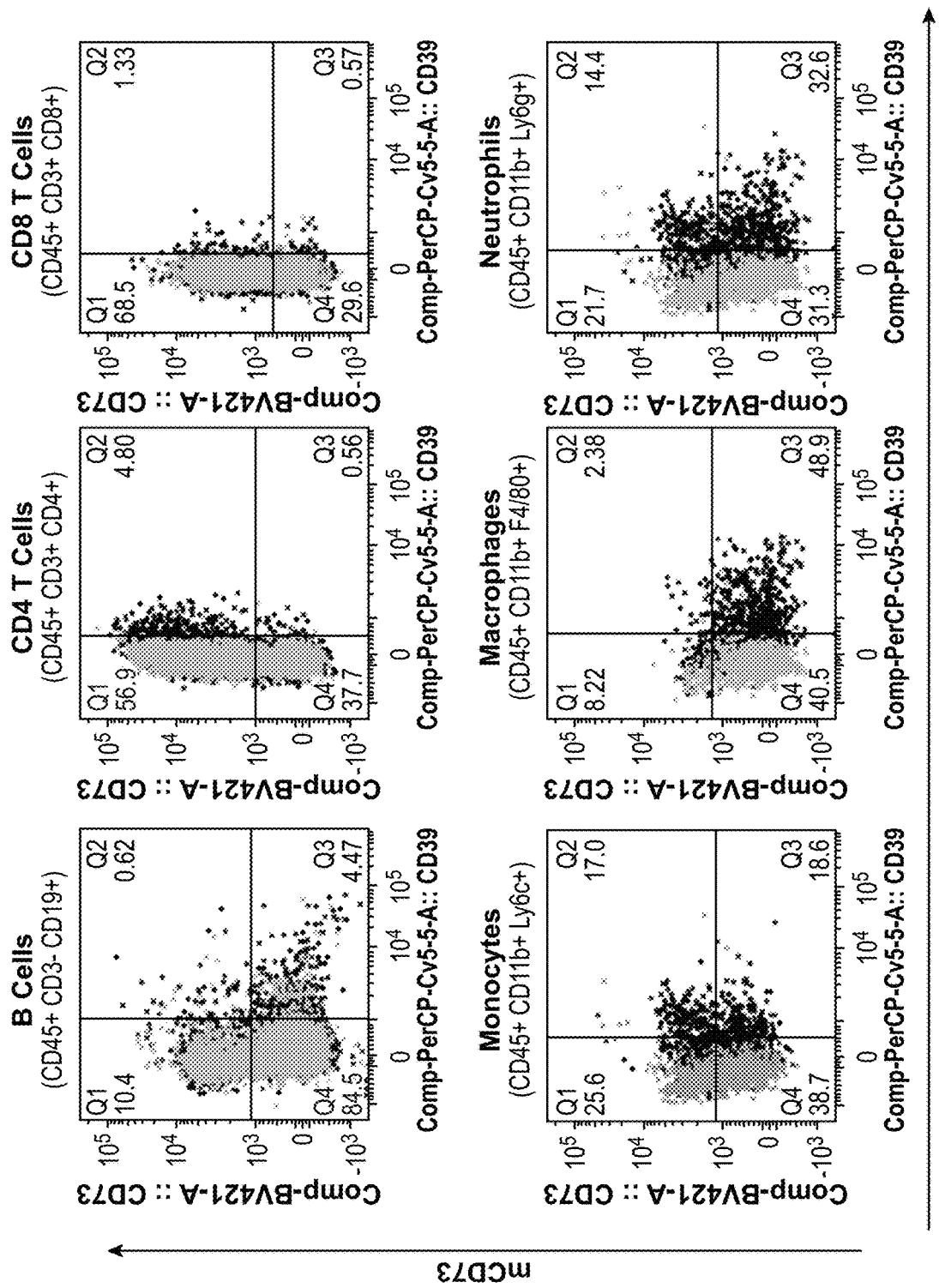
FIG. 17A depicts flow cytometry scatter plots showing expression levels of human CD39 (x-axis) and mouse CD73 (y-axis) on immune subpopulations from tumor derived lymph nodes in vehicle-treated hCD39KI mice. Gates were set on isotype controls (hCD39 isotype control in grey) and applied to each group (black).
Figure 17A:
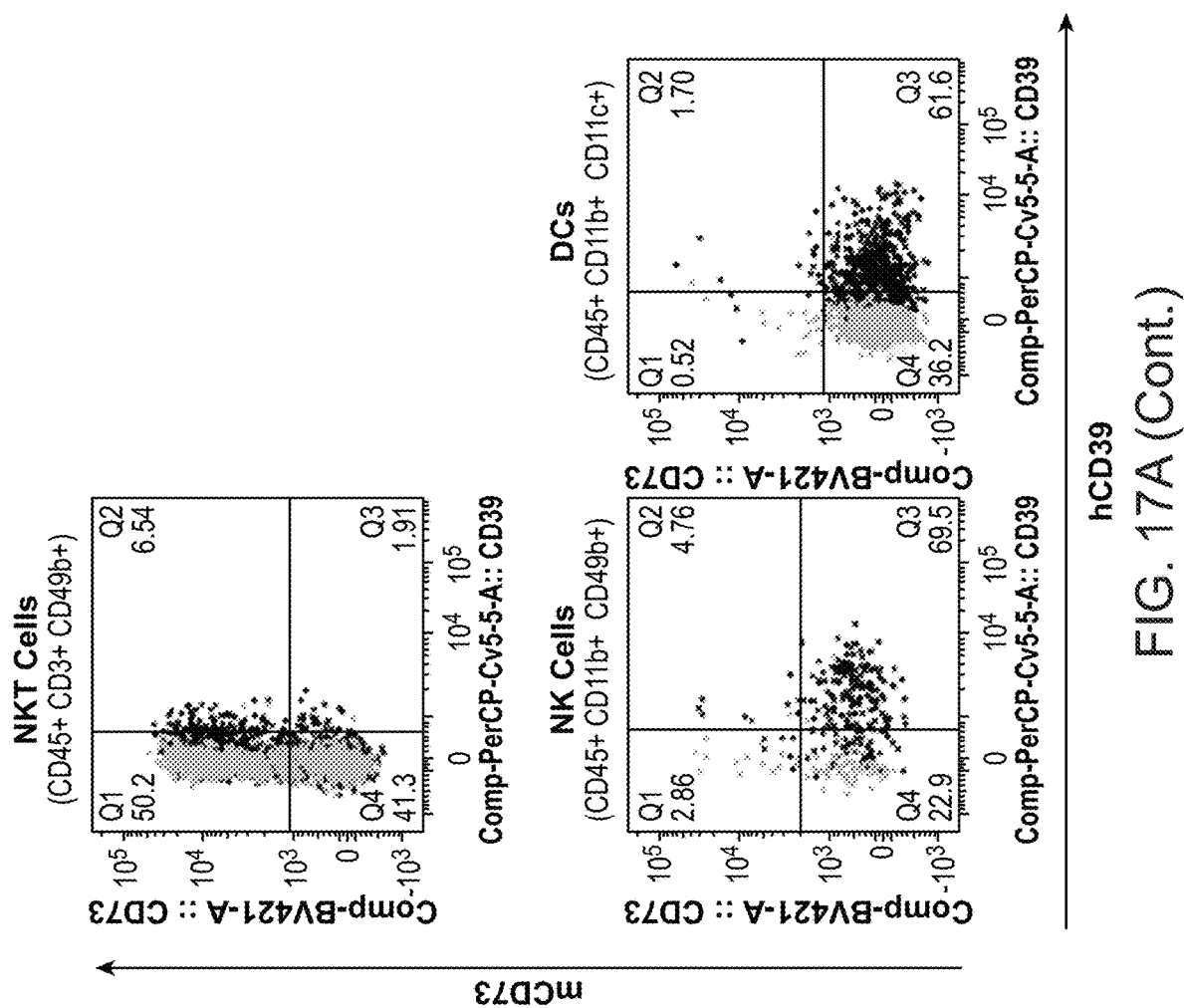
Figure 17B:
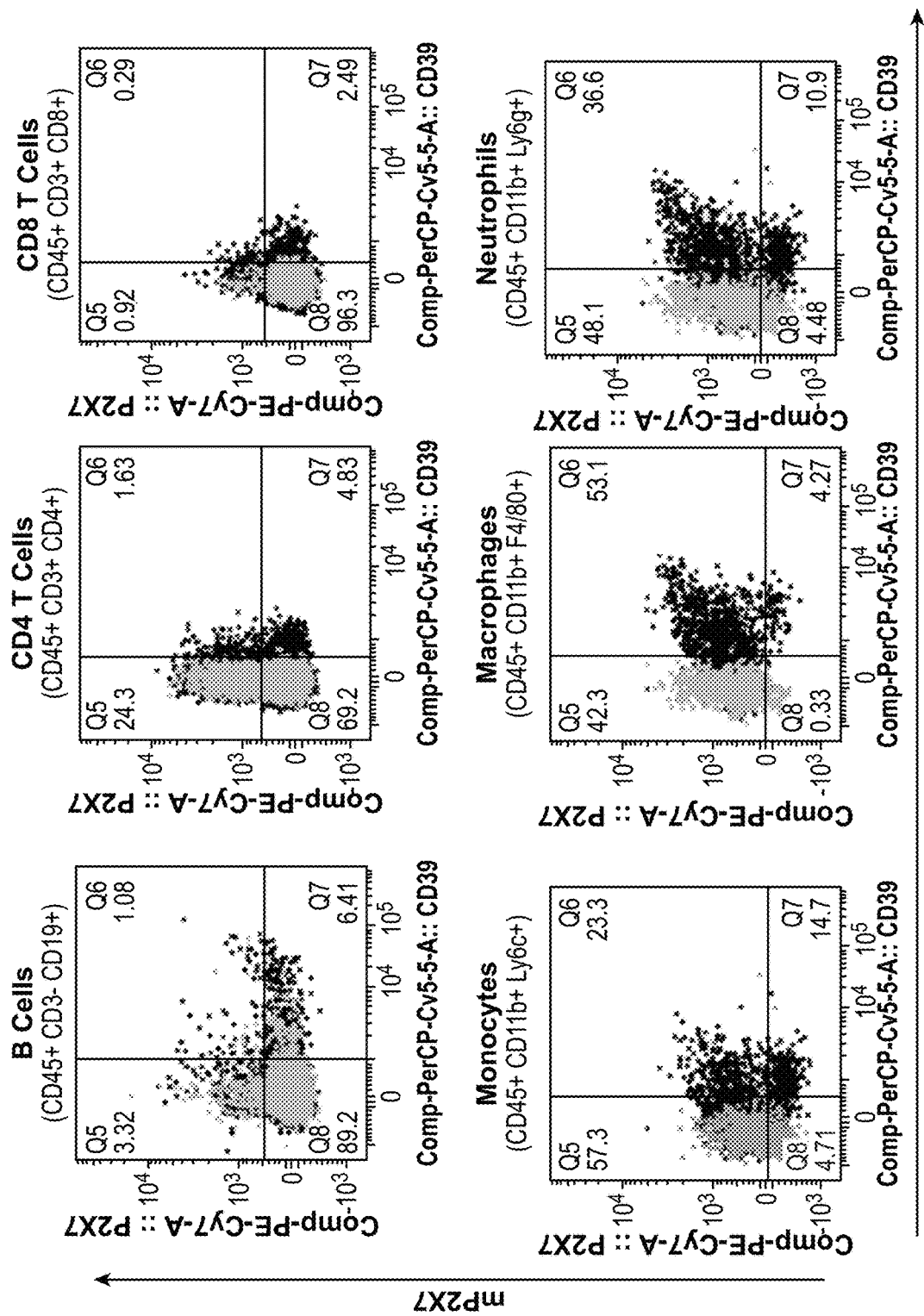
FIG. 17B depicts flow cytometry scatter plots showing expression levels of human CD39 (x-axis) and mouse P2X7 (y-axis) on immune subpopulations from tumor derived lymph nodes in vehicle-treated hCD39KI mice. Gates were set on isotype controls (hCD39 isotype control in grey) and applied to each group (black).
Figure 17B:
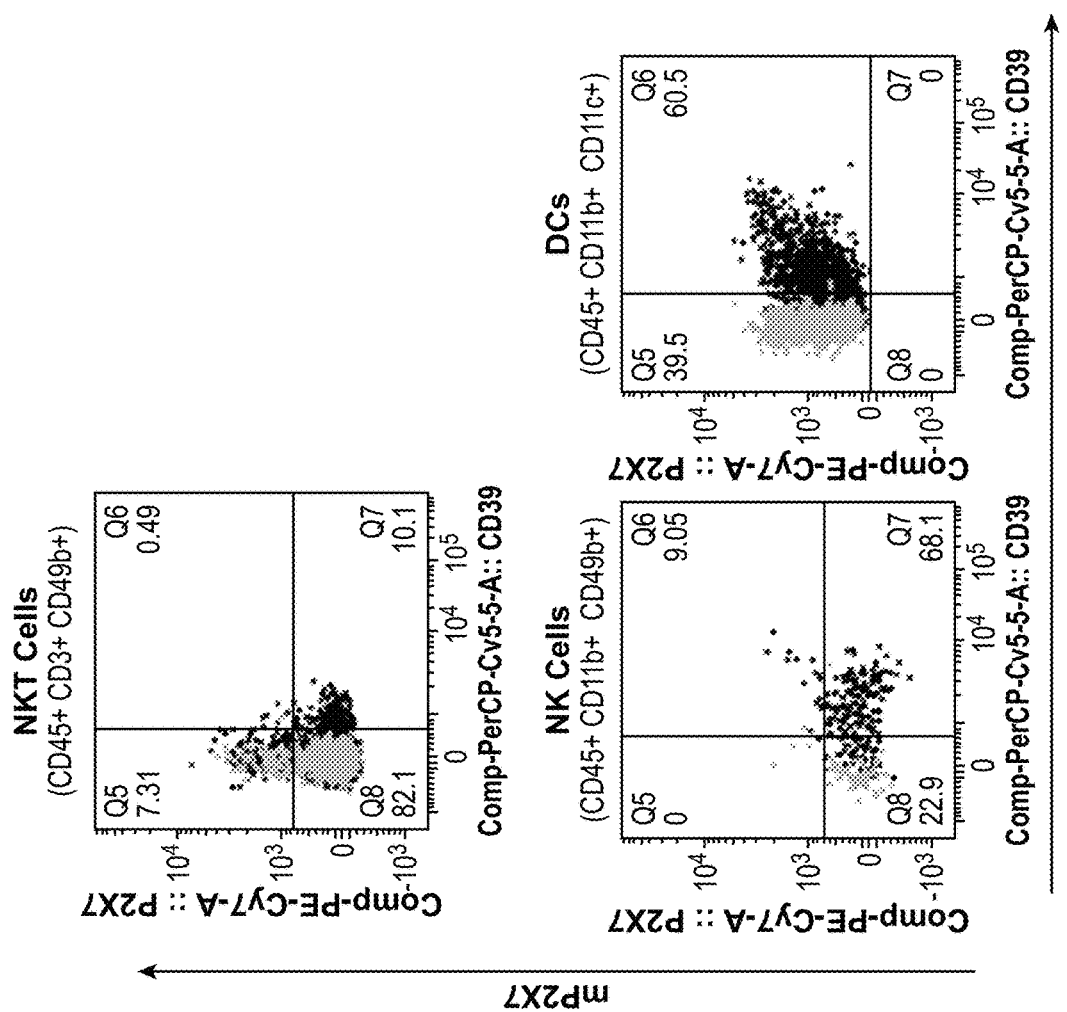
Figure 17C:
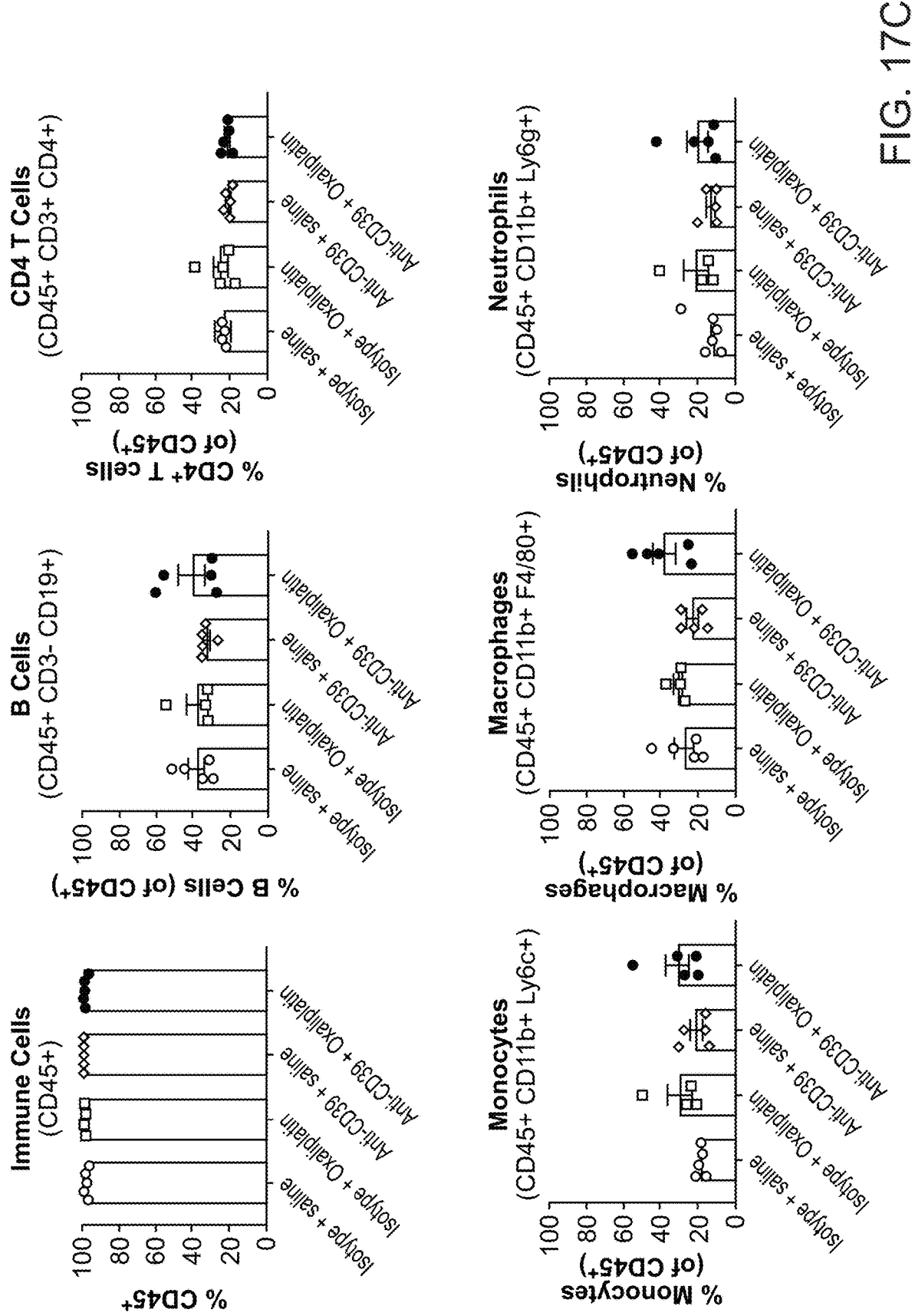
FIG. 17C depicts graphs showing immune subpopulation percentages observed following treatment as indicated along the x-axis. No significant changes in immune subpopulation percentages were observed with anti-CD39 treatment. Statistical analysis was performed with a One-way ANOVA (Dunnett's multiple comparison test, with a single pooled variance), *P<0.05, P<0.01, *P<0.001, ****P<0.0001, each symbol represents and individual mouse, bar height is the mean and error bars are +/− the SEM.
Figure 17C:
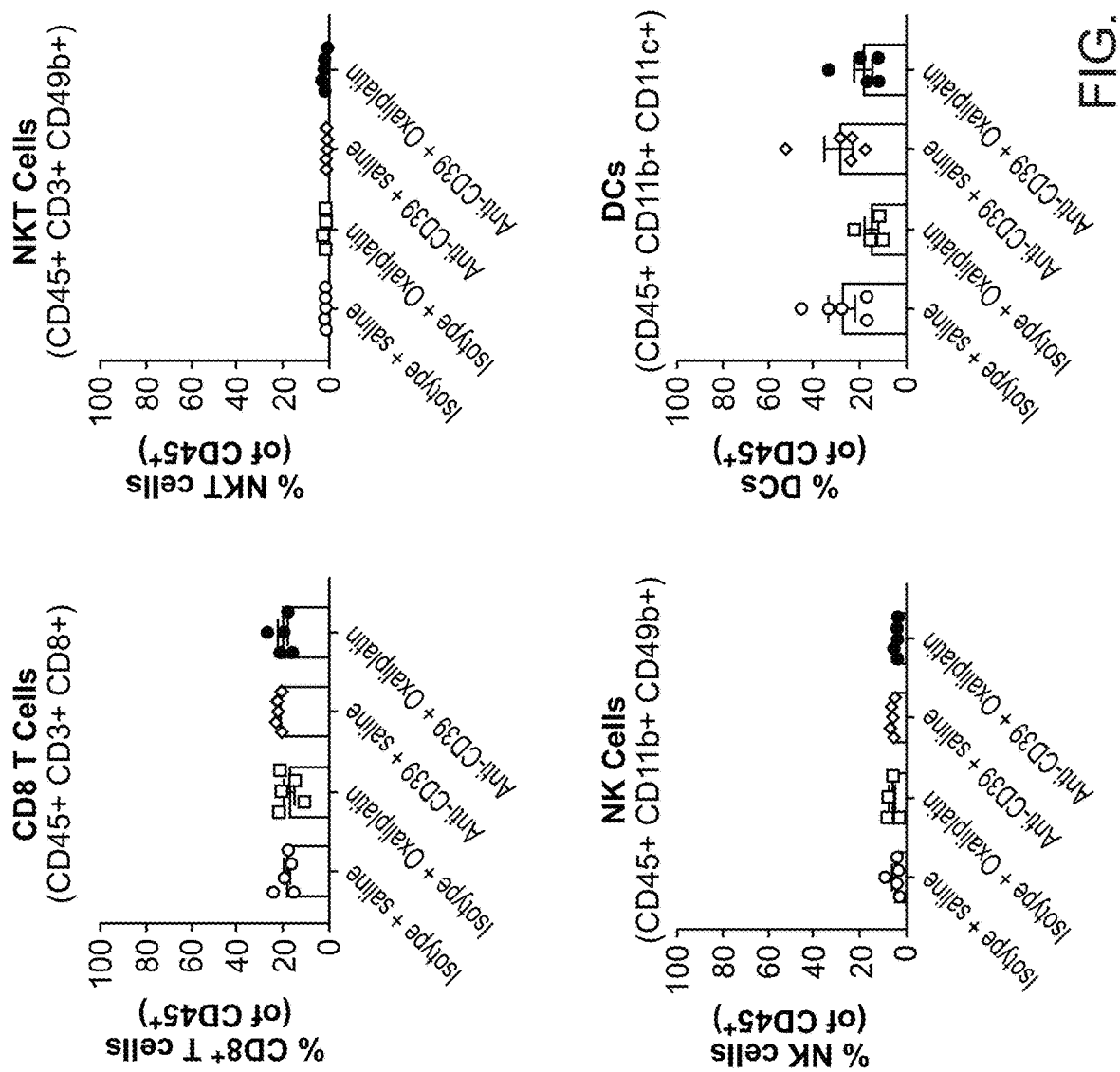
Figure 17D:
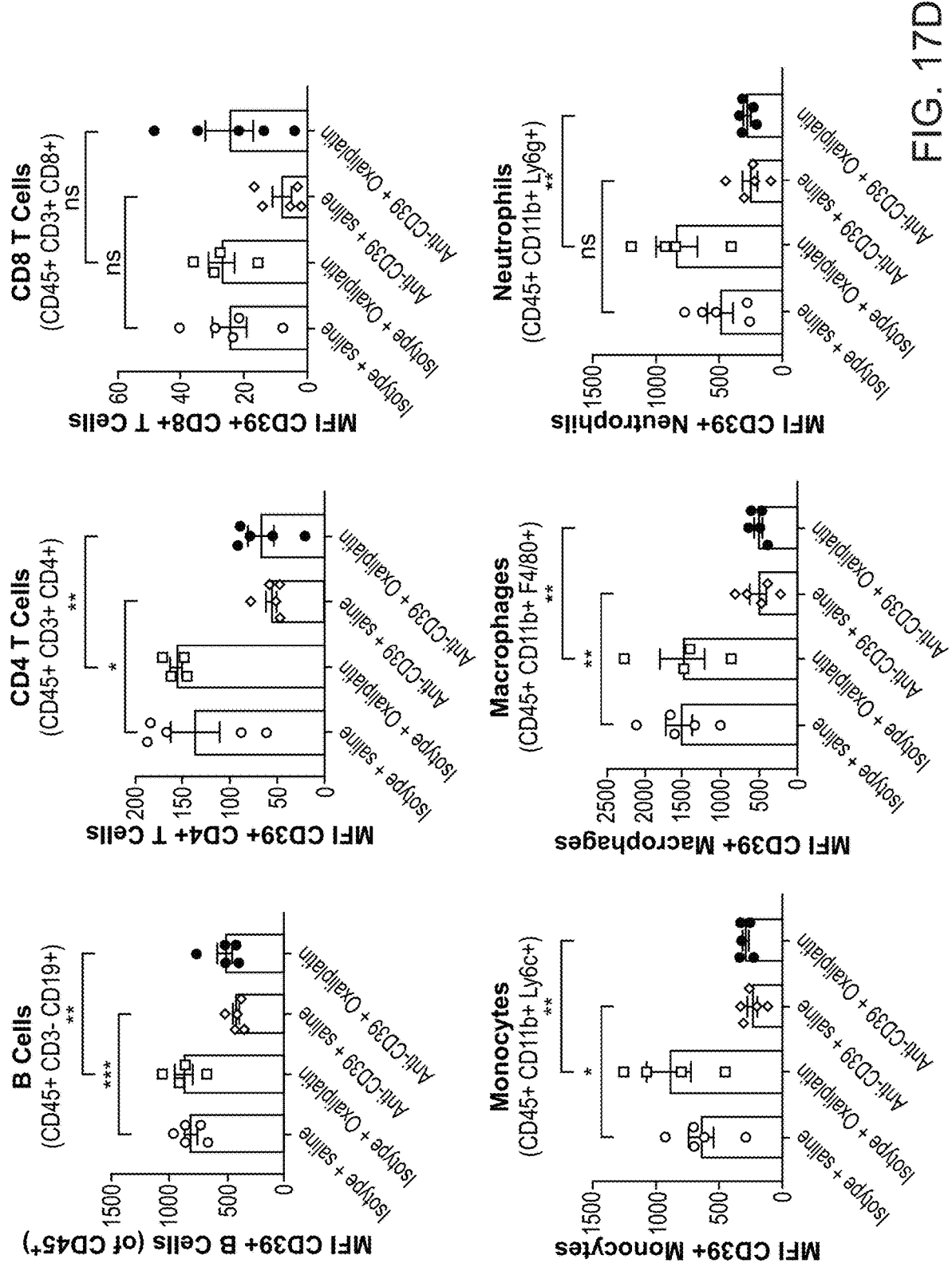
FIG. 17D depicts graphs showing CD39 cell surface expression observed following treatment as indicated along the x-axis. A significant decrease in CD39 cell surface expression was observed with anti-CD39 treatment in almost all immune sub-populations. Statistical analysis was performed with a One-way ANOVA (Dunnett's multiple comparison test, with a single pooled variance), *P<0.05, P<0.01, *P<0.001, ****P<0.0001, each symbol represents and individual mouse, bar height is the mean and error bars are +/− the SEM.
Figure 17D:
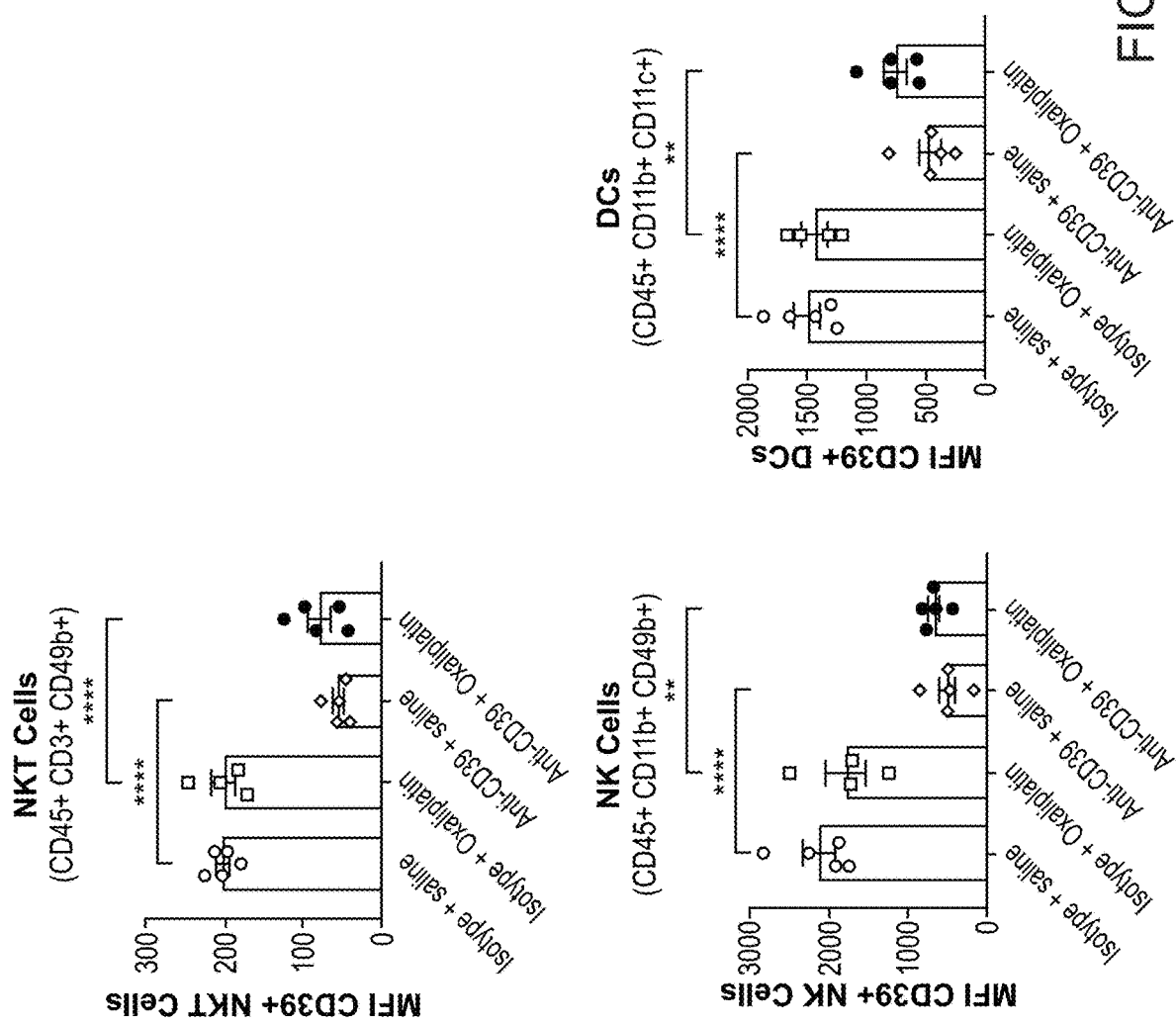
Figure 17E:
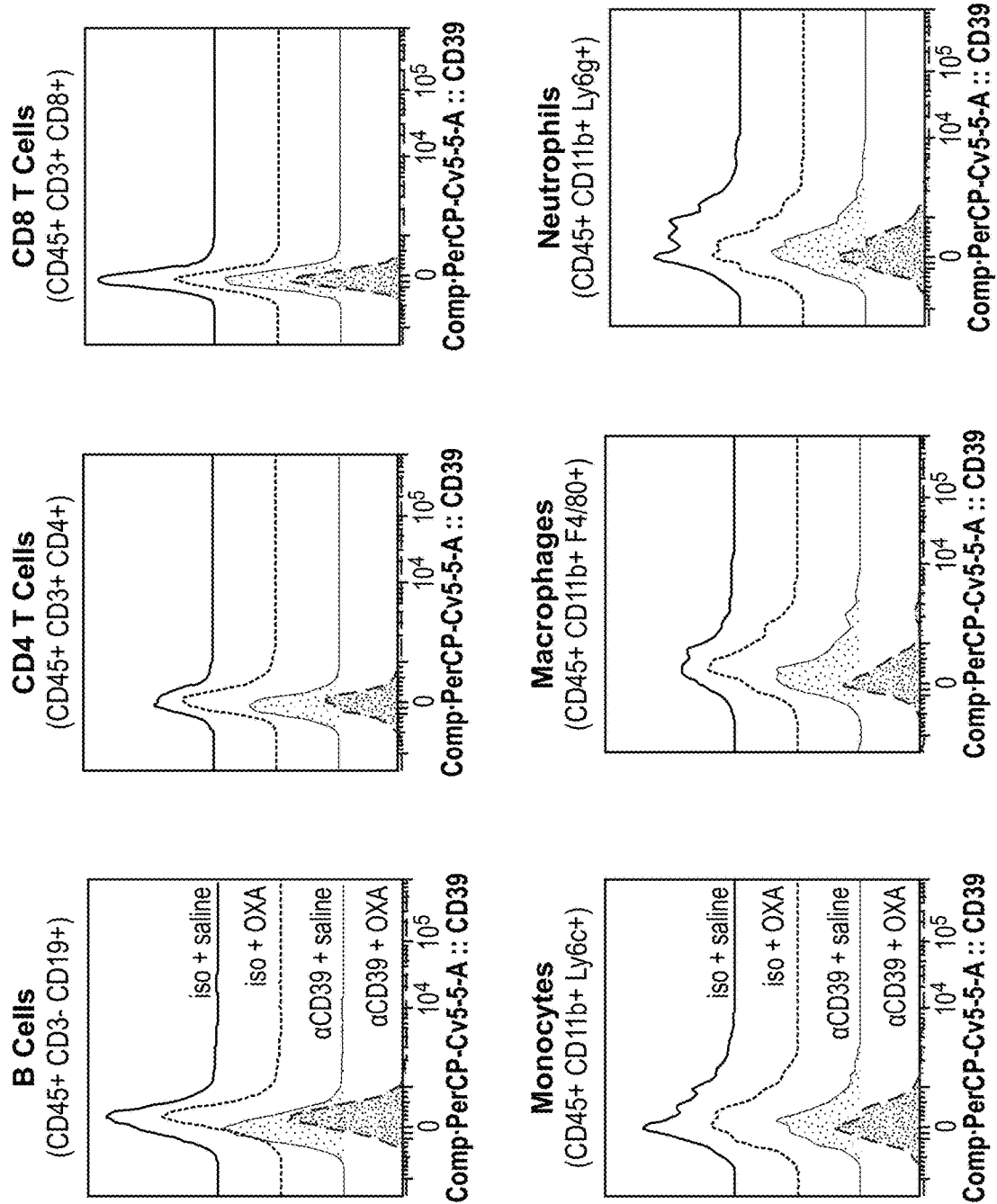
FIG. 17E are histogram overlays for each immune subpopulation showing the decrease in CD39 cell surface expression on a representative animal from each treatment group (isotype+saline (grey open histogram), isotype+oxaliplatin (black open histogram), anti-CD39+saline (grey filled histogram) and anti-CD39+oxaliplatin (black filled histogram).
Figure 17E:
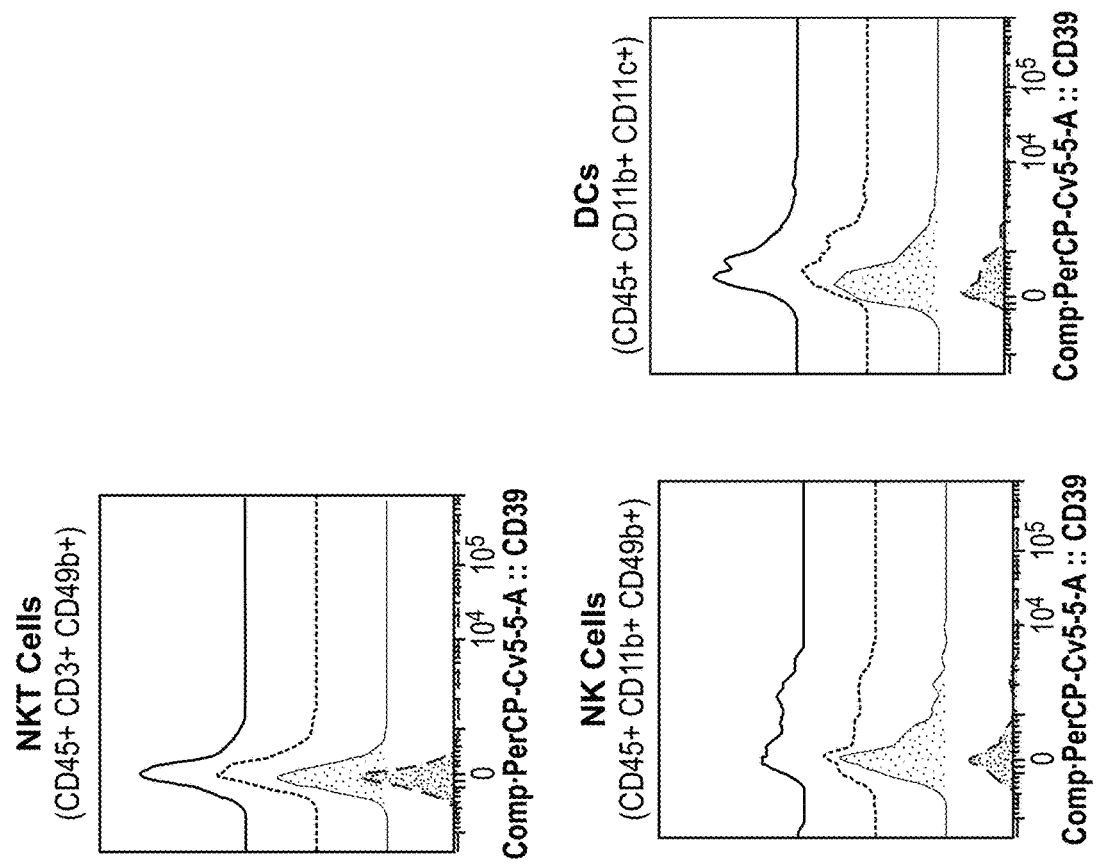

Cell surface CD39 decreases with anti-CD39 treatment in tumor draining lymph nodes of hCD39KI mice. Tumor draining lymph nodes (TLDNs) (right inguinal lymph node) were also collected at the end of the C57BL/6 hCD39KI MC38 mouse study described above. Lymph nodes were dissociated in a 37° C. water bath in RPMI 1640 (Gibco, Cat. No. 11875119) containing of 0.6 mg/mL Collagenase P (Roche, Cat. No. 11213865001), 2.4 mg/mL Dispase II (Sigma, Cat. No. D4693), and 0.3 mg/mL DNAse I (Thermo Scientific, Cat. No. J62229 MB) for 30 minutes with gentle agitation. The dissociated lymph nodes were counted and $2 \times 10^5$ cells per well were plated in a 96-well polypropylene v-bottom plate. Cells were washed in PBS (Gibco, Cat. No. 14190-144) and resuspended in a PBS solution containing 1:25 Fc Block (BD, Cat. No. 564220) and 1:250 Near JR Fluorescent Reactive Dye (Invitrogen, Cat. No. L34976A) for 15 minutes in the dark. After the incubation, the cells were stained with an antibody cocktail (Table 20) and incubated for 30 minutes at 4° C. After the incubation, the cells were pelleted, supernatant removed, and 100 µL of fixation buffer (efioscience, Cat. No. 00-8222-49) was added for 1 hour. The cells were washed, resuspended in 200 µL of PBS, and filtered with a 40 m filter plate (Fisher Scientific, Cat. No. NC0726512) prior to acquisition on the BD LSR Fortessa X-20 Cell Analyzer and analysis with FAowJo™ v1.8 Software (BD Life Sciences) to define immune subpopulations. Human CD39, mouse CD73, and mouse P2X7 expression on the defined immune subpopulations are shown in FIG. 17A and FIG. 17B. Anti-CD39 antibody, ch39mIGG2A.AAG, as a single agent or in combination with oxaliplatin treatment, did not result in significant changes in the immune subpopulation percentages in the tumor draining lymph nodes of hCD39KI mice inoculated with MC38 tumor cells (FIG. 17C). Despite this lack of change in immune populations, anti-CD39 treatment resulted in a significant reduction in human CD39 on the surface of almost all immune subpopulations identified from the tumor draining lymph nodes (FIG. 17D). Representative histograms are shown in FIG. 17E.

TABLE 20

Flow cytometry stain information

| Manufacturer | Catalog # | Fluorochrome | Marker | Clone |
| --- | --- | --- | --- | --- |
| ThermoFisher | 11-4801-82 | FITC | F4/80 | BM8 |
| ThermoFisher | 12-5971-83 | PE | CD49b | DX5 |
| Biolegend | 328218 | PerCPCy5.5 | hCD39 | A1 |
| Biolegend | 400149 | PerCPCy5.5 | IgG1, κ Isotype Ctrl | MOPC-21 |
| Biolegend | 148708 | PECy7 | P2X7 | 1F11 |
| Biolegend | 400617 | PECy7 | IgG2b, κ Isotype Ctrl | RTK4530 |
| ThermoFisher | L34975 | APCCy7 | LD-NIR | n/a |
| Biolegend | 127217 | BV421 | CD73 | TY/11.8 |
| Biolegend | 400429 | BV421 | IgG1, κ Isotype Ctrl | RTK2071 |
| BD | 744178 | BV510 | CD11c | N418 |
| BD | 563005 | BV605 | Ly6g | 1A8-Ly6g |
| Biolegend | 128049 | BV650 | Ly6c | HK1.4 |
| Biolegend | 115555 | BV711 | CD19 | 6D5 |
| Biolegend | 100750 | BV785 | CD8 | 53-6.7 |
| BD | 563553 | BUV396 | CD11b | M1/70 |
| BD | 612843 | BUV737 | CD4 | RM4.5 |
| BD | 748370 | BUV805 | CD45 | 30-F11 |

Figure 18:
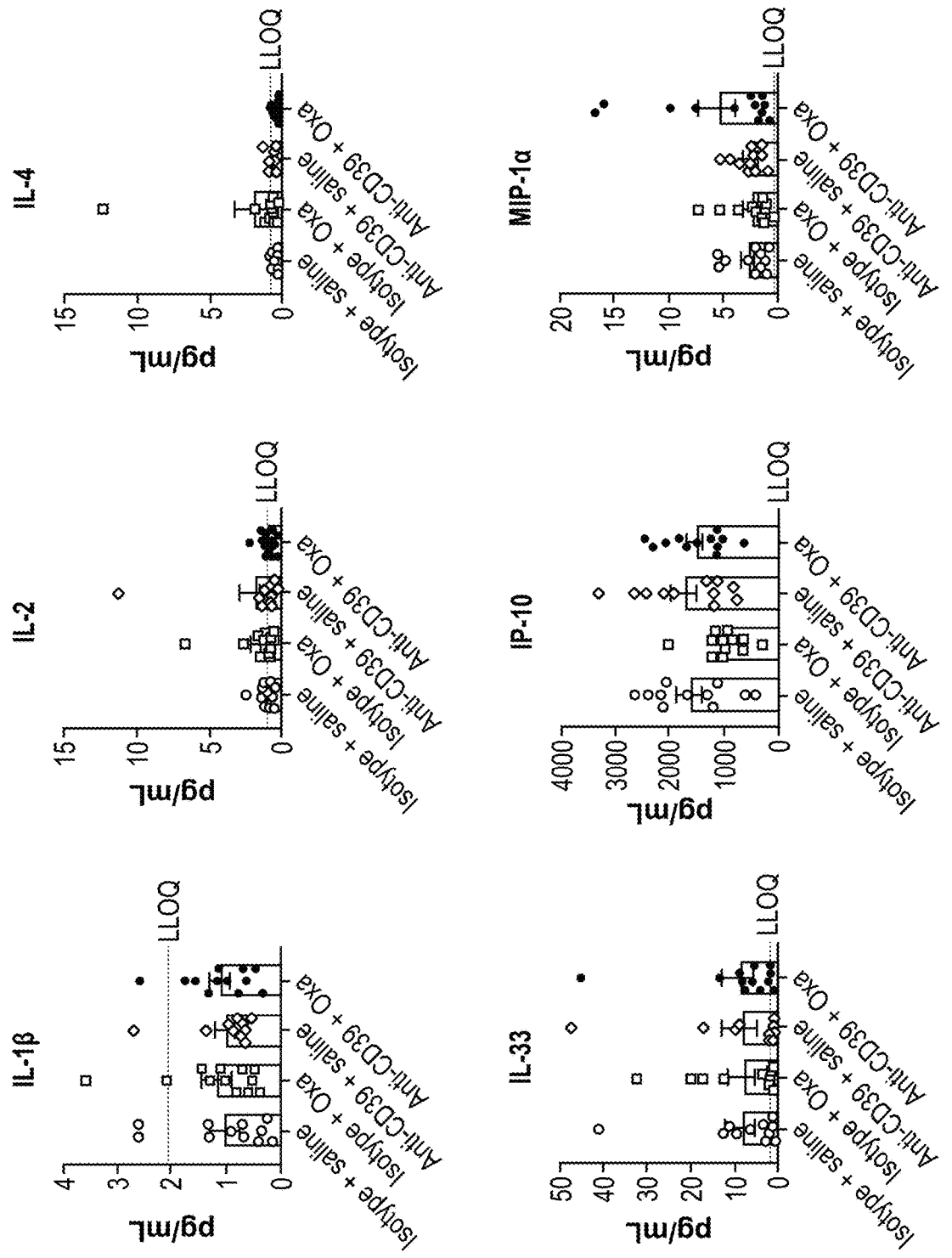
FIG. 18 depicts graphs showing peripheral cytokine levels in plasma derived from hCD39KI mice bearing MC38 tumors at the conclusion of the experiment described in Example 9. Data are presented as mean±SEM with a total of 11-12 mice per treatment group. Statistical analyses were performed using ANOVA with Tukey's multiple comparison test.
Figure 18:
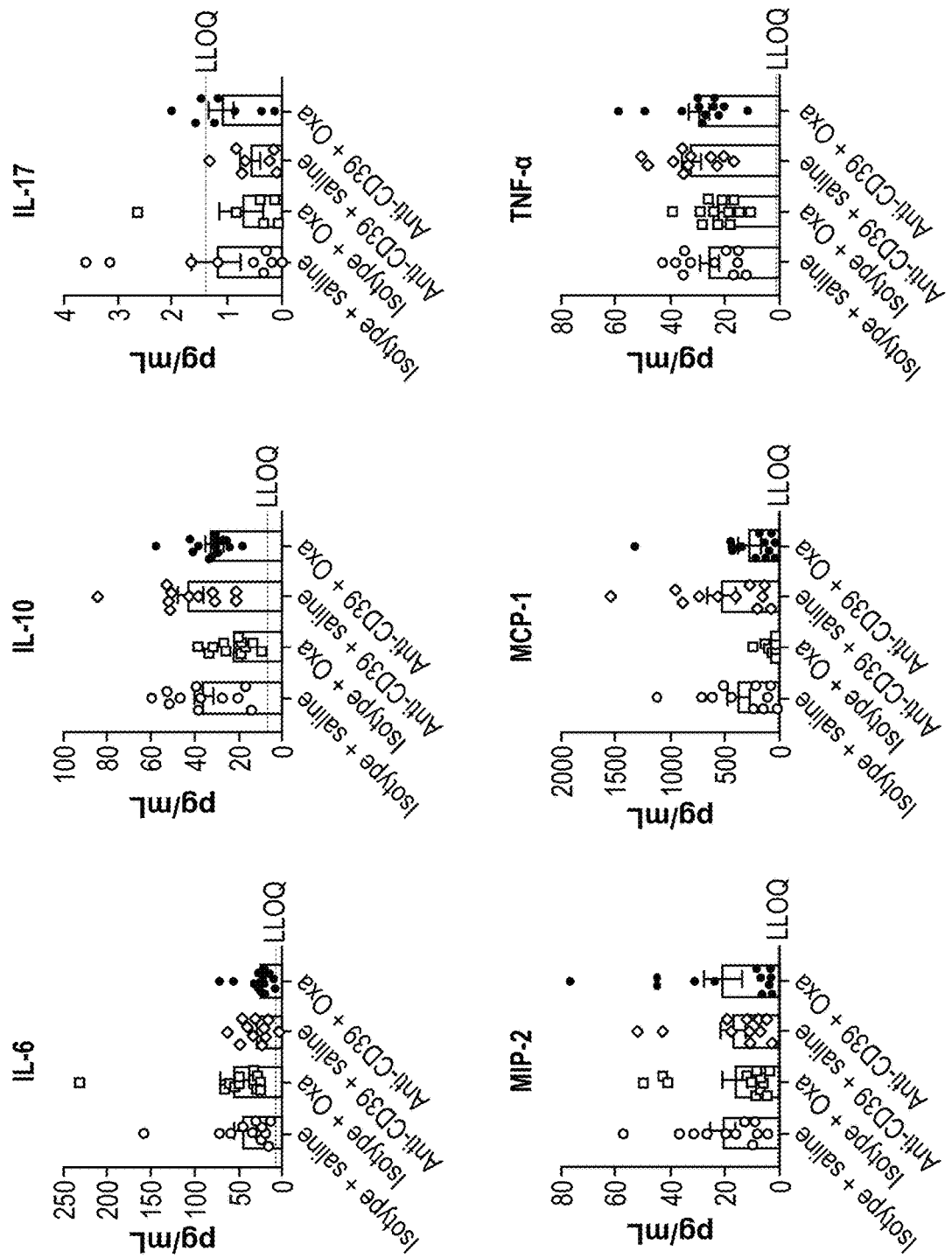

Anti-CD39 treatment does not alter peripheral cytokine levels. A terminal bleed of the mice bearing MC38 tumors were collected into BD Vacutainer® Heparin Tubes (BD Biosciences, Cat. No. 367871), centrifuged at 2000×g for 15 minutes, and supernatant plasma samples were collected. Cytokine levels in the plasma samples were analyzed using MSD following manufacturer's instructions. No elevation in the peripheral cytokine levels was observed in the anti-CD39-treated mice. Data are presented as mean±SEM with a total of 11-12 mice per treatment group (FIG. 18). Statistical analyses were performed using an ANOVA with Tukey's multiple comparison test.

Example 10: Use of Anti-CD39 Antibody in Combination with an Immunogenic Cell Death (ICD) Inducing Therapies The ICD-inducing potential of chemotherapeutic agents was characterized in the absence or presence of an anti-CD39 antibody. This study used three metrics to measure ICD-inducing potential, (1) cytotoxicity, (2) extracellular HMGB1 release, and (3) extracellular ATP release.

Figure 19A:
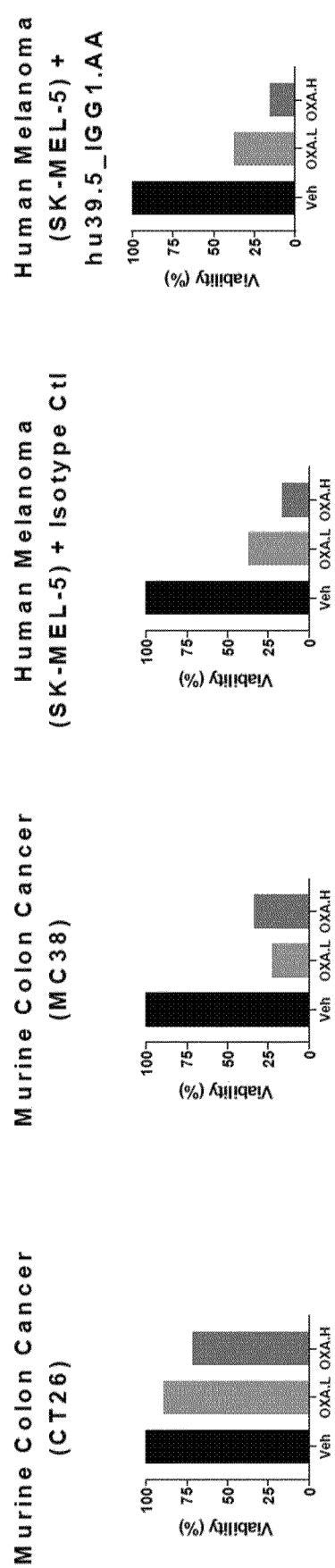
FIG. 19A depicts graphs showing cellular viability of CT26 cells, MC38 cells, SK-MEL-5 cells and isotype control antibody, and SK-MEL-5 cells and hu39.5_IGG1.AA antibody after 24 hours following treatment with vehicle control (Veh), 100 µM oxaliplatin (OXA.L) or 250 µM oxaliplatin (OXA.H).
Figure 19B:
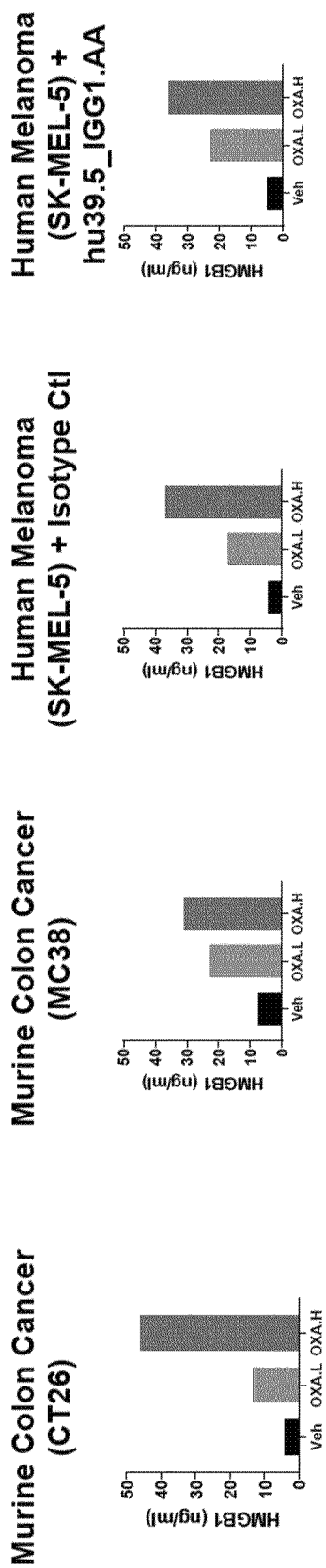
FIG. 19B depicts graphs showing HMGB1 levels in the culture supernatants of CT26 cells, MC38 cells, SK-MEL-5 cells and isotype control antibody, and SK-MEL-5 cells and hu39.5_IGG1.AA antibody after 24 hours following treatment with vehicle control (Veh), 100 µM oxaliplatin (OXA.L) or 250 µM oxaliplatin (OXA.H).
Figure 19C:
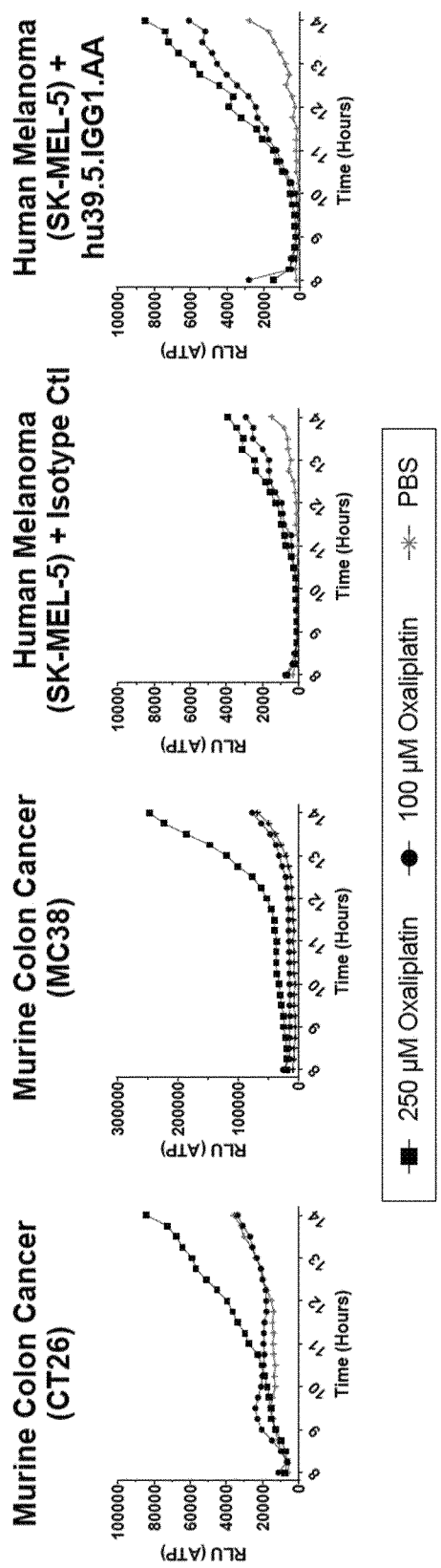
FIG. 19C depicts graphs showing extracellular ATP release by CT26 cells, MC38 cells, SK-MEL-5 cells and isotype control antibody, and SK-MEL-5 cells and hu39.5_IGG1.AA antibody after treatment with vehicle (PBS), 100 µM oxaliplatin, or 250 µM oxaliplatin for 8 hours.

To evaluate cellular ATP release following oxaliplatin treatment, murine colon carcinoma cell lines CT26 and MC38 and human melanoma cell line SK-MEL-5 were defrosted, rinsed, and resuspended in their respective culture media. Culture media for CT26 and MC38 is RPMI+10% FBS+1% glutamax+1% penicillin-streptomycin+1% sodium pyruvate. Culture media for SK-MEL-5 is EMEM+ 10% FBS+1% glutamax+1% penicillin-streptomycin+1% sodium pyruvate. Cells were plated at $2.5 \times 10^4$ cells per well in a 96-well plate and incubated overnight at 37° C., 5% $CO_2$. The following day, the cells were treated with the vehicle (PBS), 100 µM or 250 µM oxaliplatin. SK-MEL-5 cells received an additional treatment of 100 nM hu39.5_IGG1.AA or IgG1 Fc silent isotype control antibody (Absolute Antibody, Cat. No. Ab00178-10.3). To determine cellular viability, the cells were incubated with treatments for 24 hours at 37° C., 5% $CO_2$. At the end of the incubation period, viability was determined using luminescence-based Cell Titer Glo 2.0 assay (Promega, Cat. No. G9242). Data are presented as viability normalized to untreated vehicle controls (FIG. 19A). To determine HMGB1 release, the cells were incubated with treatment for 24 hours at 37° C., 5% $CO_2$. At the end of the incubation period, the plates were centrifuged at 400×g for 5 minutes and supernatants were collected. HMGB1 levels in the culture supernatants were then determined using Lumit HMGB1 Kit (Promega, Cat. No. CS3030B01) following manufacturer's instructions (FIG. 19B). To examine ATP release, the cells were then incubated with treatment for 8 hours at 37° C., 5% $CO_2$. At the end of the incubation period, 4× RealTime-Glo™ Extracellular ATP Assay (Promega Cat. No. GA5010) was added to the cells. Extracellular ATP was measured kinetically by detecting luminescence at 15 minute intervals over a period of 6 hours using a Flexstation® 3 microplate reader. All three cell lines demonstrated ATP release upon treatment with 250 µM oxaliplatin (FIG. 19C). In SK-MEL-5 cells, hu39.5_IGG1.AA treatment led to a greater accumulation of extracellular ATP compared to isotype control-treated cells (FIG. 19C).

Figure 20A:
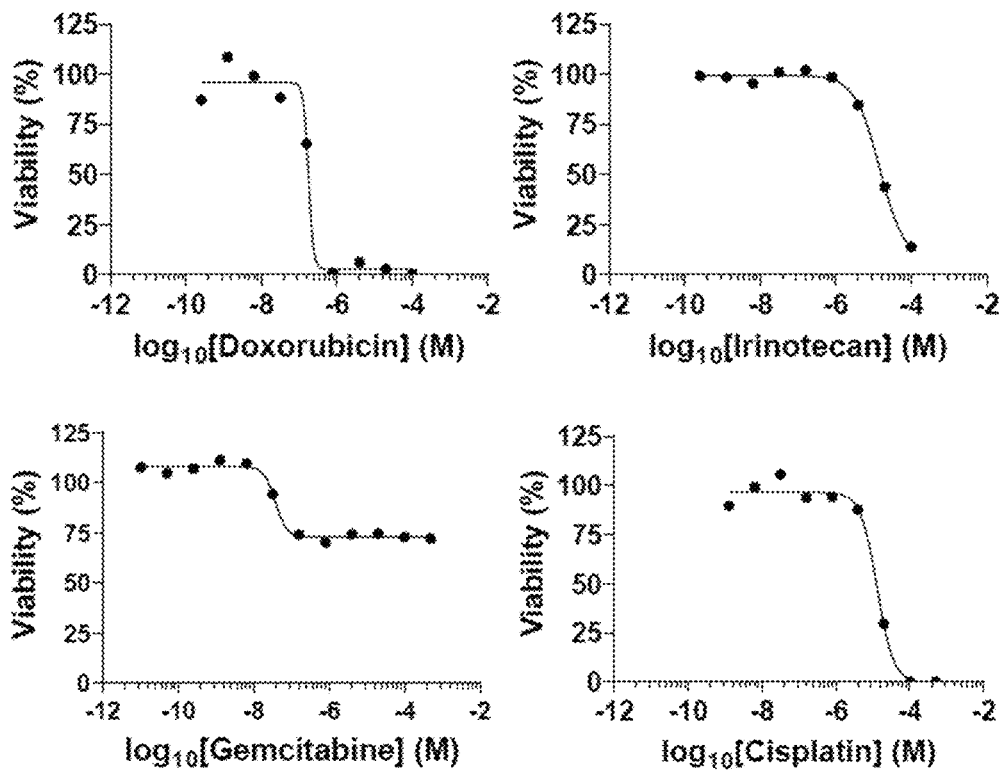
FIG. 20A depicts graphs showing cellular viability of SK-MEL-5 cells after treatment with the indicated chemotherapeutic agents for 48 hours.
Figure 20B:
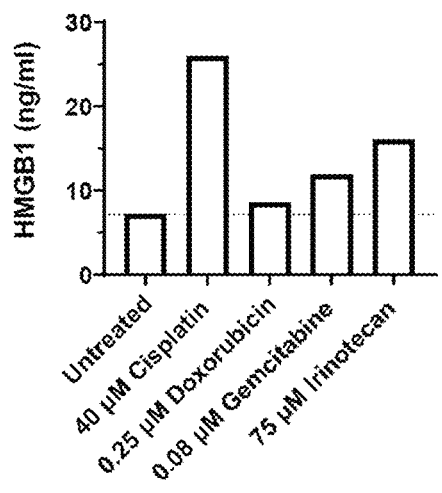
FIG. 20B depicts graphs showing HMGB1 levels in culture supernatant of SK-MEL-5 cells after treatment with the indicated chemotherapeutic agents for 48 hours.
Figure 20C:
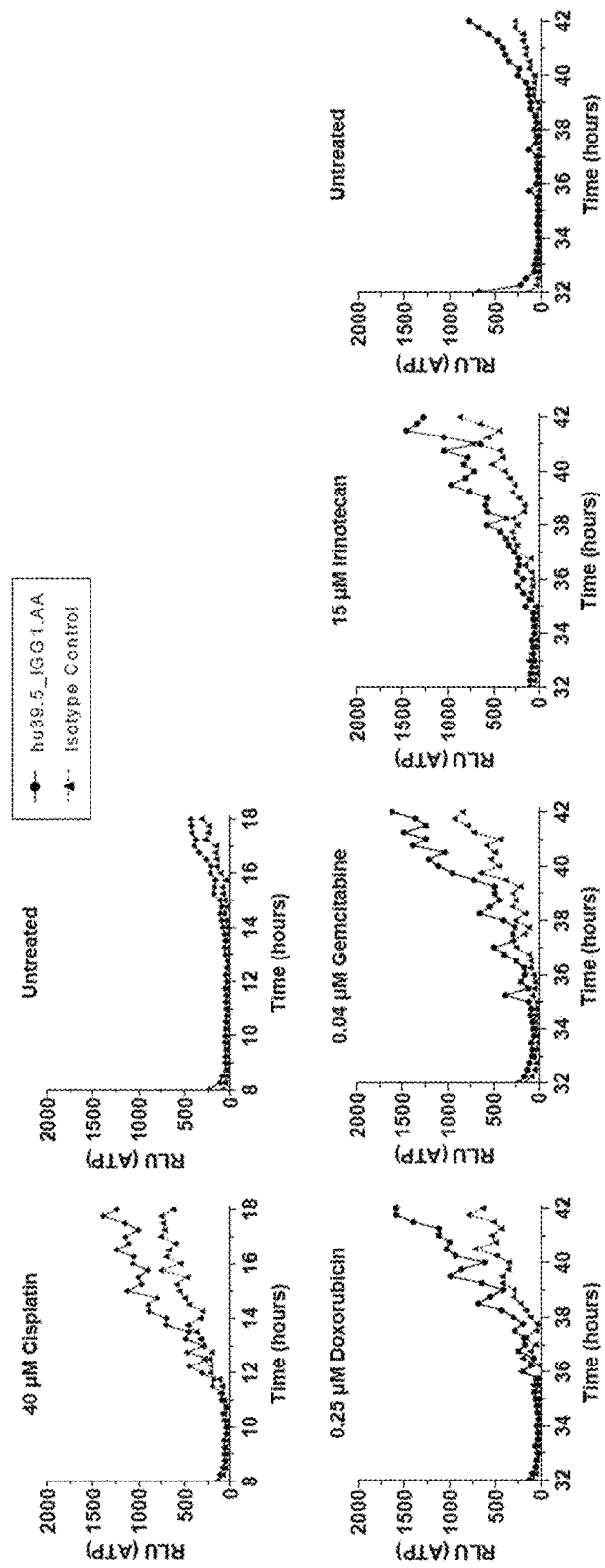
FIG. 20C depicts graphs showing extracellular ATP release by SK-MEL-5 cells after treatment with the indicated chemotherapeutic agents for either 8 or 32 hours.

The ICD-inducing potential of additional chemotherapeutic agents was characterized on the human melanoma cell line SK-MEL-5. Cells were defrosted, rinsed, and resuspended in a culture media of EMEM+10% FBS+1% glutamax+1% penicillin-streptomycin+1% sodium pyruvate. Cells were plated at $2.5 \times 10^4$ cells per well in a 96-well plate and incubated overnight at 37° C., 5% $CO_2$. The following day, the cells were treated with the chemotherapeutic agents doxorubicin (vehicle: DMSO), irinotecan (vehicle: DMSO), gemcitabine (vehicle: PBS) and cisplatin (vehicle: PBS) at the indicated concentration and incubated for 48 hours at 37° C., 5% $CO_2$. (1) To assess cytotoxicity, at the end of the incubation period, cellular viability was determined using luminescence-based Cell Titer Glo 2.0 assay (Promega, Cat. No. G9242). Data are presented as viability normalized to untreated vehicle controls (FIG. 20A). (2) To measure HMGB1 release, at the end of the incubation period, the plates were centrifuged at 400×g for 5 minutes and supernatants were collected. HMGB1 levels in the culture supernatants were then determined using Lumit HMGB1 Kit (Promega, Cat. No. CS3030B01) following manufacturer's instructions (FIG. 20B). (3) Extracellular ATP release was quantified with the chemotherapeutic agents with and without the addition of 100 nM hu39.5_IGG1.AA or IgG1 Fc-silent isotype control antibody (Absolute Antibody, Cat. No. Ab00178-10.3) and incubated for 8 hours or 32 hours. At the end of the incubation period, 4× RealTime-Glo™ Extracellular ATP Assay (Promega Cat. No. GA5010) was added to the cells. Extracellular ATP release was then measured kinetically by detecting luminescence at 15-minute intervals over a period of 10 hours using a Flexstation® 3 microplate reader. All chemotherapy treated groups show an increase in ATP release relative to untreated cells. The addition of hu39.5_IGG1.AA results in higher levels of extracellular ATP (FIG. 20C).

Example 11: Characterization of CD39 and CD39-Related Markers in Human Cells

Figure 21:
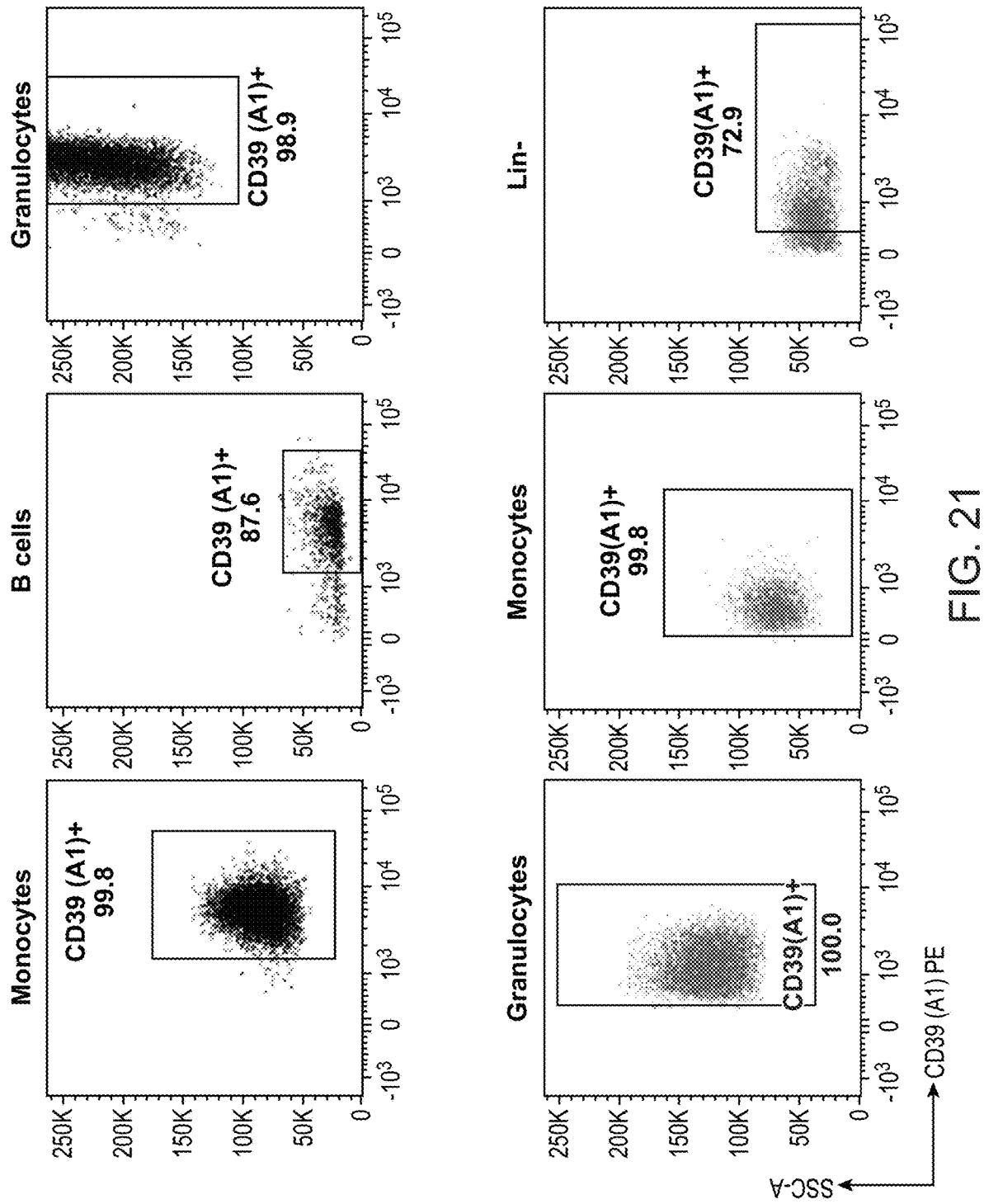
FIG. 21 depicts graphs showing relative expression of CD39 on peripheral immune cells in human (top row) and C57BL/6 hCK39KI MC38 mice (bottom row).
Figure 21:
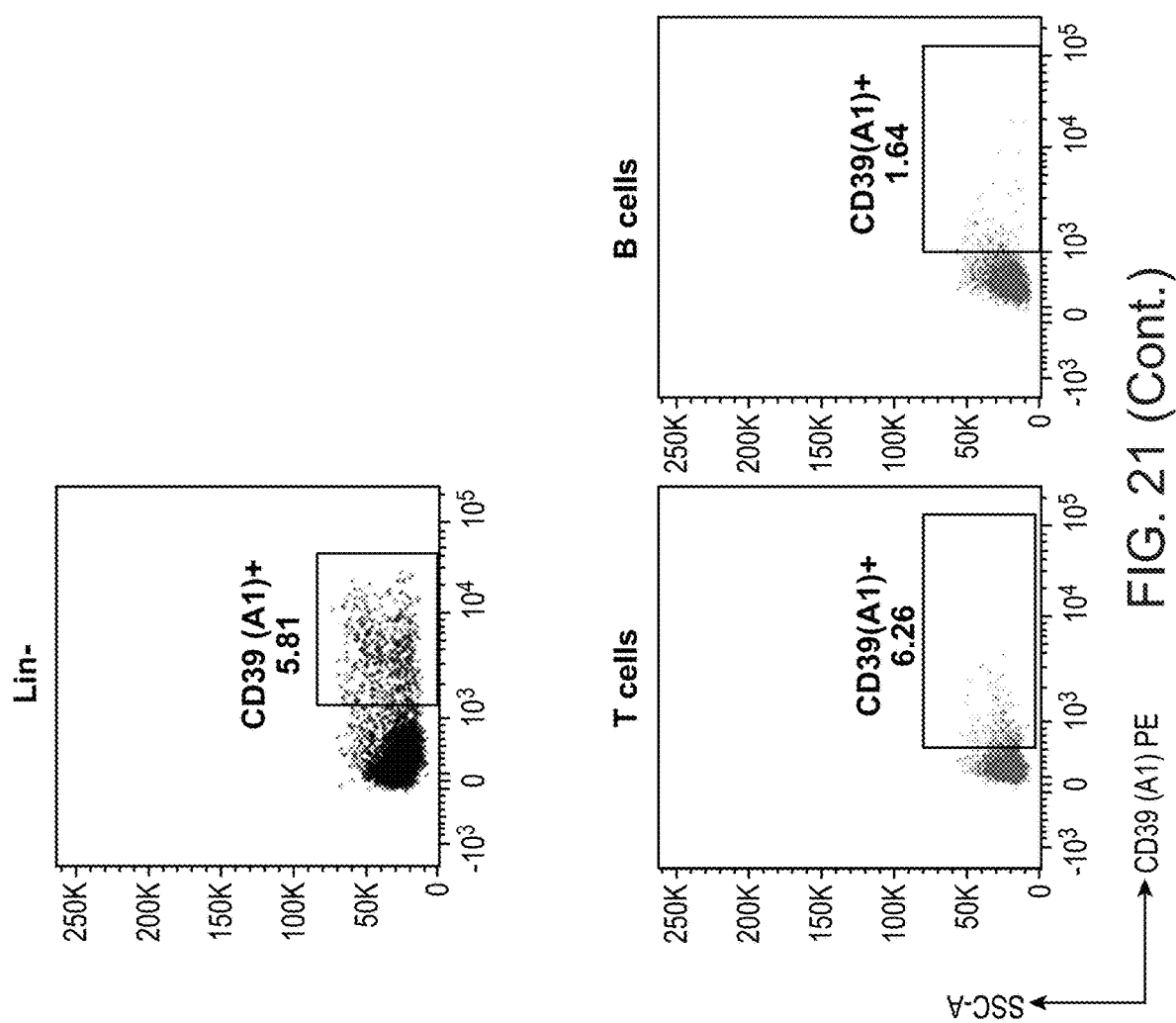

CD39 whole blood (WB) receptor occupancy (RO) flow cytometry assays were used to assess CD39 expression on various cell types in human, cyno, and hCD39KI mouse WB. A description of the hCD39KI RO assay is described in Example 9. Human whole blood samples were analyzed by the same method as described for hCD39KI mouse samples but incorporated species-specific cell lineage markers for monocytes and B cells. The human CD39 WB RO panel consisted of the following antibodies: hu39.5_IGG1.AA-AF647 (competitive to anti-CD39), anti-CD39 A1 PE (non-competitive to anti-CD39), anti-CD14 61D3 FITC, and anti-CD19 H1B19 eFluor450. As shown in FIG. 21, relative expression of CD39 on peripheral immune cells varies between humans and C57BL/6 hCD39KI MC38 mice. While monocytes have the highest level of CD39 expression amongst the cell types assayed in human blood, granulocytes had highest CD39 expression in hCD39KI mice. B cell expression varies most significantly between species. Human peripheral B cells express very high levels of CD39, whereas hCD39KI mouse B cells have low to no CD39 expression.

CD39 and CD39-related markers were also characterized in human in vitro differentiated myeloid cells such as M0-, M1-, M2-polarized macrophages, and monocyte-derived dendritic cells (moDCs), and in primary human myeloid cells such as CD14$^+$ monocytes and myeloid dendritic cell (DC) subsets from the peripheral blood of 4 healthy donors. To generate in vitro differentiated macrophages, positively selected CD14$^+$ monocytes were resuspended in RPMI supplemented with 10% heat-inactivated FBS, 1% GlutaMax, 1% Penicillin/Streptomycin and 50 ng/mL of recombinant human M-CSF (R&D, Cat. No. 216-MCC/CF) and seeded at $4 \times 10^6$ cells per well in a total of 2 mL in 6-well plates (Falcon, Cat. No. 353046). Cells were replenished with 2 mL of fresh RPMI-supplemented media containing 2× M-CSF on day 4. On day 6, cells were polarized to M1 macrophages, using 100 ng/mL LPS (Invivogen, Cat. No. tlr-peklps) and 20 ng/mL recombinant human IFN-γ (Peprotech, Cat. No. 300-02) while M2 macrophages were polarized with 20 ng/mL recombinant human IL-4 (Peprotech, Cat. No. 200-04). No additional cytokines were added for M0 macrophages. To generate moDCs, positively selected CD14$^+$ monocytes were resuspended in RPMI supplemented with 10% heat-inactivated FBS, 1% GlutaMax, 1% Penicillin/Streptomycin and 100 ng/mL of recombinant human GM-CSF (R&D, Cat. No. 215-GM/CF) and 100 ng/mL of recombinant human IL-4 and seeded at $4 \times 10^6$ cells per well in a total of 2 mL in 6-well plates (Falcon, Cat. No. 353046). Cells were replenished with 2 mL of fresh RPMI-supplemented media containing 2× GM-CSF/IL-4 on day 4. On day 7, M0-, M1-, M2-polarized macrophages and moDCs were collected, counted and aliquoted into U-bottom 96-well plates for flow cytometry or into 1.5 mL Eppendorf tubes for RNA. Primary $CD14^+$ monocytes isolated using a positive selection kit and myeloid DCs enriched using a negative selection kit were also aliquoted into U-bottom 96-well plates for flow cytometry or 1.5 mL Eppendorf tubes for RNA.

Flow cytometry quality control staining was performed to determine the purity of the primary $CD14^+$ monocyte isolation, the purity of the primary myeloid dendritic cell (DC) enrichment, and the distribution of DC subsets in the cells resulting from the primary myeloid DC enrichment. Monocytes were defined by $CD14^+$ expression. The purity of $CD14^+$ monocyte isolation was ~99%. Enrichment of primary dendritic cells from the peripheral blood of four human donors showed an enriched population of 48.5% dendritic cells, defined as HLA-DR+ CD11c+ and pDCs. The enriched DCs were composed of 2.8% plasmacytoid DCs (pDCs defined as $HLA^-DR^+$ $CD11c^{neg}$ $CD123^+$), 3.0% conventional DC1 (cDC1 defined as $HLA^-DR^+$ $CD11c^+$ $CD141^+$ $Clec9a^+$), 30.4% conventional DC2 (cDC2 defined as $HLA^-DR^+$ $CD11c^+$ $CD1c^+$ $CD141^{neg}$ $Clec9a^{neg}$) and 12.0% other DC (defined as $HLA^-DR^+$ $CD11c^+$ $CD1c^{neg}$ $CD141^{neg}$ $Clec9^{neg}$).

Figure 22A:
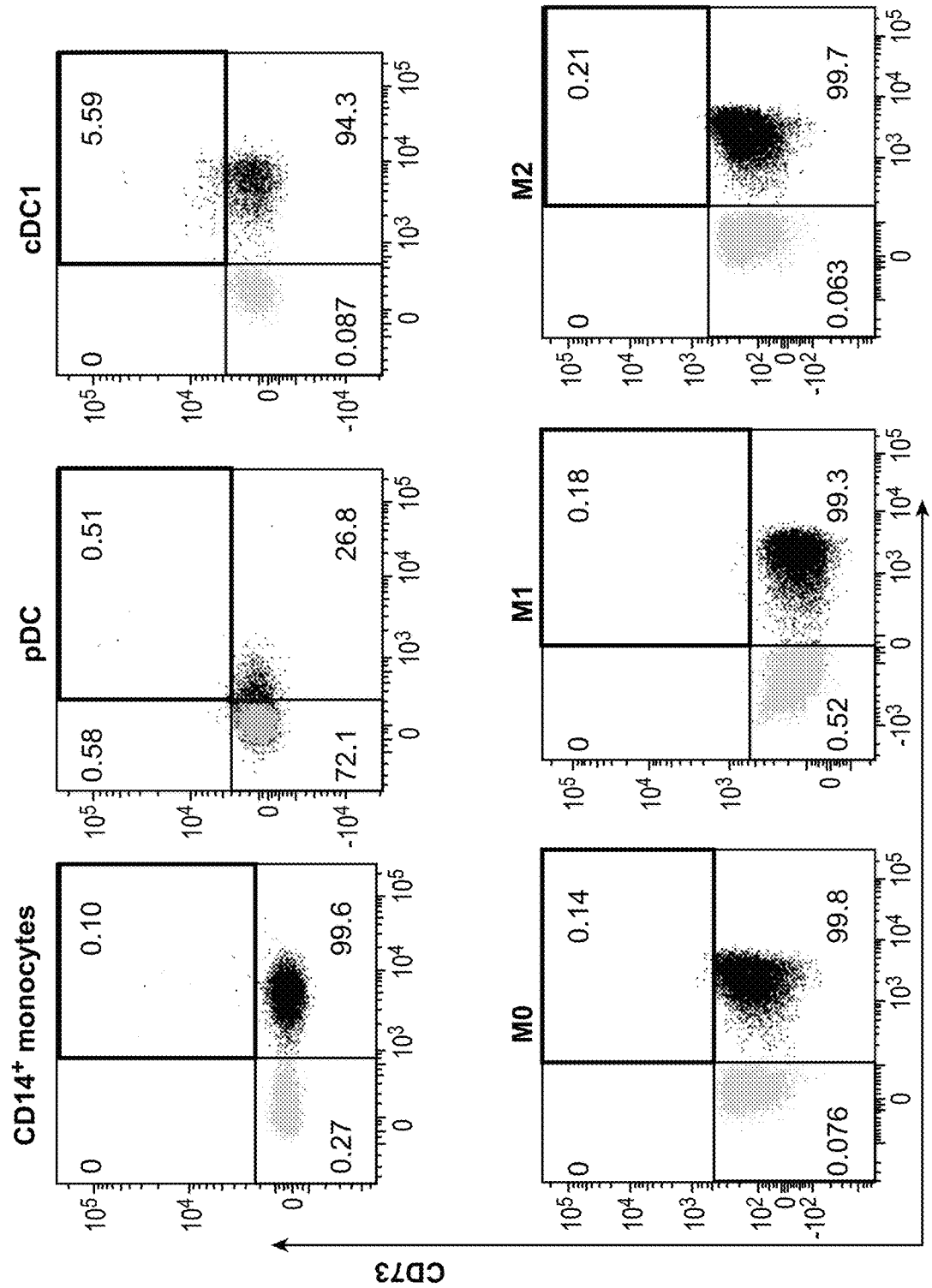
FIG. 22A depicts flow cytometry scatter plots from a representative donor showing the distribution of CD39 and CD73 on different myeloid cell types. CD14$^+$ monocytes were directly isolated from peripheral human blood. DCs enriched from peripheral human blood were further subtyped into pDCs, cDC1, cDC2, and other DCs. M0, M1, M2 and moDC subpopulations were derived from CD14$^+$ monocytes as described in the examples.
Figure 22A:
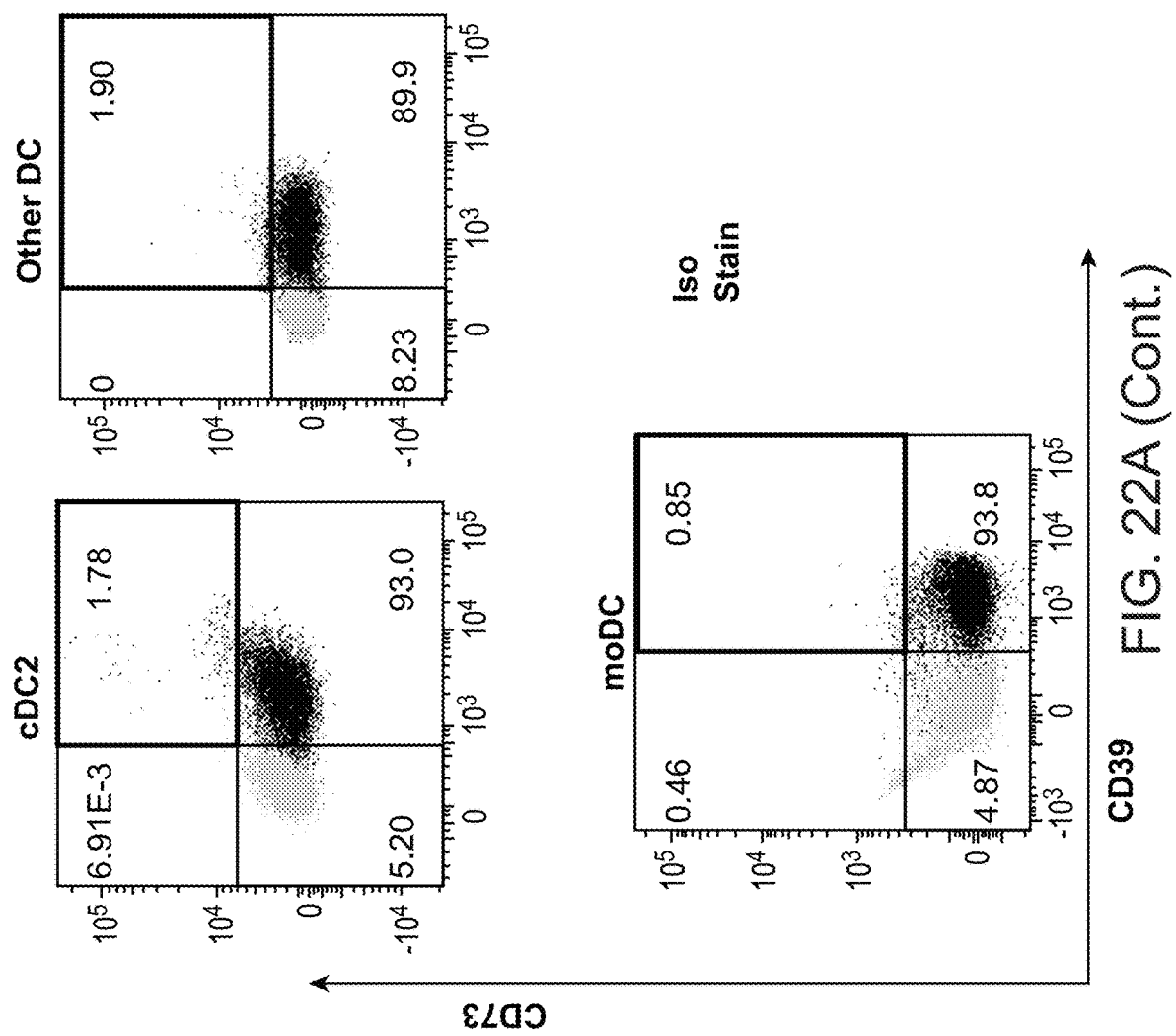
Figure 22B:
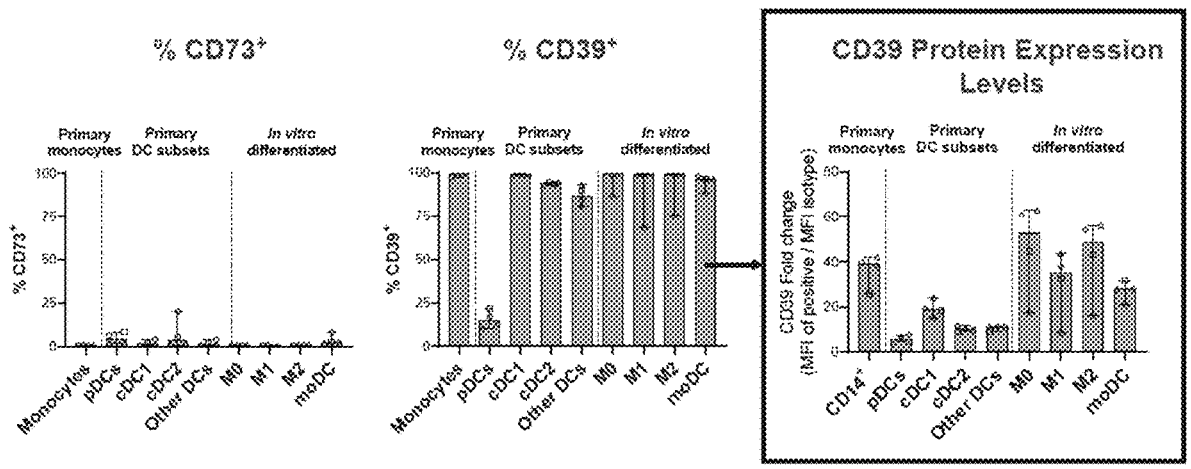
FIG. 22B depicts graphs showing CD73 percent positivity (left panel) and CD39 percent positivity (middle panel) and CD39 protein expression (right panel) as evaluated by flow cytometry on human peripheral blood CD14$^+$ monocytes, primary dendritic cell (DC) subsets including plasmacytoid DCs (pDCs defined as HLA−DR$^+$ CD11c$^{neg}$ CD123$^+$), conventional DC 1s (cDC1 defined as HLA−DR$^+$ CD11c$^+$ CD141$^+$ Clec9a$^+$), conventional DC 2s (cDC2 defined as HLA−DR$^+$ CD11c$^+$ CD1c$^+$ CD141$^{neg}$ Clec9a$^{neg}$) and other DCs (defined as HLA−DR$^+$ CD11c$^+$ CD1c$^{neg}$ CD141$^{neg}$ Clec9a$^{neg}$) and in vitro differentiated monocyte-derived myeloid cells including macrophages (M0) polarized macrophages (M1, M2) and DCs (moDC). For the CD39 protein expression level, the mean fluorescence intensity of the CD39$^+$ cells was divided by the mean fluorescence intensity of the isotype control. Each symbol is a unique donor, the height of the bar is the median and the error bars are the range.

For flow cytometric evaluation of CD39 and CD73 (FIG. 22A and FIG. 22B), $CD14^+$ monocytes, enriched myeloid DCs, M0, M1, M2 macrophages and moDCs were aliquoted into a 96-well plate and resuspended in 50 µL/well of 1:25 Fc block (BD, Cat. No. 564220) and 1:250 aqua viability dye (Invitrogen, Cat. No. L34966A) in DPBS and incubated for 15 minutes at room temperature in the dark. Cells were then stained in 50 µL/well with the following antibodies [0.25 µg/test of CD39 PE-Cy7 (eBiosciences, Cat. No. 25-0399-42) and 0.5 µg/test of CD73 BUV737 (BD, Cat. No. 612812) or the corresponding isotype controls, mouse IgG1 PE-Cy7 (BD, Cat. No. 557647) and mouse IgG1 BUV737 (BD, Cat. No. 612758)] for 30 minutes at 4° C. After one wash in DPBS, cells were fixed with 50 µL IC Fixation Buffer (Invitrogen, Cat. No. 00-8222-49) for 20 minutes at room temperature. Cells were then washed and resuspended in DPBS and subjected to flow cytometry using the BD LSR Fortessa X-20 Cell Analyzer. Percent positivity of CD39 and CD73 on the $CD14^+$ monocytes, enriched myeloid DCs subtypes, M0, M1, M2 macrophages and moDCs were assessed by comparison to an isotype control. The $CD14^+$ monocytes, all in vitro-derived subsets (M0, M1, M2 macrophages and moDCs), and the primary enriched DC subsets cDC1, cDC2 and other DCs, all had high CD39 percent positivity and low CD73 percent positivity (FIG. 22A and FIG. 22B). Relatively few (15%) pDCs were positive for CD39. Given that the majority of the cell types had >90% CD39 percent positivity, CD39 expression level was further explored by looking at the intensity of CD39 staining compared to the isotype control (FIG. 22B). Although variable across donors, CD39 expression was higher on $CD14^+$ monocytes, in vitro derived macrophages, moDCs compared to primary DCs. Of the primary DCs, cDC1s have the highest expression of cell surface CD39.

Figure 22C:
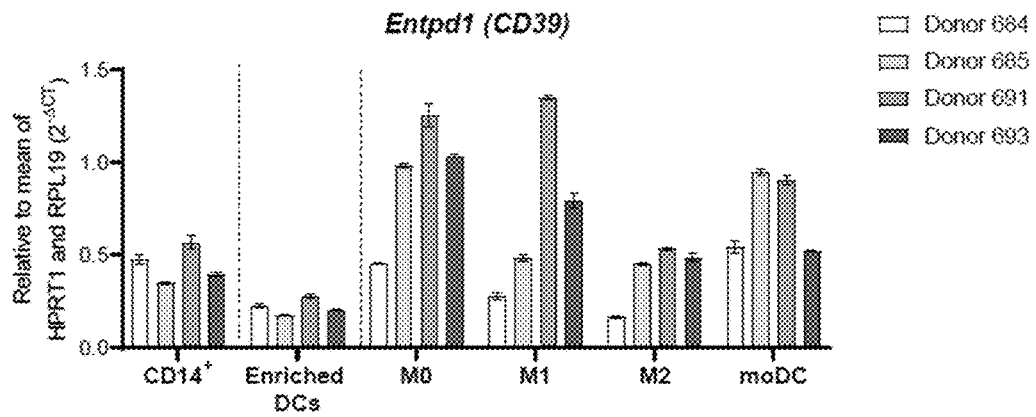
FIG. 22C and FIG. 22D depict graphs showing mRNA expression of ENTPD1 (CD39) (FIG. 22C) and NT5E (CD73) (FIG. 22D) evaluated on human peripheral blood CD14$^+$ monocytes, an enriched population of primary dendritic cell subsets (enriched DCs) and in vitro differentiated monocyte-derived myeloid cells including macrophages (M0) polarized macrophages (M1, M2) and DCs (moDC) obtained from four donors.
Figure 22D:
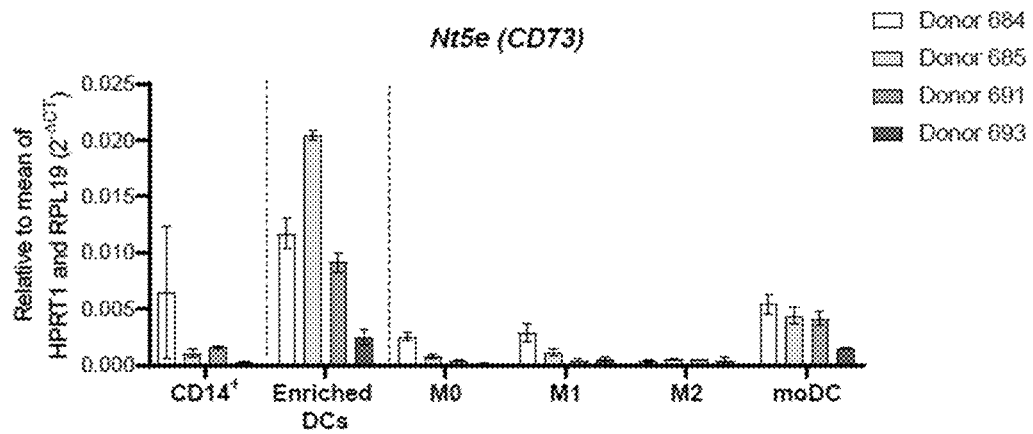

ENTPD1 (CD39) and NT5E (CD73) gene expression were analyzed by qPCR using standard methods (FIG. 22C and FIG. 22D). Levels of ENTPD1 gene expression were greater than levels of NT5E gene expression across all cell types. The enriched DC population had the lowest relative expression of ENTPD1 and the highest relative expression of NT5E. For evaluation of a wider range of CD39-related gene expression in these human myeloid subsets, a custom NanoString panel was designed and utilized. RNA from each of the myeloid cell subsets were isolated using the Qiagen RNeasy Mini kit (Cat. No. 74106) following the manufacturer's instructions. RNA was then quantified on the Nanodrop and 70 ng of RNA was utilized for NanoString. For hybridization of the RNA to the custom NanoString codeset, 70 µL of the hybridization buffer was added to the reporter codeset and 8 µL was added to 5 µL of RNA for each sample. Two microliters of the capture probeset was then added to each sample and incubated in the thermocycler at 65° C. for 16 hours. Samples were then topped up to 30 µL with RNase-free water and loaded into the sample loading ports of the nCounter SPRINT Cartridge (NanoString, Cat. No. SPRINT-CAR-1.0). The cartridge was then run on the NanoString nCounter SPRINT Profiler. A quality control metric was run on the data from each sample, and samples passing the quality control test were normalized to the 3 housekeeping genes included within the custom NanoString panel to evaluate gene expression.

Figure 22E:
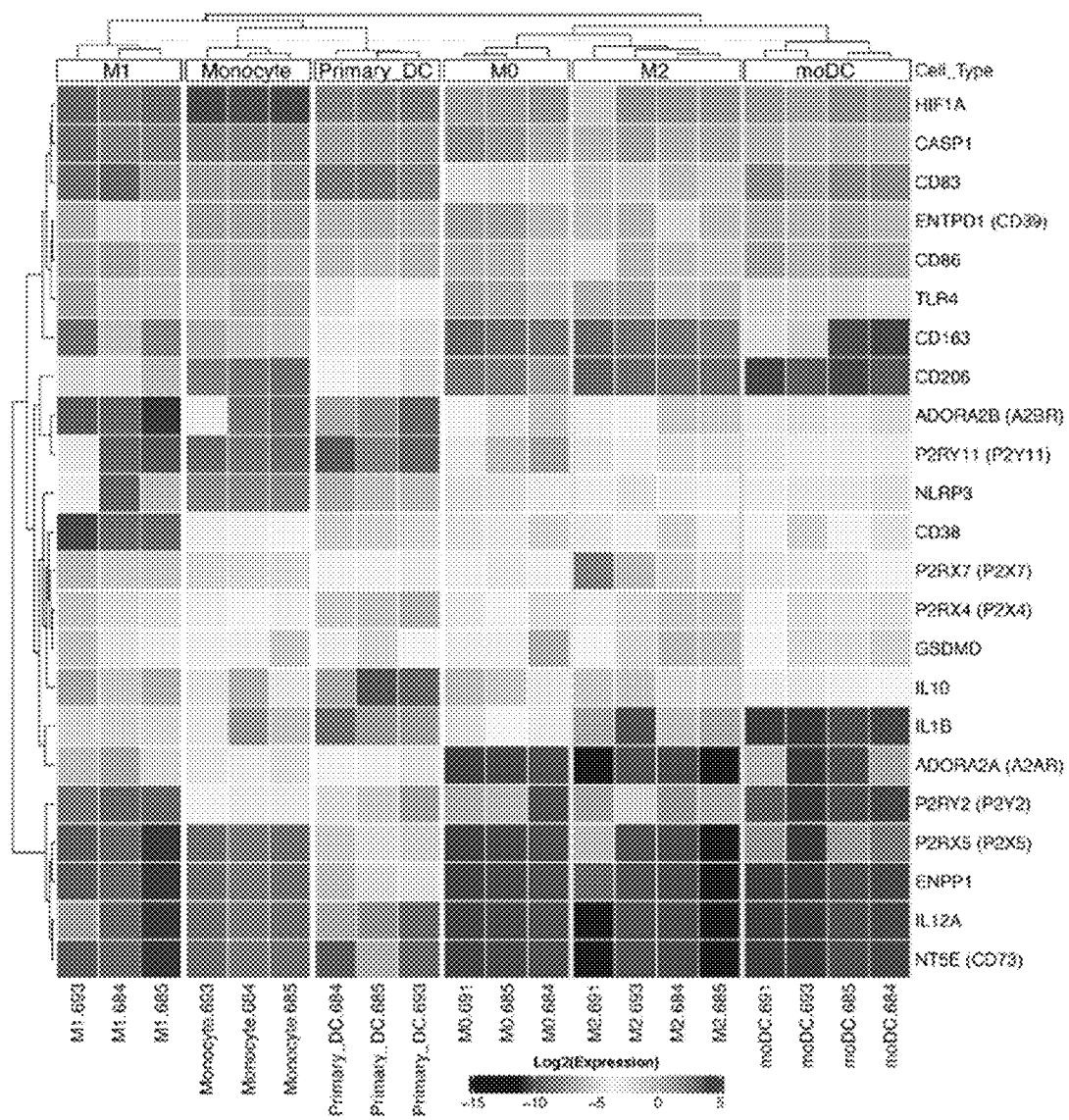
FIG. 22E is a heatmap showing unsupervised clustering of housekeeping genes-normalized expression of CD39, adenosine, and inflammasome pathway genes using a custom NanoString panel in cell populations from four healthy donors described in 279. Low quality wells flagged by low counts or aberrant control probes were removed from this analysis. Specific donor ID appended at the end of the cell type label. Dotted horizontal line in the top dendrogram shows samples split but does not affect unsupervised nature of the clustering.

A heatmap showing unsupervised clustering of housekeeping genes-normalized expression of CD39, adenosine, and inflammasome pathway genes using the custom NanoString panel is shown in FIG. 22E. Low quality wells flagged by low counts or aberrant control probes were removed from this analysis. Specific donor ID appended at the end of the cell type label. Dotted horizontal line in the top dendrogram shows samples split but does not affect unsupervised nature of the clustering. CD39 is expressed across all profiled immune populations. Cell types form distinct clusters given the consistent expression of genes in these pathways within each cell type. Monocytes, M1 macrophages, and enriched primary DCs cluster together, driven by expression on IL-1β, P2X7, and A2AR. M0, M1 macrophages, and moDCs form the other cluster with higher expression of CD206, A2BR, and P2Y11.

Example 12: P2Y11 Antagonism Reduces ATP-Driven Dendritic Cell Activation

The effect of P2X1, P2X7, and P2Y11 inhibitors was examined on the activation of monocyte-derived dendritic cells (MoDCs). MoDCs were generated from positively selected human monocytes cultured with GM-CSF and IL-4 as described in Example 11. On day 7, the 6-well plates were incubated on ice for 5 minutes and scraped to detach and count cells. Cells were resuspended in fresh media with GM-CSF and IL-4 and 125,000 cells in 100 µL were plated per well in a 96-well flat-bottomed Upcell plate (Nunc, Cat. No. 174897). Ten micromolar of each compound [P2X1 inhibitor, NF023, Millipore Sigma, Cat. No. 104869-31-0; P2X7 inhibitor, A-740003, Millipore Sigma, Cat. No. 861393-28-4; P2Y11 inhibitor NF340, APExBIO, Cat. No. B7508; P2Y11 inhibitor NF157, APExBIO Cat. No. B7060] or vehicle-control (0.1% DMSO) was added, mixed gently, and incubated for 1 h at 37° C. 5% $CO_2$. Subsequently, 0 or 300 µM ATP was added, mixed gently, and incubated for 18 h at 37° C. 5% $CO_2$. For flow cytometric evaluation, cells were detached from the plates and transferred to a 96-well polypropylene v-bottom plate. Cells were washed in PBS (Gibco, Cat. No. 14190-144) and resuspended in a PBS solution containing 2% FBS, viability dye (LD-NIR, Invitrogen, Cat. No. L34994), Fc block, and staining antibodies [BV510 anti-CD80 (BD Horizon, Cat. No. 563084), PE-Cy7 anti-CD83 (BD Horizon, Cat. No. 561132) and BV605 anti-CD86 (BD Horizon, Cat. No. 562999)]. Cells were incubated at room temperature for 60 min, stain was washed out and cells were fixed with BD Phosphoflow FIX Buffer I (BD, Cat. No. 557870) and incubated for 15 min. Fixation buffer was removed, cells were washed with PBS, and stored at 4° C. until acquisition on the BD LSR Fortessa X-20 Cell Analyzer and analysis with FlowJo™ v10.8 Software (BD Life Sciences).

Figure 23:
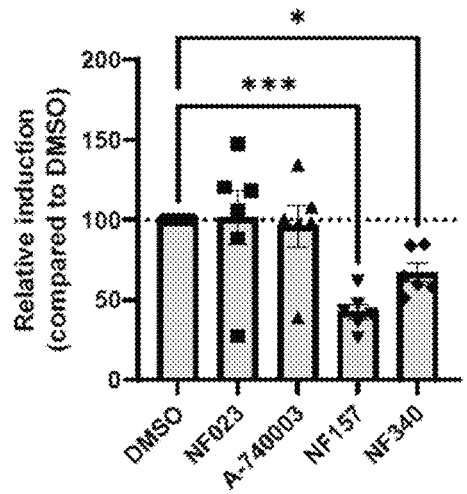
FIG. 23 depicts graphs showing relative induction (compared to DMSO) of cell surface marker expression following treatment with the indicated inhibitor for 1 hour followed by 0 or 300 µM ATP for 18 hours. Cell surface expression of CD86 (top panel), CD83 (middle panel), and CD80 (bottom panel) was assessed by flow cytometry. The induction of activation marker expression from 0 to 300 µM ATP was compared between inhibitor-treated and DMSO-treated cells. The height of the bars is the mean and error bars are the SEM. Each dot represents one donor. Statistical analyses were performed using an ANOVA with Tukey's multiple comparison test, *P<0.05, ***P<0.001.
Figure 23:
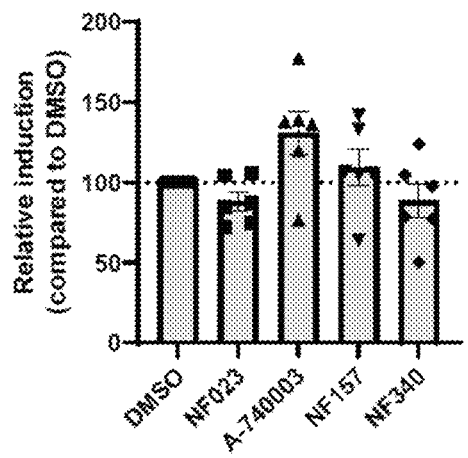
Figure 23:
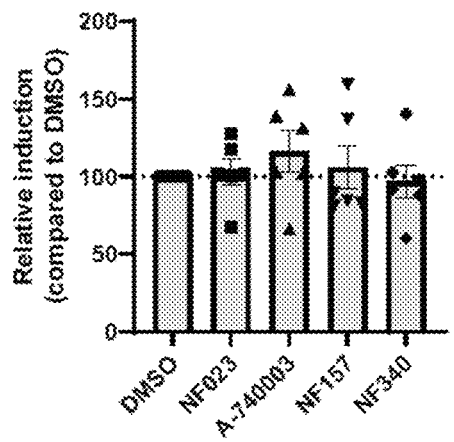

Within each inhibitor group, fold change was calculated between the ATP and non-ATP-treated group to calculate the induction of each surface marker in the presence of ATP. The induction level of the inhibitor-treated groups was then normalized to the DMSO-treated group. The results show that P2Y11 inhibitors suppress CD86 induction by ATP, but not CD80 or CD83 (FIG. 23).

Figure 24A:
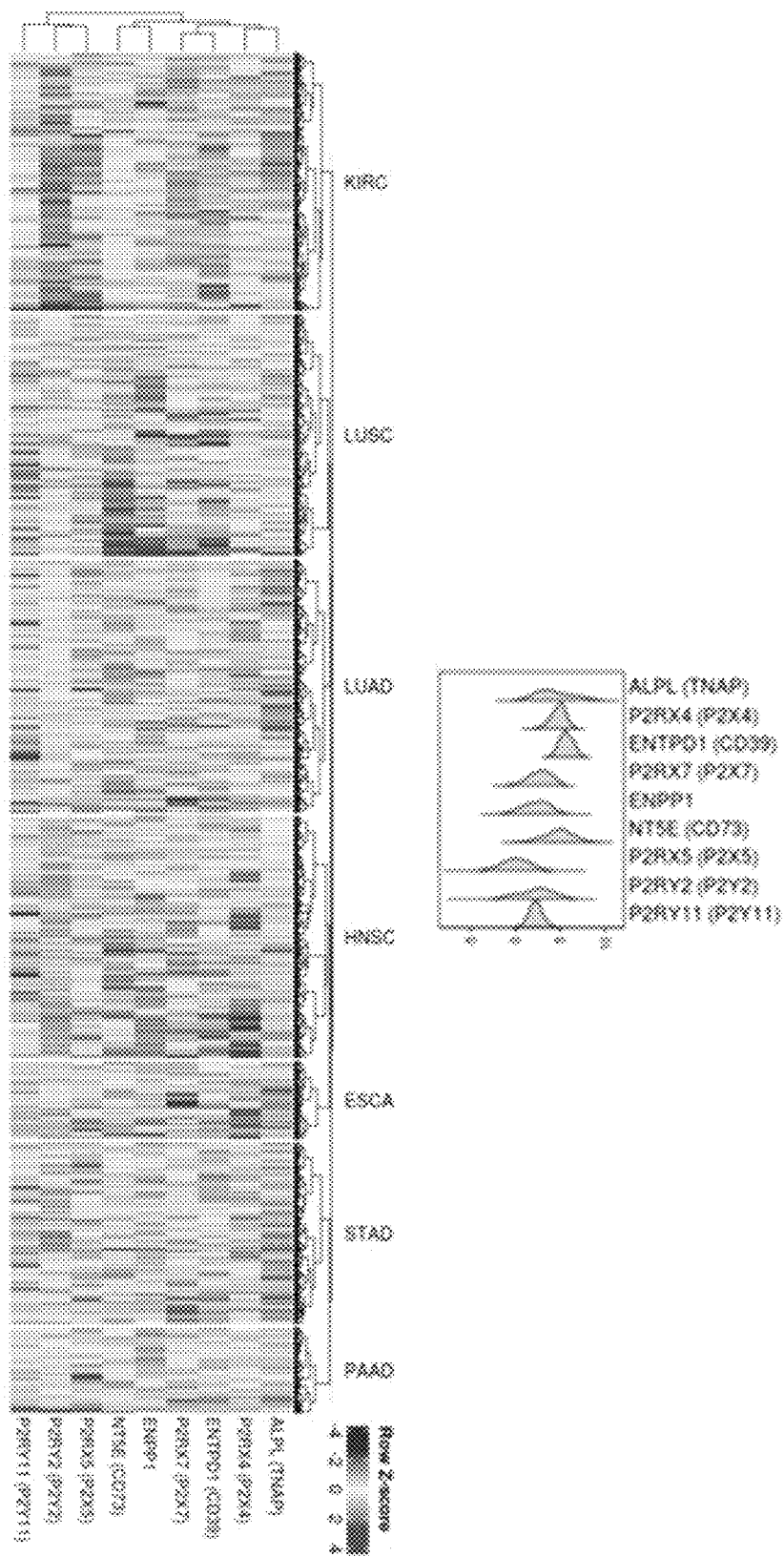
FIG. 24A is a heatmap showing TCGA RNA expression analysis in tumors (Kidney renal clear cell carcinoma (KIRC), Lung squamous cell carcinoma (LUSC), Lung adenocarcinoma (LUAD), Head and neck squamous cell carcinoma (HNSC), Esophageal carcinoma (ESCA), Stomach adenocarcinoma (STAD), and Pancreatic adenocarcinoma (PAAD)) normalized on a per gene basis. The protein encoded by the gene is indicated in parentheses. Proteins and genes observed include: ALPL (TNAP), P2RX4 (P2X4), ENTPD1 (CD39), ENPP1, NT5E (CD73), P2RX5 (P2X5), P2RY2 (P2Y2), and P2RY11 (P2Y11). Distribution is shown in the histograms to the right.
Figure 24B:
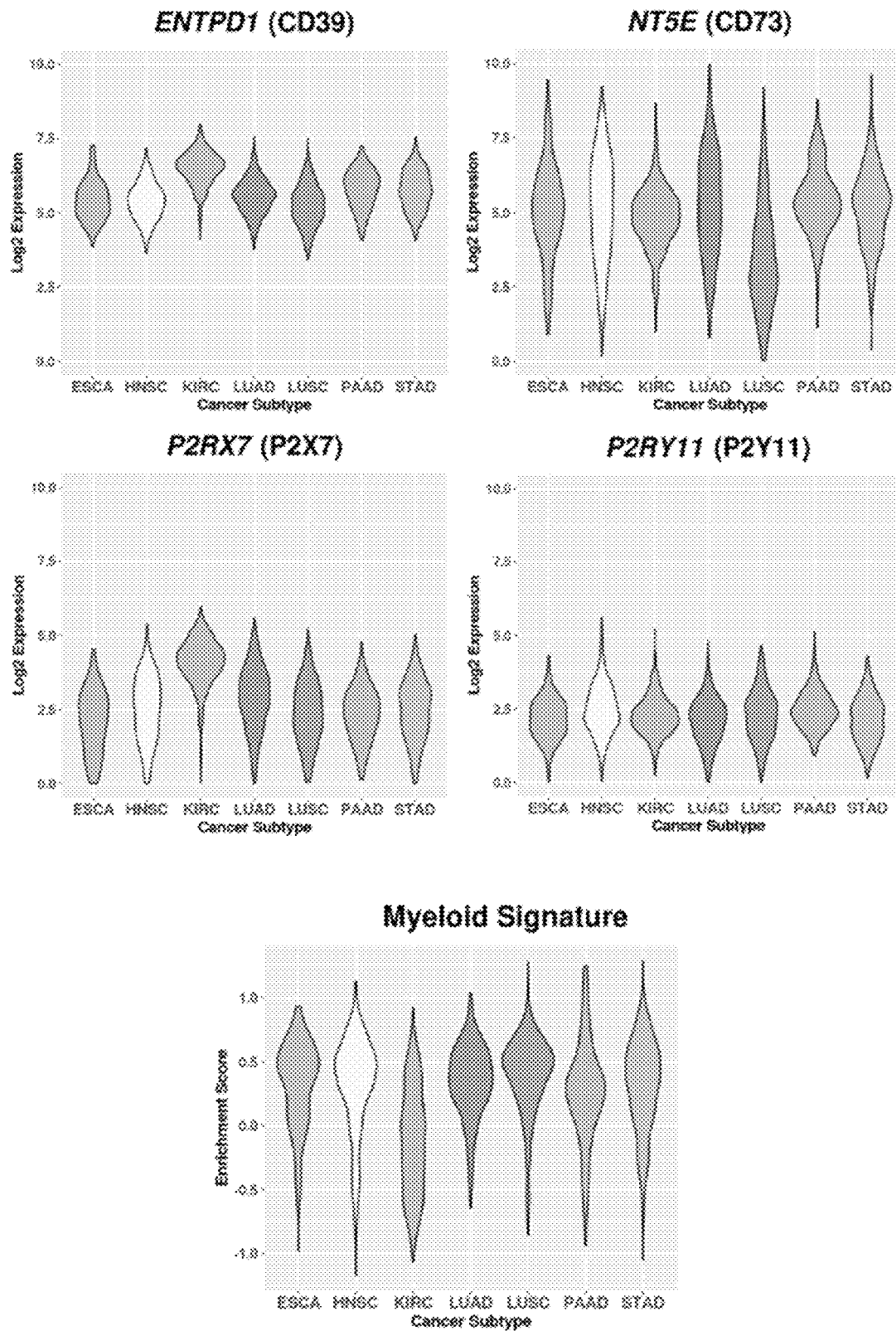
FIG. 24B depicts violin plots. The violin plots outline the kernel probability density (the width of the shaded area represents the proportion of the data located there) of the normalized log 2 gene expression (y-axis) of the following genes (proteins): ENTPD1 (CD39), NT5E (CD73), P2RX7 (P2X7), and P2RY11 (P2Y11) among a subset of TCGA samples. Along the x-axis violin plots are grouped by specific TCGA subtypes: Esophageal carcinoma (ESCA), Head and neck squamous cell carcinoma (HNSC), Kidney renal clear cell carcinoma (KIRC), Lung adenocarcinoma (LUAD), Lung squamous cell carcinoma (LUSC), Pancreatic adenocarcinoma (PAAD), and Stomach adenocarcinoma (STAD). Also shown is a pathway enrichment score (y-axis) for a myeloid signature for the same subset of TCGA cancer subtypes.

Example 13: Solid Tumors Express the Machinery for Response to Elevated ATP as a Result of CD39 Inhibition ATP response machinery was evaluated in a subset of solid tumors. Briefly, TCGA RNA expression was analyzed in tumor types of interest and expression normalized on a per gene basis (FIG. 24A). Violin plots in FIG. 24B outline the kernel probability density (the width of the shaded area represents the proportion of the data located there) of the normalized log 2 gene expression (y-axis) of the following genes (proteins): ENTPD1 (CD39), NT5E (CD73), P2RX7 (P2X7), and P2RY11 (P2Y11) among a subset of TCGA samples. Along the x-axis violin plots are grouped by specific TCGA subtypes: Esophageal carcinoma (ESCA), Head and neck squamous cell carcinoma (HNSC), Kidney renal clear cell carcinoma (KIRC), Lung adenocarcinoma (LUAD), Lung squamous cell carcinoma (LUSC), Pancreatic adenocarcinoma (PAAD), and Stomach adenocarcinoma (STAD). Also shown in FIG. 24B is a pathway enrichment score (y-axis) for a myeloid gene signature (IL-6, CXCL2, CXCL2, CXCL3, CXCL8, and PTGS2), calculated using gene set enrichment analysis, for the same subset of TCGA cancer subtypes. Using this metric, values >0 indicate upregulation and values <0 indicate downregulation. All tumors have high levels of CD39 and myeloid infiltration. All tumors also share similar levels of P2X7 and P2Y11, indicating they can respond to elevated ATP in the tumor microenvironment.

EXAMPLES OF DISCLOSED EMBODIMENTS

Embodiment 1: An anti-CD39 antibody that specifically binds to human CD39, comprising: (a) a heavy chain variable region comprising a complementarity determining region 1 (H1) having at least 80% sequence identity to SEQ ID NO: 10, a complementarity determining region 2 (H2) having at least 80% sequence identity to SEQ ID NO: 11, and a complementarity determining region 3 (H3) having at least 80% sequence identity to SEQ ID NO: 12; and a light chain variable region comprising a complementarity determining region 1 (L1) having at least 80% sequence identity to SEQ ID NO: 14, a complementarity determining region 2 (L2) having at least 80% sequence identity to SEQ ID NO: 15, and a complementarity determining region 3 (L3) having at least 80% sequence identity to SEQ ID NO: 16; (b) a heavy chain variable region comprising an H1 having at least 80% sequence identity to SEQ ID NO: 18, an H2 having at least 80% sequence identity to SEQ ID NO: 19, and an H3 having at least 80% sequence identity to SEQ ID NO: 20; and a light chain variable region comprising an L1 having at least 80% sequence identity to SEQ ID NO: 22, SEQ ID NO: 23, or SEQ ID NO: 24, an L2 having at least 80% sequence identity to SEQ ID NO: 25, and an L3 having at least 80% sequence identity to SEQ ID NO: 26; or (c) a heavy chain variable region comprising an H1 having at least 80% sequence identity to SEQ ID NO: 28, an H2 having at least 80% sequence identity to SEQ ID NO: 29, and an H3 having at least 80% sequence identity to SEQ ID NO: 30; and a light chain variable region comprising an L1 having at least 80% sequence identity to SEQ ID NO: 32, an L2 having at least 80% sequence identity to SEQ ID NO: 33, and an L3 having at least 80% sequence identity to SEQ ID NO: 34.

Embodiment 2: The anti-CD39 antibody of embodiment 1, comprising: (a) a heavy chain variable region comprising an H1 having at least 90% sequence identity or at least 95% sequence identity to SEQ ID NO: 10, an H2 having at least 90% sequence identity or at least 95% sequence identity to SEQ ID NO: 11, and an H3 having at least 90% sequence identity or at least 95% sequence identity to SEQ ID NO: 12; and a light chain variable region comprising an L1 having at least 90% sequence identity or at least 95% sequence identity to SEQ ID NO: 14, an L2 having at least 90% sequence identity or at least 95% sequence identity to SEQ ID NO: 15, and an L3 having at least 90% sequence identity or at least 95% sequence identity to SEQ ID NO: 16; (b) a heavy chain variable region comprising an H1 having at least 90% sequence identity or at least 95% sequence identity to SEQ ID NO: 18, an H2 having at least 90% sequence identity or at least 95% sequence identity to SEQ ID NO: 19, and an H3 having at least 90% sequence identity or at least 95% sequence identity to SEQ ID NO: 20; and a light chain variable region comprising an L1 having at least 90% sequence identity or at least 95% sequence identity to SEQ ID NO: 22, SEQ ID NO: 23, or SEQ ID NO: 24, an L2 having at least 90% sequence identity or at least 95% sequence identity to SEQ ID NO: 25, and an L3 having at least 90% sequence identity or at least 95% sequence identity to SEQ ID NO: 26; or (c) a heavy chain variable region comprising an H1 having at least 90% sequence identity or at least 95% sequence identity to SEQ ID NO: 28, an H2 having at least 90% sequence identity or at least 95% sequence identity to SEQ ID NO: 29, and an H3 having at least 90% sequence identity or at least 95% sequence identity to SEQ ID NO: 30; and a light chain variable region comprising an L1 having at least 90% sequence identity or at least 95% sequence identity to SEQ ID NO: 32, an L2 having at least 90% sequence identity or at least 95% sequence identity to SEQ ID NO: 33, and an L3 having at least 90% sequence identity or at least 95% sequence identity to SEQ ID NO: 34.

Embodiment 3: An anti-CD39 antibody that specifically binds to human CD39, comprising: (a) a heavy chain variable region comprising an H1 having an amino acid sequence comprising SEQ ID NO: 10, an H2 having an amino acid sequence comprising SEQ ID NO: 11, and an H3 having an amino acid sequence comprising SEQ ID NO: 12; and a light chain variable region comprising a L1 having an amino acid sequence comprising SEQ ID NO: 14, an L2 having an amino acid sequence comprising SEQ ID NO: 15, and an L3 having an amino acid sequence comprising ID NO: 16; (b) a heavy chain variable region comprising an H1 having an amino acid sequence comprising SEQ ID NO: 18, an H2 having an amino acid sequence comprising SEQ ID NO: 19, and an H3 having an amino acid sequence comprising SEQ ID NO: 20; and a light chain variable region comprising an L1 having an amino acid sequence comprising SEQ ID NO: 22, SEQ ID NO: 23, or SEQ ID NO: 24, an L2 having an amino acid sequence comprising SEQ ID NO: 25, and an L3 having an amino acid sequence comprising SEQ ID NO: 26; or (c) a heavy chain variable region comprising an H1 having an amino acid sequence comprising SEQ ID NO: 28, an H2 having an amino acid sequence comprising SEQ ID NO: 29, and an H3 having an amino acid sequence comprising SEQ ID NO: 30; and a light chain variable region comprising an L1 having an amino acid sequence comprising SEQ ID NO: 32, an L2 having an amino acid sequence comprising SEQ ID NO: 33, and an L3 having an amino acid sequence comprising SEQ ID NO: 34.

Embodiment 4: The anti-CD39 antibody of any one of embodiments 1, 2 or 3, wherein the antibody has a heavy chain variable region and a light chain variable region according to embodiment 1(a) and the heavy chain variable region has at least 90% sequence identity to SEQ ID NO: 9, and a light chain variable region has at least 90% sequence identity to SEQ ID NO: 13; or wherein the antibody has a heavy chain variable region and a light chain variable region according to embodiment 1(b) and the heavy chain variable region having at least 90% sequence identity to SEQ ID NO: 17, and a light chain variable region having at least 90% sequence identity to SEQ ID NO: 21; the heavy chain variable region having at least 90% sequence identity to SEQ ID NO: 43, and a light chain variable region having at least 90% sequence identity to SEQ ID NO: 45; the heavy chain variable region having at least 90% sequence identity to SEQ ID NO: 43, and a light chain variable region having at least 90% sequence identity to SEQ ID NO: 46; the heavy chain variable region having at least 90% sequence identity to SEQ ID NO: 43, and a light chain variable region having at least 90% sequence identity to SEQ ID NO: 47; the heavy chain variable region having at least 90% sequence identity to SEQ ID NO: 43, and a light chain variable region having at least 90% sequence identity to SEQ ID NO: 48; the heavy chain variable region having at least 90% sequence identity to SEQ ID NO: 43, and a light chain variable region having at least 90% sequence identity to SEQ ID NO: 49; the heavy chain variable region having at least 90% sequence identity to SEQ ID NO: 44, and a light chain variable region having at least 90% sequence identity to SEQ ID NO: 48; or the heavy chain variable region having at least 90% sequence identity to SEQ ID NO: 44, and a light chain variable region having at least 90% sequence identity to SEQ ID NO: 49; wherein the antibody has a heavy chain variable region and a light chain variable region according to embodiment 1(c) and the heavy chain variable region having at least 90% sequence identity to SEQ ID NO: 27, and a light chain variable region having at least 90% sequence identity to SEQ ID NO: 31; the heavy chain variable region having at least 90% sequence identity to SEQ ID NO: 58, and a light chain variable region having at least 90% sequence identity to SEQ ID NO: 60; the heavy chain variable region having at least 90% sequence identity to SEQ ID NO: 58, and a light chain variable region having at least 90% sequence identity to SEQ ID NO: 61; the heavy chain variable region having at least 90% sequence identity to SEQ ID NO: 58, and a light chain variable region having at least 90% sequence identity to SEQ ID NO: 62; the heavy chain variable region having at least 90% sequence identity to SEQ ID NO: 58, and a light chain variable region having at least 90% sequence identity to SEQ ID NO: 63; the heavy chain variable region having at least 90% sequence identity to SEQ ID NO: 59, and a light chain variable region having at least 90% sequence identity to SEQ ID NO: 61; the heavy chain variable region having at least 90% sequence identity to SEQ ID NO: 59, and a light chain variable region having at least 90% sequence identity to SEQ ID NO: 60; the heavy chain variable region having at least 90% sequence identity to SEQ ID NO: 59, and a light chain variable region having at least 90% sequence identity to SEQ ID NO: 62; or the heavy chain variable region having at least 90% sequence identity to SEQ ID NO: 59, and a light chain variable region having at least 90% sequence identity to SEQ ID NO: 63.

Embodiment 5: The anti-CD39 antibody of any one of embodiments 1 to 4, wherein the anti-CD39 antibody or antigen binding fragment thereof:
(a) has an equilibrium binding constant ($K_D$) of about $0.001 \times 10^{-11}$ M to about $100 \times 10^{-11}$ M, about $0.01 \times 10^{-11}$ M to about $100 \times 10^{-11}$ M, about $0.1 \times 10^{-11}$ M to about $100 \times 10^{-11}$ M, about $0.1 \times 10^{-11}$ M to about $10 \times 10^{-11}$ M, about $1 \times 10^{-11}$ M to about $100 \times 10^{-11}$ M or about $1 \times 10^{-11}$ M to about $10 \times 10^{-11}$ M, measured by surface plasmon resonance;
(b) inhibits human CD39 enzymatic activity with an $IC_{50}$ of at least about 1 nM or less, optionally wherein (i) inhibition is measured in the presence of 20 µM ATP or 400 µM ATP, and/or (ii) the CD39 is expressed on the surface of a human cell, optionally wherein the human cell is a primary monocyte as described in Example 5; or
(c) any combination of (a) or (b).

Embodiment 6: The anti-CD39 antibody of embodiment 5, wherein the anti-CD39 antibody or antigen binding fragment thereof inhibits CD39 enzymatic activity with an $IC_{50}$ of about 0.05 nM to about 0.5 nM, or about 0.05 nM to about 0.4 nM, or about 0.05 nM to about 0.3 nM, optionally wherein (i) inhibition is measured in the presence of 20 µM ATP or 400 µM ATP, and/or (ii) the CD39 is expressed on the surface of a human cell, optionally wherein the human cell is a primary monocyte as described in Example 5.

Embodiment 7: The anti-CD39 antibody of embodiment 5, wherein the anti-CD39 antibody or antigen binding fragment thereof inhibits CD39 enzymatic activity with an $IC_{50}$ of about 0.3 nM to about 1 nM, or about 0.3 nM to 1 nM, or about 0.5 nM to about 1 nM, or about 0.5 nM to 1 nM, optionally wherein (i) inhibition is measured in the presence of 20 µM ATP or 400 µM ATP, and/or (ii) the CD39 is expressed on the surface of a human cell, optionally wherein the human cell is a primary monocyte as described in Example 5.

Embodiment 8: The anti-CD39 antibody of any one of embodiments 1-7, wherein the anti-CD39 antibody is a monoclonal antibody or an antigen-binding fragment thereof.

Embodiment 9: The anti-CD39 antibody of any one of embodiments 1-8, wherein the anti-CD39 antibody is a chimeric, humanized, or veneered antibody or an antigen-binding fragment thereof.

Embodiment 10: The anti-CD39 antibody of any one of embodiments 1-8, wherein the anti-CD39 antibody is a human antibody or an antigen-binding fragment thereof.

Embodiment 11: The anti-CD39 antibody of any one of the proceeding embodiments, wherein the antibody further comprises a variant heavy chain constant region selected from variant human IgG1, variant human IgG2, variant human IgG3, or variant human IgG4, and optionally a human light chain constant region.

Embodiment 12: The anti-CD39 antibody of embodiment 11, wherein the variant heavy chain constant region has enhanced or decreased effector function with reference to the wild-type heavy chain constant region.

Embodiment 13: The anti-CD39 antibody of embodiment 11, wherein the variant human IgG heavy chain constant region comprises SEQ ID NO: 2, SEQ ID NO: 3, or SEQ ID NO: 5.

Embodiment 14: The anti-CD39 antibody of any one of embodiments 1-10, wherein the antibody further comprises a wild-type human IgG heavy chain constant region, and optionally a human light chain constant region.

Embodiment 15: The anti-CD39 antibody of embodiment 14, wherein the wild-type human IgG heavy chain constant region comprises SEQ ID NO: 1 or SEQ ID NO: 4.

Embodiment 16: The anti-CD39 antibody of any one of embodiments 11-15 comprising a human light chain kappa constant region, optionally wherein the human light chain constant region comprises SEQ ID NO: 6.

Embodiment 17: The anti-CD39 antibody of any one of embodiments 1-3, wherein the antibody has a heavy chain comprising the heavy chain variable region and a light chain comprising the light chain variable region, wherein
(a) the heavy chain has an amino acid sequence comprising SEQ ID NO: 50, and the light chain has an amino acid sequence comprising SEQ ID NO: 53;
(b) the heavy chain has an amino acid sequence comprising SEQ ID NO: 50, and the light chain has an amino acid sequence comprising SEQ ID NO: 54;
(c) the heavy chain has an amino acid sequence comprising SEQ ID NO: 50, and the light chain has an amino acid sequence comprising SEQ ID NO: 55;
(d) the heavy chain has an amino acid sequence comprising SEQ ID NO: 50, and the light chain has an amino acid sequence comprising SEQ ID NO: 56;
(e) the heavy chain has an amino acid sequence comprising SEQ ID NO: 51, and the light chain has an amino acid sequence comprising SEQ ID NO: 56;
(f) the heavy chain has an amino acid sequence comprising SEQ ID NO: 50, and the light chain has an amino acid sequence comprising SEQ ID NO: 57;
(g) the heavy chain has an amino acid sequence comprising SEQ ID NO: 52, and the light chain has an amino acid sequence comprising SEQ ID NO: 56; or
(h) the heavy chain has an amino acid sequence comprising SEQ ID NO: 52, and the light chain has an amino acid sequence comprising SEQ ID NO: 57.

Embodiment 18: The anti-CD39 antibody of any one of embodiments 1-3, wherein the antibody has a heavy chain comprising the heavy chain variable region and a light chain comprising the light chain variable region, wherein
(a) the heavy chain has an amino acid sequence comprising SEQ ID NO: 64, and the light chain has an amino acid sequence comprising SEQ ID NO: 67;
(b) the heavy chain has an amino acid sequence comprising SEQ ID NO: 64, and the light chain has an amino acid sequence comprising SEQ ID NO: 68;
(c) the heavy chain has an amino acid sequence comprising SEQ ID NO: 64, and the light chain has an amino acid sequence comprising SEQ ID NO: 69;
(d) the heavy chain has an amino acid sequence comprising SEQ ID NO: 64, and the light chain has an amino acid sequence comprising SEQ ID NO: 70;
(e) the heavy chain has an amino acid sequence comprising SEQ ID NO: 65, and the light chain has an amino acid sequence comprising SEQ ID NO: 68;
(f) the heavy chain has an amino acid sequence comprising SEQ ID NO: 65, and the light chain has an amino acid sequence comprising SEQ ID NO: 67;
(g) the heavy chain has an amino acid sequence comprising SEQ ID NO: 66, and the light chain has an amino acid sequence comprising SEQ ID NO: 67;
(h) the heavy chain has an amino acid sequence comprising SEQ ID NO: 65, and the light chain has an amino acid sequence comprising SEQ ID NO: 69; or
(i) the heavy chain has an amino acid sequence comprising SEQ ID NO: 65, and the light chain has an amino acid sequence comprising SEQ ID NO: 70.

Embodiment 19: The anti-CD39 antibody of embodiment 17 or embodiment 18, wherein the anti-CD39 antibody or antigen binding fragment thereof:
(a) has an equilibrium binding constant ($K_D$) of about $0.001 \times 10^{-11}$ M to about $100 \times 10^{-11}$ M, about $0.01 \times 10^{-11}$ M to about $100 \times 10^{-11}$ M, about $0.1 \times 10^{-11}$ M to about $100 \times 10^{-11}$ M, about $0.1 \times 10^{-11}$ M to about $10 \times 10^{-11}$ M, about $1 \times 10^{-11}$ M to about $100 \times 10^{-11}$ M or about $1 \times 10^{-11}$ M to about $10 \times 10^{-11}$ M, measured by surface plasmon resonance;
(b) inhibits human CD39 enzymatic activity with an $IC_{50}$ of at least about 1 nM or less, optionally wherein (i) inhibition is measured in the presence of 20 μM ATP or 400 μM ATP, and/or (ii) the CD39 is expressed on the surface of a human cell, optionally wherein the human cell is a primary monocyte as described in Example 5; or
(c) any combination of (a) or (b).

Embodiment 20: The anti-CD39 antibody of embodiment 19, wherein the anti-CD39 antibody or antigen binding fragment thereof inhibits CD39 enzymatic activity with an $IC_{50}$ of about 0.05 nM to about 0.5 nM, or about 0.05 nM to about 0.4 nM, or about 0.05 nM to about 0.3 nM, optionally wherein (i) inhibition is measured in the presence of 20 μM ATP or 400 μM ATP, and/or (ii) the CD39 is expressed on the surface of a human cell, optionally wherein the human cell is a primary monocyte as described in Example 5.

Embodiment 21: The anti-CD39 antibody of embodiment 19, wherein the anti-CD39 antibody or antigen binding fragment thereof inhibits CD39 enzymatic activity with an $IC_{50}$ of about 0.3 nM to about 1 nM, or about 0.3 nM to 1 nM, or about 0.5 nM to about 1 nM, or about 0.5 nM to 1 nM, optionally wherein (i) inhibition is measured in the presence of 20 μM ATP or 400 μM ATP, and/or (ii) the CD39 is expressed on the surface of a human cell, optionally wherein the human cell is a primary monocyte as described in Example 5.

Embodiment 22: The anti-CD39 antibody of any one of embodiments 1-21, wherein the antibody competes with a reference antibody for binding to human CD39 by at least about 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% as measured in a competition flow assay, wherein the reference antibody is (a) an antibody of embodiment 17; (b) an antibody of embodiment 18; (c) an antibody comprising a heavy chain having an amino acid sequence comprising SEQ ID NO: 37 and a light chain having an amino acid sequence comprising SEQ ID NO: 38; or (d) an antibody comprising a heavy chain having an amino acid sequence comprising SEQ ID NO: 39 and a light chain having an amino acid sequence comprising SEQ ID NO: 40.

Embodiment 23: A method of inhibiting CD39 enzymatic activity comprising contacting CD39 with the anti-CD39 antibody of any one of preceding embodiments.

Embodiment 24: A method for increasing extracellular ATP or activating the immune system in a subject in need thereof comprising administering to the subject an effective regime or a therapeutically effective amount of any one of the anti-CD39 antibodies of any one of embodiments 1-22.

Embodiment 25: A method of treating or effecting prophylaxis of cancer comprising administering to a subject having or at risk of cancer an effective regime or a therapeutically effective amount of any one of the anti-CD39 antibodies of any one of embodiments 1-22.

Embodiment 26: The method of embodiment 25, wherein the cancer is a hematological malignancy or a solid tumor.

Embodiment 27: The method of embodiment 25, wherein the cancer is breast cancer, gastrointestinal cancer, genitourinary tract cancer, lung cancer, lymphoma, or ovarian cancer.

Embodiment 28: The method of embodiment 27, wherein the cancer is acute myeloid lymphoma, colorectal cancer, gastric cancer, esophageal cancer, castration-resistant prostate cancer, non-small cell lung cancer, ovarian cancer, pancreatic cancer, or triple negative breast cancer.

Embodiment 29: The method of embodiment 25, wherein the cancer is non-small cell lung cancer, gastric cancer, or gastroesophageal cancer.

Embodiment 30: The method of embodiment 25, wherein the cancer is lung cancer, head and neck cancer, thyroid cancer, pancreatic cancer, kidney cancer, or skin cancer.

Embodiment 31: The method of embodiment 30, wherein the cancer is non-small cell lung cancer, head and neck squamous cell carcinoma, pancreatic ductal adenocarcinoma, clear cell renal carcinoma, or melanoma.

Embodiment 32: The method of any one of embodiments 24-31, further comprising administering one or more additional therapeutic agents to the subject.

Embodiment 33: A combination comprising an anti-CD39 antibody of any one of embodiments 1-22 and one or more additional therapeutic agent.

Embodiment 34: The method of embodiment 32 or the combination of embodiment 33, wherein each additional therapeutic agent is independently selected from the group consisting of a chemotherapeutic agent, a radiopharmaceutical, an agent that induces immunogenic cell death, an antagonist of an inhibitory or co-inhibitory immune checkpoint, an agonist of a stimulatory or co-stimulatory immune checkpoint, and an ATP-adenosine axis-targeting agent.

Embodiment 35: The method of embodiment 32 or the combination of embodiment 33, wherein at least one additional therapeutic agent is a chemotherapeutic agent or an agent that induces immunogenic cell death, and at least one additional therapeutic agent is an antagonist of an inhibitory or co-inhibitory immune checkpoint or an ATP-adenosine axis-targeting agent.

Embodiment 36: The method of embodiment 32 or the combination of embodiment 33, wherein at least one additional therapeutic agent is an antagonist of an inhibitory or co-inhibitory immune checkpoint, and at least one additional therapeutic agent is an ATP-adenosine axis-targeting agent.

Embodiment 37: The method or combination of any one of embodiments 32-36, wherein the agent that induces immunogenic cell death is radiation therapy.

Embodiment 38: The method or combination of any one of embodiments 32-36, wherein the agent that induces immunogenic cell death is (a) a chemotherapeutic agent, optionally selected from the group consisting of bortezomib, cyclophosphamide, doxorubicin, epirubicin, idarubicin, mitoxantrone, oxaliplatin, and any combination thereof, or (b) bleomycin, bortezomib, carboplatin, cetuximab, crizotinib, cyclophosphamide, docetaxel, doxorubicin, epirubicin, gemcitabine, idarubicin, irinotecan, mitoxantrone, oxaliplatin, paclitaxel, vemurafenib, vorinostat, and any combination thereof.

Embodiment 39: The method or combination of any one of embodiments 32-38, wherein each chemotherapeutic agent is selected from the group consisting of an alkylating agent, an anthracycline, a platinum agent, a taxane, and a proteasome inhibitor.

Embodiment 40: The method or combination of any one of embodiments 32-39, wherein the antagonist of an inhibitory or co-inhibitory immune checkpoint blocks the activity of at least one of PD-1, PD-L1, BTLA, LAG-3, a B7 family member, TIM-3, TIGIT or CTLA-4.

Embodiment 41: The method or combination of any one of embodiments 32-40, wherein the antagonist of an inhibitory or co-inhibitory immune checkpoint blocks the activity of at least one of PD-1, PD-L1, or TIGIT.

Embodiment 42: The method or combination of any one of embodiments 32-41, wherein the antagonist of an inhibitory or co-inhibitory immune checkpoint is an antagonistic anti-PD-1 antibody, an antagonistic anti-PD-L1 antibody, or an antagonistic anti-TIGIT antibody.

Embodiment 43: The method or combination of any one of embodiments 32-42, wherein each antagonist of an inhibitory or co-inhibitory immune checkpoint is independently selected from the group consisting of zimberelimab, domvanalimab, and AB308.

Embodiment 44: The method or combination of any one of embodiments 32-43, wherein each ATP-adenosine axis-targeting agent is independently selected from the group consisting of an $A_{2a}R$ antagonist, an $A_{2b}R$ antagonist, an $A_{2a/2b}R$ antagonist, and a CD73 inhibitor.

Embodiment 45: The method or combination of any one of embodiments 32-44, wherein each ATP-adenosine axis-targeting agent is independently selected from the group consisting of etrumadenant and quemliclustat.

Embodiment 46: The method of embodiment 25, wherein the cancer is non-small cell lung cancer and the method further comprises administering the anti-CD39 antibody in combination with pemetrexed, carboplatin, and either an antagonist anti-PD-1 antibody or an antagonist anti-PD-L1 antibody.

Embodiment 47: The method of embodiment 25, wherein the cancer is gastric cancer or gastroesophageal cancer and the method further comprises administering the anti-CD39 antibody in combination with FOLFOX and either an antagonist anti-PD-1 antibody or an antagonist anti-PD-L1 antibody.

Embodiment 48: The method of embodiment 46 or 47, further comprising administering one or more additional agent selected from the group consisting of an antagonistic anti-TIGIT antibody, an $A_{2a}R$ antagonist, an $A_{2b}R$ antagonist, an $A_{2a/2b}R$ antagonist, and a CD73 inhibitor, optionally where the additional agents are selected from the group consisting of domvanalimab, AB308, etrumadenant, and quemliclustat.

Embodiment 49: The combination of embodiment 33, wherein the one or more additional therapeutic agents includes (a) pemetrexed, carboplatin, and either an antagonist anti-PD-1 antibody or an antagonist anti-PD-L1 antibody, or (b) FOLFOX and either an antagonist anti-PD-1 antibody or an antagonist anti-PD-L1 antibody.

Embodiment 50: A pharmaceutical composition comprising the antibody or antigen-binding fragment thereof of any one of embodiments 1-19 and a pharmaceutically acceptable carrier.

Embodiment 51: An isolated polynucleotide encoding the antibody or antigen binding fragment thereof of any one of embodiments 1-22.

Embodiment 52: A vector comprising the isolated polynucleotide of embodiment 51.

Embodiment 53: A host cell comprising the vector of embodiment 52.

Embodiment 54: A method of expressing the antibody or antigen-binding fragment thereof of any one of embodiments 1-22, comprising culturing the host cell of embodiment 53 under the condition at which the polynucleotide of embodiment 51 is expressed.

Embodiment 55: A kit comprising the antibody or antigen-binding fragment thereof of any one of embodiments 1-22.

SEQUENCE LISTING TABLE

| SEQ ID NO | Amino Acid Sequence | Comments |
|---|---|---|
| 1 | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSCDKTHTCPPCPAPEL LGGPSVFLFPPKPKDTLMISRTPEVTCVVVDVSHEDPEV KFNWYVDGVEVHNAKTKPREEQYNSTYRVVSVLTVLHQD WLNGKEYKCKVSNKALPAPIEKTISKAKGQPREPQVYTL PPSRDELTKNQVSLTCLVKGFYPSDIAVEWESNGQPENN YKTTPPVLDSDGSFFLYSKLTVDKSRWQQGNVFSCSVMH EALHNHYTQKSLSLSPGK | HEAVY CHAIN CONSTANT REGION IGG1; WILD-TYPE IMGT ALLELE IGHG1*01-EU NUMBERING 118-447 |
| 2 | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSCDKTHTCPPCPAPEA AGGPSVFLFPPKPKDTLMISRTPEVTCVVVDVSHEDPEV KFNWYVDGVEVHNAKTKPREEQYNSTYRVVSVLTVLHQD WLNGKEYKCKVSNKALPAPIEKTISKAKGQPREPQVYTL PPSRDELTKNQVSLTCLVKGFYPSDIAVEWESNGQPENN YKTTPPVLDSDGSFFLYSKLTVDKSRWQQGNVFSCSVMH EALHNHYTQKSLSLSPGK | HEAVY CHAIN CONSTANT REGION IGG1.AA; IMGT ALLELE IGHG1*01 (L234A, L235A) EU NUMBERING |
| 3 | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSCDKTHTCPPCPAPEL LGGPDVFLFPPKPKDTLMISRTPEVTCVVVDVSHEDPEV KFNWYVDGVEVHNAKTKPREEQYNSTYRVVSVLTVLHQD WLNGKEYKCKVSNKALPLPEEKTISKAKGQPREPQVYTL PPSRDELTKNQVSLTCLVKGFYPSDIAVEWESNGQPENN YKTTPPVLDSDGSFFLYSKLTVDKSRWQQGNVFSCSVMH EALHNHYTQKSLSLSPGK | HEAVY CHAIN CONSTANT REGION IGG1.DLE; IMGT ALLELE IGHG1*01 (S239D, A330L, I332E) EU NUMBERING |
| 4 | ASTKGPSVFPLAPCSRSTSESTAALGCLVKDYFPEPVTV SWNSGALTSGVHTFPAVLQSSGLYSLSSVVTVPSSSLGT KTYTCNVDHKPSNTKVDKRVESKYGPPCPSCPAPEFLGG PSVFLFPPKPKDTLMISRTPEVTCVVVDVSQEDPEVQFN WYVDGVEVHNAKTKPREEQFNSTYRVVSVLTVLHQDWLN GKEYKCKVSNKGLPSSIEKTISKAKGQPREPQVYTLPPS QEEMTKNQVSLTCLVKGFYPSDIAVEWESNGQPENNYKT TPPVLDSDGSFFLYSRLTVDKSRWQEGNVFSCSVMHEAL HNHYTQKSLSLSLGK | HEAVY CHAIN CONSTANT REGION IGG4; WILD-TYPE; IMGT ALLELE IGHG4*01-EU NUMBERING |
| 5 | ASTKGPSVFPLAPCSRSTSESTAALGCLVKDYFPEPVTV SWNSGALTSGVHTFPAVLQSSGLYSLSSVVTVPSSSLGT KTYTCNVDHKPSNTKVDKRVESKYGPPCPPCPAPEFLGG PSVFLFPPKPKDTLMISRTPEVTCVVVDVSQEDPEVQFN WYVDGVEVHNAKTKPREEQFNSTYRVVSVLTVLHQDWLN GKEYKCKVSNKGLPSSIEKTISKAKGQPREPQVYTLPPS QEEMTKNQVSLTCLVKGFYPSDIAVEWESNGQPENNYKT TPPVLDSDGSFFLYSRLTVDKSRWQEGNVFSCSVMHEAL HNHYTQKSLSLSLGK | HEAVY CHAIN CONSTANT REGION IGG4.P; IMGT ALLELE IGHG4*01 (S228P) EU NUMBERING |
| 6 | RTVAAPSVFIFPPSDEQLKSGTASVVCLLNNFYPREAKV QWKVDNALQSGNSQESVTEQDSKDSTYSLSSTLTLSKAD YEKHKVYACEVTHQGLSSPVTKSFNRGEC | LIGHT CHAIN CONSTANT REGION, KAPPA IMGT ALLELE IGKC*01 |
| 7 | MEDTKESNVKTFCSKNILAILGFSSIIAVIALLAVGLTQ NKALPENVKYGIVLDAGSSHTSLYIYKWPAEKENDTGVV HQVEECRVKGPGISKFVQKVNEIGIYLTDCMERAREVIP RSQHQETPVYLGATAGMRLLRMESEELADRVLDVVERSL SNYPFDFQGARIITGQEEGAYGWITINYLLGKFSQKTRW FSIVPYETNNQETFGALDLGGASTQVTFVPQNQTIESPD NALQFRLYGKDYNVYTHSFLCYGKDQALWQKLAKDIQVA SNEILRDPCFHPGYKKVVNVSDLYKTPCTKRFEMTLPFQ QFEIQGIGNYQQCHQSILELFNTSYCPYSQCAFNGIFLP | Human CD39 (UniProtKB reference: P49961) |

SEQUENCE LISTING TABLE-continued

| SEQ ID NO | Amino Acid Sequence | Comments |
|---|---|---|
| | PLQGDFGAFSAFYFVMKFLNLTSEKVSQEKVTEMMKKFC AQPWEEIKTSYAGVKEKYLSEYCFSGTYILSLLLQGYHF TADSWEHIHFIGKIQGSDAGWTLGYMLNLTNMIPAEQPL STPLSHSTYVFLMVLFSLVLFTVAIIGLLIFHKPSYFWK DMV | |
| 8 | MKGTKDLTSQQKESNVKTFCSKNILAILGFSSIIAVIAL LAVGLTQNKALPENIKYGIVLDAGSSHTSLYIYKWPAEK ENDTGVVHQVEECRVKGPGISKYVQKVNEIGIYLTDCME RAREVIPRSQHQETPVYLGATAGMRLLRMESEELADRVL DVVERSLSNYPFDFQGARIITGQEEGAYGWITINYLLGK FSQKTRWFSIVPYETNNQETFGALDLGGASTQITFVPQN QTTESPDNALQFRLYGKDYNVYTHSFLCYGKDQALWQKL AKDIQVASNEILRDPCFHPGYKKVVNVSDLYKTPCTKRF EMTLPFQQFEIQGIGNYQQCHQSVLELFNTSYCPYSQCA FNGIFLPPLQGDFGAFSAFYFVMNFLNLTSEKVSQEKVT EMMKKFCSQPWEEIKTSYAGVKEKYLSEYCFSGTYILSL LLQGYHFTADSWEHIHFIGKIQGSDAGWTLGYMLNLTNM IPAEQPLSTPLSHSTYVFLMVLFSLVLVIVAIIGLLIFH KPSYFWKDMV | Cynomolgus monkey CD39 (UniProtKB reference: G7PDM2) |
| 9 | QVQLKETGPGLVQPTQTLSITCTVSGFSLTSYFTQWVRQ TPGKGLEWMGFIRSGGSTQYNSAFKSRLSISRDTSKNQV FLKMNSLKTEDTGVYYCARDRPDYHDGTYGVLDVWG QGASVTVSS | 19 HCVR (mature peptide) ch19_IGG4.P HCVR (mature peptide) |
| 10 | GFSLTSYFTQ | 19 HC CDR1 ch19_IGG4.P HC CDR1 |
| 11 | FIRSGGSTQYNSAFKS | 19 HC CDR2 ch19_IGG4.P HC CDR2 |
| 12 | DRPDYHDGTYGVLDV | 19 HC CDR3 ch19_IGG4.P HC CDR3 |
| 13 | DIRMTQSPASLSASLGETVNIECLASEDIDSDLAWYQKK PGKSPQLLIYNGNALQNGVPSRFSGSGSGTHFSLKINSL QSEDVATYFCQQYINYPYTFGGGTKLELR | 19 LCVR (mature peptide) ch19_IGG4.P LCVR (mature peptide) |
| 14 | LASEDIDSDLA | 19 LC CDR1 ch19_IGG4.PLC CDR1 |
| 15 | NGNALQN | 19 LC CDR2 ch19_IGG4.PLC CDR2 |
| 16 | QQYINYPYT | 19 LC CDR3 ch19_IGG4.PLC CDR3 |
| 17 | EVHLQQSGAALVRPGTSVKLPCKVSGDSITAYFMHFVRQ RPGQGLEWMGRIDPDHERTKYAEKFKNRASLTSETSSNT VFLQLTSLTSEDTATYFCTTERVPGFETDYWGQGVMVTV SS | 31 HCVR (mature peptide) ch31_IGG4.P HCVR (mature peptide) |
| 18 | GDSITAYFMH | 31 HC CDR1 ch31_IGG4.P HC CDR1 hu31.1_IGG4.P HC CDR1 hu31.2_IGG4.P HC CDR1 hu31.3_IGG4.P HC CDR1 hu31.4_IGG4.P HC CDR1 hu31.4_IGG1.AA HC CDR1 hu31.5_IGG4.P HC CDR1 hu31.6_IGG4.P HC CDR1 hu31.7_IGG4.P HC CDR1 |
| 19 | RIDPDHERTKYAEKFKN | 31 HC CDR2 ch31_IGG4.P HC CDR2 hu31.1_IGG4.P HC CDR2 hu31.2_IGG4.P HC CDR2 hu31.3_IGG4.P HC CDR2 hu31.4_IGG4.P HC CDR2 hu31.4_IGG1.AA HC CDR2 hu31.5_IGG4.P HC CDR2 hu31.6_IGG4.P HC CDR2 hu31.7_IGG4.P HC CDR2 |

SEQUENCE LISTING TABLE-continued

| SEQ ID NO | Amino Acid Sequence | Comments |
|---|---|---|
| 20 | ERVPGFETDY | 31 HC CDR3<br>ch31_IGG4.P HC CDR3<br>hu31.1_IGG4.P HC CDR3<br>hu31.2_IGG4.P HC CDR3<br>hu31.3_IGG4.P HC CDR3<br>hu31.4_IGG4.P HC CDR3<br>hu31.4_IGG1.AA HC CDR3<br>hu31.5_IGG4.P HC CDR3<br>hu31.6_IGG4.P HC CDR3<br>hu31.7_IGG4.P HC CDR3 |
| 21 | DIVLTQSPTLAVSLGQRATISCRTNQTVDHYGTTYMNWY<br>QQKPGQQPKLLIYLASSLASGIPARFSGRGSGTDFTLTI<br>DPVEADDTATYYCQQSRNLWTFGGGTKLELK | 31 LCVR (mature peptide)<br>ch31_IGG4.P LCVR (mature peptide) |
| 22 | RTNQTVDHYGTTYMN | 31 LC CDR1<br>ch31_IGG4.PLC CDR1 |
| 23 | RTNPTVDHYGTTYMN | hu31.1_IGG4.PLC CDR1<br>hu31.3_IGG4.PLC CDR1 |
| 24 | RTQQTVDHYGTTYMN | hu31.2_IGG4.PLC CDR1<br>hu31.4_IGG4.PLC CDR1<br>hu31.4_IGG1.AA LC CDR1<br>hu31.5_IGG4.PLC CDR1<br>hu31.6_IGG4.PLC CDR1<br>hu31.7_IGG4.PLC CDR1 |
| 25 | LASSLAS | 31 LC CDR2<br>ch31_IGG4.PLC CDR2<br>hu31.1_IGG4.PLC CDR2<br>hu31.2_IGG4.P LC CDR2<br>hu31.3_IGG4.PLC CDR2<br>hu31.4_IGG4.PLC CDR2<br>hu31.4_IGG1.AA LC CDR2<br>hu31.5_IGG4.PLC CDR2<br>hu31.6_IGG4.PLC CDR2<br>hu31.7_IGG4.PLC CDR2 |
| 26 | QQSRNLWT | 31 LC CDR3<br>ch31_IGG4.PLC CDR3<br>hu31.1_IGG4.PLC CDR3<br>hu31.2_IGG4.PLC CDR3<br>hu31.3_IGG4.PLC CDR3<br>hu31.4_IGG4.PLC CDR3<br>hu31.4_IGG1.AA LC CDR3<br>hu31.5_IGG4.PLC CDR3<br>hu31.6_IGG4.PLC CDR3<br>hu31.7_IGG4.PLC CDR3 |
| 27 | EVQLVESGGGLVQPGRSLKLSCLASGFTFNNYGMNWIRQ<br>APGKGLEWVASFSSSSTYISYADTVKGRFTISRENAKNT<br>LYLQMTSLRSEDTALYYCVRHGRYGGYGGFYFDYWGQGV<br>MVTVSS | 39 HCVR (mature peptide)<br>ch39_mIGG2A.AAG HCVR (mature peptide)<br>ch39_IGG4.P HCVR (mature peptide) |
| 28 | GFTFNNYGMN | 39 HC CDR1<br>ch39_mIGG2A.AAG HC CDR1<br>ch39_IGG4.P HC CDR1<br>hu39.1_IGG4.P HC CDR1<br>hu39.2_IGG4.P HC CDR1<br>hu39.3_IGG4.P HC CDR1<br>hu39.4_IGG4.P HC CDR1<br>hu39.5_IGG4.P HC CDR1<br>hu39.5_IGG1.AA HC CDR1<br>hu39.6_IGG4.P HC CDR1<br>hu39.7_IGG4.P HC CDR1<br>hu39.8_IGG4.P HC CDR1 |
| 29 | SFSSSSTYISYADTVKG | 39 HC CDR2<br>ch39_mIGG2A.AAG HC CDR2<br>ch39_IGG4.P HC CDR2<br>hu39.1_IGG4.P HC CDR2<br>hu39.2_IGG4.P HC CDR2<br>hu39.3_IGG4.P HC CDR2<br>hu39.4_IGG4.P HC CDR2 |

SEQUENCE LISTING TABLE-continued

| SEQ ID NO | Amino Acid Sequence | Comments |
|---|---|---|
| | | hu39.5_IGG4.P HC CDR2<br>hu39.5_IGG1.AA HC CDR2<br>hu39.6_IGG4.P HC CDR2<br>hu39.7_IGG4.P HC CDR2<br>hu39.8_IGG4.PHC CDR2 |
| 30 | HGRYGGYGGFYFDY | 39 HC CDR3<br>ch39_mIGG2A.AAG HC CDR3<br>ch39_IGG4.P HC CDR3<br>hu39.1_IGG4.P HC CDR3<br>hu39.2_IGG4.P HC CDR3<br>hu39.3_IGG4.P HC CDR3<br>hu39.4_IGG4.P HC CDR3<br>hu39.5_IGG4.P HC CDR3<br>hu39.5_IGG1.AA HC CDR3<br>hu39.6_IGG4.P HC CDR3<br>hu39.7_IGG4.P HC CDR3<br>hu39.8_IGG4.P HC CDR3 |
| 31 | DTVLTQSPALAVSPGERVSISCRASEGVKSYMHWYQQKP GQQPKLLIYKASNLASGVPARFSGSGSGTDFTLTIDPVE ADDTATYFCQQSWNDPTFGAGTKLELK | 39 LCVR (mature peptide)<br>ch39_mIGG2A.AAG LCVR (mature peptide)<br>ch39_IGG4.P LCVR (mature peptide) |
| 32 | RASEGVKSYMH | 39 LC CDR1<br>ch39_mIGG2A.AAGLC CDR1<br>ch39_IGG4.PLC CDR1<br>hu39.1_IGG4.PLC CDR1<br>hu39.2_IGG4.PLC CDR1<br>hu39.3_IGG4.PLC CDR1<br>hu39.4_IGG4.PLC CDR1<br>hu39.5_IGG4.PLC CDR1<br>hu39.5_IGG1.AA LC CDR1<br>hu39.6_IGG4.PLC CDR1<br>hu39.7_IGG4.P LC CDR1<br>hu39.8_IGG4.PLC CDR1 |
| 33 | KASNLAS | 39 LC CDR2<br>ch39_mIGG2A.AAGLC CDR2<br>ch39_IGG4.PLC CDR2<br>hu39.1_IGG4.PLC CDR2<br>hu39.2_IGG4.PLC CDR2<br>hu39.3_IGG4.PLC CDR2<br>hu39.4_IGG4.PLC CDR2<br>hu39.5_IGG4.PLC CDR2<br>hu39.5_IGG1.AA LC CDR2<br>hu39.6_IGG4.PLC CDR2<br>hu39.7_IGG4.PLC CDR2<br>hu39.8_IGG4.PLC CDR2 |
| 34 | QQSWNDPT | 39 LC CDR3<br>ch39_mIGG2A.AAG LC CDR3<br>ch39_IGG4.PLC CDR3<br>hu39.1_IGG4.PLC CDR3<br>hu39.2_IGG4.PLC CDR3<br>hu39.3_IGG4.PLC CDR3<br>hu39.4_IGG4.PLC CDR3<br>hu39.5_IGG4.PLC CDR3<br>hu39.5_IGG1.AA LC CDR3<br>hu39.6_IGG4.PLC CDR3<br>hu39.7_IGG4.PLC CDR3<br>hu39.8_IGG4.PLC CDR3 |
| 35 | QVQLKETGPGLVQPTQTLSITCTVSGFSLTSYFTQWVRQ TPGKGLEWMGFIRSGGSTQYNSAFKSRLSISRDTSKNQV FLKMNSLKTEDTGVYYCARDRPDYHDGTYGVLDVWGQGA SVTVSSASTKGPSVFPLAPCSRSTSESTAALGCLVKDYF PEPVTVSWNSGALTSGVHTFPAVLQSSGLYSLSSVVTVP SSSLGTKTYTCNVDHKPSNTKVDKRVESKYGPPCPPCPA PEFLGGPSVFLFPPKPKDTLMISRTPEVTCVVVDVSQED PEVQFNWYVDGVEVHNAKTKPREEQFNSTYRVVSVLTVL HQDWLNGKEYKCKVSNKGLPSSIEKTISKAKGQPREPQV YTLPPSQEEMTKNQVSLTCLVKGFYPSDIAVEWESNGQP ENNYKTTPPVLDSDGSFFLYSRLTVDKSRWQEGNVFSCS VMHEALHNHYTQKSLSLSLGK | ch19_IGG4.P HC |

SEQUENCE LISTING TABLE-continued

| SEQ ID NO | Amino Acid Sequence | Comments |
|---|---|---|
| 36 | DIRMTQSPASLSASLGETVNIECLASEDIDSDLAWYQKK PGKSPQLLIYNGNALQNGVPSRFSGSGSGTHFSLKINSL QSEDVATYFCQQYINYPYTFGGGTKLELRRTVAAPSVFI FPPSDEQLKSGTASVVCLLNNFYPREAKVQWKVDNALQS GNSQESVTEQDSKDSTYSLSSTLTLSKADYEKHKVYACE VTHQGLSSPVTKSFNRGEC | ch19_IGG4.PLC |
| 37 | EVHLQQSGAALVRPGTSVKLPCKVSGDSITAYFMHFVRQ RPGQGLEWMGRIDPDHERTKYAEKFKNRASLTSETSSNT VFLQLTSLTSEDTATYFCTTERVPGFETDYWGQGVMVTV SSASTKGPSVFPLAPCSRSTSESTAALGCLVKDYFPEPV TVSWNSGALTSGVHTFPAVLQSSGLYSLSSVVTVPSSSL GTKTYTCNVDHKPSNTKVDKRVESKYGPPCPPCPAPEFL GGPSVFLFPPKPKDTLMISRTPEVTCVVVDVSQEDPEVQ FNWYVDGVEVHNAKTKPREEQFNSTYRVVSVLTVLHQDW LNGKEYKCKVSNKGLPSSIEKTISKAKGQPREPQVYTLP PSQEEMTKNQVSLTCLVKGFYPSDIAVEWESNGQPENNY KTTPPVLDSDGSFFLYSRLTVDKSRWQEGNVFSCSVMHE ALHNHYTQKSLSLSLGK | ch31_IGG4.P HC |
| 38 | DIVLTQSPTLAVSLGQRATISCRTNQTVDHYGTTYMNWY QQKPGQQPKLLIYLASSLASGIPARFSGRGSGTDFTLTI DPVEADDTATYYCQQSRNLWTFGGGTKLELKRTVAAPSV FIFPPSDEQLKSGTASVVCLLNNFYPREAKVQWKVDNAL QSGNSQESVTEQDSKDSTYSLSSTLTLSKADYEKHKVYA CEVTHQGLSSPVTKSFNRGEC | ch31_IGG4.PLC |
| 39 | EVQLVESGGGLVQPGRSLKLSCLASGFTFNNYGMNWIRQ APGKGLEWVASFSSSSTYISYADTVKGRFTISRENAKNT LYLQMTSLRSEDTALYYCVRHGRYGGYGGFYFDYWGQGV MVTVSSASTKGPSVFPLAPCSRSTSESTAALGCLVKDYF PEPVTVSWNSGALTSGVHTFPAVLQSSGLYSLSSVVTVP SSSLGTKTYTCNVDHKPSNTKVDKRVESKYGPPCPPCPA PEFLGGPSVFLFPPKPKDTLMISRTPEVTCVVVDVSQED PEVQFNWYVDGVEVHNAKTKPREEQFNSTYRVVSVLTVL HQDWLNGKEYKCKVSNKGLPSSIEKTISKAKGQPREPQV YTLPPSQEEMTKNQVSLTCLVKGFYPSDIAVEWESNGQP ENNYKTTPPVLDSDGSFFLYSRLTVDKSRWQEGNVFSCS VMHEALHNHYTQKSLSLSLGK | ch39_IGG4.P HC |
| 40 | DTVLTQSPALAVSPGERVSISCRASEGVKSYMHWYQQKP GQQPKLLIYKASNLASGVPARFSGSGSGTDFTLTIDPVE ADDTATYFCQQSWNDPTFGAGTKLELKRTVAAPSVFIFP PSDEQLKSGTASVVCLLNNFYPREAKVQWKVDNALQSGN SQESVTEQDSKDSTYSLSSTLTLSKADYEKHKVYACEVT HQGLSSPVTKSFNRGEC | ch39_IGG4.PLC |
| 41 | EVQLVESGGGLVQPGRSLKLSCLASGFTFNNYGMNWIRQ APGKGLEWVASFSSSSTYISYADTVKGRFTISRENAKNT LYLQMTSLRSEDTALYYCVRHGRYGGYGGFYFDYWGQGV MVTVSSAKTTAPSVYPLAPVCGDTTGSSVTLGCLVKGYF PEPVTLTWNSGSLSSGVHTFPAVLQSDLYTLSSSVTVTS STWPSQSITCNVAHPASSTKVDKKIEPRGPTIKPCPPCK CPAPNAAGGPSVFIFPPKIKDVLMISLSPIVTCVVVDVS EDDPDVQISWFVNNVEVHTAQTQTHREDYNSTLRVVSAL PIQHQDWMSGKEFKCKVNNKDLGAPIERTISKPKGSVRA PQVYVLPPPEEEMTKKQVTLTCMVTDFMPEDIYVEWTNN GKTELNYKNTEPVLDSDGSYFMYSKLRVEKKNWVERNSY SCSVVHEGLHNHHTTKSFSRTPGK | ch39_mIGG2A.AAG HC |
| 42 | DTVLTQSPALAVSPGERVSISCRASEGVKSYMHWYQQKP GQQPKLLIYKASNLASGVPARFSGSGSGTDFTLTIDPVE ADDTATYFCQQSWNDPTFGAGTKLELKRADAAPTVSIFP PSSEQLTSGGASVCFLNNFYPKDINVKWKIDGSERQNG VLNSWTDQDSKDSTYSMSSTLTLTKDEYERHNSYTCEAT HKTSTSPIVKSFNRNEC | ch39_mIGG2A.AAGLC |
| 43 | QVQLVQSGAEVKKPGASVKVSCKVSGDSITAYFMHWVRQ APGKGLEWMGRIDPDHERTKYAEKFKNRVTMTSDTSTNT VYMELSSLRSEDTAVYYCATERVPGFETDYWGQGTMVTV SS | hu31.1_IGG4.P HCVR (mature peptide) hu31.2_IGG4.P HCVR (mature peptide) hu31.3_IGG4.P HCVR (mature peptide) hu31.4_IGG4.P HCVR (mature peptide) hu31.4_IGG1.AA HCVR (mature peptide) hu31.5_IGG4.P HCVR (mature peptide) |

SEQUENCE LISTING TABLE-continued

| SEQ ID NO | Amino Acid Sequence | Comments |
|---|---|---|
| 44 | EVQLVQSGAEVKKPGATVKISCKVSGDSITAYFMHWVQQ APGKGLEWMGRIDPDHERTKYAEKFKNRVTITADTSTNT VYMELSSLRSEDTAVYYCATERVPGFETDYWGQGVMVTV SS | hu31.6_IGG4.P HCVR (mature peptide) hu31.7_IGG4.P HCVR (mature peptide) |
| 45 | DIVLTQSPALAVSPGQRATITCRTNPTVDHYGTTYMNWY QQKPGQPPKLLIYLASSLASGVPARFSGSGSGTDFTLTI NPVEANDTANYYCQQSRNLWTFGGGTKVEIK | hu31.1_IGG4.P LCVR (mature peptide) |
| 46 | DIVLTQSPALAVSPGQRATITCRTQQTVDHYGTTYMNWY QQKPGQPPKLLIYLASSLASGVPARFSGSGSGTDFTLTI NPVEANDTANYYCQQSRNLWTFGGGTKVEIK | hu31.2_IGG4.P LCVR (mature peptide) |
| 47 | DIVLTQSPALAVSPGQRATITCRTNPTVDHYGTTYMNWY QQKPGQPPKLLIYLASSLASGVPARFSGSGSGTDFTLTI NPVEADDTANYYCQQSRNLWTFGGGTKVEIK | hu31.3_IGG4.P LCVR (mature peptide) |
| 48 | DIVLTQSPALAVSPGQRATITCRTQQTVDHYGTTYMNWY QQKPGQPPKLLIYLASSLASGVPARFSGSGSGTDFTLTI NPVEADDTANYYCQQSRNLWTFGGGTKVEIK | hu31.4_IGG4.P LCVR (mature peptide) hu31.4_IGG1.AA LCVR (mature peptide) hu31.6_IGG4.P LCVR (mature peptide) |
| 49 | DIVMTQSPDLAVSLGERATINCRTQQTVDHYGTTYMNWY QQKPGQPPKLLIYLASSLASGVPDRFSGSGSGTDFTLTI SSLQAEDVAVYYCQQSRNLWTFGGGTKVEIK | hu31.5_IGG4.P LCVR (mature peptide) hu31.7_IGG4.P LCVR (mature peptide) |
| 50 | QVQLVQSGAEVKKPGASVKVSCKVSGDSITAYFMHWVRQ APGKGLEWMGRIDPDHERTKYAEKFKNRVTMTSDTSTNT VYMELSSLRSEDTAVYYCATERVPGFETDYWGQGVMVTV SSASTKGPSVFPLAPCSRSTSESTAALGCLVKDYFPEPV TVSWNSGALTSGVHTFPAVLQSSGLYSLSSVVTVPSSSL GTKTYTCNVDHKPSNTKVDKRVESKYGPPCPPCPAPEFL GGPSVFLFPPKPKDTLMISRTPEVTCVVVDVSQEDPEVQ FNWYVDGVEVHNAKTKPREEQFNSTYRVVSVLTVLHQDW LNGKEYKCKVSNKGLPSSIEKTISKAKGQPREPQVYTLP PSQEEMTKNQVSLTCLVKGFYPSDIAVEWESNGQPENNY KTTPPVLDSDGSFFLYSRLTVDKSRWQEGNVFSCSVMHE ALHNHYTQKSLSLSLGK | hu31.1_IGG4.P HC (mature peptide) hu31.2_IGG4.P HC (mature peptide) hu31.3_IGG4.P HC (mature peptide) hu31.4_IGG4.P HC (mature peptide) hu31.5_IGG4.P HC (mature peptide) |
| 51 | QVQLVQSGAEVKKPGASVKVSCKVSGDSITAYFMHWVRQ APGKGLEWMGRIDPDHERTKYAEKFKNRVTMTSDTSTNT VYMELSSLRSEDTAVYYCATERVPGFETDYWGQGVMVTV SSASTKGPSVFPLAPSSKSTSGGTAALGCLVKDYFPEPV TVSWNSGALTSGVHTFPAVLQSSGLYSLSSVVTVPSSSL GTQTYICNVNHKPSNTKVDKKVEPKSCDKTHTCPPCPAP EAAGGPSVFLFPPKPKDTLMISRTPEVTCVVVDVSHEDP EVKFNWYVDGVEVHNAKTKPREEQYNSTYRVVSVLTVLH QDWLNGKEYKCKVSNKALPAPIEKTISKAKGQPREPQVY TLPPSRDELTKNQVSLTCLVKGFYPSDIAVEWESNGQPE NNYKTTPPVLDSDGSFFLYSKLTVDKSRWQQGNVFSCSV MHEALHNHYTQKSLSLSPGK | hu31.4_IGG1.AA HC (mature peptide) |
| 52 | EVQLVQSGAEVKKPGATVKISCKVSGDSITAYFMHWVQQ APGKGLEWMGRIDPDHERTKYAEKFKNRVTITADTSTNT VYMELSSLRSEDTAVYYCATERVPGFETDYWGQGVMVTV SSASTKGPSVFPLAPCSRSTSESTAALGCLVKDYFPEPV TVSWNSGALTSGVHTFPAVLQSSGLYSLSSVVTVPSSSL GTKTYTCNVDHKPSNTKVDKRVESKYGPPCPPCPAPEFL GGPSVFLFPPKPKDTLMISRTPEVTCVVVDVSQEDPEVQ FNWYVDGVEVHNAKTKPREEQFNSTYRVVSVLTVLHQDW LNGKEYKCKVSNKGLPSSIEKTISKAKGQPREPQVYTLP PSQEEMTKNQVSLTCLVKGFYPSDIAVEWESNGQPENNY KTTPPVLDSDGSFFLYSRLTVDKSRWQEGNVFSCSVMHE ALHNHYTQKSLSLSLGK | hu31.6_IGG4.P HC (mature peptide) hu31.7_IGG4.P HC (mature peptide) |
| 53 | DIVLTQSPALAVSPGQRATITCRTNPTVDHYGTTYMNWY QQKPGQPPKLLIYLASSLASGVPARFSGSGSGTDFTLTI NPVEANDTANYYCQQSRNLWTFGGGTKVEIKRTVAAPSV FIFPPSDEQLKSGTASVVCLLNNFYPREAKVQWKVDNAL QSGNSQESVTEQDSKDSTYSLSSTLTLSKADYEKHKVYA CEVTHQGLSSPVTKSFNRGEC | hu31.1_IGG4.PLC (mature peptide) |
| 54 | DIVLTQSPALAVSPGQRATITCRTQQTVDHYGTTYMNWY QQKPGQPPKLLIYLASSLASGVPARFSGSGSGTDFTLTI NPVEANDTANYYCQQSRNLWTFGGGTKVEIKRTVAAPSV FIFPPSDEQLKSGTASVVCLLNNFYPREAKVQWKVDNAL | hu31.2_IGG4.PLC (mature peptide) |

SEQUENCE LISTING TABLE-continued

| SEQ ID NO | Amino Acid Sequence | Comments |
|---|---|---|
| | QSGNSQESVTEQDSKDSTYSLSSTLTLSKADYEKHKVYA<br>CEVTHQGLSSPVTKSFNRGEC | |
| 55 | DIVLTQSPALAVSPGQRATITCRTNPTVDHYGTTYMNWY<br>QQKPGQPPKLLIYLASSLASGVPARFSGSGSGTDFTLTI<br>NPVEADDTANYYCQQSRNLWTFGGGTKVEIKRTVAAPSV<br>FIFPPSDEQLKSGTASVVCLLNNFYPREAKVQWKVDNAL<br>QSGNSQESVTEQDSKDSTYSLSSTLTLSKADYEKHKVYA<br>CEVTHQGLSSPVTKSFNRGEC | hu31.3_IGG4.PLC (mature peptide) |
| 56 | DIVLTQSPALAVSPGQRATITCRTQQTVDHYGTTYMNWY<br>QQKPGQPPKLLIYLASSLASGVPARFSGSGSGTDFTLTI<br>NPVEADDTANYYCQQSRNLWTFGGGTKVEIKRTVAAPSV<br>FIFPPSDEQLKSGTASVVCLLNNFYPREAKVQWKVDNAL<br>QSGNSQESVTEQDSKDSTYSLSSTLTLSKADYEKHKVYA<br>CEVTHQGLSSPVTKSFNRGEC | hu31.4_IGG4.PLC (mature peptide)<br>hu31.4_IGG1.AA LC (mature peptide)<br>hu31.6_IGG4.PLC (mature peptide) |
| 57 | DIVMTQSPDLAVSLGERATINCRTQQTVDHYGTTYMNWY<br>QQKPGQPPKLLIYLASSLASGVPDRFSGSGSGTDFTLTI<br>SSLQAEDVAVYYCQQSRNLWTFGGGTKVEIKRTVAAPSV<br>FIFPPSDEQLKSGTASVVCLLNNFYPREAKVQWKVDNAL<br>QSGNSQESVTEQDSKDSTYSLSSTLTLSKADYEKHKVYA<br>CEVTHQGLSSPVTKSFNRGEC | hu31.5_IGG4.PLC (mature peptide)<br>hu31.7_IGG4.PLC (mature peptide) |
| 58 | EVQLVESGGGLVQPGRSLRLSCAASGFTFNNYGMNWVRQ<br>APGKGLEWVSSFSSSSTYISYADTVKGRFTISRDNAKNS<br>LYLQMNSLRAEDTALYYCARHGRYGGYGGFYFDYWGQGT<br>MVTVSS | hu39.1_IGG4.P HCVR (mature peptide)<br>hu39.2_IGG4.P HCVR (mature peptide)<br>hu39.3_IGG4.P HCVR (mature peptide)<br>hu39.8_IGG4.P HCVR (mature peptide) |
| 59 | QVQLVESGGGVVQPGRSLRLSCAASGFTFNNYGMNWVRQ<br>APGKGLEWVASFSSSSTYISYADTVKGRFTISRDNSKNT<br>LYLQMSSLRAEDTAVYYCARHGRYGGYGGFYFDYWGQG<br>TMVTVSS | hu39.4_IGG4.P HCVR (mature peptide)<br>hu39.5_IGG4.P HCVR (mature peptide)<br>hu39.5_IGG1.AA HCVR (mature peptide)<br>hu39.6_IGG4.P HCVR (mature peptide)<br>hu39.7_IGG4.P HCVR (mature peptide) |
| 60 | DTVLTQSPASLAVSPGQRATITCRASEGVKSYMHWYQQK<br>PGQPPKLLIYKASNLASGVPARFSGSGSGTDFTLTINPV<br>EADDTANYYCQQSWNDPTFGQGTKLEIK | hu39.1_IGG4.P LCVR (mature peptide)<br>hu39.5_IGG4.P LCVR (mature peptide)<br>hu39.5_IGG1.AA LCVR (mature peptide) |
| 61 | DIVLTQSPASLAVSPGQRATITCRASEGVKSYMHWYQQK<br>PGQPPKLLIYKASNLASGVPARFSGSGSGTDFTLTINPV<br>EADDTANYYCQQSWNDPTFGQGTKLEIK | hu39.2_IGG4.P LCVR (mature peptide)<br>hu39.4_IGG4.P LCVR (mature peptide) |
| 62 | EIVMTQSPATLSVSPGERATLSCRASEGVKSYMHWYQQK<br>PGQAPRLLIYKASNLASGIPARFSGSGSGTEFTLTISSL<br>QSEDFAVYYCQQSWNDPTFGQGTKLELK | hu39.3_IGG4.P LCVR (mature peptide)<br>hu39.6_IGG4.P LCVR (mature peptide) |
| 63 | ETVMTQSPATLSVSPGERATLSCRASEGVKSYMHWYQQK<br>PGQAPRLLIYKASNLASGIPARFSGSGSGTEFTLTISSL<br>QSEDFAVYYCQQSWNDPTFGQGTKLELK | hu39.7_IGG4.P LCVR (mature peptide)<br>hu39.8_IGG4.P LCVR (mature peptide) |
| 64 | EVQLVESGGGLVQPGRSLRLSCAASGFTFNNYGMNWVRQ<br>APGKGLEWVSSFSSSSTYISYADTVKGRFTISRDNAKNS<br>LYLQMNSLRAEDTALYYCARHGRYGGYGGFYFDYWGQGT<br>MVTVSSASTKGPSVFPLAPCSRSTSESTAALGCLVKDYF<br>PEPVTVSWNSGALTSGVHTFPAVLQSSGLYSLSSVVTVP<br>SSSLGTKTYTCNVDHKPSNTKVDKRVESKYGPPCPPCPA<br>PEFLGGPSVFLFPPKPKDTLMISRTPEVTCVVVDVSQED<br>PEVQFNWYVDGVEVHNAKTKPREEQFNSTYRVVSVLTVL<br>HQDWLNGKEYKCKVSNKGLPSSIEKTISKAKGQPREPQV<br>YTLPPSQEEMTKNQVSLTCLVKGFYPSDIAVEWESNGQP<br>ENNYKTTPPVLDSDGSFFLYSRLTVDKSRWQEGNVFSCS<br>VMHEALHNHYTQKSLSLSLGK | hu39.1_IGG4.P HC (mature peptide)<br>hu39.2_IGG4.P HC (mature peptide)<br>hu39.3_IGG4.P HC (mature peptide)<br>hu39.8_IGG4.P HC (mature peptide) |
| 65 | QVQLVESGGGVVQPGRSLRLSCAASGFTFNNYGMNWVRQ<br>APGKGLEWVASFSSSSTYISYADTVKGRFTISRDNSKNT<br>LYLQMSSLRAEDTAVYYCARHGRYGGYGGFYFDYWGQGT<br>MVTVSSASTKGPSVFPLAPCSRSTSESTAALGCLVKDYF<br>PEPVTVSWNSGALTSGVHTFPAVLQSSGLYSLSSVVTVP<br>SSSLGTKTYTCNVDHKPSNTKVDKRVESKYGPPCPPCPA<br>PEFLGGPSVFLFPPKPKDTLMISRTPEVTCVVVDVSQED<br>PEVQFNWYVDGVEVHNAKTKPREEQFNSTYRVVSVLTVL<br>HQDWLNGKEYKCKVSNKGLPSSIEKTISKAKGQPREPQV<br>YTLPPSQEEMTKNQVSLTCLVKGFYPSDIAVEWESNGQP<br>ENNYKTTPPVLDSDGSFFLYSRLTVDKSRWQEGNVFSCS<br>VMHEALHNHYTQKSLSLSLGK | hu39.4_IGG4.P HC (mature peptide)<br>hu39.5_IGG4.P HC (mature peptide)<br>hu39.6_IGG4.P HC (mature peptide)<br>hu39.7_IGG4.P HC (mature peptide) |

SEQUENCE LISTING TABLE-continued

| SEQ ID NO | Amino Acid Sequence | Comments |
|---|---|---|
| 66 | QVQLVESGGGVVQPGRSLRLSCAASGFTFNNYGMNWVRQ APGKGLEWVASFSSSSTYISYADTVKGRFTISRDNSKNT LYLQMSSLRAEDTAVYYCARHGRYGGYGGFYFDYWGQGT MVTVSSASTKGPSVFPLAPSSKSTSGGTAALGCLVKDYF PEPVTVSWNSGALTSGVHTFPAVLQSSGLYSLSSVVTVP SSSLGTQTYICNVNHKPSNTKVDKKVEPKSCDKTHTCPP CPAPEAAGGPSVFLFPPKPKDTLMISRTPEVTCVVVDVS HEDPEVKFNWYVDGVEVHNAKTKPREEQYNSTYRVVSL TVLHQDWLNGKEYKCKVSNKALPAPIEKTISKAKGQPRE PQVYTLPPSRDELTKNQVSLTCLVKGFYPSDIAVEWESN GQPENNYKTTPPVLDSDGSFFLYSKLTVDKSRWQQGNVF SCSVMHEALHNHYTQKSLSLSPGK | hu39.5_IGG1.AA HC (mature peptide) |
| 67 | DTVLTQSPASLAVSPGQRATITCRASEGVKSYMHWYQQK PGQPPKLLIYKASNLASGVPARFSGSGSGTDFTLTINPV EADDTANYYCQQSWNDPTFGQGTKLEIKRTVAAPSVFIF PPSDEQLKSGTASVVCLLNNFYPREAKVQWKVDNALQSG NSQESVTEQDSKDSTYSLSSTLTLSKADYEKHKVYACEV THQGLSSPVTKSFNRGEC | hu39.1_IGG4.PLC (mature peptide) hu39.5_IGG4.PLC (mature peptide) hu39.5_IGG1.AA LC (mature peptide) |
| 68 | DIVLTQSPASLAVSPGQRATITCRASEGVKSYMHWYQQK PGQPPKLLIYKASNLASGVPARFSGSGSGTDFTLTINPV EADDTANYYCQQSWNDPTFGQGTKLEIKRTVAAPSVFIF PPSDEQLKSGTASVVCLLNNFYPREAKVQWKVDNALQSG NSQESVTEQDSKDSTYSLSSTLTLSKADYEKHKVYACEV THQGLSSPVTKSFNRGEC | hu39.2_IGG4.PLC (mature peptide) hu39.4_IGG4.PLC (mature peptide) |
| 69 | EIVMTQSPATLSVSPGERATLSCRASEGVKSYMHWYQQK PGQAPRLLIYKASNLASGIPARFSGSGSGTEFTLTISSL QSEDFAVYYCQQSWNDPTFGQGTKLELKRTVAAPSVFIF PPSDEQLKSGTASVVCLLNNFYPREAKVQWKVDNALQSG NSQESVTEQDSKDSTYSLSSTLTLSKADYEKHKVYACEV THQGLSSPVTKSFNRGEC | hu39.3_IGG4.PLC (mature peptide) hu39.6_IGG4.PLC (mature peptide) |
| 70 | ETVMTQSPATLSVSPGERATLSCRASEGVKSYMHWYQQK PGQAPRLLIYKASNLASGIPARFSGSGSGTEFTLTISSL QSEDFAVYYCQQSWNDPTFGQGTKLELKRTVAAPSVFIF PPSDEQLKSGTASVVCLLNNFYPREAKVQWKVDNALQSG NSQESVTEQDSKDSTYSLSSTLTLSKADYEKHKVYACEV THQGLSSPVTKSFNRGEC | hu39.7_IGG4.PLC (mature peptide) hu39.8_IGG4.P LC (mature peptide) |
| 71 | MEDIKDSKVKRFCSKNILIILGFTSILAVIALIAVGLTQ NKPLPENVKYGIVLDAGSSHTNLYIYKWPAEKENDTGVV QQLEECQVKGPGISKYAQKTDEIGAYLAECMELSTELIP TSKHHQTPVYLGATAGMRLLRMESEQSADEVLAAVSTSL KSYPFDFQGAKIITGQEEGAYGWITINYLLGRFTQEQSW LSLISDSQKQETFGALDLGGASTQITFVPQNSTIESPEN SLQFRLYGEDYTVYTHSFLCYGKDQALWQKLAKDIQVSS GGVLKDPCFNPGYEKVVNVSELYGTPCTKRFEKKLPFDQ FRIQGTGDYEQCHQSILELFNNSHCPYSQCAFNGVFLPP LHGSFGAFSAFYFVMDFFKKVAKNSVISQEKMTEITKNF CSKSWEETKTSYPSVKEKYLSEYCFSGAYILSLLQGYNF TDSSWEQIHFMGKIKDSNAGWTLGYMLNLTNMIPAEQPL SPPLPHSTYIGLMVLFSLLLVAVAITGLFIYSKPSYFWK EAV | Mouse CD39 (UniProtKB reference: P55772) |
| 72 | TQNKALPENVKYGIVLDAGSSHTSLYIYKWPAEKENDTG VVHQVEECRVKGPGISKFVQKVNEIGIYLTDCMERAREV IPRSQHQETPVYLGATAGMRLLRMESEELADRVLDVVER SLSNYPFDFQGARIITGQEEGAYGWITINYLLGKFSQKT RWFSIVPYETNNQETFGALDLGGASTQVTFVPQNQTIES PDNALQFRLYGKDYNVYTHSFLCYGKDQALWQKLAKDIQ VASNEILRDPCFHPGYKKVVNVSDLYKTPCTKRFEMTLP FQQFEIQGIGNYQQCHQSILELFNTSYCPYSQCAFNGIF LPPLQGDFGAFSAFYFVMKFLNLTSEKVSQEKVTEMMKK FCAQPWEEIKTSYAGVKEKYLSEYCFSGTYILSLLLQGY HFTADSWEHIHFIGKIQGSDAGWTLGYMLNLTNMIPAEQ PLSTPLSHSTYVAHHHHHHHHHH | Human CD39 extracellular domain, His-tagged |
| 73 | QVQLVQSGAEVKKPGASVKVSCKASGYTFTDYNMHWVRQ APGQRLEWIGYIVPLNGGSTFNQKFKGRATITVDTSART AYMELSSLRSEDTAVYYCARGGTRFPAYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTHTCPPCPAPEAE | huBMK2_IGG1.AEASS HC (mature peptide) |

SEQUENCE LISTING TABLE-continued

| SEQ ID NO | Amino Acid Sequence | Comments |
|---|---|---|
| | GAPSVFLFPPKPKDTLMISRTPEVTCVVVDVSHEDPEVK<br>FNWYVDGVEVHNAKTKPREEQYNSTYRVVSVLTVLHQDW<br>LNGKEYKCKVSNKALPSSIEKTISKAKGQPREPQVYTLP<br>PSREEMTKNQVSLTCLVKGFYPSDIAVEWESNGQPENNY<br>KTTPPVLDSDGSFFLYSKLTVDKSRWQQGNVFSCSVMHE<br>ALHNHYTQKSLSLSPGK | |
| 74 | DIVMTQSPDSLAVSLGERATINCRASESVDNFGVSFMYW<br>FQQKPGQPPKLLIYGASNQGSGVPDRFSGSGSGTDFTLT<br>ISSLQAEDVAVYYCQQTKEVPYTFGGGTKVEIKRTVAAP<br>SVFIFPPSDEQLKSGTASVVCLLNNFYPREAKVQWKVDN<br>ALQSGNSQESVTEQDSKDSTYSLSSTLTLSKADYEKHKV<br>YACEVTHQGLSSPVTKSFNRGEC | huBMK2_IGG1.AEASS LC (mature peptide) |

We claim:

1. An anti-CD39 antibody that specifically binds to human CD39, comprising a heavy chain variable region comprising a complementarity determining region 1 (H1) comprising SEQ ID NO: 28, a complementarity determining region 2 (H2) comprising SEQ ID NO: 29, and a complementarity determining region 3 (H3) comprising SEQ ID NO: 30; and a light chain variable region comprising a complementarity determining region 1 (L1) comprising SEQ ID NO: 32, a complementarity determining region 2 (L2) comprising SEQ ID NO: 33, and a complementarity determining region 3 (L3) comprising SEQ ID NO: 34.

2. The anti-CD39 antibody of claim 1, wherein the antibody has a heavy chain variable region and a light chain variable region according to claim 1 and:
   the heavy chain variable region has at least 90% sequence identity to SEQ ID NO: 27, and the light chain variable region has at least 90% sequence identity to SEQ ID NO: 31;
   the heavy chain variable region has at least 90% sequence identity to SEQ ID NO: 58, and the light chain variable region has at least 90% sequence identity to SEQ ID NO: 60;
   the heavy chain variable region has at least 90% sequence identity to SEQ ID NO: 58, and the light chain variable region has at least 90% sequence identity to SEQ ID NO: 61;
   the heavy chain variable region has at least 90% sequence identity to SEQ ID NO: 58, and the light chain variable region has at least 90% sequence identity to SEQ ID NO: 62;
   the heavy chain variable region has at least 90% sequence identity to SEQ ID NO: 58, and the light chain variable region has at least 90% sequence identity to SEQ ID NO: 63;
   the heavy chain variable region has at least 90% sequence identity to SEQ ID NO: 59, and the light chain variable region has at least 90% sequence identity to SEQ ID NO: 61;
   the heavy chain variable region has at least 90% sequence identity to SEQ ID NO: 59, and the light chain variable region has at least 90% sequence identity to SEQ ID NO: 60;
   the heavy chain variable region has at least 90% sequence identity to SEQ ID NO: 59, and the light chain variable region has at least 90% sequence identity to SEQ ID NO: 62; or
   the heavy chain variable region has at least 90% sequence identity to SEQ ID NO: 59, and the light chain variable region has at least 90% sequence identity to SEQ ID NO: 63.

3. The anti-CD39 antibody of claim 1, wherein the anti-CD39 antibody is a monoclonal antibody or an antigen-binding fragment thereof.

4. The anti-CD39 antibody of claim 1, wherein the anti-CD39 antibody is a human, chimeric, humanized, or veneered antibody or an antigen-binding fragment thereof.

5. The anti-CD39 antibody of claim 1, wherein the antibody further comprises a variant heavy chain constant region selected from a variant human IgG1 constant region, a variant human IgG2 constant region, a variant human IgG3 constant region, or a variant human IgG4 constant region.

6. The anti-CD39 antibody of claim 5, wherein the variant human IgG heavy chain constant region comprises SEQ ID NO: 2, SEQ ID NO: 3, or SEQ ID NO: 5.

7. The anti-CD39 antibody of claim 1, wherein the antibody further comprises a wild-type human IgG heavy chain constant region.

8. The anti-CD39 antibody of claim 7, wherein the wild-type human IgG heavy chain constant region comprises SEQ ID NO: 1 or SEQ ID NO: 4.

9. The anti-CD39 antibody of claim 5 comprising a human light chain kappa constant region.

10. The anti-CD39 antibody of claim 1, wherein the antibody has a heavy chain comprising the heavy chain variable region and a light chain comprising the light chain variable region, wherein
   (a) the heavy chain comprises SEQ ID NO: 64, and the light chain comprises SEQ ID NO: 67;
   (b) the heavy chain comprises SEQ ID NO: 64, and the light chain comprises SEQ ID NO: 68;
   (c) the heavy chain comprises SEQ ID NO: 64, and the light chain comprises SEQ ID NO: 69;
   (d) the heavy chain comprises SEQ ID NO: 64, and the light chain has comprises SEQ ID NO: 70;
   (e) the heavy chain comprises SEQ ID NO: 65, and the light chain comprises SEQ ID NO: 68;
   (f) the heavy chain comprises SEQ ID NO: 65, and the light chain comprises SEQ ID NO: 67;
   (g) the heavy chain comprises SEQ ID NO: 66, and the light chain comprises SEQ ID NO: 67;
   (h) the heavy chain comprises SEQ ID NO: 65, and the light chain comprises SEQ ID NO: 69; or
   (i) the heavy chain comprises SEQ ID NO: 65, and the light chain comprises SEQ ID NO: 70.

11. A pharmaceutical composition comprising the antibody of claim 1 and a pharmaceutically acceptable carrier.

12. The anti-CD39 antibody of claim 1, wherein the antibody has a heavy chain variable region and a light chain variable region according to claim 1 and:
   the heavy chain variable region has at least 95% sequence identity to SEQ ID NO: 27, and the light chain variable region has at least 95% sequence identity to SEQ ID NO: 31;
   the heavy chain variable region has at least 95% sequence identity to SEQ ID NO: 58, and the light chain variable region has at least 95% sequence identity to SEQ ID NO: 60;
   the heavy chain variable region has at least 95% sequence identity to SEQ ID NO: 58, and the light chain variable region has at least 95% sequence identity to SEQ ID NO: 61;
   the heavy chain variable region has at least 95% sequence identity to SEQ ID NO: 58, and the light chain variable region has at least 95% sequence identity to SEQ ID NO: 62;
   the heavy chain variable region has at least 95% sequence identity to SEQ ID NO: 58, and the light chain variable region has at least 95% sequence identity to SEQ ID NO: 63;
   the heavy chain variable region has at least 95% sequence identity to SEQ ID NO: 59, and the light chain variable region has at least 95% sequence identity to SEQ ID NO: 61;
   the heavy chain variable region has at least 95% sequence identity to SEQ ID NO: 59, and the light chain variable region has at least 95% sequence identity to SEQ ID NO: 60;
   the heavy chain variable region has at least 95% sequence identity to SEQ ID NO: 59, and the light chain variable region has at least 95% sequence identity to SEQ ID NO: 62; or
   the heavy chain variable region has at least 95% sequence identity to SEQ ID NO: 59, and the light chain variable region has at least 95% sequence identity to SEQ ID NO: 63.

13. The anti-CD39 antibody of claim 1, wherein the antibody has a heavy chain variable region and a light chain variable region according to claim 1 and:
   the heavy chain variable region has at least 99% sequence identity to SEQ ID NO: 27, and the light chain variable region has at least 99% sequence identity to SEQ ID NO: 31;

the heavy chain variable region has at least 99% sequence identity to SEQ ID NO: 58, and the light chain variable region has at least 99% sequence identity to SEQ ID NO: 60;

the heavy chain variable region has at least 99% sequence identity to SEQ ID NO: 58, and the light chain variable region has at least 99% sequence identity to SEQ ID NO: 61;

the heavy chain variable region has at least 99% sequence identity to SEQ ID NO: 58, and the light chain variable region has at least 99% sequence identity to SEQ ID NO: 62;

the heavy chain variable region has at least 99% sequence identity to SEQ ID NO: 58, and the light chain variable region has at least 99% sequence identity to SEQ ID NO: 63;

the heavy chain variable region has at least 99% sequence identity to SEQ ID NO: 59, and the light chain variable region has at least 99% sequence identity to SEQ ID NO: 61;

the heavy chain variable region has at least 99% sequence identity to SEQ ID NO: 59, and the light chain variable region has at least 99% sequence identity to SEQ ID NO: 60;

the heavy chain variable region has at least 99% sequence identity to SEQ ID NO: 59, and the light chain variable region has at least 99% sequence identity to SEQ ID NO: 62; or the heavy chain variable region has at least 99% sequence identity to SEQ ID NO: 59, and the light chain variable region has at least 99% sequence identity to SEQ ID NO: 63.

\* \* \* \* \*

UNITED STATES PATENT AND TRADEMARK OFFICE
CERTIFICATE OF CORRECTION

| | | |
|---|---|---|
| PATENT NO. | : 11,970,543 B2 | Page 1 of 1 |
| APPLICATION NO. | : 18/177729 | |
| DATED | : April 30, 2024 | |
| INVENTOR(S) | : Christine Elizabeth Bowman et al. | |

It is certified that error appears in the above-identified patent and that said Letters Patent is hereby corrected as shown below:

On the Title Page

Please insert the foreign priority information:
--(30) Foreign Application Priority Data
Mar. 3, 2022 (WO) ............... PCT/CN2022/079021
Oct. 19, 2022 (WO) ............... PCT/CN2022/126070--

Signed and Sealed this
Second Day of July, 2024

Katherine Kelly Vidal
*Director of the United States Patent and Trademark Office*